(12) United States Patent
Chhikara et al.

(10) Patent No.: US 10,406,072 B2
(45) Date of Patent: Sep. 10, 2019

(54) PRESSURE-REGULATING FLUID TRANSFER SYSTEMS AND METHODS

(71) Applicant: ICU Medical, Inc., San Clemente, CA (US)

(72) Inventors: Bhupinder Chhikara, Draper, UT (US); Srinath Lingutla, Salt Lake City, UT (US); Brandon Eads, Taylorsville, UT (US)

(73) Assignee: ICU Medical, Inc., San Clemente, CA (US)

( * ) Notice: Subject to any disclaimer, the term of this patent is extended or adjusted under 35 U.S.C. 154(b) by 593 days.

(21) Appl. No.: 14/997,231

(22) Filed: Jan. 15, 2016

(65) Prior Publication Data
US 2016/0206512 A1 Jul. 21, 2016

Related U.S. Application Data

(63) Continuation of application No. PCT/US2014/046735, filed on Jul. 15, 2014.
(Continued)

(51) Int. Cl.
*A61J 1/20* (2006.01)
*A61J 1/22* (2006.01)
(Continued)

(52) U.S. Cl.
CPC ............. *A61J 1/22* (2013.01); *A61J 1/2048* (2015.05); *A61J 1/2072* (2015.05); *A61J 1/2096* (2013.01);
(Continued)

(58) Field of Classification Search
CPC ...... A61J 1/2048; A61J 1/2072; A61J 1/2096; A61J 1/22; A61M 5/162; A61M 5/1782; A61M 5/1787; A61M 5/19; A61M 5/3129; A61M 5/3145; A61M 5/31513; A61M 5/3298; A61M 2005/1787;
(Continued)

(56) References Cited

U.S. PATENT DOCUMENTS 2,074,223 A 3/1937 Horiuchi et al.
2,409,734 A 10/1946 Bucher et al.
(Continued)

FOREIGN PATENT DOCUMENTS

AU 2008242160 A1 10/2008
AU 2013200393 A1 2/2013
(Continued)

OTHER PUBLICATIONS

U.S. Appl. No. 14/932,794, filed Nov. 4, 2015, Warren et al.
(Continued)

*Primary Examiner* — Benjamin J Klein
(74) *Attorney, Agent, or Firm* — Knobbe, Martens, Olson & Bear, LLP

(57) ABSTRACT

Various systems and methods for the pressure-regulated transfer of medical fluids are disclosed. The system can include an adapter assembly that connects with a medical container and with a syringe assembly. The syringe assembly can include a first reservoir and a second reservoir. In various embodiments, when the adapter assembly and the syringe assembly are coupled, the first reservoir and the container can exchange regulating fluid and the second reservoir and the container can exchange medical liquid from the medical container.

12 Claims, 86 Drawing Sheets

Related U.S. Application Data

(60) Provisional application No. 61/936,785, filed on Feb. 6, 2014, provisional application No. 61/856,593, filed on Jul. 19, 2013.

(51) Int. Cl.
*A61M 5/162* (2006.01)
*A61M 5/178* (2006.01)
*A61M 5/31* (2006.01)
*A61M 5/315* (2006.01)
*A61M 5/32* (2006.01)

(52) U.S. Cl.
CPC .......... *A61M 5/162* (2013.01); *A61M 5/1782* (2013.01); *A61M 5/3129* (2013.01); *A61M 5/3145* (2013.01); *A61M 5/31513* (2013.01); *A61M 5/3298* (2013.01); *A61M 2005/1623* (2013.01); *A61M 2005/1787* (2013.01); *A61M 2005/3114* (2013.01); *A61M 2005/3123* (2013.01); *A61M 2005/3128* (2013.01); *A61M 2005/3132* (2013.01); *A61M 2005/31598* (2013.01); *A61M 2205/75* (2013.01)

(58) Field of Classification Search
CPC .. A61M 2005/3114; A61M 2005/3123; A61M 2005/3128; A61M 2005/3132; A61M 2005/31598; A61M 2005/75
See application file for complete search history.

(56) References Cited

U.S. PATENT DOCUMENTS

| | | |
|---|---|---|
| 2,419,401 A | 4/1947 | Hinds |
| 2,668,533 A | 2/1954 | Evans |
| 2,673,013 A | 3/1954 | Hester |
| 2,999,500 A | 9/1961 | Schurer |
| 3,291,151 A | 12/1966 | Loken |
| 3,584,770 A | 6/1971 | Taylor |
| 3,797,521 A | 3/1974 | King |
| 3,822,700 A | 7/1974 | Pennington |
| 3,844,283 A | 10/1974 | Dabney |
| 3,923,058 A | 12/1975 | Weingarten |
| 3,980,082 A | 9/1976 | Miller |
| 3,993,063 A | 11/1976 | Larrabee |
| 4,046,291 A | 9/1977 | Goda |
| 4,058,121 A | 11/1977 | Choski et al. |
| 4,143,853 A | 3/1979 | Abramson |
| 4,240,433 A | 12/1980 | Bordow |
| 4,240,833 A | 12/1980 | Myles |
| 4,262,671 A | 4/1981 | Kersten |
| 4,301,799 A | 11/1981 | Pope, Jr. et al. |
| 4,312,349 A | 1/1982 | Cohen |
| 4,349,035 A | 9/1982 | Thomas et al. |
| 4,376,634 A | 3/1983 | Prior et al. |
| 4,381,776 A | 5/1983 | Latham, Jr. |
| 4,410,321 A | 10/1983 | Pearson et al. |
| 4,475,915 A | 10/1984 | Sloane |
| 4,493,348 A | 1/1985 | Lemmons |
| 4,505,709 A | 3/1985 | Froning et al. |
| 4,534,758 A | 8/1985 | Akers et al. |
| 4,588,403 A | 5/1986 | Weiss et al. |
| 4,600,040 A | 7/1986 | Naslund |
| 4,673,404 A | 6/1987 | Gustavsson |
| 4,735,608 A | 4/1988 | Sardam |
| 4,743,243 A | 5/1988 | Vaillancourt |
| 4,768,568 A | 9/1988 | Fournier et al. |
| 4,798,578 A | 1/1989 | Ranford |
| 4,929,230 A | 5/1990 | Pfleger |
| 5,176,673 A | 1/1993 | Marrucchi |
| 5,349,984 A | 9/1994 | Weinheimer et al. |
| 5,478,337 A | 12/1995 | Okamoto et al. |
| 5,660,796 A | 8/1997 | Sheehy |
| 5,725,500 A | 3/1998 | Micheler |
| 5,772,079 A | 6/1998 | Gueret |
| 5,803,311 A | 9/1998 | Fuchs |
| 5,833,213 A | 11/1998 | Ryan |
| 6,139,534 A | 10/2000 | Niedospial et al. |
| 6,159,192 A | 12/2000 | Fowles et al. |
| 6,551,299 B2 | 4/2003 | Miyoshi et al. |
| 6,572,256 B2 | 6/2003 | Seaton et al. |
| 6,715,520 B2 | 4/2004 | Andreasson et al. |
| 6,719,719 B2 | 4/2004 | Carmel et al. |
| 6,997,910 B2 | 2/2006 | Howlett et al. |
| 6,997,917 B2 | 2/2006 | Niedospial, Jr. et al. |
| 7,004,926 B2 | 2/2006 | Navia et al. |
| 7,048,720 B1 | 5/2006 | Thorne, Jr. et al. |
| 7,086,431 B2 | 8/2006 | D'Antonio et al. |
| 7,101,354 B2 | 9/2006 | Thorne, Jr. et al. |
| 7,306,584 B2 | 2/2007 | Wessman et al. |
| 7,192,423 B2 | 3/2007 | Wong |
| 7,291,131 B2 | 11/2007 | Call |
| 7,354,427 B2 | 4/2008 | Fangrow |
| 7,507,227 B2 | 3/2009 | Fangrow |
| 7,510,547 B2 | 3/2009 | Fangrow |
| 7,510,548 B2 | 3/2009 | Fangrow |
| 7,513,895 B2 | 4/2009 | Fangrow |
| 7,534,238 B2 | 5/2009 | Fangrow |
| 7,547,300 B2 | 6/2009 | Fangrow |
| 7,569,043 B2 | 8/2009 | Fangrow |
| 7,618,408 B2 | 11/2009 | Yandell |
| 7,632,261 B2 | 12/2009 | Zinger et al. |
| 7,645,271 B2 | 1/2010 | Fangrow |
| 7,654,995 B2 | 2/2010 | Warren et al. |
| 7,658,733 B2 | 2/2010 | Fangrow |
| 7,743,799 B2 | 6/2010 | Mosler et al. |
| 7,758,560 B2 | 7/2010 | Connell et al. |
| 7,883,499 B2 | 2/2011 | Fangrow |
| 7,900,659 B2 | 3/2011 | Whitley et al. |
| 7,963,954 B2 | 6/2011 | Kavazov |
| 7,972,321 B2 | 7/2011 | Fangrow |
| 7,998,106 B2 | 8/2011 | Thorne, Jr. et al. |
| 8,122,923 B2 | 2/2012 | Kraus et al. |
| 8,123,736 B2 | 2/2012 | Kraushaar et al. |
| 8,141,601 B2 | 3/2012 | Fehr et al. |
| 8,162,914 B2 | 4/2012 | Kraushaar et al. |
| 8,167,863 B2 | 5/2012 | Yow |
| 8,196,614 B2 | 6/2012 | Kriheli |
| 8,197,459 B2 | 6/2012 | Jansen et al. |
| 8,206,367 B2 | 6/2012 | Warren et al. |
| 8,211,082 B2 | 7/2012 | Hasegawa et al. |
| 8,225,826 B2 | 7/2012 | Horppu et al. |
| 8,231,567 B2 | 7/2012 | Tennican et al. |
| 8,241,265 B2 | 8/2012 | Moy et al. |
| 8,267,127 B2 | 9/2012 | Kriheli |
| 8,267,913 B2 | 9/2012 | Fangrow |
| 8,287,513 B2 | 10/2012 | Ellstrom et al. |
| 8,336,587 B2 | 12/2012 | Rosenquist et al. |
| 8,356,644 B2 | 1/2013 | Chong et al. |
| 8,356,645 B2 | 1/2013 | Chong et al. |
| 8,357,137 B2 | 1/2013 | Yandell |
| 8,381,776 B2 | 2/2013 | Horppu |
| 8,403,905 B2 | 3/2013 | Yow |
| 8,409,164 B2 | 4/2013 | Fangrow |
| 8,409,165 B2 | 4/2013 | Niedsopial et al. |
| 8,414,554 B2 | 4/2013 | Garfield et al. |
| 8,425,487 B2 | 4/2013 | Beiriger et al. |
| 8,449,521 B2 | 5/2013 | Thorne, Jr. et al. |
| 8,469,939 B2 | 6/2013 | Fangrow |
| 8,506,548 B2 | 8/2013 | Okiyama |
| 8,511,352 B2 | 8/2013 | Kraus et al. |
| 8,512,307 B2 | 8/2013 | Fangrow |
| 8,522,832 B2 | 9/2013 | Lopez et al. |
| 8,523,838 B2 | 9/2013 | Tornqvist |
| 8,540,692 B2 | 9/2013 | Fangrow |
| 8,608,723 B2 | 12/2013 | Lev et al. |
| 8,622,985 B2 | 1/2014 | Ellstrom |
| 8,657,803 B2 | 2/2014 | Helmerson et al. |
| 8,684,994 B2 | 4/2014 | Lev et al. |
| 8,701,696 B2 | 4/2014 | Guala |
| 8,702,675 B2 | 4/2014 | Imai |
| 8,720,496 B2 | 5/2014 | Huwiler et al. |
| 8,721,614 B2 | 5/2014 | Takemoto et al. |
| 8,753,325 B2 | 6/2014 | Lev et al. |

(56) References Cited

U.S. PATENT DOCUMENTS

| | | |
|---|---|---|
| 8,795,231 B2 | 8/2014 | Chong et al. |
| 8,821,436 B2 | 9/2014 | Mosler et al. |
| 8,827,977 B2 | 9/2014 | Fangrow |
| 8,864,725 B2 | 10/2014 | Ranalletta et al. |
| 8,864,737 B2 | 10/2014 | Hasegawa et al. |
| 8,870,832 B2 | 10/2014 | Raday et al. |
| 8,882,738 B2 | 11/2014 | Fangrow et al. |
| 8,945,084 B2 | 2/2015 | Warren et al. |
| 8,974,433 B2 | 3/2015 | Fangrow |
| 8,979,792 B2 | 3/2015 | Lev et al. |
| 8,992,501 B2 | 3/2015 | Seifert et al. |
| 9,005,179 B2 | 4/2015 | Fangrow et al. |
| 9,005,180 B2 | 4/2015 | Seifert et al. |
| 9,060,921 B2 | 6/2015 | Seifert et al. |
| 9,072,657 B2 | 7/2015 | Seifert et al. |
| 9,089,474 B2 | 7/2015 | Cederschiöld |
| 9,089,475 B2 | 7/2015 | Fangrow |
| 9,101,717 B2 | 8/2015 | Mansaar et al. |
| 9,107,808 B2 | 8/2015 | Fangrow |
| 9,107,809 B2 | 8/2015 | Garfield et al. |
| 9,132,062 B2 | 9/2015 | Fangrow |
| 9,144,646 B2 | 9/2015 | Barron, III et al. |
| 9,198,832 B2 | 12/2015 | Moy et al. |
| 9,211,231 B2 | 12/2015 | Mansour et al. |
| 9,351,905 B2 | 5/2016 | Fangrow et al. |
| 9,381,135 B2 | 7/2016 | Reynolds et al. |
| 9,381,339 B2 | 7/2016 | Wu et al. |
| 9,585,812 B2 | 3/2017 | Browka et al. |
| 9,610,217 B2 | 4/2017 | Fangrow |
| 9,615,997 B2 | 4/2017 | Fangrow |
| 9,662,272 B2 | 5/2017 | Warren et al. |
| 9,763,855 B2 | 9/2017 | Fangrow et al. |
| 10,022,302 B2 | 7/2018 | Warran et al. |
| 10,071,020 B2 | 9/2018 | Warren et al. |
| 10,117,807 B2 | 11/2018 | Fangrow |
| 2002/0095133 A1 | 7/2002 | Gillis et al. |
| 2002/0193777 A1 | 12/2002 | Aneas |
| 2003/0153895 A1 | 8/2003 | Leinsing |
| 2003/0216695 A1 | 11/2003 | Yang |
| 2003/0229330 A1 | 12/2003 | Hickle |
| 2005/0131357 A1 | 6/2005 | Denton et al. |
| 2005/0148992 A1 | 7/2005 | Simas, Jr. et al. |
| 2006/0025747 A1 | 2/2006 | Sullivan et al. |
| 2006/0106360 A1 | 5/2006 | Wong |
| 2006/0111667 A1 | 5/2006 | Matsuura et al. |
| 2006/0149309 A1 | 7/2006 | Paul et al. |
| 2007/0208320 A1 | 9/2007 | Muramatsu et al. |
| 2008/0045919 A1 | 2/2008 | Jakob et al. |
| 2008/0142388 A1 | 6/2008 | Whitley et al. |
| 2010/0305548 A1 | 12/2010 | Kraushaar |
| 2011/0062703 A1 | 3/2011 | Lopez et al. |
| 2011/0175347 A1 | 7/2011 | Okiyama |
| 2011/0224611 A1 | 9/2011 | Lum et al. |
| 2011/0257621 A1 | 10/2011 | Fangrow |
| 2012/0109077 A1 | 5/2012 | Ryan |
| 2012/0298254 A1 | 11/2012 | Brem et al. |
| 2012/0302986 A1 | 11/2012 | Brem et al. |
| 2013/0053815 A1 | 2/2013 | Mucientes et al. |
| 2013/0066293 A1 | 3/2013 | Garfield et al. |
| 2013/0110053 A1 | 5/2013 | Yoshino et al. |
| 2013/0130197 A1 | 5/2013 | Jessop et al. |
| 2013/0180618 A1 | 7/2013 | Py |
| 2013/0218121 A1 | 8/2013 | Waller et al. |
| 2013/0226128 A1 | 8/2013 | Fangrow |
| 2014/0011963 A1 | 1/2014 | McCauley et al. |
| 2014/0150925 A1 | 6/2014 | Sjogren et al. |
| 2014/0261727 A1 | 8/2014 | Mansour et al. |
| 2014/0231876 A1 | 9/2014 | Mansour et al. |
| 2014/0261876 A1 | 9/2014 | Mansour et al. |
| 2014/0261877 A1 | 9/2014 | Ivosevic et al. |
| 2014/0276386 A1 | 9/2014 | Mansour et al. |
| 2014/0276649 A1 | 9/2014 | Ivosevic et al. |
| 2015/0000787 A1 | 1/2015 | Fangrow |
| 2015/0065987 A1 | 3/2015 | Fangrow |
| 2015/0068640 A1 | 3/2015 | Garfield et al. |
| 2015/0082746 A1 | 3/2015 | Ivosevic et al. |
| 2015/0123398 A1 | 5/2015 | Sanders et al. |
| 2015/0126958 A1 | 5/2015 | Sanders et al. |
| 2015/0136271 A1 | 5/2015 | Warren |
| 2015/0202121 A1 | 7/2015 | Seifert |
| 2015/0209230 A1 | 7/2015 | Lev et al. |
| 2015/0209233 A1 | 7/2015 | Fukuoka |
| 2015/0209572 A1 | 7/2015 | Garfield et al. |
| 2015/0250680 A1 | 9/2015 | Browka et al. |
| 2015/0250681 A1 | 9/2015 | Lev et al. |
| 2015/0265500 A1 | 9/2015 | Russo et al. |
| 2015/0297451 A1 | 10/2015 | Marici et al. |
| 2015/0297453 A1 | 10/2015 | Kim et al. |
| 2015/0297454 A1 | 10/2015 | Sanders et al. |
| 2015/0297456 A1 | 10/2015 | Marici et al. |
| 2015/0297459 A1 | 10/2015 | Sanders |
| 2015/0297460 A1 | 10/2015 | Mansour et al. |
| 2015/0297461 A1 | 10/2015 | Fangrow |
| 2015/0297839 A1 | 10/2015 | Sanders et al. |
| 2015/0320642 A1 | 11/2015 | Fangrow |
| 2015/0359709 A1 | 12/2015 | Kriheli et al. |
| 2015/0366758 A1 | 12/2015 | Noguchi et al. |
| 2016/0000653 A1 | 1/2016 | Kramer |
| 2016/0008534 A1 | 1/2016 | Cowan et al. |
| 2016/0081878 A1 | 3/2016 | Marks et al. |
| 2016/0101020 A1 | 4/2016 | Guala |
| 2016/0120753 A1 | 5/2016 | Warren et al. |
| 2016/0120754 A1 | 5/2016 | Fangrow |
| 2016/0136051 A1 | 5/2016 | Lavi |
| 2016/0136412 A1 | 5/2016 | McKinnon et al. |
| 2016/0206511 A1 | 7/2016 | Garfield et al. |
| 2016/0213568 A1 | 7/2016 | Mansour et al. |
| 2016/0250102 A1 | 9/2016 | Garfield et al. |
| 2016/0262981 A1 | 9/2016 | Carrez et al. |
| 2016/0338911 A1 | 11/2016 | Fangrow |
| 2017/0095404 A1 | 4/2017 | Fangrow |
| 2017/0196772 A1 | 7/2017 | Seifert |
| 2017/0196773 A1 | 7/2017 | Fangrow |
| 2017/0202744 A1 | 7/2017 | Fangrow |
| 2017/0202745 A1 | 7/2017 | Seifert |
| 2017/0239140 A1 | 8/2017 | Fangrow |
| 2017/0296431 A1 | 10/2017 | Fangrow |
| 2017/0312176 A1 | 11/2017 | Fangrow |
| 2017/0333288 A1 | 11/2017 | Fangrow |
| 2018/0125759 A1 | 5/2018 | Fangrow |
| 2018/0250195 A1 | 9/2018 | Fangrow |
| 2018/0280240 A1 | 10/2018 | Fangrow |
| 2019/0000717 A1 | 1/2019 | Fangrow |

FOREIGN PATENT DOCUMENTS

| | | |
|---|---|---|
| CA | 2 684 745 | 10/2008 |
| EP | 2 606 872 | 6/2013 |
| EP | 2 139 442 | 4/2014 |
| GB | 2 000 685 | 1/1979 |
| JP | 39-17386 | 8/1961 |
| JP | 45-20604 | 8/1970 |
| JP | 57-208362 | 12/1982 |
| JP | H06-66682 | 9/1994 |
| WO | WO 84/04673 | 12/1984 |
| WO | WO 1984/04672 | 12/1984 |
| WO | WO 1997/02853 | 1/1997 |
| WO | WO 2000/035517 | 6/2000 |
| WO | WO 2005/065626 | 7/2005 |
| WO | WO 2007/120641 | 10/2007 |
| WO | WO 2008/048777 | 4/2008 |
| WO | WO 2008/081424 | 7/2008 |
| WO | WO 2008/129550 | 10/2008 |
| WO | WO 2008/153459 | 12/2008 |
| WO | WO 2009/097146 | 8/2009 |
| WO | WO 2010/069359 | 6/2010 |
| WO | WO 2010/120953 | 10/2010 |
| WO | WO 2014/122643 | 8/2014 |
| WO | WO 2014/163851 | 10/2014 |
| WO | WO 2014/181320 | 11/2014 |

(56) References Cited

FOREIGN PATENT DOCUMENTS

| | | |
|---|---|---|
| WO | WO 2015/029018 | 3/2015 |
| WO | WO 2015/009746 | 4/2015 |

OTHER PUBLICATIONS

U.S. Appl. No. 14/932,813, filed Nov. 4, 2015, Fangrow et al.
ICU Medical, Inc., Clave® Needlefree Connector Brochure, 2012.
ICU Medical, Inc., Genie® Closed Vial Access Device Brochure, 2012.
ICU Medical, Inc., Spiros® Closed Male Luer Brochure, 2012.
Equashield, Hazardous Drugs Closed System Transfer Device, http://www.equashield.com/system_components.php, downloaded Jul. 22, 2013.
International Search Report and Written Opinion for PCT Application No. PCT/US2014/046735, dated Feb. 10, 2015.
International Preliminary Report on Patentability and Written Opinion for PCT Application No. PCT/US2014/046735, dated Jan. 19, 2016.
Clave—NeedleFree Connector, 2-page brochure, Jan. 2012 ICU Medical, Inc. (M1-1065 Rev. 04).
Genie—Closed Vial Access Device, 2-page brochure, Jan. 2012 ICU Medical, Inc. (M1-1186 Rev. 11).
Spiros—Closed Male Luer, 2-page brochure, Jan. 2012 ICU Medical, Inc. (M1-1184 Rev. 11).

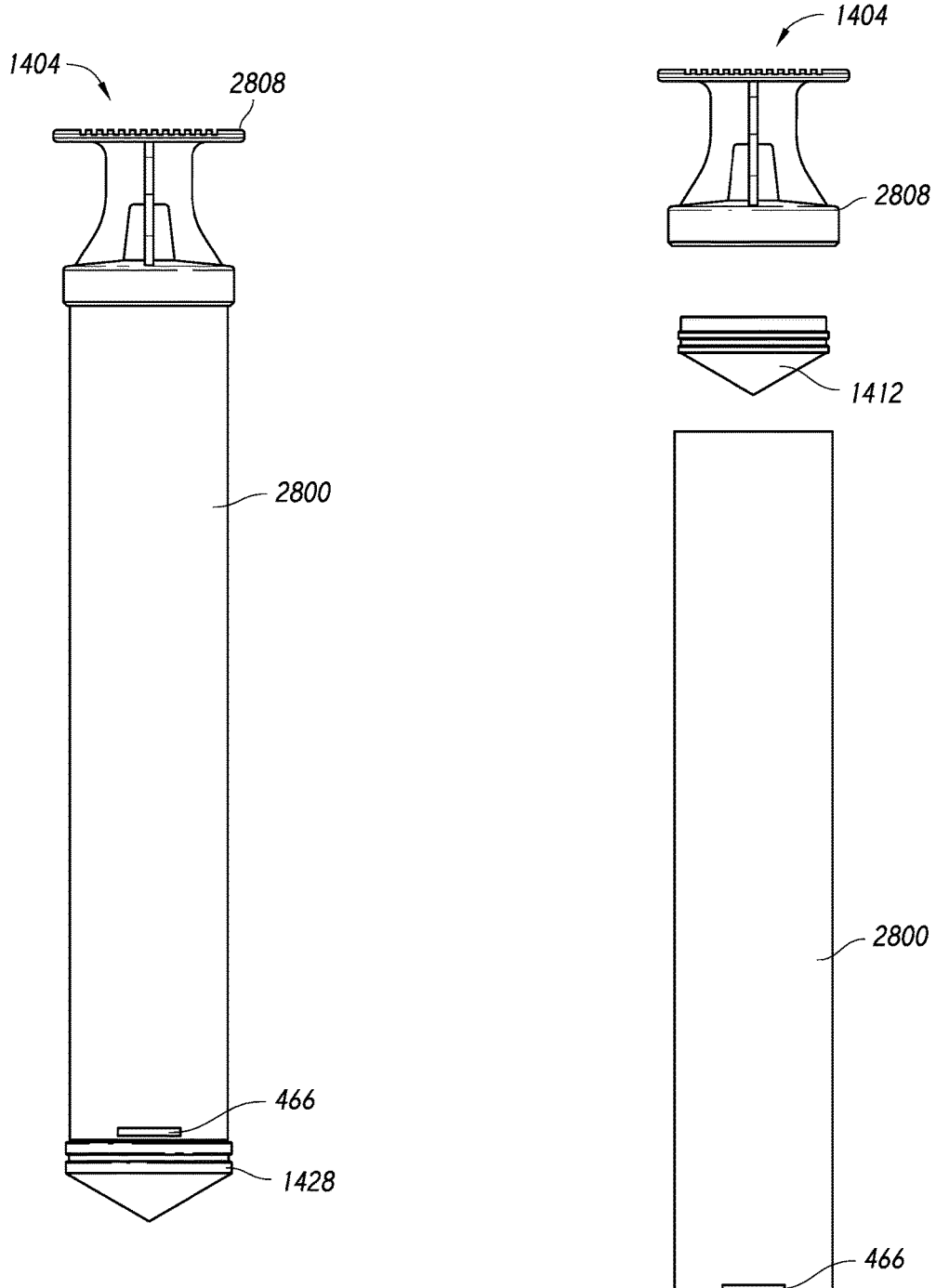

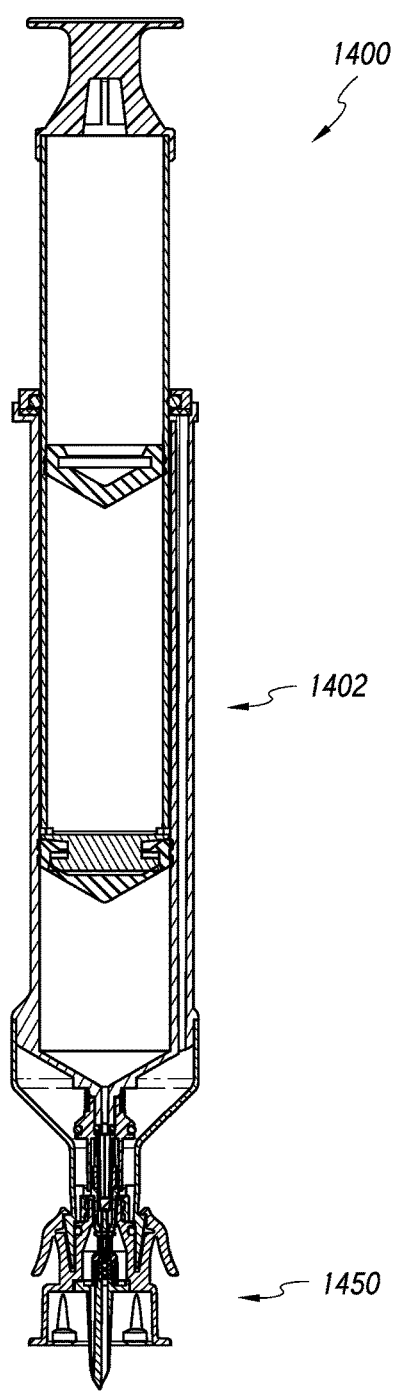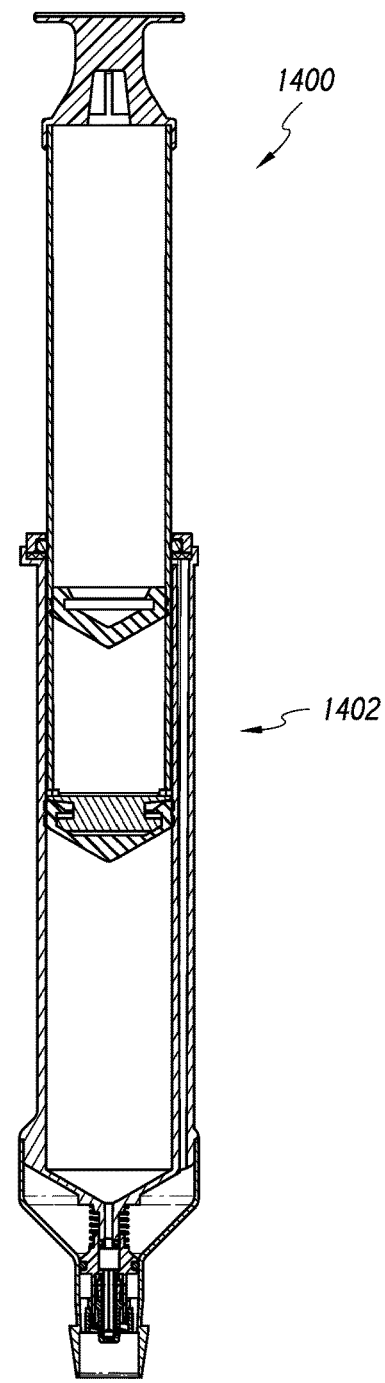
FIG. 42
FIG. 43

PRESSURE-REGULATING FLUID TRANSFER SYSTEMS AND METHODS

RELATED APPLICATIONS

This application claims the benefit under 35 U.S.C. § 120 and 35 U.S.C. § 365(c) as a continuation of International Application No. PCT/US2014/046735, designating the United States, with an international filing date of Jul. 15, 2014, titled PRESSURE-REGULATING FLUID TRANSFER SYSTEMS AND METHODS, which claims the benefit of U.S. Provisional Application No. 61/856,593, filed Jul. 19, 2013, titled PRESSURE-REGULATING FLUID TRANSFER SYSTEMS AND METHODS, and U.S. Provisional Application No. 61/936,785, filed Feb. 6, 2014, titled PRESSURE-REGULATING FLUID TRANSFER SYSTEMS AND METHODS. The entirety of each of the applications indicated above is incorporated by reference herein and made a part of this specification.

BACKGROUND

Field

Certain embodiments disclosed herein relate to pressure-regulating systems for coupling with medicinal containers (e.g., vials and/or bags), and components thereof, and methods to contain vapors and/or to aid in regulating pressures within medicinal containers. Some embodiments relate to pressure-regulating syringe assemblies.

Description of the Related Art

Medicines and other medically related fluids are commonly stored in vials or other containers. In some instances, the medicines or fluids stored in vials or other containers are therapeutic if injected into the bloodstream of certain patients, but are harmful if inhaled or if contacted by exposed skin of non-patients, such as healthcare providers. Certain known systems for extracting potentially harmful medicines from vials suffer from various drawbacks. Thus, there is a need to store and/or control medicines such that they can be properly administered to patients without being inadvertently administered to non-patients.

BRIEF SUMMARY

In some embodiments, a syringe assembly can include a housing and a plunger slidably coupled to the housing. The housing can have a distal portion and a proximal portion. The plunger can have a distal plunger seal, a proximal plunger seal, and an inner channel, wherein the proximal plunger seal is configured to slide in a distal direction inside the inner channel and/or in a proximal direction inside the inner channel. A syringe assembly can include a first reservoir located in a distal portion of the inner channel of the plunger and a second reservoir located in the distal portion of the housing.

In several embodiments, a syringe assembly can include a third reservoir located in a proximal portion of the inner channel of the plunger and separated (e.g., sealed) from the first reservoir by the proximal plunger seal. The plunger or another portion of the syringe can have a hole configured to fluidly couple the third reservoir with an ambient environment outside of the syringe assembly. The plunger can have a vent configured to equalize pressure inside of the third reservoir with ambient pressure. In some embodiments, the plunger can include a vent configured to regulate pressure inside of the third reservoir relative to ambient pressure. The proximal plunger seal can be configured to slide inside the inner channel in response to a difference in pressure between a proximal side of the proximal plunger seal and a distal side of the proximal plunger seal.

In some embodiments, a syringe assembly can include a housing with a distal portion and a proximal portion. Syringe assemblies can have a plunger slidably coupled to the housing. The plunger can have a distal plunger seal and a proximal plunger seal. Syringe assemblies can include a first reservoir. In some embodiments, syringe assemblies can include a second reservoir located in the distal portion of the housing. A first passage can be configured to communicate fluid from the first reservoir to the distal portion of the housing. The first passage can be located radially outward from the first reservoir and can be configured to be fluidly isolated from the second reservoir.

In several embodiments, the first reservoir can be located in a portion of the plunger. The plunger can have an inner channel and the proximal plunger seal can be configured to slide in a distal direction inside the inner channel. In some embodiments, the first reservoir and the second reservoir are volumetrically independent. In some embodiments, the first fluid reservoir regulates gas pressure inside of a container. The second fluid reservoir receives liquid from the container and/or adds liquid to the container. In several embodiments, the first fluid reservoir has a first maximum volume and the second fluid reservoir has a second maximum volume. The first maximum volume can be at least half as large as the second maximum volume.

In some embodiments, the second fluid reservoir is located distally relative to the first fluid reservoir and/or the first fluid reservoir is located distally relative to the third fluid reservoir. The plunger can include an inner channel. A seal can be slidably coupled inside the inner channel. The first fluid reservoir can be located distally relative to the seal and the third fluid reservoir can be located proximally relative to the seal.

In several embodiments, the first fluid reservoir has an outer diameter and the third fluid reservoir can have an outer diameter. The outer diameter of the first fluid reservoir can be approximately equal to the outer diameter of the third fluid reservoir. In several embodiments, the first fluid reservoir and the third fluid reservoir are approximately isodiametric. The second fluid reservoir can have an outer diameter that is larger than the outer diameter of the first fluid reservoir and larger than the outer diameter of the third fluid reservoir. In some variants, the plunger includes a third fluid reservoir (e.g., an ambient portion), which can be fluidly coupled with an ambient environment. The third fluid reservoir can be separated from the first fluid reservoir by one or more of the seals.

In some embodiments, the plunger includes a barrel, which can delineate at least part of the second fluid reservoir. The plunger can be slidably coupled to the barrel and can be configured to slide inside at least a portion of the barrel. The syringe assembly can include a distal end configured to be coupled to a container. In several embodiments, the syringe assembly includes a first passage configured to fluidly couple the first fluid reservoir to the distal end and a second passage configured to fluidly couple the second fluid reservoir to the distal end.

In some embodiments, one or more of the seals includes a rigid inner body and a compliant sealing member. The sealing member fluidly seal against an inner surface of the plunger. The compliant sealing member can be positioned around at least a portion of the rigid inner body. In several embodiments, the first fluid reservoir has a proximal end and the proximal end is configured to move when the seal slides within the plunger.

In some implementations, the plunger includes an expandable and contractable container, such as a bag, balloon, or the like. A first fluid reservoir can be located inside of the bag.

In several embodiments, an expansion chamber can be configured to be placed in fluid communication with a second passage. The expansion chamber can be configured to expand from a first volume to a second volume when the syringe assembly is uncoupled from a device (e.g., an adapter assembly) that couples the syringe assembly to a container. The second volume can be larger than the first volume.

In several embodiments, a syringe assembly can be configured to couple with an adapter assembly that is configured to couple with a container. The syringe assembly can include a housing having a distal portion. Syringe assemblies can also include a plunger having an inner channel and a distal seal. Plungers can be slidably coupled to the housing. Syringe assemblies can also include a first reservoir located in the inner channel of the plunger and configured to contain a regulating fluid. In some embodiments, syringe assemblies can include a second reservoir located in the distal portion of the housing. The distal seal of the plunger can be configured to slide within the housing to vary the volume of the second reservoir. Syringe assemblies can also include a proximal seal configured to slide in the inner channel of the plunger and thereby vary the volume of the first reservoir.

In several embodiments, when the syringe assembly is coupled to the container via the adapter assembly, the first reservoir can be configured to deliver at least a portion of a regulating fluid to the container and the second reservoir can be configured to receive at least a portion of liquid from the container. In several embodiments, when the syringe assembly is coupled to the container via the adapter assembly, the first reservoir can be configured to receive gas from the container and the second reservoir can be configured to deliver liquid to the container. In some embodiments, when the syringe assembly is not coupled to the adapter assembly, the first reservoir and the second reservoir are configured to be substantially and/or effectively sealed from each other and/or from the ambient environment.

In some embodiments, the first reservoir can be located between the distal seal and the proximal seal. The second reservoir can be located distally relative to the distal seal. Some systems can include a regulating channel configured to communicate regulating fluid from the first reservoir to the container. In some embodiments, at least a portion of the regulating channel can be located radially outward from the first reservoir. In some embodiments, at least a portion of the regulating channel can be located radially outward from the second reservoir. Some systems include an extraction channel configured to communicate liquid from the container to the second reservoir.

In several embodiments, syringe assemblies include a first spring and a regulating channel seal. The first spring can be configured to apply an axial force to press the regulating channel seal against a sealing surface to seal the regulating channel. Several embodiments include a regulating channel configured to communicate the regulating fluid from the first reservoir to the container. Some systems include a first spring and a regulating channel seal. The first spring can be configured to apply an axial force to press the regulating channel seal against a sealing surface to seal the regulating channel.

Several embodiments include piercing members. The piercing member can be located on the adapter, which can be coupled with the syringe assembly and with a medical container, such as a vial. The piercing member can pierce a septum on the vial when the adapter is coupled with the vial. Several embodiments of the syringe assembly and/or the adapter assembly do not include a needle.

In some embodiments, a syringe assembly can be configured to couple to the adapter assembly without requiring a specific rotational orientation of the syringe assembly relative to the adapter assembly.

In several embodiments, a pressure-regulating system for the transfer of medical fluids can include an adapter assembly. The adaptor assembly can be connectable with a medical vial and with a syringe assembly. The syringe assembly can be configured to connect (e.g., permanently or releasably) with the adapter assembly.

In some embodiments, the syringe assembly includes a housing having a distal portion and a first reservoir. The first reservoir can be located in an inner channel of the syringe assembly and can contain an amount of regulating fluid, such as a gas and/or a liquid. The syringe assembly can include a second reservoir located in the distal portion of the housing. The syringe assembly can include a proximal seal configured to slide in the inner channel to vary the volume of the first reservoir in order to regulate pressure inside of a container. Some syringe assembly embodiments include a plunger slidably coupled to the housing. Plungers can include a distal seal configured to slide in the housing and thereby vary the volume of the second reservoir. In some embodiments, when the adapter assembly and the syringe assembly are coupled, the first reservoir is configured to deliver a flow of the regulating fluid to the medical vial and the second reservoir is configured to receive a flow of liquid from the vial.

In several embodiments, when the adapter assembly and the syringe assembly are not coupled (e.g., are spaced apart, separated, detached, disengaged, or otherwise), the first reservoir and the second reservoir are each substantially sealed from the ambient environment and/or effectively sealed from the ambient environment. As used herein, the phrase "substantially sealed from the ambient environment" means preventing clinically relevant flow to the ambient environment during normal operating conditions. As used herein, the phrase "effectively sealed from the ambient environment" means blocking the transfer of pharmaceuticals to the ambient environment during normal operating conditions for a normal operating period of time.

Some embodiments have a regulating channel configured to communicate the regulating fluid from the first reservoir to the vial. Some embodiments include a first spring and a regulating channel seal. The first spring can be configured to apply an axial force to press the regulating channel seal against a sealing surface to seal the regulating channel.

In several embodiments, an adapter assembly includes a distally protruding piercing member configured to enable fluid communication with an internal portion of a vial. An adapter assembly can include a proximally protruding member configured to compress the first spring to unseal the regulating channel. An adapter assembly can include a passage capable of fluid communication with an internal portion of the vial. In some embodiments, an adapter assembly includes a second spring axially coupled to an adapter seal. The second spring can be configured to move the adapter seal to seal the passage of the adapter assembly. In several embodiments, a syringe assembly and an adapter assembly are configured to connect without requiring a specific rotational orientation of the syringe assembly relative to the adapter assembly.

In some embodiments, a syringe assembly is configured to regulate pressure in a container. A syringe assembly can include a plunger comprising a first fluid reservoir capable of holding a pressure regulating gas. A syringe assembly can include a barrel comprising a second fluid reservoir capable of holding a liquid, such as a medical liquid. The plunger can be slidably coupled to the barrel and configured to slide inside at least a portion of the barrel. A syringe assembly can include a regulator channel capable of placing the first fluid reservoir in fluid communication with the container such that the syringe assembly is capable of communicating the pressure regulating gas to regulate pressure inside of the container. A syringe assembly can include an extractor channel capable of placing the second fluid reservoir in fluid communication with the container such that the syringe assembly is capable of extracting the medical liquid from the container and moving the medical liquid into the second fluid reservoir.

In several embodiments, a syringe assembly is configured such that changing a volume of the second fluid reservoir does not necessarily change a volume of the first fluid reservoir because the second fluid reservoir is located inside of the barrel and the first fluid reservoir is located inside of the plunger. A syringe assembly can be configured such that moving the plunger distally reduces the volume of the second fluid reservoir but does not necessarily change the volume of the first fluid reservoir.

Any of the structures, materials, steps, or other features disclosed above, or disclosed elsewhere herein, can be used in any of the embodiments in this disclosure. Any of the structures, materials, steps, or other features that are shown and/or described herein can be used in combination with any other of the structures, materials, steps, or other features that shown and/or described herein.

Neither the preceding summary nor the following detailed description purports to limit or define the scope of protection. The scope of protection is defined by the claims.

BRIEF DESCRIPTION OF THE DRAWINGS

The abovementioned and other features of the embodiments disclosed herein are described below with reference to the drawings of the embodiments. The illustrated embodiments are intended to illustrate, but not to limit the embodiments. Various structures, materials, steps, or other features of the disclosed embodiments can be combined to form further embodiments, which are part of this disclosure.

FIGS. 29B and 29C illustrate assembled and exploded side views of the plunger of FIG. 29, including a proximal plunger seal, distal plunger seal, plunger body, and grip.

FIG. 42 illustrates the syringe assembly of FIG. 41 mechanically and fluidly coupled to the adapter assembly of FIG. 41.

FIG. 43 illustrates the syringe assembly of FIG. 41 mechanically and fluidly uncoupled from the adapter assembly of FIG. 41.

DETAILED DESCRIPTION

Figure 1:
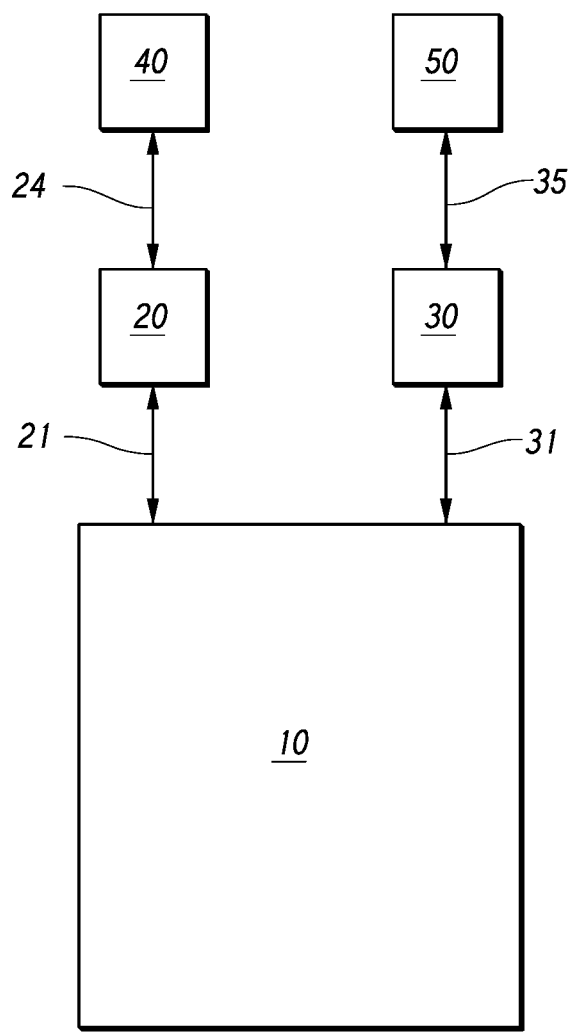
FIG. 1 schematically illustrates a system for removing fluid from and/or injecting fluid into a container.

Although certain embodiments and examples are disclosed herein, inventive subject matter extends beyond the examples in the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent. The structures, systems, and/or devices described herein may be embodied as integrated components or as separate components. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein. No feature, benefit, advantage, structure, or step disclosed herein is essential or indispensable.

The drawings illustrate certain embodiments and are not intended to be limiting. The drawings can be semi-diagrammatic and not to scale. For clarity of presentation and discussion, some portions of and/or dimensions in the drawings are shown greatly exaggerated.

For expository purposes, the term "horizontal" as used herein is defined as a plane parallel to the plane or surface of the floor of the area in which the device being described is used or the method being described is performed, regardless of its orientation. The term "floor" can be interchanged with the term "ground." The term "vertical" refers to a direction perpendicular to the horizontal as just defined. Terms such as "above," "below," "bottom," "top," "side," "higher," "lower," "upper," "over," and "under," are defined with respect to the horizontal plane unless otherwise indicated.

Numerous medicines and other therapeutic fluids are stored and distributed in medicinal vials or other containers of various shapes and sizes. These vials are sometimes hermetically sealed to prevent contamination or leaking of the stored fluid. The pressure differences between the interior of the sealed vials and the particular atmospheric pressure in which the fluid is later removed often give rise to various problems, as well as the release of potentially harmful vapors. As used in the embodiments below, "vial" can be any type of container used to store medicines, drugs, fluids used in medical care, or powders used in medical care.

For instance, introducing a piercing member of a vial adapter through the septum of a vial can cause the pressure within the vial to rise (or fall, in some cases). This pressure increase can cause fluid to leak from the vial at the interface of the septum and piercing member or at the attachment interface of the adapter and a medical device, such as a syringe. Also, it can be difficult to withdraw an accurate amount of fluid from a sealed vial using an empty syringe, or other medical instrument, because the fluid may be naturally urged back into the vial when the syringe plunger is released. Furthermore, as the syringe is decoupled from the vial, pressure differences can cause an amount of fluid to spurt from the syringe or the vial.

Moreover, in some instances, introducing a fluid into the vial can cause the pressure to rise in the vial. For example, in certain cases it can be desirable to introduce a solvent (such as sterile saline) into the vial, e.g., to reconstitute a lyophilized pharmaceutical in the vial. Such introduction of fluid into the vial can cause the pressure in the vial to rise above the pressure of the surrounding environment, which can result in fluid leaking from the vial at the interface of the septum and piercing member or at the attachment interface of the adapter and a medical device, such as a syringe. Further, the increased pressure in the vial can make it difficult to introduce an accurate amount of the fluid into the vial with a syringe, or other medical instrument. Also, should the syringe be decoupled from the vial when the pressure inside the vial is greater than the surrounding pressure (e.g., atmospheric), the pressure gradient can cause a portion of the fluid to spurt from the vial.

Additionally, in some instances, air bubbles are drawn into the syringe as fluid is withdrawn from the vial. Such bubbles are generally undesirable as they could result in an embolus if injected into a patient. To rid a syringe of bubbles after removal from the vial, medical professionals sometimes "flick" the syringe, gather all bubbles near the opening of the syringe, and then force the bubbles out. In so doing, a small amount of liquid is usually expelled from the syringe as well. Medical personnel generally do not take the extra step to re-couple the syringe with the vial before expelling the bubbles and fluid. In some instances, this may even be prohibited by laws and regulations. Such laws and regulations may also necessitate expelling overdrawn fluid at some location outside of the vial in certain cases. Moreover, even if extra air or fluid were attempted to be reinserted in the vial, pressure differences can sometimes lead to inaccurate measurements of withdrawn fluid.

To address these problems caused by pressure differentials, medical professionals frequently pre-fill an empty syringe with a precise volume of ambient air corresponding to the volume of fluid that they intend to withdraw from the vial. The medical professionals then pierce the vial and expel this ambient air into the vial, temporarily increasing the pressure within the vial. When the desired volume of fluid is later withdrawn, the pressure differential between the interior of the syringe and the interior of the vial is generally near equilibrium. Small adjustments of the fluid volume within the syringe can then be made to remove air bubbles without resulting in a demonstrable pressure differential between the vial and the syringe. However, a significant disadvantage to this approach is that ambient air, especially in a hospital setting, may contain various airborne viruses, bacteria, dust, spores, molds, and other unsanitary and harmful contaminants. The pre-filled ambient air in the syringe may contain one or more of these harmful substances, which may then mix with the medicine or other therapeutic fluid in the vial. If this contaminated fluid is injected directly into a patient's bloodstream, it can be particularly dangerous because it circumvents many of the body's natural defenses to airborne pathogens. Moreover, patients who need the medicine and other therapeutic fluids are more likely to be suffering from a diminished infection-fighting capacity.

In the context of oncology and certain other drugs, all of the foregoing problems can be especially serious. Such drugs, although helpful when injected into the bloodstream of a patient, can be extremely harmful if inhaled or touched. Accordingly, such drugs can be dangerous if allowed to spurt unpredictably from a vial due to pressure differences. Furthermore, these drugs are often volatile and may instantly aerosolize when exposed to ambient air. Accordingly, expelling a small amount of such drugs in order to clear a syringe of bubbles or excess fluid, even in a controlled manner, is generally not a viable option, especially for medical personnel who may repeat such activities numerous times each day.

FIG. 1 is a schematic illustration of a container 10, such as a medicinal vial, that can be coupled with an accessor 20 and a regulator 30. In certain arrangements, the regulator 30 allows the removal of some or all of the contents of the container 10 via the accessor 20 without a significant change of pressure within the container 10.

In general, the container 10 can be hermetically sealed to preserve the contents of the container 10 in a sterile environment. The container 10 can be evacuated or pressurized upon sealing. In some instances, the container 10 is partially or completely filled with a liquid, such as a drug or other medical fluid. In such instances, one or more gases can also be sealed in the container 10. In some instances, a solid or powdered substance, such as a lyophilized pharmaceutical, is disposed in the container 10.

The accessor 20 can provide access to the contents of the container 10 such that the contents may be removed or added to. In certain arrangements, the accessor 20 includes an opening between the interior and exterior of the container 10. The accessor 20 can have a passageway between the interior and exterior of the container 10. In some configurations, the passageway of the accessor 20 can be selectively opened and closed. In some arrangements, the accessor 20 includes a conduit extending through a surface of the container 10. The accessor 20 can be integrally formed with the container 10 prior to the sealing thereof or introduced to the container 10 after the container 10 has been sealed.

In some configurations, the accessor 20 is in fluid communication with the container 10, as indicated by an arrow 21. In certain of these configurations, when the pressure inside the container 10 varies from that of the surrounding environment, the introduction of the accessor 20 to the container 10 causes a transfer through the accessor 20. For example, in some arrangements, the pressure of the environment that surrounds the container 10 exceeds the pressure within the container 10, which may cause ambient air from the environment to ingress through the accessor 20 upon insertion of the accessor 20 into the container 10. In other arrangements, the pressure inside the container 10 exceeds that of the surrounding environment, causing the contents of the container 10 to egress through the accessor 20.

In some configurations, the accessor 20 is coupled with an exchange device 40. In certain instances, the accessor 20 and the exchange device 40 are separable. In some instances, the accessor 20 and the exchange device 40 are integrally formed. The exchange device 40 is configured to accept fluids and/or gases from the container 10 via the accessor 20, to introduce fluids and/or gases to the container 10 via the accessor 20, or to do some combination of the two. In some arrangements, the exchange device 40 is in fluid communication with the accessor 20, as indicated by an arrow 24. In certain configurations, the exchange device 40 includes a medical instrument, such as a syringe or syringe assembly.

With continued reference to FIG. 1, in some instances, the exchange device 40 is configured to remove some or all of the contents of the container 10 via the accessor 20. In certain arrangements, the exchange device 40 can remove the contents independent of pressure differences, or lack thereof, between the interior of the container 10 and the surrounding environment. For example, in instances where the pressure outside of the container 10 exceeds that within the container 10, an exchange device 40 comprising a syringe can remove the contents of the container 10 if sufficient force is exerted to extract the plunger from the syringe. The exchange device 40 can similarly introduce fluids and/or gases to the container 10 independent of pressure differences between the interior of the container 10 and the surrounding environment.

In certain configurations, the regulator 30 is coupled with the container 10. The regulator 30 generally regulates the pressure within the container 10. As used herein, the term "regulate," or any derivative thereof, is a broad term used in its ordinary sense and includes, unless otherwise noted, any active, affirmative, or positive activity, or any passive, reactive, respondent, accommodating, or compensating activity that tends to effect a change. In some instances, the regulator 30 substantially maintains a pressure difference or equilibrium, between the interior of the container 10 and the surrounding environment. As used herein, the term "maintain," or any derivative thereof, is a broad term used in its ordinary sense and includes the tendency to preserve an original condition for some period, with some small degree of variation permitted as may be appropriate in the circumstances. In some instances, the regulator 30 maintains a substantially constant pressure within the container 10. In certain instances, the pressure within the container 10 varies by no more than about 1 psi, no more than about 2 psi, no more than about 3 psi, no more than about 4 psi, or no more than about 5 psi. In still further instances, the regulator 30 equalizes pressures exerted on the contents of the container 10. As used herein, the term "equalize," or any derivative thereof, is a broad term used in its ordinary sense and includes the tendency for causing quantities to be the same or close to the same, with some small degree of variation permitted as may be appropriate in the circumstances. In certain configurations, the regulator 30 is coupled with the container 10 to allow or encourage equalization of a pressure difference between the interior of the container 10 and some other environment, such as the environment surrounding the container 10 or an environment within the exchange device 40. In some arrangements, a single device includes the regulator 30 and the accessor 20. In other arrangements, the regulator 30 and the accessor 20 are separate units.

As illustrated in FIG. 1, the regulator 30 is generally in communication with the container 10, as indicated by an arrow 31, and a reservoir 50, as indicated by another arrow 35. In some configurations, the reservoir 50 includes at least a portion of the environment surrounding the container 10. In some embodiments, the reservoir 50 is configured to change volume. In some implementations, the reservoir 50 and the exchange device 40 are part of a medical device assembly, such as a pressure regulating syringe assembly. In certain configurations, the reservoir 50 includes a chamber, container, canister, bag, or other holder. As used herein, the term "bag," or any derivative thereof, is a broad term used in its ordinary sense and includes, for example, any sack, balloon, bladder, receptacle, enclosure, diaphragm, or membrane capable of expanding and/or contracting, including structures comprising a flexible, supple, pliable, resilient, elastic, and/or expandable material. In some embodiments, the reservoir 50 includes a gas and/or a liquid. As used herein, the term "flexible," or any derivative thereof, is a broad term used in its ordinary sense and describes, for example, the ability of a component to bend, expand, contract, fold, unfold, or otherwise substantially deform or change shape when fluid is flowing into or out of the container 10 (e.g., via the accessor 20). Also, as used herein, the term "rigid," or any derivative thereof, is a broad term used in its ordinary sense and describes, for example, the ability of a component to generally avoid substantial deformation under normal usage such as when fluid is flowing into or out of the container 10 (e.g., via the accessor 20). In some embodiments, the reservoir 50 is bounded by at least one rigid wall. In certain implementations, the reservoir 50 is bounded by at least one movable wall. The movement of the movable wall can change the volume of the reservoir 50.

In certain embodiments, the regulator 30 provides fluid communication between the container 10 and the reservoir 50. In certain of such embodiments, the fluid in the reservoir 50 includes mainly gas so as not to appreciably dilute liquid contents of the container 10. In some arrangements, the regulator 30 includes a filter to purify or remove contaminants from the gas or liquid entering the container 10, thereby reducing the risk of contaminating the contents of the container 10. In certain arrangements, the filter is hydrophobic such that air can enter the container 10 but fluid cannot escape therefrom. In some configurations, the regulator 30 includes an orientation-actuated or orientation-sensitive check valve which selectively inhibits fluid communication between the container 10 and the filter. In some configurations, the regulator 30 includes a check valve which selectively inhibits fluid communication between the container 10 and the filter when the valve and/or the container 10 are oriented so that the regulator 30 is held above (e.g., further from the floor than) the regulator 30.

In some embodiments, the regulator 30 prevents fluid communication between the container 10 and the reservoir 50. In certain of such embodiments, the regulator 30 serves as an interface between the container 10 and the reservoir 50. In some arrangements, the regulator 30 includes a substantially impervious bag for accommodating ingress of gas and/or liquid to the container 10 or egress of gas and/or liquid from the container 10.

Figure 2:
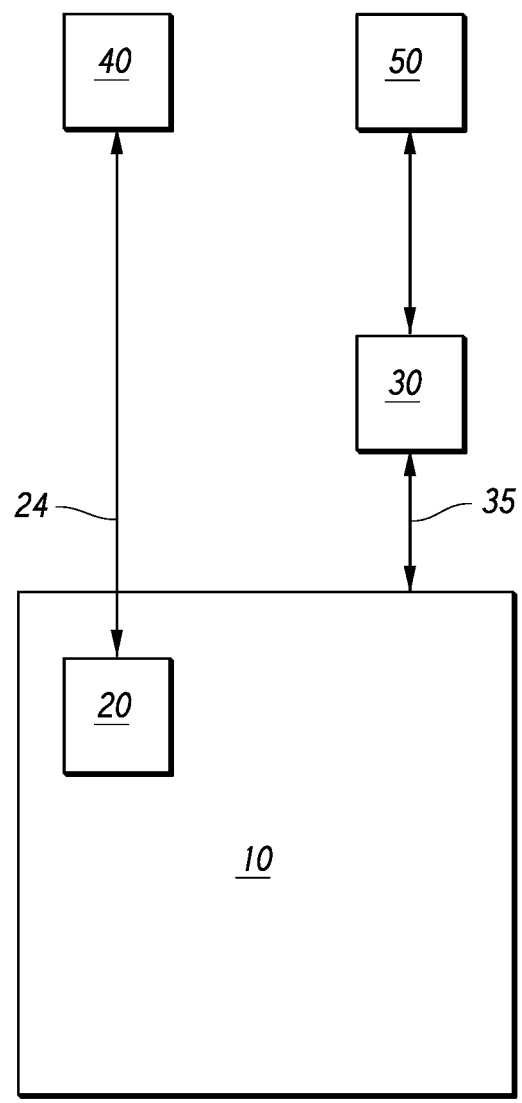
FIG. 2 schematically illustrates another system for removing fluid from and/or injecting fluid into a container.

As schematically illustrated in FIG. 2, in certain embodiments, the accessor 20, or some portion thereof, is located within the container 10. As detailed above, the accessor 20 can be integrally formed with the container 10 or separate therefrom. In some embodiments, the regulator 30, or some portion thereof, is located outside the container 10. In some arrangements, the regulator 30 is integrally formed with the container 10. It is possible to have any combination of the accessor 20, or some portion thereof, entirely within, partially within, or outside of the container 10 and/or the regulator 30, or some portion thereof, entirely within, partially within, or outside of the container 10.

In certain embodiments, the accessor 20 is in fluid communication with the container 10. In further embodiments, the accessor 20 is in fluid communication with the exchange device 40, as indicated by the arrow 24.

The regulator 30 can be in fluid or non-fluid communication with the container 10. In some embodiments, the regulator 30 is located entirely outside the container 10. In certain embodiments, the regulator 30 includes a closed bag configured to expand or contract external to the container 10 to maintain a substantially constant pressure within the container 10. In some variants, the regulator 30 includes a variable volume chamber (e.g., bounded by at least one movable piston). In some embodiments, the regulator 30 is in communication, either fluid or non-fluid, with the reservoir 50, as indicated by the arrow 35.

Figure 3:
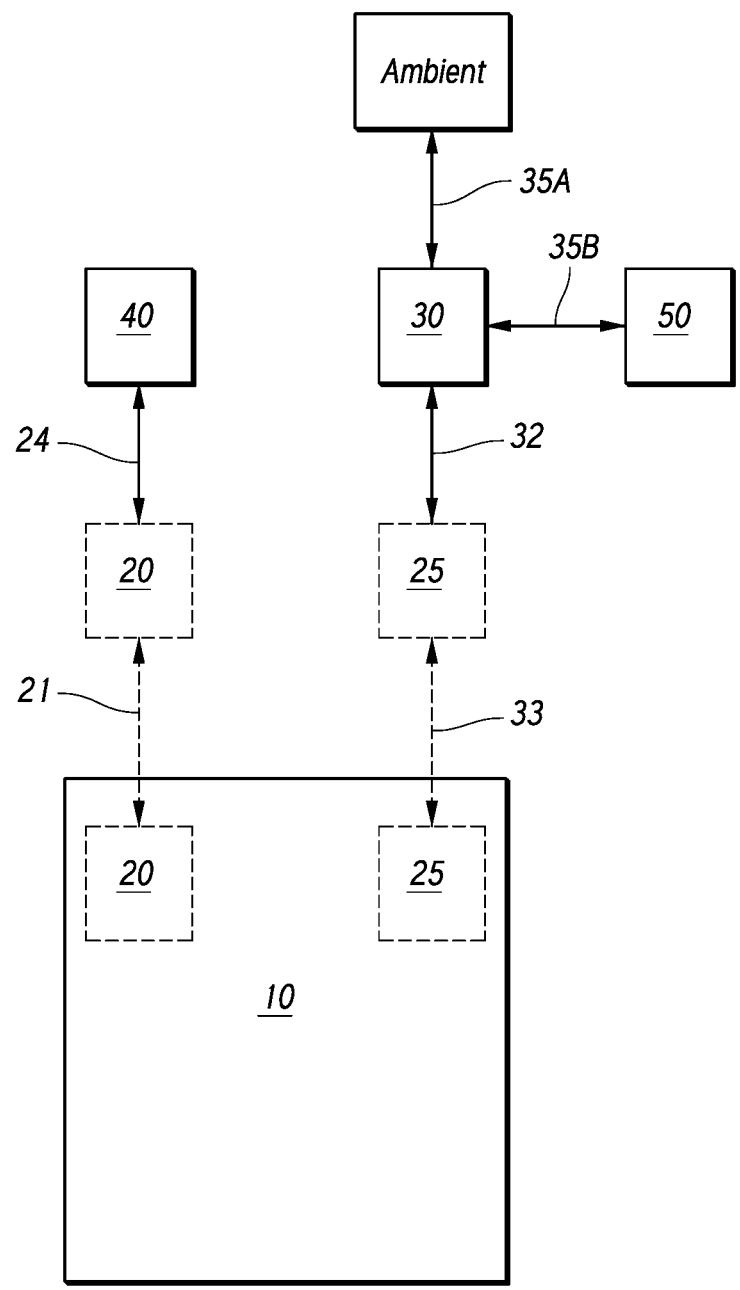
FIG. 3 schematically illustrates another system for removing fluid from and/or injecting fluid into a container.

As schematically illustrated in FIG. 3, in certain embodiments, the accessor 20, or some portion thereof, can be located within the container 10. In some embodiments, the accessor 20, or some portion thereof, can be located outside the container 10. In some embodiments, a valve 25, or some portion thereof, can be located outside the container 10. In some embodiments, the valve 25, or some portion thereof, can be located within the container 10. In some embodiments, the regulator 30 is located entirely outside the container 10. In some embodiments, the regulator 30, or some portion thereof, can be located within the container 10. It is possible to have any combination of the accessor 20, or some portion thereof, entirely within, partially within, or outside of the container 10 and/or the valve 25, or some portion thereof, entirely within, partially within, or outside of the container 10. It is also possible to have any combination of the accessor 20, or some portion thereof, entirely within, partially within, or outside of the container 10 and/or the regulator 30, or some portion thereof, entirely within, partially within, or outside of the container 10.

The accessor 20 can be in fluid communication with the container 10, as indicated by the arrow 21. In some embodiments, the accessor 20 can be in fluid communication with the exchange device 40, as indicated by the arrow 24.

In certain embodiments, the regulator 30 can be in fluid or non-fluid communication with a valve 25, as indicated by the arrow 32. In some embodiments, the valve 25 can be integrally formed with the container 10 or separate therefrom. In some embodiments, the valve 25 can be integrally formed with the regulator 30 or separate therefrom. In certain embodiments, the valve 25 can be in fluid or non-fluid communication with the container 10, as indicated by the arrow 33.

In some embodiments, the regulator 30 can be in fluid or non-fluid communication with the ambient surroundings, as indicated by the arrow 35A in FIG. 3. In some embodiments, the regulator 30 can be in fluid or non-fluid communication with a reservoir 50, as indicated by the arrow 35B. In some embodiments, the reservoir 50 can include a bag or other flexible enclosure. In some embodiments, the reservoir 50 includes a rigid container surrounding a flexible enclosure. In some embodiments, the reservoir 50 includes a partially-rigid enclosure. In several embodiments, the reservoir 50 includes an enclosure with rigid walls and a moveable member, wherein movement of the moveable member changes the internal volume of the reservoir 50.

According to some configurations, the regulator 30 can have a filter. In some embodiments, the filter can selectively inhibit passage of fluids, gases, liquids, and/or contaminants between the valve 25 and the reservoir 50 or the ambient surroundings. In some embodiments, the filter can selectively inhibit passage of fluids, gases, liquids and/or contaminants between the reservoir 50 and the valve 25 and/or between the ambient surroundings and the valve 25.

In some embodiments, the valve 25 can be a one-way check valve. In some embodiments, the valve 25 can be a two-way valve. According to some configurations, the valve 25 can selectively inhibit liquid, gas, and/or fluid communication between the filter and/or reservoir 50 and the container 10. In some embodiments, the valve 25 can selectively inhibit liquid, gas, and/or fluid communication between the container 10 and the filter and/or reservoir 50 when the container 10 is oriented or positioned above the exchange device 40.

Figure 4:
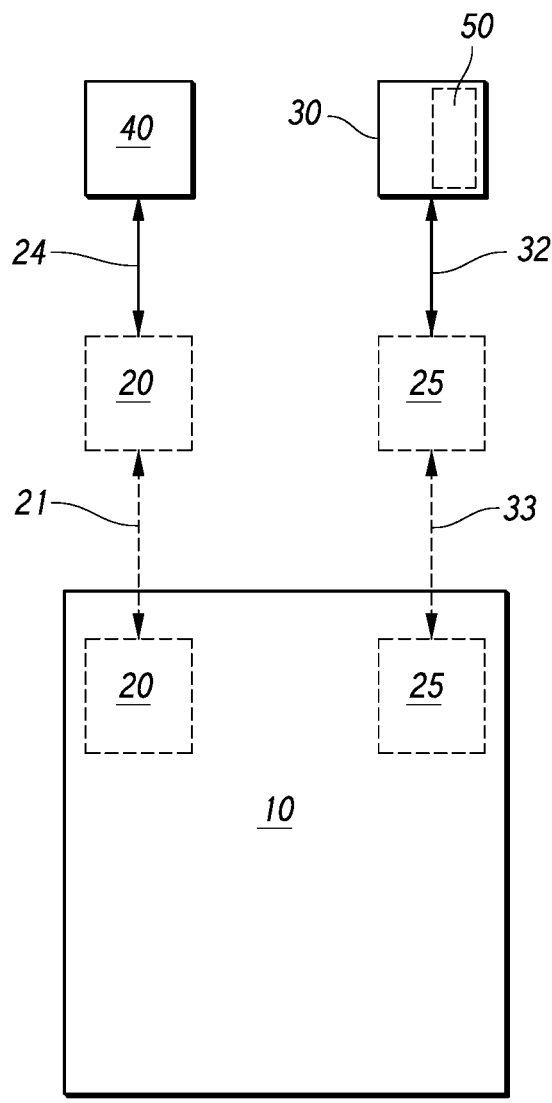
FIG. 4 schematically illustrates another system for removing fluid from and/or injecting fluid into a container, wherein the reservoir is in a contracted position.
Figure 5:
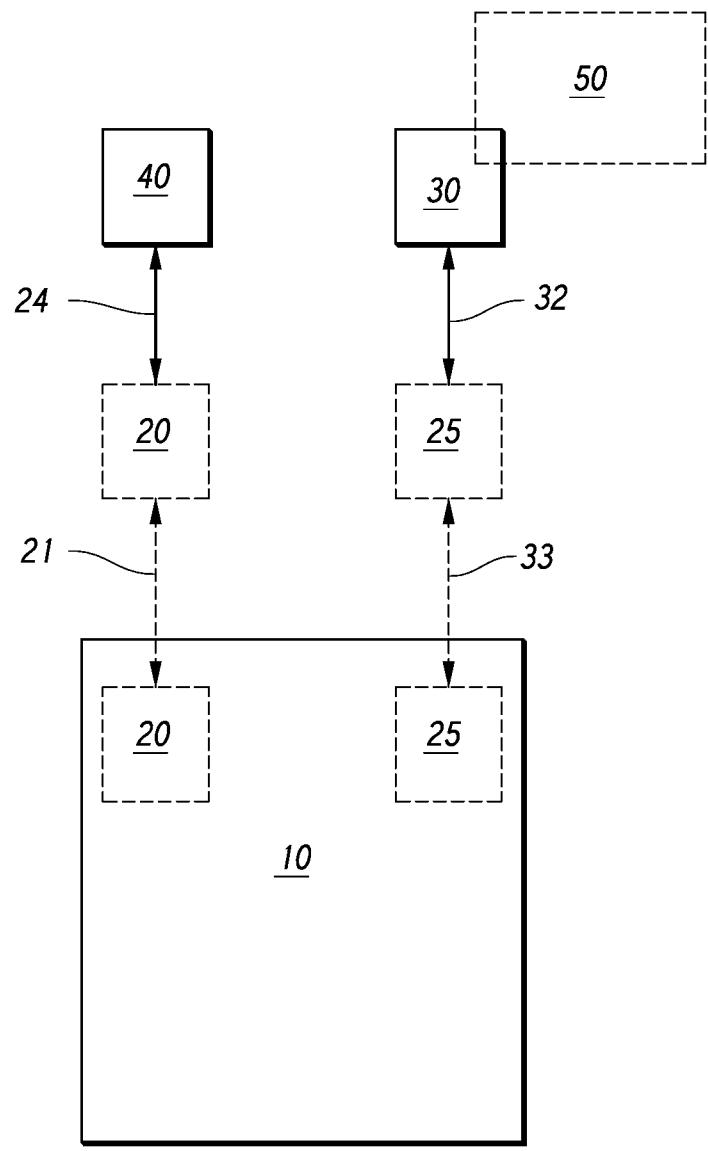
FIG. 5 schematically illustrates the system of FIG. 4, wherein the reservoir is in an expanded position.

As schematically illustrated in FIGS. 4 and 5, in certain embodiments, the reservoir 50 can be located at least partially within the regulator 30. The regulator 30 can be in fluid communication with the container 10, as illustrated by arrows 32 and 33. In some embodiments, a valve 25 is located in the fluid path between the container 10 and the regulator 30. The regulator 30 can be configured to maintain a substantially constant pressure within the container 10 as fluid is introduced into and/or withdrawn from the vial 10. For example, in some embodiments, the reservoir 50 is configured to transition from a contracted or primarily interior configuration (e.g., as illustrated in FIG. 4) to a primarily exterior or expanded configuration (e.g., as illustrated in FIG. 5), upon addition of fluid into the container 10 via the accessor 20 or otherwise. The reservoir 50 can be a flexible enclosure, such as a bag, or a variable volume rigid enclosure, such as a piston assembly (which can include a piston cylinder).

In some embodiments, the reservoir 50 is contained entirely within the regulator 30 when the reservoir 50 is in the contracted configuration. In some embodiments, a cap or other enclosing structure can confine the reservoir 50 within the regulator 30. In some embodiments, the reservoir 50 is partially enclosed within the regulator 30. The enclosing structure and/or regulator 30 can limit or prevent access to (e.g., physical contact with) the reservoir 50 when the reservoir 50 is in the contracted configuration.

In some embodiments, the volume of the reservoir 50 in the contracted configuration is substantially smaller than the volume of the container 10. For example, the volume of the contracted reservoir 50 can be less than or equal to about 20% of the volume within the container 10 and/or greater than or equal to about 2% of the volume within the container 10. In some embodiments, the volume of the contracted reservoir 50 is approximately 5% of the volume of the container 10. The volume of the portion of the regulator 30 in which the contracted reservoir 50 is contained can be approximately equal to the volume of the contracted reservoir 50. In some embodiments, the volume of the portion of the regulator 30 in which the contracted reservoir 50 is contained is greater than or equal to about 105% of the volume of the contracted reservoir 50 and/or less than about 120% of the volume of the contracted reservoir 50.

At least a portion of the reservoir 50 can expand outside of the regulator 30 when the reservoir transitions to the expanded configuration. In some embodiments, as illustrated in FIG. 5, substantially all of the volume-enclosing region of the reservoir can move to the exterior of the regulator 30 in the primarily exterior position. The volume of the reservoir 50 in this configuration can be substantially greater than the volume of the reservoir 50 in the contracted configuration. For example, the volume of the reservoir 50 in the expanded configuration can be greater than or equal to about 15% of the volume of the container 10 and/or less than about 70% of the volume of the container 10. In some embodiments, the volume of the expanded reservoir 50 is approximately 50% of the volume of the container 10. Many variations are possible.

Figure 6:
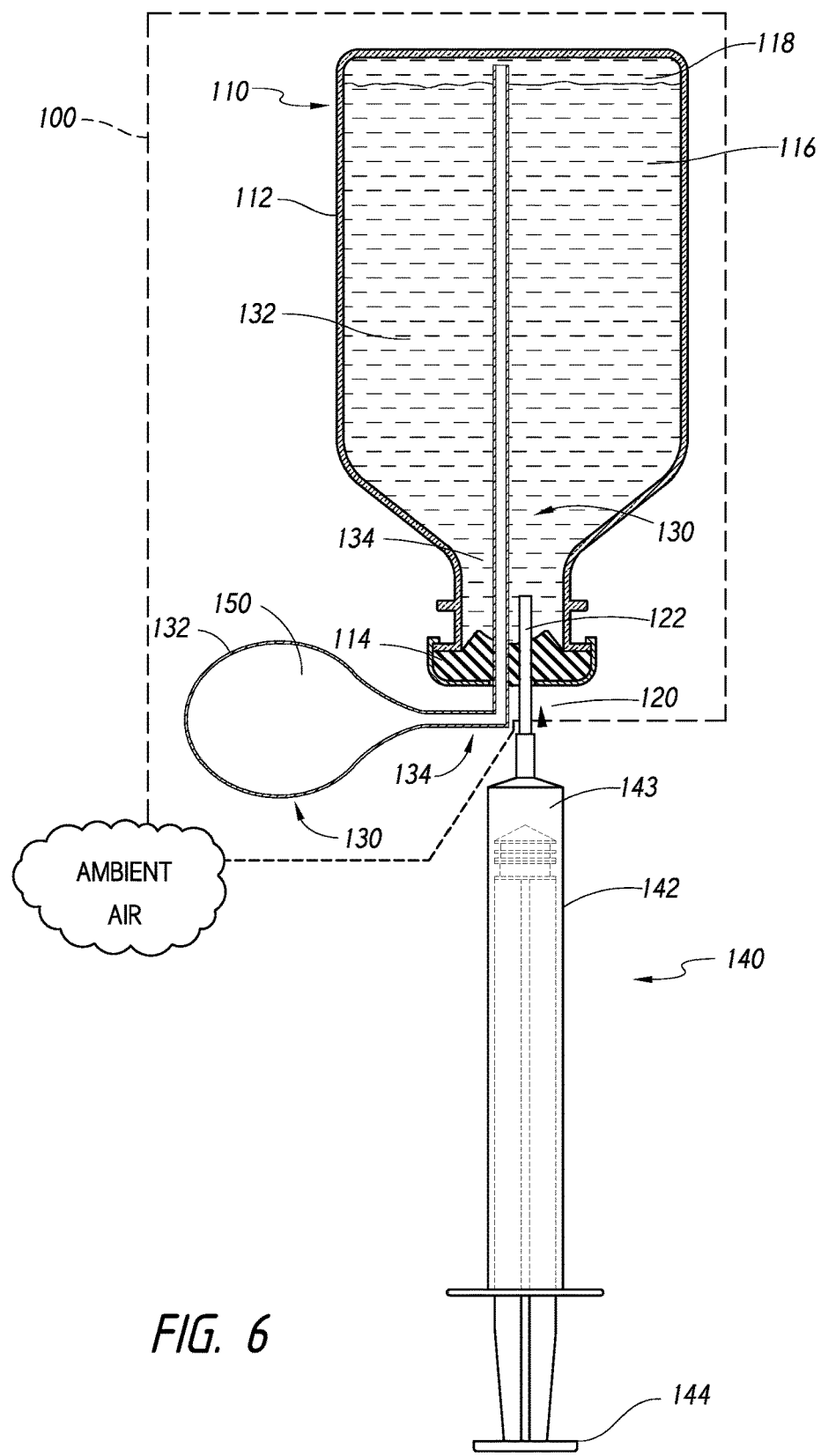
FIG. 6 illustrates a side view of another system for removing fluid from a container and/or injecting fluid into a container.

FIG. 6 illustrates an embodiment of a system 100 comprising a vial 110, an accessor 120, and a regulator 130. The vial 110 includes a body 112 and a cap 114. In the illustrated embodiment, the vial 110 contains a medical fluid 116 and a relatively small amount of sterilized air 118. In certain arrangements, the fluid 116 is removed from the vial 110 when the vial 110 is oriented with the cap 114 facing downward (e.g., the cap 114 is between the fluid and the floor). The accessor 120 includes a conduit 122 fluidly connected at one end to an exchange device 140, such as a syringe 142 with a plunger 144. The conduit 122 extends through the cap 114 and into the fluid 116. The regulator 130 can include a reservoir 132 and a conduit 134. The reservoir 132 can be a chamber, such as a bag, or a cavity with a piston movable relative to the cavity. The reservoir 132 can be located at least partially inside of a rigid enclosure 124.

The reservoir 132 and the conduit 134 are in fluid communication with a reservoir interior 150, which includes an amount of cleaned and/or sterilized air. In certain implementations, the reservoir 132 has a bag. In several embodiments, the reservoir 132 has one or more rigid walls and at least one movable wall 136. At least some of the outside surface of the reservoir 132 can be in contact with the ambient air surrounding the system 100. For example, an outside surface of the moveable wall 136 can be in contact with the ambient air. The reservoir 132 can be substantially impervious such that the fluid 116, the air 118 inside the vial 110, and the reservoir interior 150 do not contact the ambient air.

As shown in FIG. 6, areas outside of the vial 110 are at atmospheric pressure. Accordingly, the pressure on the syringe plunger 144 is equal to the pressure on the interior of the reservoir 132, and the system 100 is in general equilibrium.

The plunger 144 can be withdrawn to fill a portion of the syringe 142 with the fluid 116. Withdrawing the plunger 144 can increase the effective volume inside the syringe 142, thereby decreasing the pressure inside the syringe 142. Such a decrease of pressure within the syringe 142 increases the difference in pressure between the inside of the vial 110 and the inside of the syringe 142, which causes the fluid 116 to flow into the syringe 142. As the fluid 116 flows from the vial 110 to the syringe 142, the pressure inside the vial 110 drops below the pressure of the reservoir interior 150, which causes at least a portion of the reservoir interior 150 to flow into the vial 110. The flow from the vial 110 into the syringe 142 and from the reservoir interior 150 into the vial 110 continues until the difference in pressures inside the vial 110, the syringe 142, and the reservoir interior 150 are too small to cause flow. The pressure differential necessary to cause flow depends on the viscosity of the flow liquid (or gas) and the geometry of the structures through which the fluid flows. Some embodiments are optimized to reduce flow resistance.

The decrease of pressure within the vial 110 increases the difference in pressure between the interior and exterior of the reservoir 132, which causes the reservoir 132 to decrease in internal volume or contract, which in turn encourages an amount of regulatory fluid through the conduit 134 and into the vial 110. In effect, the reservoir 132 contracts outside the vial 110 to a new volume that compensates for the volume of the fluid 116 withdrawn from the vial 110. Thus, when the plunger 144 ceases being withdrawn from the vial 110, the system is again in equilibrium. As the system 100 operates near equilibrium, withdrawal of the fluid 116 can be facilitated. Furthermore, due to the equilibrium of the system 100, the plunger 144 remains at the position to which it has been withdrawn, thereby allowing removal of an accurate amount of the fluid 116 from the vial 110.

In certain arrangements, the decreased volume of the reservoir 132 is approximately equal to the volume of liquid removed from the vial 110. In some arrangements, the volume of the reservoir 132 decreases at a slower rate as greater amounts of fluid are withdrawn from the vial 110 such that the volume of fluid withdrawn from the vial 110 is greater than the decreased volume of the reservoir 132.

In some arrangements, the reservoir 132 can be substantially and/or completely collapsed or deflated, such that there is substantially no volume inside the reservoir 132. For example, in an embodiment with a front wall, sidewalls, and a movable piston, the piston can traverse so as to substantially abut the front wall, thereby collapsing the reservoir 132 and providing substantially no volume inside. In some instances, such collapsing of the reservoir 132 prevents the reservoir 132 from allowing the pressure inside the vial 110 to reach ambient pressure. Thus, when the reservoir 132 is completely collapsed, there can be a vacuum (relative to ambient) inside the vial 110. In some instances, such collapsing of the reservoir 132 creates substantially no restoring force that tends to create a pressure differential between the inside of the reservoir 132 and the inside of the vial 110, such as when the reservoir 132 is generally non-resilient, rigid, or completely rigid.

With continued reference to FIG. 6, in certain embodiments, the syringe 142 has fluid contents 143. A portion of the fluid contents 143 can be introduced into the vial 110 by depressing the plunger 144 (toward the vial), which can be desirable in certain instances. For example, in some instances, it is desirable to introduce a solvent and/or compounding fluid into the vial 110. In certain instances, more of the fluid 116 than desired initially might be withdrawn inadvertently. In some instances, some of the air 118 in the vial 110 initially might be withdrawn, creating unwanted bubbles within the syringe 142. It may thus be desirable to inject some of the withdrawn fluid 116 and/or air 118 back into the vial 110.

Depressing the plunger 144 encourages the fluid contents 143 of the syringe into the vial 110, which decreases the effective volume of the vial 110, thereby increasing the pressure within the vial 110. An increase of pressure within the vial 110 increases the difference in pressure between the inside of the vial 110 and the inside of the reservoir 132, which can cause the air 118 to flow into the reservoir 132, which in turn causes the reservoir 132 to expand. In effect, the reservoir 132 expands or increases to a new volume that compensates for the volume of the contents 143 of the syringe 142 introduced into the vial 110. Thus, when the plunger 144 stops moving toward the vial 110, the system is again in equilibrium. As the system 100 operates near equilibrium, introduction of the contents 143 can be facilitated. Moreover, due to the equilibrium of the system 100, the plunger 144 generally remains at the position to which it is depressed, thereby allowing introduction of an accurate amount of the contents 143 of the syringe 142 into the vial 110.

If the pressure inside the syringe 142 is larger or smaller than the pressure inside the vial 110, the plunger 144 may move inadvertently if the pressure differential is large enough to overcome frictional forces. In some embodiments, temporary pressure differentials are used to prevent fluid from dripping out of, for example, a syringe after it is disconnected from a vial. For example, a portion of the syringe can increase in effective volume, thereby reducing the local pressure and drawing at least some fluid into that region of added volume. Some embodiments, however, minimize temporary pressure differentials.

In certain arrangements, the increased volume of the reservoir 132 is approximately equal to the volume of air 118 removed from the vial 110. In some arrangements, the volume of the reservoir 132 increases at a slower rate as greater amounts of the contents 143 are introduced into the vial 110, such that the volume of the contents 143 introduced into the vial 110 is greater than the increased volume of the reservoir 132.

In some arrangements, the reservoir 132 can stretch, expand, or otherwise increase in volume to expand beyond a resting volume. In some instances, the expansion gives rise to a restorative force that effectively creates a difference in pressure between the inside of the reservoir 132 and the inside of the vial 110. For example, a slight overpressure (relative to ambient) inside the vial 110 can be created when the reservoir 132 is stretched or expanded.

Many of the components described herein can be molded as individual components and/or can be integrated with other molded components. For example, in some cases, multiple components can be molded at the same time in a single molding press. Some of the components can be injection molded with medical-grade plastic. Some components are made from acrylic plastic, ABS plastic, or polycarbonate plastic. Some components can be made from metal, such as stainless steel. Many of the metal components can be machined with a computer numerical control ("CNC") mill.

Expandable reservoirs, such as some bags, can be configured to unfold, unroll, expand, contract, inflate, deflate, compress, and/or decompress. Reservoirs can include any of a wide variety of flexible and/or expandable materials (although some reservoirs are inflexible and rigid). For example, in certain embodiments, reservoirs or bags include polyester, polyethylene, polypropylene, saran, latex rubber, polyisoprene, silicone rubber, vinyl, polyurethane, or other materials. In certain embodiments, reservoirs or bags include a material having a metal component to further inhibit fluid (including gas or air) leakage through the material of the bag, e.g., metalized biaxially-oriented polyethylene terephthalate (also known as "PET" and available under the trade name Mylar®). In some embodiments, reservoirs and bags include a laminate. Reservoirs and bags can include a metal material. For example, reservoirs and bags can be constructed of a layer of 0.36 Mil (7.8#) metalized (e.g., aluminum) PET film and a layer of 0.65 Mil (9.4#) linear low-density polyethylene. In some embodiments, reservoirs or bags include a material capable of forming a substantially airtight seal with a coupling. In certain embodiments, reservoirs and bags are transparent or substantially transparent. In other embodiments, reservoirs and bags are opaque. In some instances, reservoirs and bags include a material that is generally impervious to liquids, gases, and air (at least for a sufficient period of time under normal use conditions). In certain embodiments, reservoirs and bags include a material that is inert with respect to the intended contents of the vial. For example, in certain cases, reservoirs and bags include a material that does not react with certain drugs used in chemotherapy. In some embodiments, reservoirs and bags include latex-free silicone having a durometer that is greater than or equal to about 10 Shore A and/or less than or equal to about 80 Shore A.

In certain configurations, the reservoir includes a coating. For example, in some embodiments, the reservoir includes a coating that reduces its porosity. In some cases, the coating is evaporated aluminum or gold. In some cases, the coating includes a water soluble plastic configured to form a barrier to inhibit passage of gases. In certain instances, the coating is applied to the outside of the reservoir. In other instances, the coating is applied to the inside of the reservoir. In some cases, the coating is applied to the inside and the outside of the reservoir. In some embodiments, the coating is a polyolefin.

Vials can include any suitable container for storing medical fluids. For example, the vials can be any of a number of standard medical vials known in the art, such as those produced by Abbott Laboratories of Abbott Park, Ill. In some embodiments, vials are capable of being hermetically sealed. In some configurations, the vial has a body and a cap. The body can be a rigid, substantially impervious material, such as plastic or glass. In some embodiments, the cap includes a septum and a casing. The septum can be an elastomeric material capable of deforming in such a way when punctured by an item that it forms a substantially airtight seal around that item. For example, in some instances, the septum includes silicone rubber or butyl rubber. The casing can be any suitable material for sealing the vial. In some instances, the casing includes metal that is crimped around the septum and a portion of the body in order to form a substantially airtight seal between the septum and the vial. In certain embodiments, the cap has a ridge that extends outwardly from the top of the body.

As discussed in more detail below, several embodiments include seals. The seals can be formed (e.g., molded) from medical-grade silicone with a durometer between 35 and 90 Shore A. Other seals and components are molded from other flexible or semi-flexible materials.

Certain embodiments include a filter that can remove particles and/or contaminants from the gas that passes through the filter. For example, in certain embodiments, the filter is configured to remove nearly all or at least 99.9% of airborne particles 0.3 micrometers in diameter. In some cases, the filter is configured to remove microbes. In some embodiments, the filter includes nylon, polypropylene, polyvinylidene fluoride, polytetrafluoroethylene, or other plastics. In some embodiments, the filter includes activated carbon, e.g., activated charcoal. In certain configurations, the filter includes a mat of regularly or randomly arranged fibers, e.g., fiberglass. In some arrangements, the filter includes Gortex® material or Teflon® material.

In some embodiments, a filler is located inside a reservoir such as a bag. In several embodiments, at ambient pressure the diameter and thickness of the filler are about the same as the diameter D and thickness T of the bag. In certain arrangements, a filler is configured to contain a volume of gas, such as sterilized air. In certain cases, the filler is porous. In some instances, the filler is a sponge or sponge-like material. In certain arrangements, the filler includes cotton wadding. In certain configurations, the filler includes a mat of regularly or randomly arranged fibers configured to provide a network of chambers or spaces therein. In some embodiments, the filler is made of low density foam. For example, in certain embodiments, the filler is made of polyurethane-ether foam, and has a weight of, for example, about 1.05 pounds per cubic foot and an indentation load deflection ("ILD") of, for example, about 38. In some embodiments, the filler is made of polyether, polyester, polyethylene, or ether-like-ester ("ELE"). In some cases, the filler is made of nylon, polypropylene, polyvinylidene fluoride, polytetrafluoroethylene, or other plastics. In certain embodiments, the filler is a metal, e.g., aluminum or stainless steel. In certain embodiments, the filler is treated with an anti-microbial or other compound to enhance sterility. In certain cases, the filler has a sealed chamber, e.g., containing sterilized air, which is configured to open when a fluid is withdrawn from the vial. In some embodiments, the filler can be configured to bind with, absorb, generally neutralize, or otherwise chemically and/or mechanically interact with the fluid (such as vapors) entering the bag.

Figure 7:
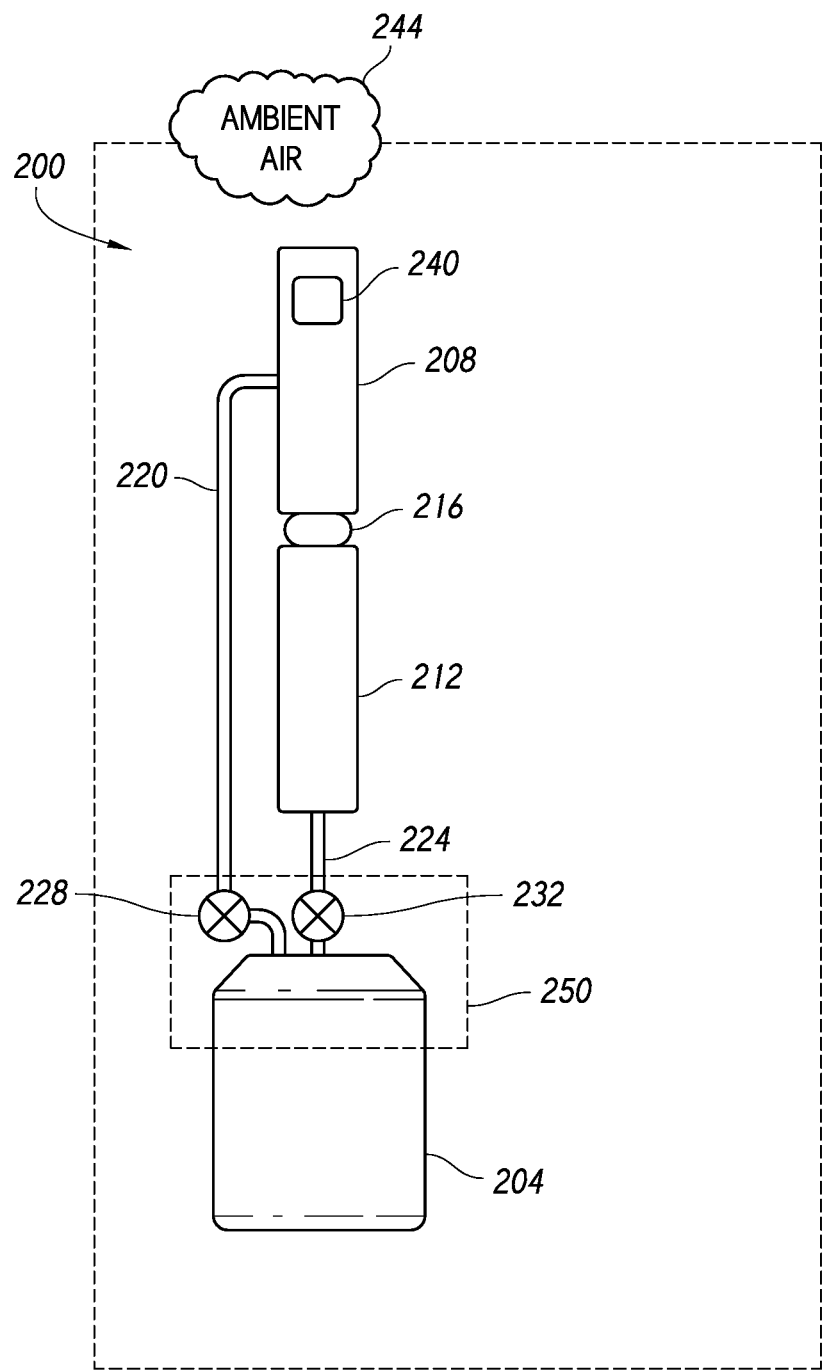
FIG. 7 schematically illustrates an embodiment of a pressure regulating syringe system coupled to a container.

FIG. 7 schematically illustrates an embodiment of a pressure regulating syringe system 200 coupled to a container 204, such as a vial. The container 204 can be configured to hold a drug, a pharmaceutical, and/or a substance used in medical care. The regulating system 200 can include a first reservoir 208 and a second reservoir 212. The first reservoir 208 and the second reservoir 212 can be configured to change in volume (e.g., individually and/or together). In some embodiments, the first reservoir 208 is configured to store a gas, which can be sterilized air, unsterilized air, or any gas. In some embodiments, the second reservoir 212 is configured to store a liquid, which can be a medicinal fluid, any fluid that contains a pharmaceutical agent, a liquid that will be injected into the container 204, water, a saline solution, or any liquid. The first reservoir 208 and the second reservoir 212 can be located in a housing, which can include a barrel and/or a plunger. The housing can be substantially rigid with low brittleness to avoid cracking. In some embodiments, the housing is made from molded plastic. The plastic can be clear and/or translucent. In any embodiment in this specification, as illustrated, the first reservoir and the second reservoir may be configured so that, during use, fluid does not pass directly between the first reservoir and the second reservoir (e.g., directly from the first reservoir to the second reservoir, or directly from the second reservoir to the first reservoir).

In many embodiments described herein, containers 204, 304 can include vials, plastic vials, glass vials, ampoules, cuvettes, packages configured to hold medicine, bags, bins, bottles, bowls, canisters, cartons, flasks, jugs, packets, pouches, receptacles, sacks, medicinal storage devices, fluid storage devices, medicinal vessels, drug repositories, test tubes, tubes, cannulas, and fluid tanks.

In some embodiments, the first reservoir 208 and/or the second reservoir includes a bag with an internal volume. The internal volume can increase or decrease. In some embodiments, the first reservoir 208 and/or the second reservoir has a rigid outer housing that can be made from plastic. The rigid outer housing can be somewhat flexible if enough force or pressure is placed on the outer housing.

As schematically illustrated in FIG. 7, certain embodiments include a dividing member, such as a seal 216. The seal 216 can be located between the first reservoir 208 and the second reservoir 212. The seal 216 can isolate (e.g., fluidly isolate) the first reservoir 208 from the second reservoir 212 such that a liquid or gas located inside the first reservoir 208 is inhibited or prevented from flowing through the area that the seal 216 blocks to the second reservoir 212, and such that a liquid or gas located inside the second reservoir 212 is inhibited or prevented from flowing through the area that the seal 216 blocks to the first reservoir 208. In some embodiments, the seal is a rubber plunger seal or a rubber O-ring.

Several embodiments include a first passage 220 (e.g., passageway, channel, lumen, or otherwise). The first passage 220 can fluidly couple the first reservoir 208 to the container 204, such that fluid and/or gas from the first reservoir 208 can flow into the container 204 and/or such that fluid and/or gas from the container 204 can flow into the first reservoir 208.

Some embodiments include a second passage 224 (e.g., passageway, channel, lumen, or otherwise). The second passage 224 can fluidly couple the second reservoir 212 to the container 204, such that fluid and/or gas from the second reservoir 212 can flow into the container 204 and/or such that fluid and/or gas from the container 204 can flow into the second reservoir 212. The first passage 220 and the second passage 224 can include lumens, channels, open areas, or any other structure capable of forming passages that can hold or communicate fluids, liquids, and/or gases. In various embodiments, the first passage 220 is called a "regulating channel" and the second passage 224 is called an "access channel" or "extraction channel."

In some embodiments, the second passage 224 is an extractor channel configured to communicate liquid, medicinal liquid, medical liquid, therapeutic fluid, and/or saline. In some embodiments, the second passage 224 is configured to communicate gas, sterilized gas, and/or air. In some embodiments, the first passage 220 is a regulator channel configured to regulate pressure in the container 204. In some embodiments, the first passage 220 is configured to communicate gas, sterilized gas, and/or air. In some embodiments, the first passage 220 is configured to communicate liquid, medicinal liquid, medical liquid, therapeutic fluid, and/or saline. In some embodiments, the first passage 220 and/or the second passage 224 are configured to communicate powder, such as a medical powder.

With continued reference to FIG. 7, some embodiments include a first flow controller 228. When in an open position, the first flow controller 228 allows fluid to flow through the first passage 220. When in a closed position, the first flow controller 228 inhibits or prevents fluid from flowing through the first passage 220. Certain embodiments have a second flow controller 232. When the second flow controller 232 is in an open position fluid can flow through the second passage 224. When the second flow controller 232 is in a closed position fluid is inhibited or prevented from flowing through the second passage 224. In some embodiments, the first flow controller 228 and the second flow controller 232 are one flow controller, such that one flow controller is capable of controlling the flow of liquids and/or gases in the first passage 220 and in the second passage 224. Some embodiments of flow controllers include seals that open and close passages. The first flow controller 228 and/or the second flow controller 232 can be and/or include a pump assembly, a valve assembly, a sealing assembly, a seal assembly, and/or a system that pumps and/or selectively seals. In some embodiments, the first flow controller 228 and/or the second flow controller 232 is a valve that has an open position to allow fluid to pass through the valve and a closed position that substantially blocks fluid from passing through the valve.

The first passage 220 can be located outside of the first reservoir 208 and the second reservoir 212. The first reservoir 208 can have a central axis that runs generally parallel to a longitudinal axis of the system 200. In some embodiments, the first passage 220 and/or a portion of the first passage 220 can be located radially outward from the central axis of the first reservoir 208. The first passage can be located radially outside of the first reservoir 208 rather than being located inside the outer perimeter of the first reservoir 208.

Several embodiments include a pressure regulator 240. The pressure regulator 240 can be configured to reduce and/or eliminate the pressure differential between the pressure of ambient air 244 (located outside of the pressure regulating syringe system 200) and the pressure inside the first reservoir 208. In various embodiments, the pressure regulator 240 can equalize the pressure between the inside of the first reservoir 208 and ambient air 244 (e.g., the pressure regulator 240 can be a pressure equalizer in some embodiments). In some embodiments, friction or cracking pressure can inhibit the pressure regulator 240 from equalizing the pressure between the ambient air 244 and the first reservoir 208. The pressure regulator 240 can be lubricated (e.g., with a medical-grade lubricant) to reduce friction and/or cracking pressure to increase the equalization ability of the pressure regulator 240. The pressure regulator 240 can be a component that changes the effective volume of the first reservoir 208. In some embodiments, the pressure regulator 240 is a bag. In some embodiments, the first reservoir 208 has an open end that is sealed by a rubber plunger and the pressure regulator 240 includes the rubber plunger that slides inside the first reservoir 208 to change the effective internal volume of the first reservoir 208. The pressure regulator 240 can be a component that allows ambient air 244 to flow into or out of the first reservoir 208. In various implementations, the pressure regulator 240 can include a valve (e.g., opened by a pressure differential) or a hole that can be covered by a cap.

In FIG. 7, the ambient air 244 is represented by a cloud with a dashed box that surrounds the pressure regulating syringe system 200. This shows that the ambient air 244 typically surrounds the pressure regulating syringe system 200. Many other figures illustrated herein include ambient air that surrounds the embodiments, but many figures do not include a dashed box in the interest of providing a clear view of other items. Ambient air is typically located outside of pressure regulating syringe systems and typically surrounds pressure regulating syringe systems.

Several embodiments include a coupling system 250 to fluidly and/or mechanically couple the pressure regulating system 200 to a container 204, which can be a vial, a glass container, a rigid plastic container, a flexible plastic container, any container used in intravenous infusion, or any other container. In some embodiments, the first flow controller 228 and the second flow controller 232 are part of the coupling system 250. In several embodiments, during the course of coupling the pressure regulating syringe system 200 to the container 204, the first flow controller 228 and/or the second flow controller 232 move from a closed position to an open position.

In several embodiments, the first reservoir 208 and the second reservoir 212 are part of a closed system that is fluidly isolated from the ambient air 244. A closed system can help prevent and/or limit the amount of pharmaceutical agents released by the pressure regulating syringe system 200 into the ambient air 244. The pressure regulating syringe system 200 can be configured to prevent liquids and gases that have been contaminated with pharmaceuticals from the container 204 from exiting the pressure regulating syringe system 200. The first flow controller 228 and the second flow controller 232 can be configured to prevent and/or limit the escape of gases and liquids from the first reservoir 208 and/or the second reservoir 212 after the pressure regulating syringe system 200 has been decoupled from the container 204.

In several embodiments, the first reservoir 208 and the second reservoir 212 are located outside of the container 204, which can be a vial. The first reservoir 208 and the second reservoir 212 can be integrated inside of a syringe and/or located inside of a syringe. In some embodiments, the first reservoir 208 is located inside of a plunger of a syringe and the second reservoir is located inside of a barrel of a syringe. The barrel can be a housing in which a plunger can slide. The plunger can form some of the outer walls of the first reservoir 208. In some embodiments, the plunger can form one or more walls of the second reservoir 212. The barrel can form some of the outer walls of the second reservoir 212.

Figure 8:
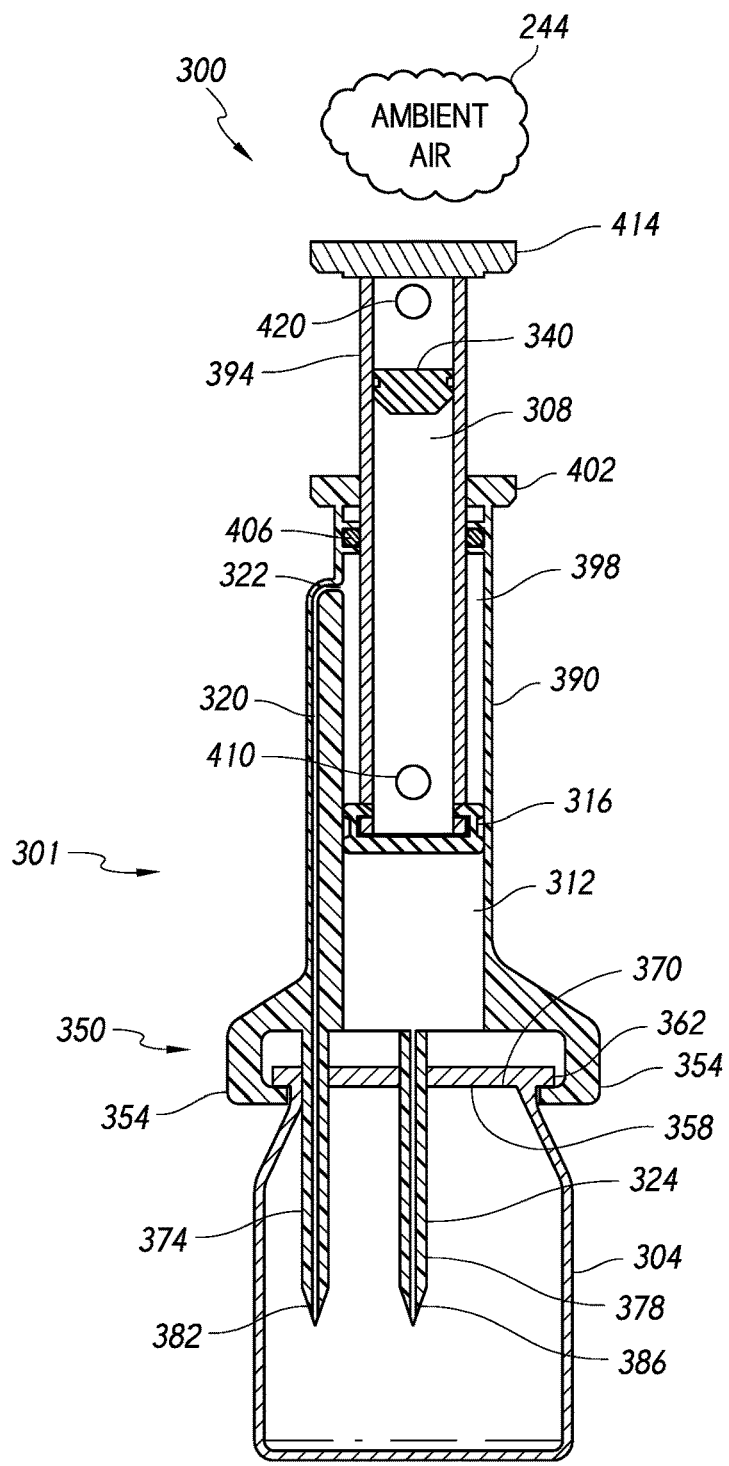
FIG. 8 illustrates a cross-sectional, side view of an embodiment of a pressure regulating syringe system coupled to a container.

FIG. 8 illustrates a cross-sectional view of another embodiment of a pressure regulating syringe system 300 coupled to a container 304, such as a vial. The system 300 can be the same or identical to any of the other pressure-regulating syringe systems described herein and can include any of the features of those other systems. The cross section illustrated in FIG. 8 runs down the central axis of the pressure regulating syringe system 300. As shown, the system 300 can include a syringe assembly 301 and a coupling system 354.

The coupling system 350 includes arms 354 that are configured to attach to the container 304 by engaging (e.g., snapping into) a neck 358 of the container 304. The arms 354 can flex radially outward as the arms 354 slide over the lip 362 of the container 304, and then the arms 354 can flex radially inward as the arms 354 mate with the neck 358 of the container. In some embodiments, the neck 358 has a smaller diameter than the lip 362. The container 304 can be a glass vial, plastic vial, or any other container. In various embodiments, the syringe assembly 301 can removably couple to the coupling system 354.

The container 304 can include a septum 370 in the neck 358 and/or lip 362 that is configured to prevent inadvertent transmission of gas or liquid. The septum 370 can prevent ambient air 244 from inadvertently entering the container 304 and can prevent gas or liquid located inside the container 304 from inadvertently escaping the container. A first passage 320 and a second passage 324 can pass through (or pierce) the septum 370, and thus, can transmit gas and fluid into and/or out of the container 304.

A portion of the first passage 320 configured to pass through the septum 370 can be located in a first piercing member 374. A portion of the second passage 324 configured to pass through the septum 370 can be located in a second piercing member 378. In some embodiments, the first piercing member 374 and the second piercing member 378 are part of a single piercing member. For example, the piercing member can be a plastic lance that includes a portion of the first passage 320 and a portion of the second passage 324. In some implementations, the lance has a pointed distal tip. In some variants, the lance has a generally rounded distal tip. A distal end 382 of the first passage 320 can exit the first piercing member 374 at a distal end of the first piercing member 374 or within about 1 centimeter of the distal end of the first piercing member 374. A distal end 386 of the second passage 324 can exit the second piercing member 378 at a distal end of the second piercing member 378 or within about 1 centimeter of the distal end of the second piercing member 378.

As illustrated in FIG. 8, the syringe system 300 can include a barrel 390 and a plunger 394. The barrel 390 can be a housing or conduit to which the plunger 394 is slidably coupled. The plunger 394 can move distally and proximally relative to the barrel 390. As used herein, the term "distal," or any derivative thereof, refers to a direction along the axial length of the syringe system and toward the end of the syringe system that engages with the container, such as the vial 304. The term "proximal," or any derivative thereof, refers to the opposite direction and is normally in the direction toward a user holding a portion of the syringe assembly. For example, in FIG. 8, the plunger 394 is located proximally relative to the vial 304 and the vial 304 is located distally relative to the plunger 394.

A distal plunger seal 316 can be coupled to the distal end of the plunger 394. In some embodiments, the volume of the second reservoir 312 is the internal space of the barrel 390 up to the distal plunger seal 316. The syringe system 300 can be configured such that pushing the plunger 394 in a distal direction (e.g., towards the container 304) reduces the volume of the second reservoir 312. The distal plunger seal 316 can be a dual wiper seal, which can be made from rubber. Pushing the plunger 394 in a distal direction can cause gas or liquid located inside the second reservoir 312 to flow through the second passage 324 and into the container 304.

The barrel 390 and the plunger 394 can have diverse shapes and sizes. In some embodiments, the barrel 390 and the plunger are generally cylindrical with generally circular cross sections. In several embodiments, the barrel 390 and the plunger 394 have generally rectangular cross sections with rounded corners to facilitate sealing. In several embodiments, the barrel 390 and the plunger 394 are sized and shaped such that the barrel 390 can receive the plunger 394.

In some embodiments, the plunger 394 has an internal volume of at least about 40 milliliters and/or less than or equal to about 100 milliliters; at least about 10 milliliters and/or less than or equal to about 300 milliliters; or at least about 55 milliliters and/or less than or equal to about 85 milliliters. In several embodiments, the first reservoir 308 (which can be a gas reservoir) has an internal volume and/or a maximum internal volume of at least about 40 milliliters and/or less than or equal to about 100 milliliters; at least about 10 milliliters and/or less than or equal to about 500 milliliters; or at least about 55 milliliters and/or less than or equal to about 85 milliliters.

In some embodiments, the barrel 390 has an internal volume of at least about 40 milliliters and/or less than or equal to about 100 milliliters; at least about 10 milliliters and/or less than or equal to about 300 milliliters; or at least about 55 milliliters and/or less than or equal to about 85 milliliters. In several embodiments, the second reservoir 312 (which can be configured to hold a liquid) has an internal volume and/or a maximum internal volume of at least about 40 milliliters and/or less than or equal to about 100 milliliters; at least about 10 milliliters and/or less than or equal to about 500 milliliters; or at least about 55 milliliters and/or less than or equal to about 85 milliliters.

In several embodiments, the second reservoir 312 has a capacity of greater than or equal to about 60 milliliters and the first reservoir 308 has a capacity of greater than or equal to 70 milliliters. The first reservoir 308 can have a maximum capacity that is larger than the maximum capacity of the second reservoir 312.

In some embodiments, the first reservoir 308 contains sterilized gas, such as sterilized air. The first reservoir 308 can be fluidly isolated (e.g., sealed) from the ambient air 244 such that the pressure regulating syringe system 300 prevents and/or hinders gas exchange between the first reservoir 308 and the ambient air 244. The second reservoir 312 can be configured to hold a pharmaceutical substance.

In some embodiments, the volume of the first reservoir 308 is the volume inside the plunger 394 from the distal plunger seal 316 to a proximal plunger seal 340. The distal plunger seal 316 can separate the first reservoir 308 from the second reservoir 312. The proximal plunger seal 340 can be a dual wiper seal, which can be made from rubber. The first reservoir 308 can in fluid communication with the first passage 320. When the syringe assembly 301 is coupled with the coupling assembly 354, and the coupling assembly 354 is coupled with the container 304, gas or other fluids located inside the first reservoir 308 can flow between the first reservoir 308 and the inside of the container 304. Gas or fluids can flow from the container 304 to the first reservoir 308. Some embodiments include one-way valves to block flow from the container 304 to the first reservoir 308 or to block flow from the first reservoir 308 to the container 304. In some embodiments, the first reservoir 308 is in fluid communication with an internal portion of the container 304.

The proximal plunger seal 340 can be located in a plunger 394 and can be slidably coupled inside of the plunger 394. The proximal plunger seal 340 can separate a distal gas reservoir from a proximal gas reservoir. The distal gas reservoir can be located on the distal side of the proximal plunger seal 340 and the proximal gas reservoir can be located on the proximal side of the proximal plunger seal 340. In some embodiments, the proximal gas reservoir can include a part of the surrounding ambient air. The proximal plunger seal 340 can seal against an inner diameter of the plunger 394. The plunger 394 can be slidably coupled to a barrel 390. The proximal plunger seal 340 can be configured to move (e.g., slide) within the plunger 394 in response to pressure differentials between the distal gas reservoir and the proximal gas reservoir. In some variants, the proximal gas reservoir is fluidly coupled with ambient air 244. In some embodiments, the pressure of the proximal gas reservoir is ambient pressure.

As shown in FIG. 8, some embodiments include a second reservoir 312. The second reservoir 312 can be configured to hold a liquid. The second reservoir 312 can be located distally relative to the distal gas reservoir of the plunger and/or distally relative to the distal plunger seal 316. The second reservoir 312 can be located inside of the barrel 390. In some variants, the second reservoir 312 is a volume bounded by the barrel 390, the distal plunger seal 316, and a distal wall of the syringe assembly 301.

In several embodiments, syringe systems have an area 398 between the barrel 390 and the plunger 394. This area can be located radially outward from the plunger 394 and radially inward from the barrel 390. A proximal seal 406, such as an O-ring, can inhibit or prevent gas or liquid from escaping from the area 398 to the ambient air 244. In some embodiments, the proximal seal 406 can be located near the barrel's finger grips 402. For example, as measured parallel to the longitudinal axis of the system 300, the proximal seal 406 can be at least about 0.01 centimeters and/or less than or equal to about 1 centimeter from the barrel's finger grips 402; or at least about 0.1 centimeters and/or less than or equal to about 4 centimeters from the barrel's finger grips 402.

In some embodiments, the proximal end of the first passage 320 can be located near the barrel's finger grips 402; at least about 0.01 centimeters and/or less than or equal to about 1 centimeter from the barrel's finger grips 402; or at least about 0.1 centimeters and/or less than or equal to about 4 centimeters from the barrel's finger grips 402. Air or gas located inside the first reservoir 308 can flow through a hole 410 in the first reservoir 308 (e.g., a hole in the plunger 394), through the area 398, and into the proximal end of the first passage 320. In some embodiments, gas or liquid flowing through the area 398 travels in one direction while gas flowing through the first passage 320 flows in an opposite direction.

As shown in FIG. 8, the area 398 can bound a passage between a portion of the barrel 390 and a portion of the plunger 394. The passage that the area 398 bounds can be oriented substantially parallel to a portion of the first passage 320. A portion of the first passage 320 can be located radially outward relative to the area 398. A portion of the first passage 320 can be located radially outward from and/or outside of the plunger 394, the first reservoir 308, the second reservoir 312, and/or the barrel 390. In some embodiments, a portion of the first passage is located inside of the plunger 394 rather than being located radially outward from the plunger 394.

The plunger 394 can have finger grips 414. In several embodiments, a user can pull the plunger's finger grips 414 proximally (e.g., away from the barrel's finger grips 402), thereby increasing the volume of the second reservoir 312 and extracting liquid from inside of the container 304 and into the second reservoir 312 via the second passage 324. Extracting liquid from inside the container 304 can cause pressure inside the container 304 to drop below ambient pressure (e.g., the pressure of the environment outside of the syringe system 300). When the pressure inside the container 304 drops below ambient pressure, gas inside the first reservoir 308 can flow into the first passage 320 and then into the container 304 to increase the pressure inside of the container 304 towards ambient pressure. This removal of gas from the first reservoir 308 can cause the pressure inside the first reservoir 308 to drop below ambient pressure. Therefore, some embodiments include a pressure equalization device to address this situation and/or to address other pressure imbalances.

As illustrated in FIG. 8, some embodiments include a proximal plunger seal 340 that can move axially within the plunger 394. The plunger 394 can include a vent 420 that allows ambient air into a portion of the plunger 394 up to the proximal plunger seal 340. The proximal plunger seal 340 can be configured to prevent and/or reduce the flow of ambient air into the first reservoir 308. For example, the proximal plunger seal 340 can form a generally gas-tight seal with the inner wall of the plunger 394. The proximal plunger seal 340 can be configured to prevent and/or reduce the flow of gas from inside first reservoir 308 to the ambient environment.

In various embodiments, the proximal plunger seal 340 facilitates pressure equalization and/or reduces pressure differences between the first reservoir 308 and ambient air 244. If the ambient pressure is higher than the pressure inside the first reservoir 308, the pressure differential can cause the proximal plunger seal 340 to move distally. For example, the proximal plunger seal 340 can move distally until the pressure differential is eliminated or reduced, such as reduced to the point that the pressure differential is insufficient to overcome other forces (such as frictional forces) to move the proximal plunger seal 340. If the ambient pressure is lower than the pressure inside the first reservoir 308, the pressure differential can cause the proximal plunger seal 340 to move proximally. For example, the proximal plunger seal 340 can move proximally until the pressure differential is eliminated or reduced, such as reduced to the point that the pressure differential is insufficient to overcome other forces (such as frictional forces) to move the proximal plunger seal 340.

Figure 9:
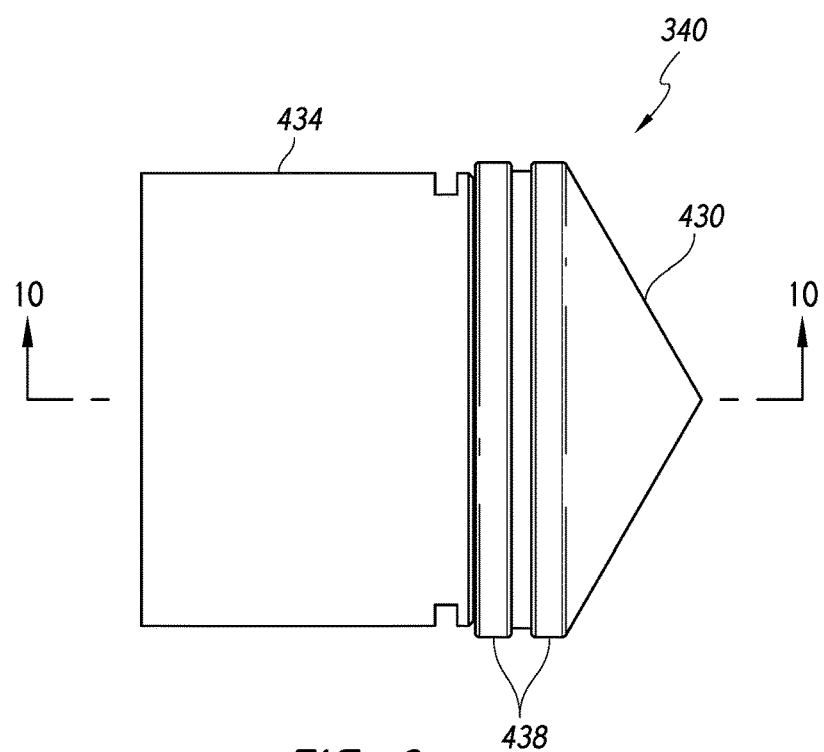
FIG. 9 illustrates a side view of a proximal plunger seal.
Figure 10:
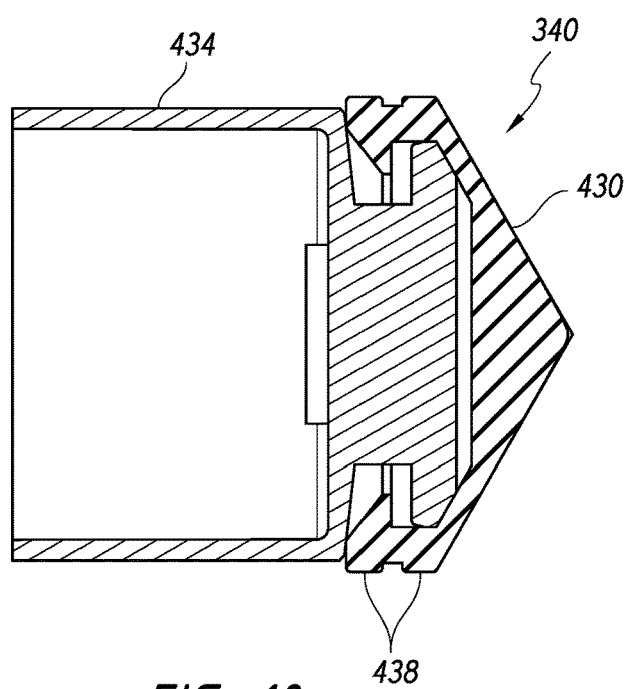
FIG. 10 illustrates a cross-sectional view along line 10-10 of FIG. 9.

FIGS. 9 and 10 illustrate side and cross-sectional views of the proximal plunger seal 340. As shown, the proximal plunger seal 340 can include a sealing member 430 and a support member 434. The sealing member 430 can include one or more sealing surfaces 438, such as wiper seals or O-rings. The sealing surfaces can be made from flexible or semiflexible materials configured to seal the proximal end of the first reservoir 308 (shown in FIG. 8). At least a portion of the sealing member 430 can be located radially outward from at least a portion of the support member 434. As shown, in some embodiments, at least a portion of the proximal plunger seal 340 (e.g., the support member 434) is hollow. In any embodiment in this specification, as illustrated, any plunger seal of any type may be configured such that fluid cannot pass directly from a proximal side to a distal side of the plunger seal, or fluid cannot pass through the plunger seal, or the plunger seal is permanently closed to the passage of fluid, or the plunger seal is valveless, or fluid cannot pass from a first reservoir in the syringe to a second reservoir in the syringe through a plunger seal.

In some embodiments, the sealing member 430 is made of medical-grade silicone rubber with a durometer between about 35 and about 95 Shore A. In some embodiments, the sealing member 430 includes a material with a durometer of at least about 35 Shore A and/or less than or equal to about 95 Shore A; at least about 45 Shore A and/or less than or equal to about 85 Shore A; or at least about 55 Shore A and/or less than or equal to about 80 Shore A. Some proximal plunger seal embodiments are constructed entirely or partially of rubber. Some proximal plunger seal embodiments include materials besides rubber, such as thermoplastics.

Certain embodiments are configured to inhibit or prevent the sealing member 430 (e.g., at least a portion of a proximal plunger seal 340) from canting, tilting, folding, or otherwise losing contact with the inside of the plunger 394 (shown in FIG. 8) to help maintain adequate sealing. The support member 434 can be made from a less flexible material than the material used to make the sealing member 430. The support member 434 can be made from a harder material than the material used to make the sealing member 430. In some embodiments, the support member 434 includes a material with a durometer of at least about 40 Shore D and/or less than or equal to about 95 Shore D; at least about 55 Shore D and/or less than or equal to about 85 Shore D; or at least about 65 Shore D and/or less than or equal to about 75 Shore D.

The support member 434 can be molded from a rigid plastic and the sealing member 430 can be molded from a compliant rubber, such as medical-grade silicone. The sealing member 430 can be coupled to the distal or proximal end of the support member 434. The outer diameter of the sealing surfaces 428 can be greater than the outer diameter of the support member 434.

Figure 11:
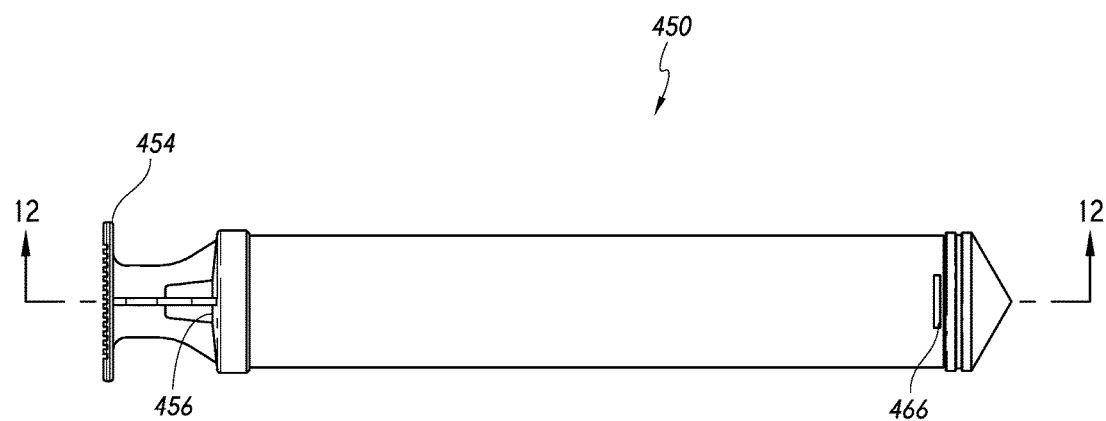
FIG. 11 illustrates a side view of a plunger.
Figure 12:
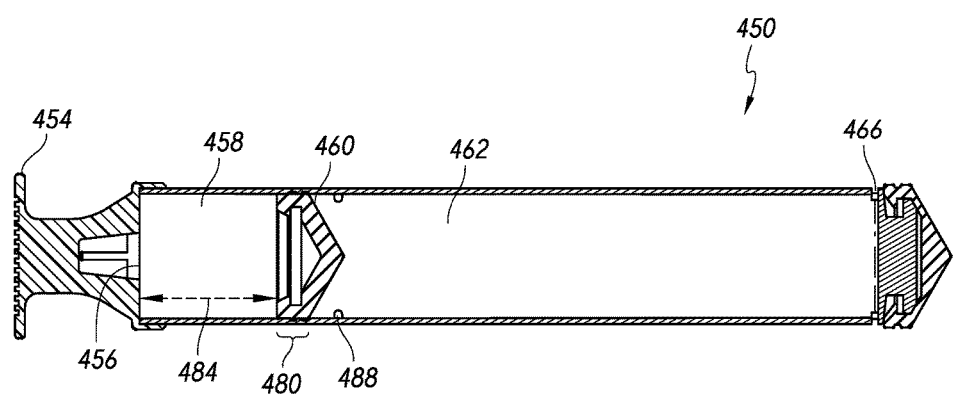
FIG. 12 illustrates a cross-sectional view along line 12-12 of FIG. 11.

FIGS. 11 and 12 illustrate side and cross-sectional views of a plunger 450 (e.g., a tube, actuator, shaft, etc.) that can be part of some or all of the syringe assemblies disclosed. The plunger 450 can include a finger grip 454 to enable a user to push the plunger 450 distally at least partially into a barrel (e.g., a housing, casing, enclosure, etc.) and pull the plunger 450 proximally at least partially out of the barrel. The plunger 450 can include a vent 456 to enable ambient air to enter a proximal portion 458 of the plunger 450 to reduce a difference in pressure between the pressure in the proximal portion 458 and the pressure in a first reservoir 462 by causing a proximal plunger seal 460 to move distally or proximally inside of the plunger 450. A hole 466 can allow gas (or liquid) to flow from the first reservoir 462 into a passage and then into a container (not shown). Some embodiments include a plurality of holes 466, which can facilitate fluid flowing into and/or out of the first reservoir 462. Many different plungers are disclosed herein. Any plunger can be used with any syringe system disclosed herein.

The proximal plunger seal 460 can have a contact region 480, which is the region of the proximal plunger seal 460 that can contact the inner diameter of the plunger 450 or another inner surface of the plunger 450 that forms the sealing surface along which the proximal plunger seal 460 slides in a distal or proximal direction. In some embodiments, the length of the contact region 480 is at least about 25% of the inner diameter of the plunger; at least about 50% of the inner diameter of the plunger; at least about 25% of the inner diameter of the plunger and/or less than or equal to about 200% of the inner diameter of the plunger; at least about 40% of the inner diameter of the plunger and/or less than or equal to about 75% of the inner diameter of the plunger; or at least about 50% of the inner diameter of the plunger and/or less than or equal to about 100% of the inner diameter of the plunger. In some embodiments, the length of the contact region 480 is at least about 0.2 centimeters and/or less than or equal to about 3 centimeters; at least about 0.5 centimeters and/or less than or equal to about 2 centimeters; or at least about 0.7 centimeters and/or less than or equal to about 1.5 centimeters.

In some embodiments, the proximal plunger seal 460 is lubricated to facilitate sliding within the plunger 450. In certain embodiments, the inner diameter of the plunger 450 can be lubricated. Petroleum-based lubricants and silicone lubricants are used in some embodiments. Some embodiments do not use lubricants.

Certain embodiments of the plunger 450 are configured to stop the proximal plunger seal 460 from moving proximally beyond a certain position (e.g., the farthest proximal position). In some embodiments, the proximal plunger seal 460 has a starting position or a shipping position that is not in the furthest proximal position. The distance between the furthest proximal position that the proximal plunger seal 460 can reach and the location of the proximal plunger seal 460 is called the gap distance 484. In some embodiments, a gap distance can help accommodate pressure changes (e.g., increases) post-manufacturing. For example, if a pressure regulating syringe system is manufactured at sea level and then used at an elevation of 2,000 meters, the first reservoir could have a pressure higher than ambient pressure at 2,000 meters if the proximal plunger seal 460 is not allowed to move sufficiently in the proximal direction. A sufficiently large gap distance 484 can accommodate decreases in ambient pressure by allowing the first reservoir 462 to increase in volume to reduce the difference in pressure between inside the first reservoir 462 and outside of the first reservoir 462. In some embodiments, the gap distance 484 is at least about 0.5 centimeters and/or less than or equal to about 10 centimeters; at least about 1 centimeter and/or less than or equal to about 5 centimeters; or at least about 1.5 centimeters and/or less than or equal to about 4 centimeters. Some methods include shipping a plunger 450 to a customer when the gap distance has one of the dimensions or dimensional ranges stated above.

As shown in FIG. 12, some embodiments of the plunger 450 include a securing or locking feature 488. This can be used to hold the proximal plunger seal 460 in a location until a sufficiently large pressure differential overcomes the locking feature 488. The locking feature 488 can be a projection and/or a protrusion (e.g., a rounded bump) that protrudes radially inward from the inner diameter of the plunger 450.

In several embodiments, the first reservoir 462 is pressurized such that its initial pressure or pressure as shipped to a customer is not ambient pressure. In some embodiments, the proximal plunger seal 460 can travel to a proximal extreme and to a distal extreme. The first reservoir 462 can be pressurized until the proximal plunger seal 460 reaches the proximal extreme (e.g., the farthest proximal position) and then can continue to be pressurized to make the pressure inside of the first reservoir 462 greater than ambient pressure.

Figure 13:
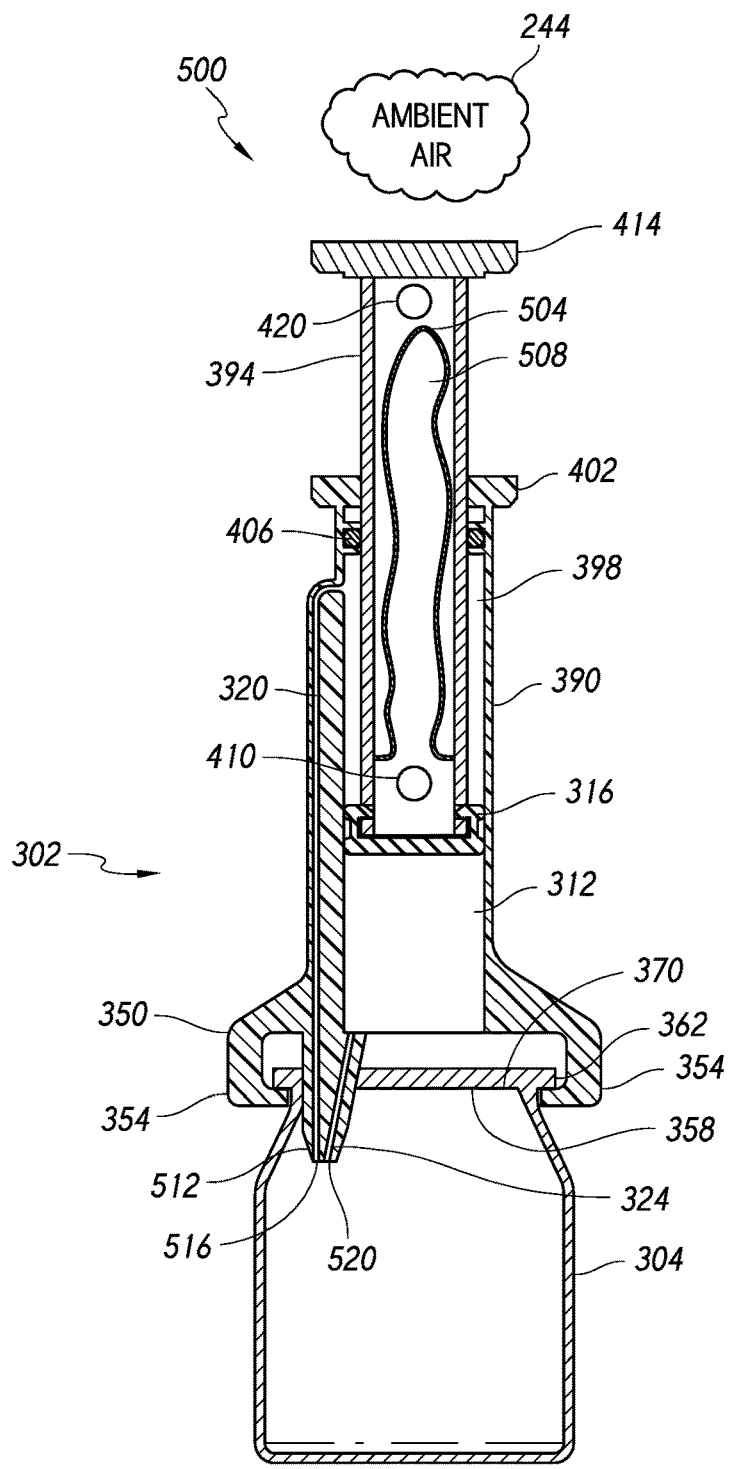
FIG. 13 illustrates a cross-sectional, side view of an embodiment of a pressure regulating syringe system coupled to a container.

FIG. 13 illustrates a cross-sectional view of an embodiment of a pressure regulating syringe system 500 coupled to a container 304, such as a vial. The system 500 can be the same or identical to any of the other pressure-regulating syringe systems described herein and can include any of the features of those other systems. The syringe system 500 can include a bag 504 that contains a first reservoir 508. The embodiment illustrated in FIG. 13 is needle-free. Rather than using needles to pierce the septum 370, the embodiment utilizes a piercing member 512 to pierce the septum 370. In some variants, the piercing member 512 can be made from molded plastic with a hardness of 50 Shore D to 85 Shore D. Some embodiments include needles.

The septum 370 can be an elastomeric material capable of deforming in such a way when punctured by an item that it forms a substantially airtight seal around that item. For example, in some instances, the septum 370 includes silicone rubber or butyl rubber.

A portion of the first passage 320 configured to pass through the septum 370 can be located in a piercing member 512. A portion of the second passage 324 configured to pass through the septum 370 can be located in the piercing member 512. In some embodiments, the piercing member 512 can be a tapered or rounded lance that includes a portion of the first passage 320 and a portion of the second passage 324. The distal end 516 of the first passage 320 can exit the piercing member 512 at the distal end of the piercing member 512 or within about 1 centimeter of the distal end of the piercing member 512. The distal end 520 of the second passage 324 can exit the piercing member 512 at the distal end of the piercing member 512 or within about 1 centimeter of the distal end of the piercing member 512.

The bag 504 can be made from a compliant material that enables an internal volume of the bag 504 to increase and decrease. As noted above, the volume inside the bag can be the first reservoir 508. In some embodiments, the inside of the bag 504 (e.g., the first reservoir 508) can be in fluid communication with the inside of the container 304. For example, in certain variants, gas and/or liquid located inside the first reservoir 508 can pass through the hole 410, move through the area 398, pass through the first passage 320, and then enter the container 304, which can be a vial.

The vent 420 can allow ambient air 244 to equalize or at least reduce differences between pressure inside the first reservoir 508 and ambient pressure. Ambient air 244 can enter the vent 420 and can contact an outer surface of the bag 504 (e.g., a surface generally opposed to the side of the bag 504 that at least partially bounds the first reservoir 508). In some embodiments, ambient air 244 cannot enter the bag 504. Expandable reservoirs, such as bag 504, can be configured to unfold, unroll, expand, contract, inflate, deflate, compress, and/or decompress. The bag 504 can change from a collapsed configuration with a first internal volume of the first reservoir 508 to an expanded configuration with a second internal volume of the first reservoir 508, wherein the second internal volume is larger than the first internal volume.

As shown in FIG. 13, in some embodiments, the bag 504 is contained within the plunger 394. In some embodiments, the bag 504 is located within the plunger 394. In some embodiments, the bag 504 is located inside a portion of the syringe assembly 302. In several embodiments, at least about 50 percent and/or less than or equal to about 90 percent of the bag is contained within the plunger 394; at least about 40 percent and/or less than or equal to about 95 percent of the bag is contained within the plunger 394; or at least about 75 percent and/or less than or equal to about 99 percent of the bag is contained within the plunger 394. The plunger 394 can contain at least a portion of the bag 504. In some variants, the plunger 394 is a rigid and/or plastic housing. The housing can be configured to encase and/or protect the bag 504.

In some embodiments, the bag 504 is configured to stretch (e.g., like a balloon made from rubber or latex). In several embodiments, the bag 504 is not configured to stretch and/or generally does not stretch. In various embodiments, the bag 504 can change from a collapsed configuration with essentially no internal volume to an expanded configuration with an internal volume.

Figure 14:
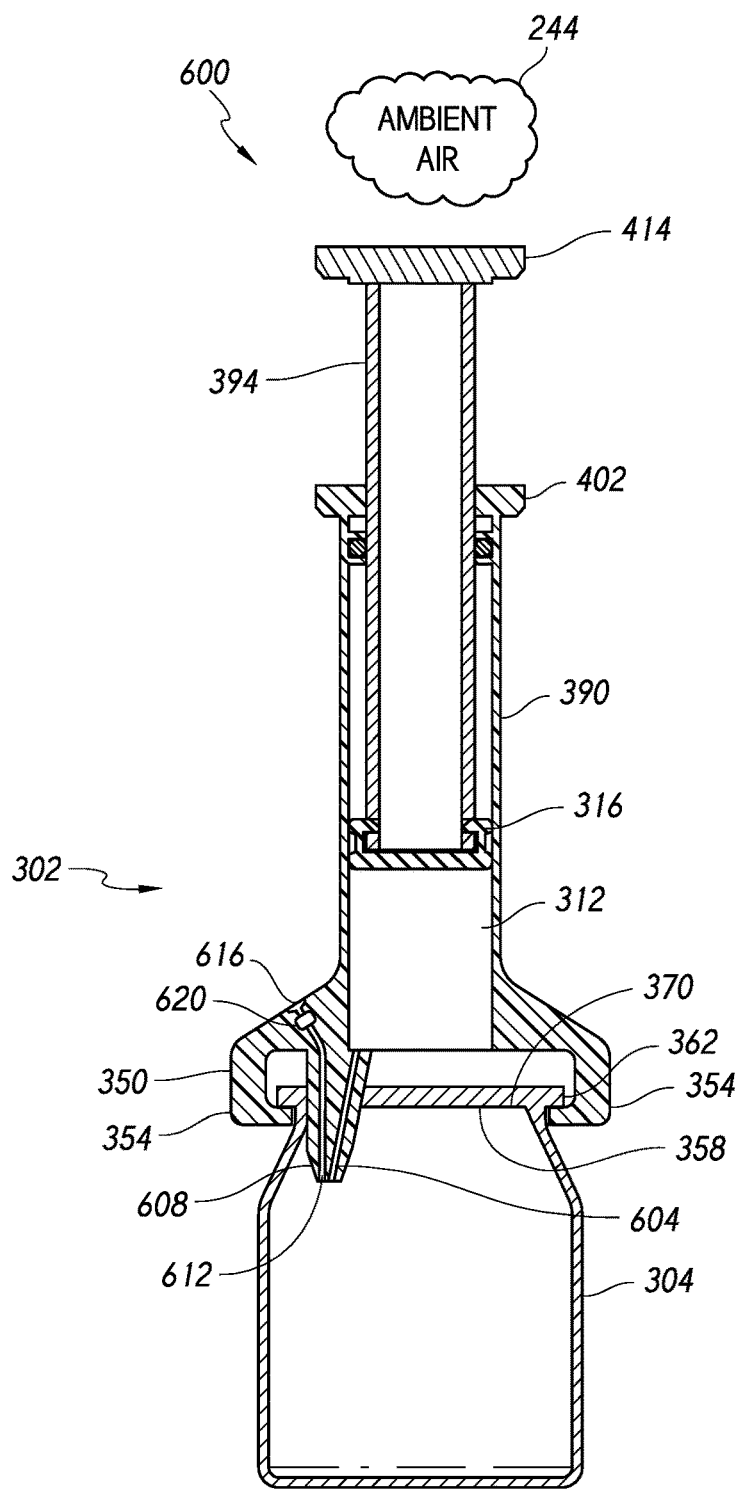
FIG. 14 illustrates a cross-sectional, side view of an embodiment of a pressure regulating syringe system coupled to a container.

FIG. 14 illustrates a cross-sectional view of an embodiment of a pressure regulating syringe system 600 coupled to a container 304, such as a vial. The system 600 can be the same or identical to any of the other pressure-regulating syringe systems described herein and can include any of the features of those other systems. The syringe system 600 can include a second passage 604 that fluidly communicates the second reservoir 312 with an internal portion of a container 304. The second passage 604 can pass through a piercing member 608.

The syringe system 600 can include a pressure equalizer that can include a first passage 612 that is configured to place an internal portion of the container 304 in communication with gas located outside of the syringe system 600, such as ambient air 244. The first passage 612 can place a vent 616 in fluid communication with an internal portion of the container 304 such that the vent 616 is configured to enable gas outside of the syringe system 600 to pass through the vent 616, then pass through the first passage 612, and then enter an internal portion of the container 304. The syringe system 600 can be configured to enable gas located inside of the container 304 to pass through the first passage 612 and then exit the syringe system 600 via the vent 616. The pressure equalizer can include a filter 620 such that gas that passes through the vent and into the container 304 also passes through the filter 620. The pressure equalizer can include a filter 620 such that gas that exits the container 304 through the vent 616 passes through the filter 620. At least a portion of the first passage 612 can be located in the piercing member 608. In some embodiments, the vent 616 exits the syringe system 600 at the coupling system 350, barrel 390, plunger 394, or finger grips 414, 402.

Figure 15:
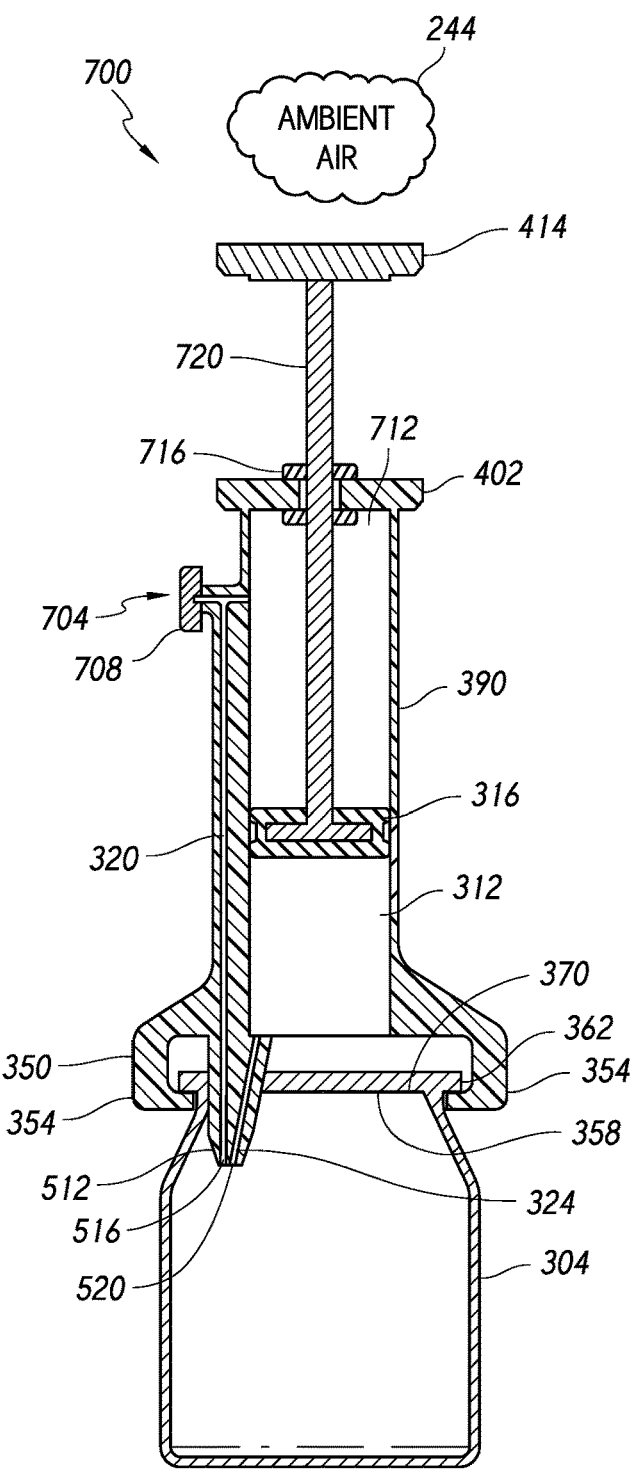
FIG. 15 illustrates a cross-sectional, side view of an embodiment of a pressure regulating syringe system coupled to a container.

FIG. 15 illustrates a cross-sectional view of an embodiment of a pressure regulating syringe system 700 coupled to a container 304, such as a vial. The system 300 can be the same or identical to any of the other pressure-regulating syringe systems described herein and can include any of the features of those other systems. The syringe system 700 includes a valve 704 with an open position and a closed position. When in the open position, the valve 704 enables gas located outside of the syringe system 700 (such as ambient air 244) to enter the first passage 320. The valve 704 can include a cap 708 that covers an entrance to the first passage 320. In some embodiments, a user can open the cap 708 with a finger by pulling one side of the cap 708 away from the barrel 390. The valve 704 can include a filter.

The barrel 390 can include a coupling system 350 at the distal end of the barrel 390. In some embodiments, the barrel 390 is removably or non-removably coupled with the coupling system 350 at the distal end of the barrel 390. The barrel 390 can include a proximal seal 716 at the proximal end of the barrel 390. The proximal seal 716 can have a hole in which a shaft of the plunger 720 is slidably disposed.

As shown in FIG. 15, a first reservoir 712 can be located inside a portion of the barrel 390 between the distal plunger seal 316 and the proximal seal 716. The proximal seal 716 can be configured to enable a portion of a plunger 720 to slide into and out of a portion of the barrel 390 without enabling gas located inside the first reservoir 712 to leak out of the first reservoir 712. In some embodiments, the proximal seal 716 can be configured to enable a plunger 720 to slide into and out of a portion of the barrel 390 while inhibiting or reducing a leakage of gas from inside the first reservoir 712. A distal end of the plunger 720 can be coupled to a dividing member, such as the distal plunger seal 316, which can be configured to separate and/or seal the second reservoir 312 from the first reservoir 712.

In some embodiments, the first reservoir 312 and the inside of the container 304 are in fluid communication. For example, gas located inside the first reservoir 712 can flow into the first passage 320 and then can flow into a portion of the container 304. Gas located inside a portion of the container 304 can flow into the first passage 320 and then can flow into the first reservoir 712. In some embodiments, the flow of gas is interrupted, impeded, and/or prevented by a valve and/or seal. The flow of gas can be temporarily inhibited or prevented until, for example, proper coupling occurs between a pressure regulating syringe system and a container, such as a vial. In some embodiments, proper coupling occurs when the arm 354 engages with the neck 358 and/or when the piercing member 512 penetrates the septum 370.

The second reservoir 312 can be configured to remove a substance (e.g., liquid medicine) from the container 304. The second reservoir 312 can be configured to add a substance (e.g., saline, a liquid solvent, water) to the container 304. The removal and/or addition of a substance can take place via the second passage 324, which can include a valve 232 (shown in FIG. 7). Although in some embodiments the first reservoir 712 and the second reservoir 312 are generally coaxial, and the first reservoir 712 is located proximally relative to the second reservoir 312, many other reservoir configurations are possible. In some embodiments, the first reservoir and the second reservoir are not coaxial. In several embodiments, the first reservoir and the second reservoir are two generally parallel (e.g., are two generally cylindrically shaped bodies). The reservoirs can be located side by side (rather than end to end). Some embodiments include three, four, and/or five reservoirs.

Figure 16:
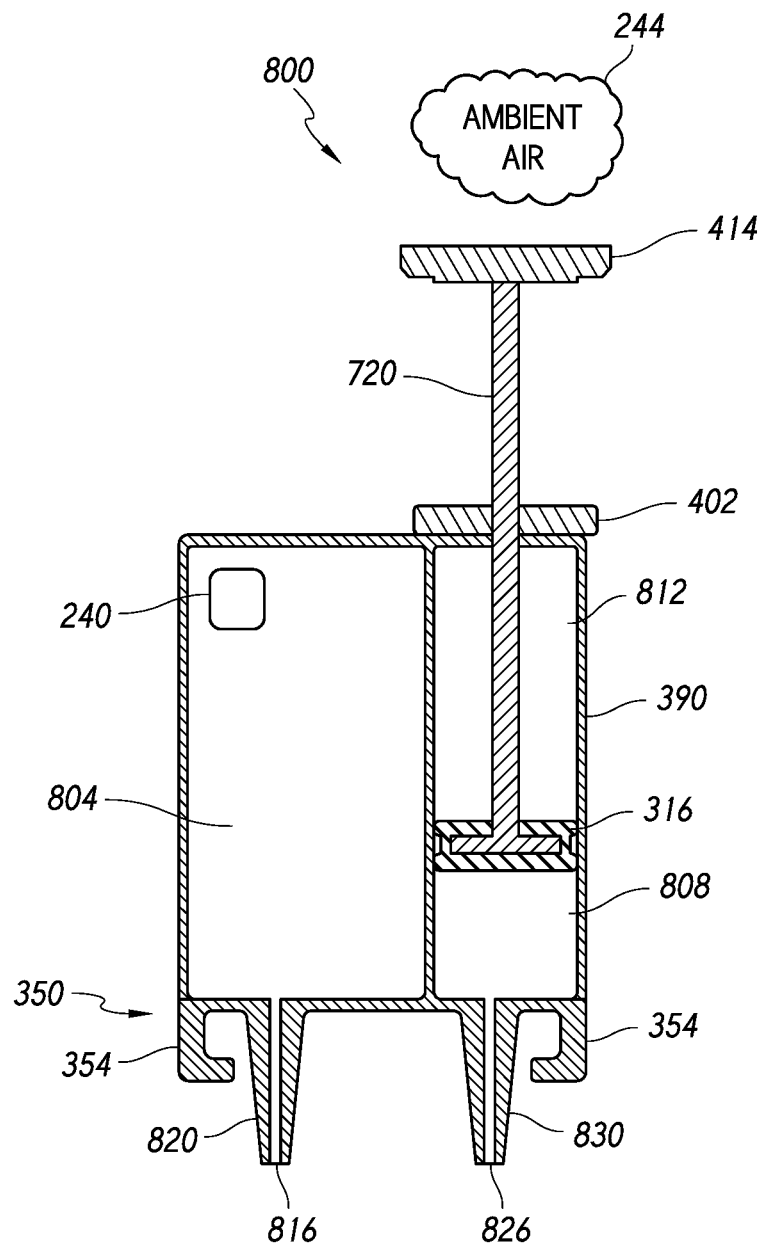
FIG. 16 illustrates a cross-sectional, side view of an embodiment of a pressure regulating syringe system.
Figure 17:
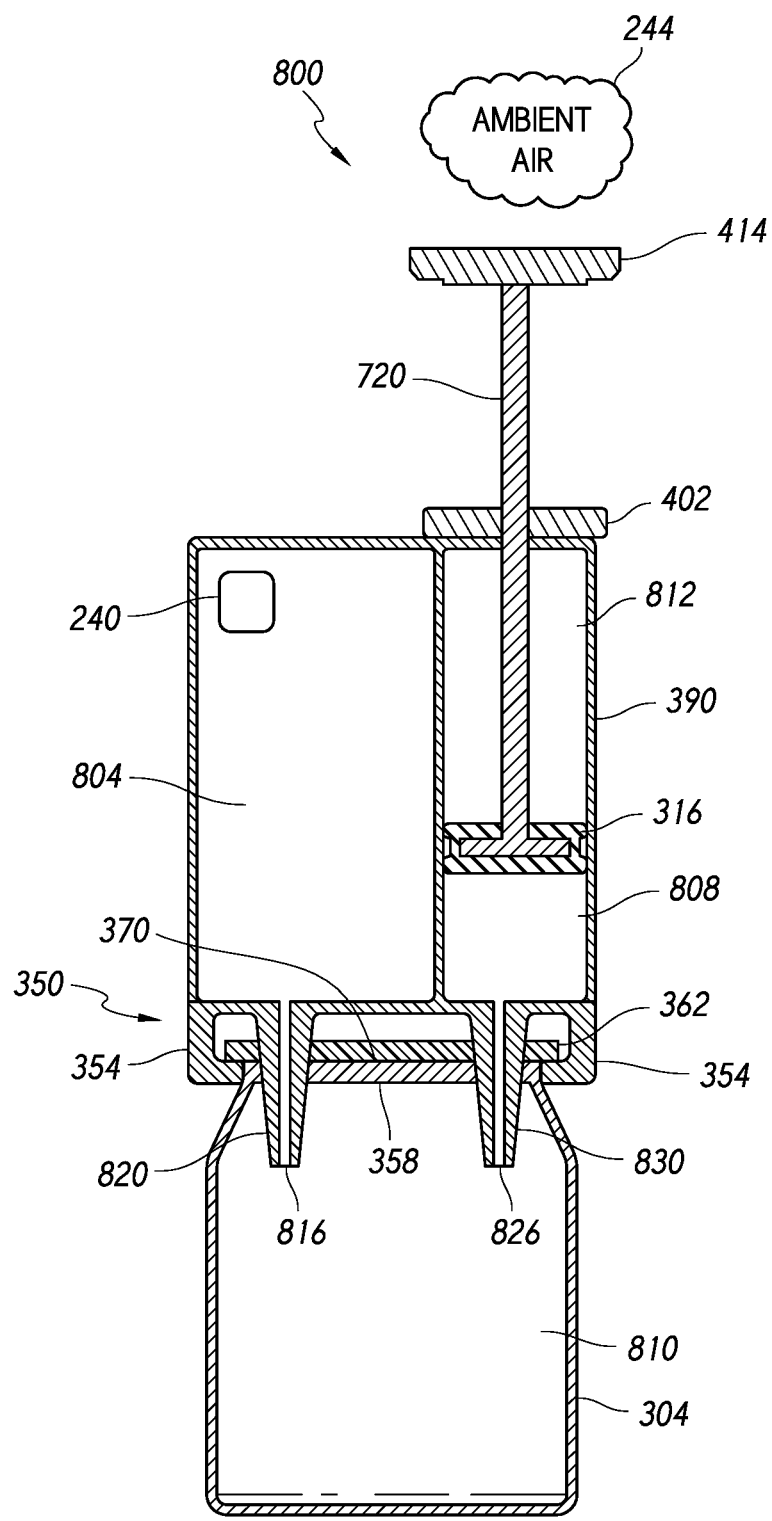
FIG. 17 illustrates a cross-sectional, side view of the pressure regulating syringe system from FIG. 16 coupled to a container.

FIGS. 16 and 17 illustrate side views of an embodiment of a pressure regulating syringe system 800. FIG. 16 illustrates the system 800 itself and FIG. 17 illustrates the system 800 coupled to a container 304, such as a vial. The system 800 can be the same or identical to any of the other pressure-regulating syringe systems described herein and can include any of the features of those other systems.

The system 800 can include a first reservoir 804 that is located to the side (e.g., radially outward) of a second reservoir 808. In some embodiments, the first reservoir 804 is configured to hold a gas such as air and the second reservoir 808 is configured to hold liquid, such as a liquid used for medical treatment, medical procedural, and/or pharmaceuticals. The syringe system 800 can include a third reservoir 812 located to the side of at least a portion of the first reservoir 804 and/or located generally coaxially relative to the second reservoir 808. In some embodiments, the third reservoir 812 is in fluid communication with the first reservoir 804 and/or an internal portion 810 of the container 304.

A first passage 816 can fluidly couple the first reservoir 804 to an internal portion of the container 304. The first passage 816 can pass through at least a portion of a first piercing member 820. A second passage 826 can fluidly couple the second reservoir 808 to an internal portion of the container 304. The second passage 826 can pass through at least a portion of a second piercing member 830, which can be a projection with a tapered or rounded tip, such as a plastic lance. Some embodiments include piercing members that are metal needles.

The first reservoir 804 can have a maximum volume that is larger than, at least 50% larger than, at least 25% larger than, smaller than, at least 25% smaller than, at least 50% smaller than, or equal to the maximum volume of the second reservoir 808.

In some embodiments, the first reservoir 804, the second reservoir 808, and/or the third reservoir 812 have a pressure regulator 240 capable of reducing the pressure difference between the ambient air and the pressure of the reservoir and/or internal portion 810 of the container 304. In several embodiments, the pressure regulator 240 is a bag with an internal volume that can change, a variable volume, a valve, and/or a seal configured to change the size of an internal volume.

Figure 18:
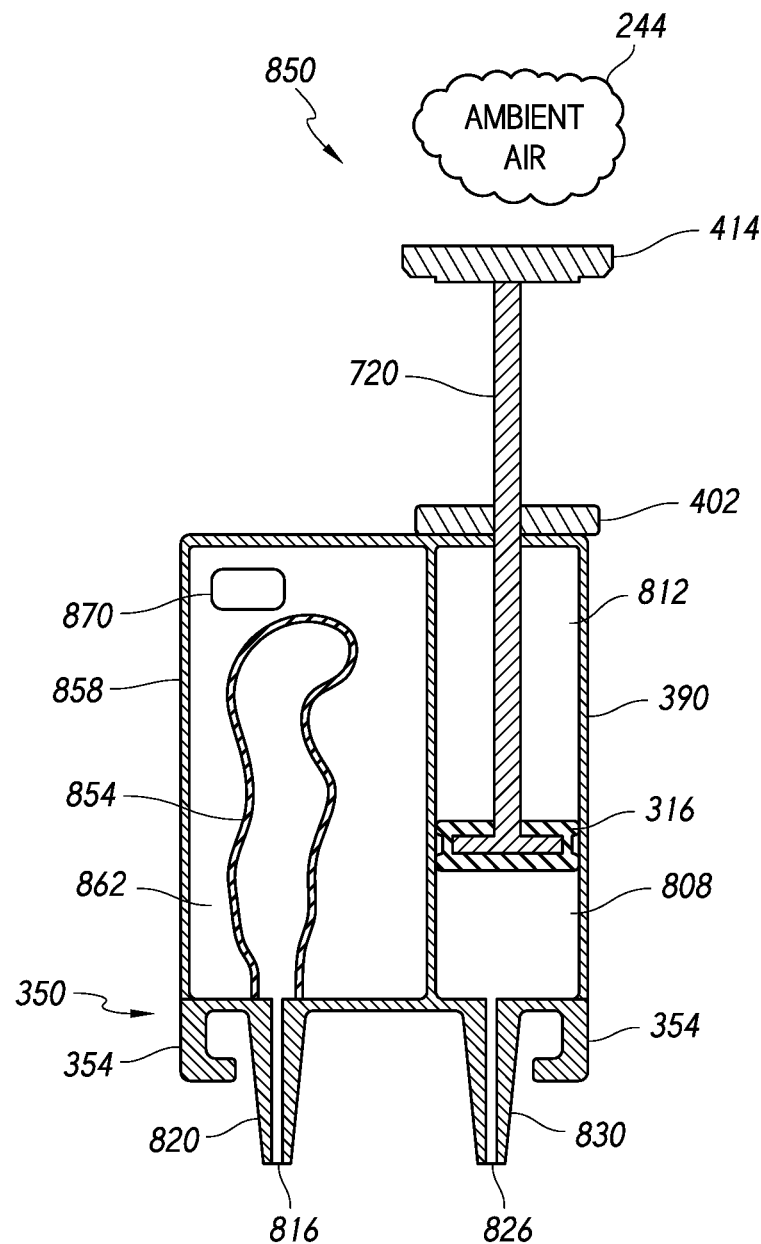
FIG. 18 illustrates a cross-sectional, side view of an embodiment of a pressure regulating syringe system that includes a bag.

FIG. 18 illustrates a side view of an embodiment of a pressure regulating syringe system 850 that includes a bag 854 located inside of a housing 858, which can be rigid. The system 850 can be the same or identical to any of the other pressure-regulating syringe systems described herein and can include any of the features of those other systems. The rigid housing 858 can be located inside the footprint of the coupling system 350 such that the rigid housing 858 does not extend radially outward from the widest portion of the coupling system 350. The bag 854 can include a first reservoir 862. The first reservoir 862 can be configured to be in fluid communication with the first passage 816. The housing 858 can include a vent 870 to allow ambient air 244 to contact an outer surface of the bag 854.

Figure 19:
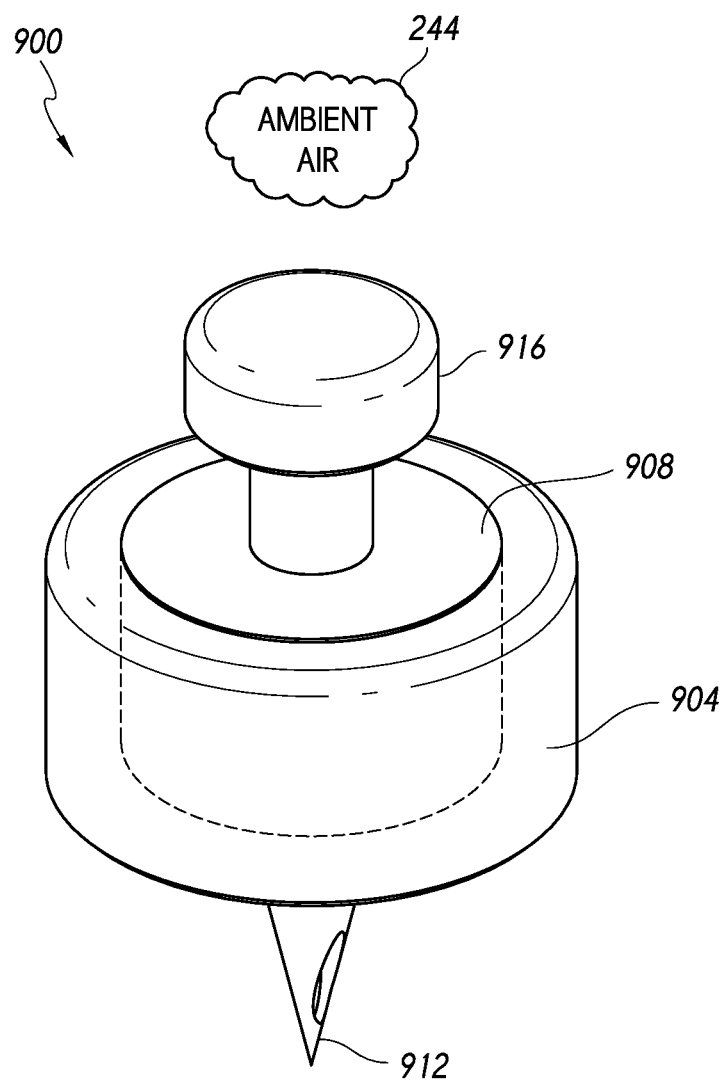
FIG. 19 illustrates a perspective view of an embodiment of a pressure regulating syringe system, wherein at least a portion of the volume of the first reservoir is located radially outward from the second reservoir.

FIG. 19 illustrates a perspective view of an embodiment of a pressure regulating syringe system 900. The pressure regulating syringe system 900 can be the same or identical to any of the other pressure-regulating syringe systems described herein and can include any of the features of those other systems. In some embodiments, the system 900 has a first reservoir 904 that is coaxial with at least a portion of a second reservoir 908. In certain variants, least a portion of and/or at least 50% of the volume of the first reservoir 904 is located radially outward from the second reservoir 908. The second reservoir 908 can be located at least partially inside the first reservoir 904. For example, the second reservoir 908 can be generally cylindrically shaped and be located partly or completely inside the first reservoir 904, which can also be generally cylindrically shaped.

The syringe system 900 can include a piercing member 912 and a plunger 916. The syringe system 900 can be connected with the container 304 (shown in FIG. 17) such that the piercing member 912 is at least partially disposed in the container 304. At least a portion of the piercing member 912 can be in fluid communication with the first reservoir 904 and the second reservoir 908.

The syringe system 900 can be configured such that moving the plunger 916 in a distal direction forces fluid from the second reservoir 908 out of the piercing member 912 and pulls fluid into the first reservoir 904 through the piercing member 912. The syringe system 900 can be configured such that moving the plunger 916 in a proximal direction forces fluid from the first reservoir 904 out of the piercing member 912 and pulls fluid into the second reservoir 908 through the piercing member 912. Syringe systems (such as any of the syringe systems described herein) can be configured such that causing fluid to enter a first reservoir causes fluid to exit a second reservoir and/or causing fluid to enter a second reservoir causes fluid to exit a first reservoir.

Figure 20:
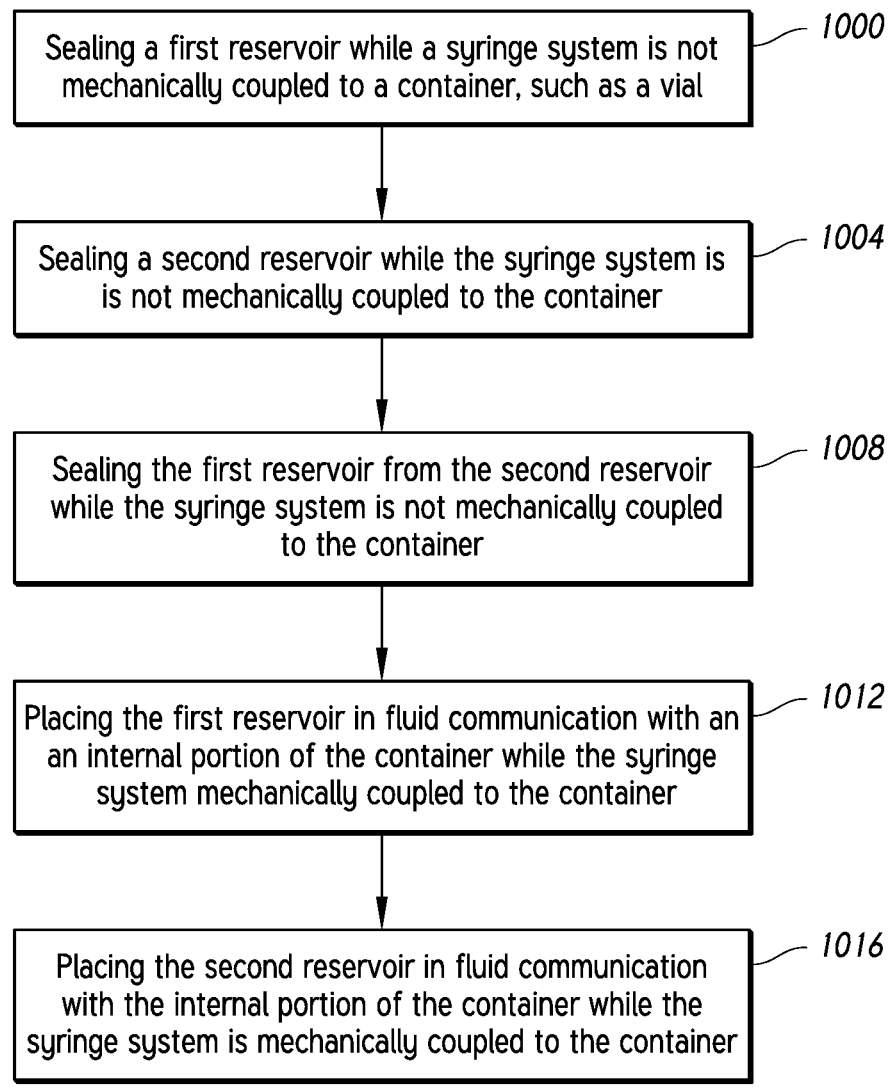
FIGS. 20-24 illustrate various methods for using syringe systems.

FIG. 20 illustrates a method for using a syringe system (such as any of the syringe systems disclosed herein). Block 1000 can include sealing a first reservoir while the syringe system is not mechanically coupled (e.g., connected) to a container, such as a vial. In some embodiments, the first reservoir is configured to hold a gas to help reduce pressure differentials between the inside and the outside of a container. Sealing the first reservoir can include blocking the flow of gas into or out of the first reservoir. Some sealing embodiments are less than perfect, and thus, some sealing embodiments include essentially sealing and/or minor leaks or diffusion into or out of the first reservoir. Sealing a reservoir can include reducing any gap leading into or out of the reservoir to less than 0.002 inches. Block 1004 can include sealing a second reservoir while the syringe system is not mechanically coupled (e.g., connected) to the container. In some embodiments, the second reservoir is configured to hold a liquid, such as a liquid used in medical treatment or procedures.

Block 1008 can include sealing the first reservoir from the second reservoir while the syringe system is not mechanically coupled (e.g., connected) to the container. In some embodiments, a first passage (in fluid communication with a first reservoir) and a second passage (in fluid communication with a second reservoir) terminate in an enclosed area. Thus, moving (e.g., pressing) a plunger can force fluid from the first reservoir to the second reservoir or from the second reservoir to the first reservoir via the enclosed area. In these embodiments, the first reservoir is not sealed from the second reservoir because fluid can flow between the reservoirs. Sealing the first reservoir from the second reservoir helps to block fluid from flowing between the reservoirs.

Block 1012 can include placing the first reservoir in fluid communication with an internal portion of the container while the syringe system is mechanically coupled (e.g., connected) to the container. The internal portion can be the internal volume of a container, such as the internal volume configured to hold a liquid or gas. Placing a reservoir in fluid communication with a container can include fluidly coupling the reservoir and the container via a passage, such as a lumen or channel. Block 1016 can include placing the second reservoir in fluid communication with the internal portion of the container while the syringe system is mechanically coupled (e.g., connected) to the container.

The various methods described herein can be performed in orders other than the orders shown in the example embodiments. Many of the embodiments of the methods described herein can include optional blocks, steps, portions, and elements. For example, some embodiments of the method of FIG. 20 include Block 1000 but do not include Block 1004. None of the elements of the various methods described herein are essential or critical.

Figure 21:
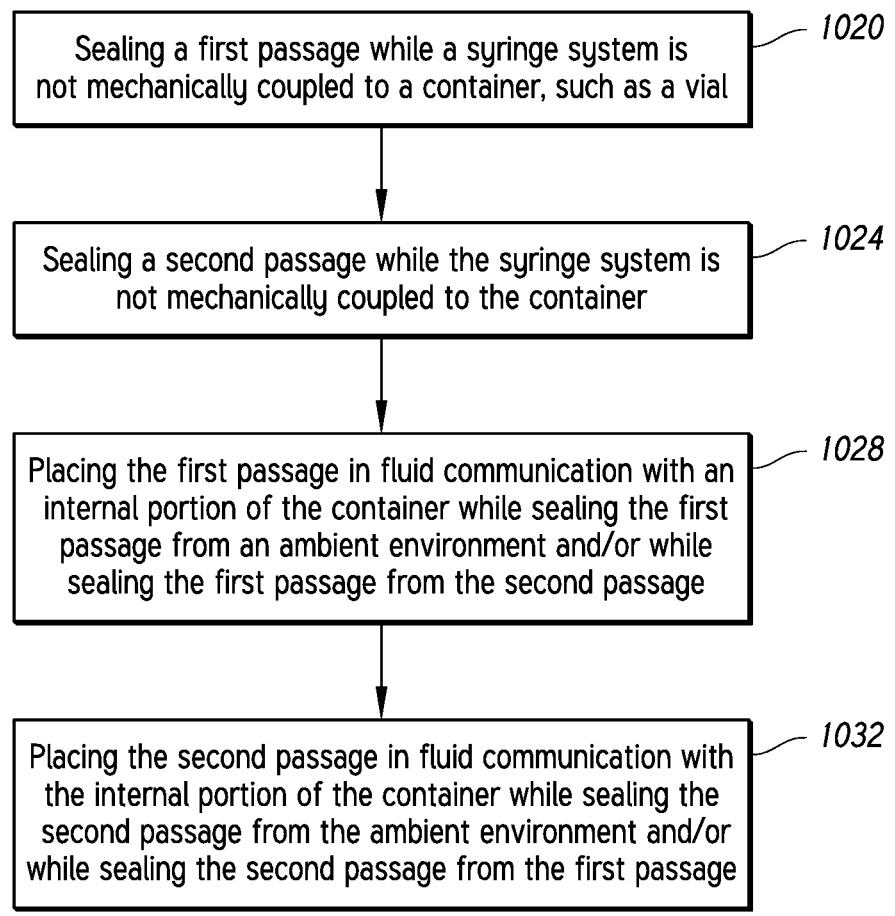

FIG. 21 illustrates a method for using a syringe system (such as any of the syringe systems disclosed herein). Block 1020 can include sealing a first passage while the syringe system is not mechanically coupled (e.g., connected) to a container, such as a vial. Block 1024 can include sealing a second passage while the syringe system is not mechanically coupled (e.g., connected) to the container. The first passage can be fluidly coupled to a first reservoir, which can be configured to hold gas. The second passage can be fluidly coupled to a second reservoir, which can be configured to hold liquid. Block 1028 can include placing the first passage in fluid communication with an internal portion of the container while sealing the first passage from an ambient environment and while sealing the first passage from the second passage. The ambient environment is the environment outside of the syringe system and outside of the container (e.g., ambient air 244 in FIG. 7). Some embodiments include sealing the first passage from the ambient environment while the first passage is in fluid communication with an internal portion of the container and/or sealing the first passage from the second passage while the first passage is in fluid communication with an internal portion of the container.

Block 1032 can include placing the second passage in fluid communication with the internal portion of the container while sealing the second passage from the ambient environment and while sealing the second passage from the first passage. Some embodiments include sealing the second passage from the ambient environment while the second passage is in fluid communication with the internal portion of the container and/or sealing the second passage from the first passage while the second passage is in fluid communication with the internal portion of the container.

Figure 22:
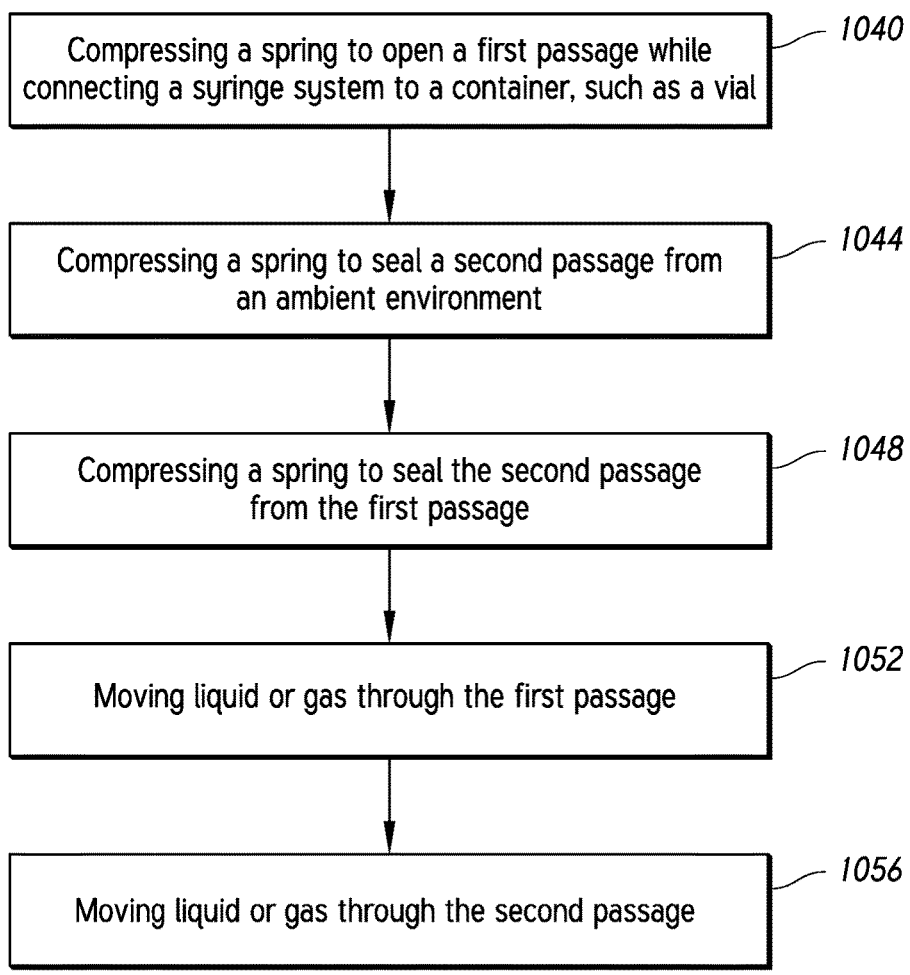

FIG. 22 illustrates a method for using a syringe system, such as any of the syringe systems disclosed herein. Block 1040 can include compressing a first biasing member (such as a first spring) to open a first passage while connecting a syringe system to a container, such as a vial. The first passage can be configured to fluidly couple a first reservoir with an internal portion of the container. Block 1044 can include compressing a second biasing member (such as a second spring) to seal a second passage from an ambient environment. Block 1048 can include compressing a third biasing member (such as a third spring) to seal the second passage from the first passage. The second passage can be configured to fluidly couple a second reservoir with the internal portion of the container. The ambient environment is the environment outside of the syringe system and outside of the container (e.g., ambient air 244 in FIG. 7). In some embodiments, the first biasing member, the second biasing member, and/or the third biasing member are actually one biasing member (e.g., one spring). In some embodiments, the second biasing member and the third biasing member are actually one biasing member (e.g., the spring 1504 in FIG. 41) and the first biasing member is another biasing member (e.g., the spring 1558 in FIG. 41).

Block 1052 can include moving liquid or gas through the first passage. Block 1056 can include moving liquid or gas through the second passage. Moving liquid and/or gas can include moving liquid and/or gas into and/or out of the syringe system. Moving liquid and/or gas can include moving liquid and/or gas into and/or out of the container, such as the container 304 in FIG. 17.

The spring can be any mechanical device, such as an elastic device, that stores energy, such as axial energy. Springs can be made from spring steel. The energy stored by a spring is sometimes proportional to the change in the spring's length. Some embodiments use helical springs, coil springs, tension springs, compression springs, torsion springs, constant springs, variable springs, flat springs, machined springs, cantilever springs, leaf springs, V-springs, Belleville springs, gas springs, mainsprings, spring washers, and wave springs. In some embodiments, springs are replaced with axially compliant members such as a silicone cylinder with a lumen running along the axis of the cylinder.

Figure 23:
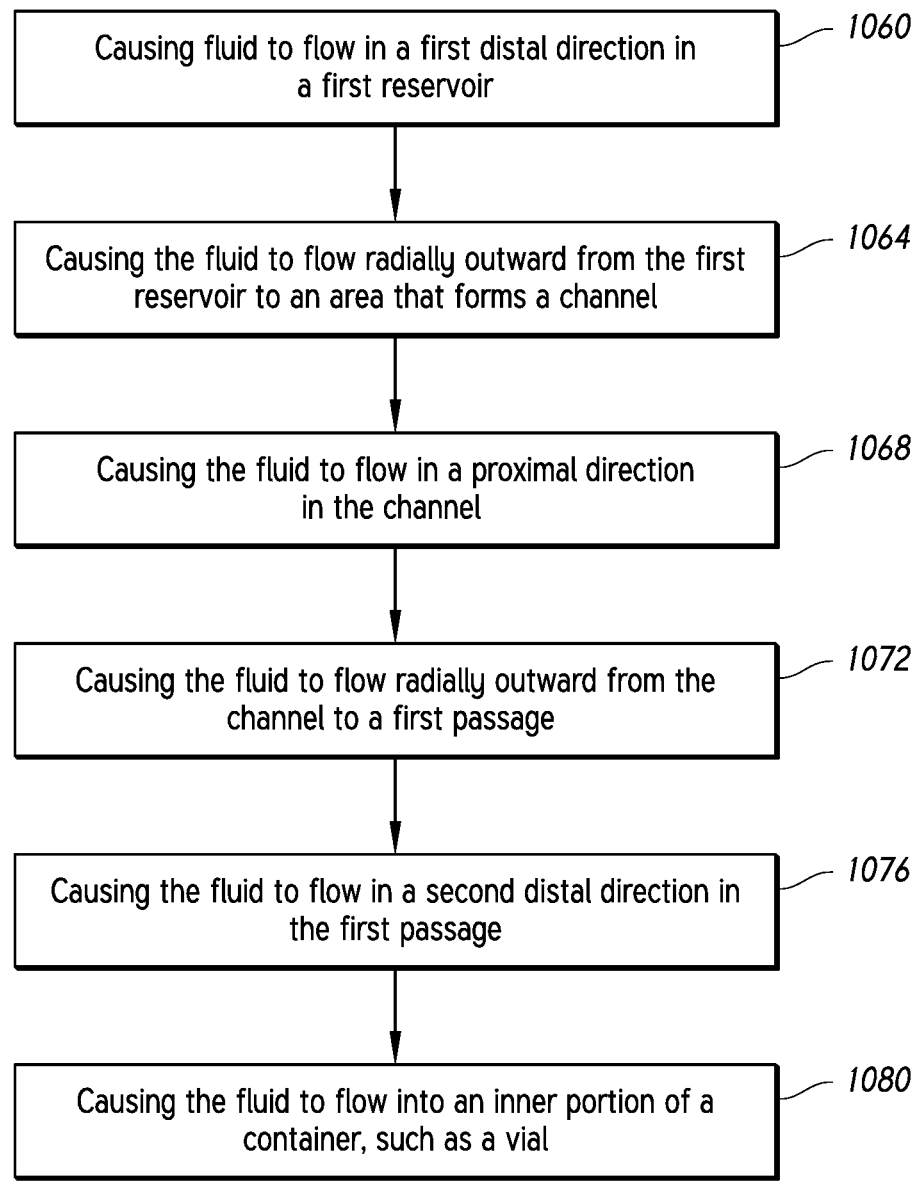

FIG. 23 illustrates a method for using a syringe system, such as any of the syringe systems disclosed herein. A user or machine can cause fluid to flow by pushing on the plunger, pulling on the plunger, and/or causing a pressure differential that drives fluid flow. Fluid can be gas or liquid. Block 1060 can include causing fluid to flow in a first distal direction in a first reservoir. For example, in FIG. 8, fluid can flow from a middle portion of the first reservoir 308 towards the hole 410. Block 1064 can include causing the fluid to flow radially outward from the first reservoir to an area that forms a channel. For example, in FIG. 8, fluid can flow from the first reservoir 308 radially outward through the hole 410 to the area 398. The area 398 forms a channel through which fluid can flow. Block 1068 can include causing the fluid to flow in a proximal direction in the channel. For example, in FIG. 8, the fluid can flow inside the area 398 from a distal portion of the area 398 (e.g., the distal portion near the hole 410) towards a proximal portion of the area 398 (e.g., the proximal portion near an entrance 322 to the first passage 320).

Block 1072 can include causing the fluid to flow radially outward from the channel to a first passage. For example, in FIG. 8, the fluid can flow radially outward from the proximal portion of the area 398, through the entrance 322, and into a proximal portion of the first passage 320. Some embodiments include causing the fluid to flow outside of the first reservoir and into a first passage. Block 1076 can include causing the fluid to flow in a second distal direction in the first passage. For example, in FIG. 8, the fluid can flow from a proximal portion of the first passage 320 towards a distal portion of the first passage 320 (e.g., towards the container 304). Block 1080 can include causing the fluid to flow into an inner portion of a container, such as a vial.

In some embodiments, each direction in Blocks 1060, 1064, 1068, 1072, 1076, and 1080 is reversed such that fluid flows from the container (e.g., 304 in FIG. 8) to the first reservoir (e.g., 308 in FIG. 8). Various embodiments of the method of FIG. 23 can include mechanically and/or fluidly coupling a syringe system to a container, such as a vial. Some embodiments use containers that are not vials.

Figure 24:
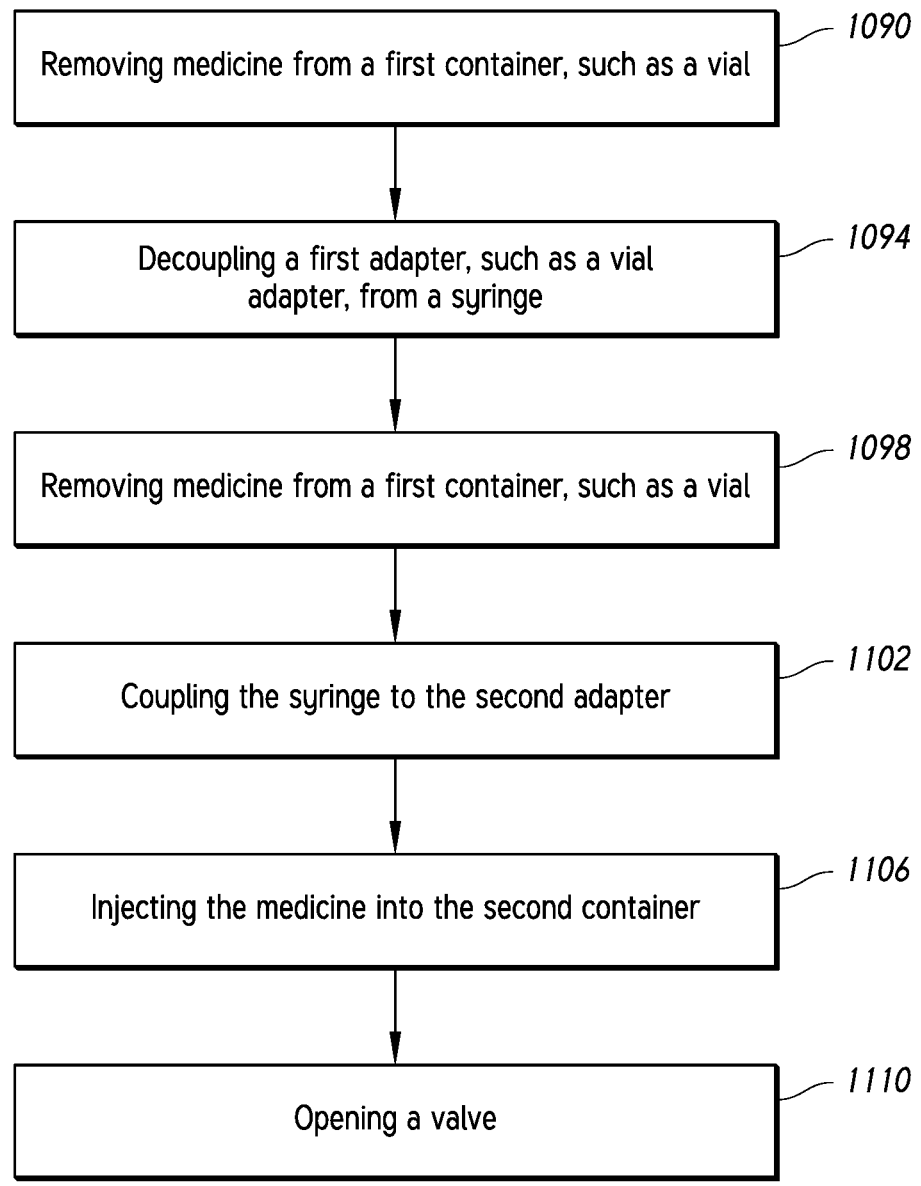

FIG. 24 illustrates a method for using a syringe system, such as any of the syringe systems disclosed herein. Block 1090 can include removing medicine from a first container, such as a vial. Some embodiments include using a vial adapter while removing medicine from the first container. Block 1094 can include decoupling a first adapter, such as a vial adapter, from a syringe. Block 1098 can include coupling a second adapter to a second container. The second container can be an intravenous therapy ("IV") bag or IV line. The second adapter can be configured to mechanically and/or fluidly couple the syringe to the second container. Block 1102 can include coupling the syringe to the second adapter. Block 1106 can include injecting the medicine into the second container. Block 1110 can include opening a valve, such as a pressure regulation valve and/or valve that allows ambient air or filtered ambient air to enter the syringe.

Figure 25:
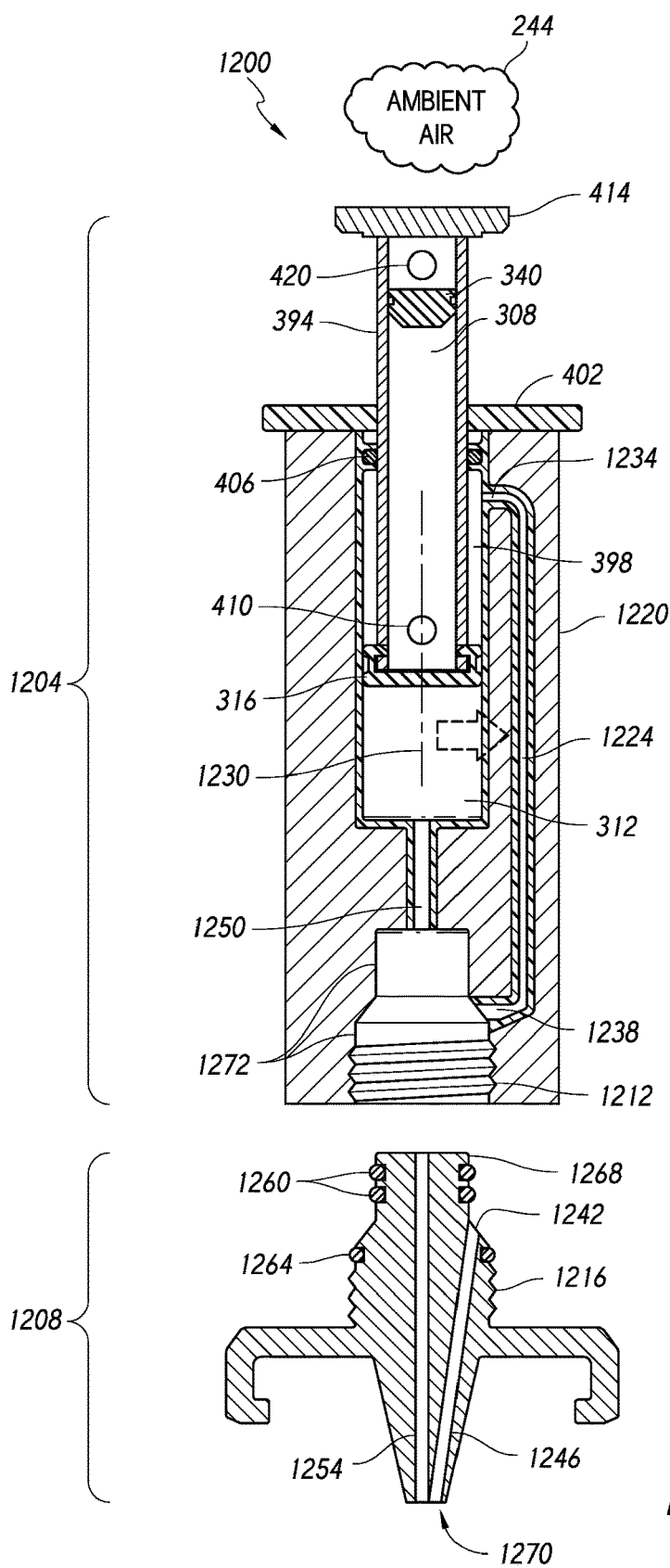
FIG. 25 illustrates a cross-sectional, side view of an embodiment of a pressure regulating syringe system that includes a coupling system.

FIG. 25 illustrates a side view of an embodiment of a pressure regulating syringe system 1200 that highlights additional coupling system details. The system 1200 can be the same or identical to any of the other pressure-regulating syringe systems described herein and can include any of the features of those other systems. The syringe system 1200 can include a syringe assembly 1204 and an adapter assembly 1208. The adapter assembly 1208 can be configured to couple the syringe assembly 1204 to a container such as a vial, IV bag, or IV line. Threads 1212 near a distal portion of the syringe assembly 1204 can couple to threads 1216 on the adapter assembly 1208. Some embodiments include screwing the syringe assembly 1204 to the adapter assembly 1208. Various implementations, such as the embodiment illustrated in FIG. 25, are capable of coupling to the adapter assembly 1208 in any rotational orientation along a central axis of the syringe assembly 1204. Thus, the syringe assembly 1204 and adapter assembly 1208 in FIG. 25 and various other embodiments do not require a particular rotation orientation. Not requiring a particular rotational orientation can facilitate simpler coupling and can reduce coupling errors. Lack of a required rotational orientation can be called "rotational independence." Many embodiments described herein have rotational independence, such as the embodiments illustrated in FIGS. 25, 40, 48, and/or 62.

The syringe assembly 1204 can include a barrel 1220. The first reservoir 308 and the second reservoir 312 can be located inside the barrel 1220. A proximal first passage 1224 can be located inside of the barrel 1220. The proximal first passage 1224 can be located outside of the first reservoir 308 and/or outside of the second reservoir 312. A central axis 1230 of the syringe assembly 1204 is illustrated as a dashed line. The proximal first passage 1224 can be located radially outward from the central axis 1230, the first reservoir 308, the second reservoir 312, and the plunger 394, as depicted by the dashed arrow. The proximal first passage 1224 includes a proximal opening 1234 and a distal opening 1238. The proximal opening 1234 can be in fluid communication with the area 398 that forms a channel. The area 398 can be in fluid communication with the first reservoir 308 via a hole 410. The distal opening 1238 is configured to be placed in fluid communication with a proximal opening 1242 of a distal first passage 1246 of the adapter assembly 1208 after the syringe assembly 1204 is coupled to the adapter assembly 1208.

The syringe assembly 1204 can have a proximal second passage 1250 configured to be placed in fluid communication with a distal second passage 1254 of the adapter assembly 1208 after the syringe assembly 1204 is coupled to the adapter assembly 1208.

As illustrated in FIG. 25, the syringe assembly 1204 and/or the adapter assembly 1208 can include seals 1260, 1264. The seals 1260, 1264 can be configured to facilitate substantially gas-tight sealing, gas-tight sealing, and/or liquid-tight sealing between any combination of the first reservoir 308, the second reservoir 312, and/or an internal portion of a container while the syringe assembly 1204 is mechanically coupled (e.g., connected) to the container. For example, the seals 1260, 1264 can seal the first passage 1224, 1246 from an ambient environment (e.g., ambient air 244) and/or can seal the first passage 1224, 1246 from the second passage 1250, 1254.

In some embodiments, the seals 1260, 1264 can be any type of sealant or gasket, such as O-rings. Some seal embodiments can be made from medical-grade silicone or neoprene. The O-rings can sit in grooves with a width that is at least 10% wider than the thickness of the O-rings. The width of the grooves can be measured in a direction parallel to the central axis of the syringe assembly 1204. The depth of the grooves can be measured in a direction perpendicular to the central axis of the syringe assembly 1204. The thickness of the O-ring can equal 50% of the outer diameter minus the inner diameter of the O-ring. The thickness can also be determined by laying an O-ring on a flat surface and then measuring how far the O-ring extends perpendicularly to the flat surface. In some embodiments, the seals 1260, 1264 are radially sealing members that seal a portion of the adapter assembly 1208 to a portion of the syringe assembly 1204. A radially sealing member, such as the seals 1260, 1264 illustrated in FIG. 25, can be located around a support 1268 (e.g., a plastic and/or rigid cylindrical support) of the adapter or syringe (e.g., the adapter assembly 1208, the syringe assembly 1204). In some embodiments, the inner diameter of the radially sealing member seals against the support 1268 and the outer diameter of the radially sealing member seals against an inner surface 1272 (e.g., an inner diameter) of the syringe or adapter.

Figure 26:
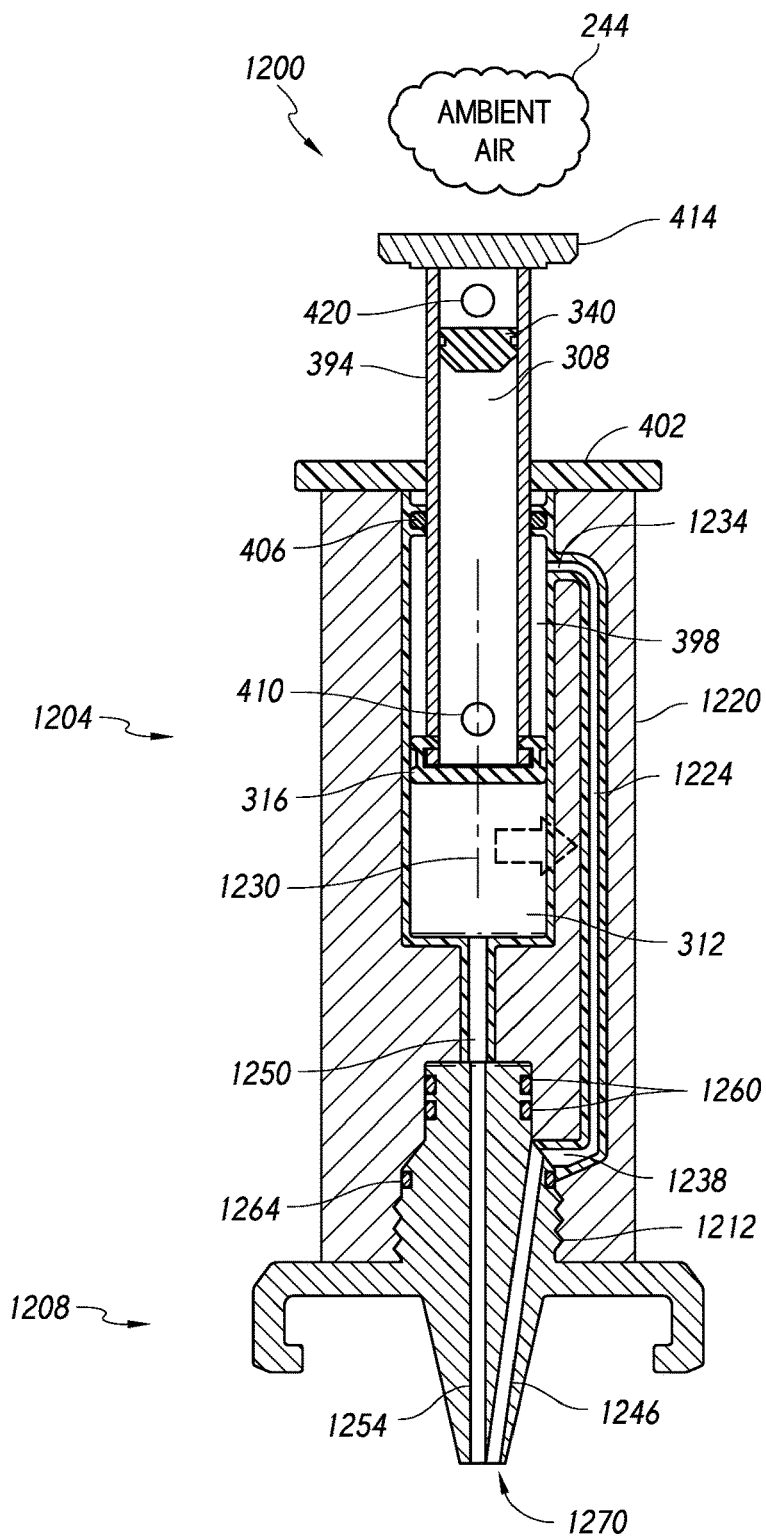
FIG. 26 illustrates the pressure regulating syringe system of FIG. 25 with the syringe assembly coupled to the adapter assembly.

FIG. 25 illustrates the pressure regulating syringe system 1200 when the syringe assembly 1204 is not coupled to the adapter assembly 1208. FIG. 26 illustrates the pressure regulating syringe system 1200 when the syringe assembly 1204 is coupled to the adapter assembly 1208. For example, the syringe assembly 1204 and the adapter assembly 1208 can be coupled by corresponding threads 1212, 1216. The proximal seals 1260 can inhibit or prevent fluid from passing between the second passage 1250, 1254 and first passage 1124, 1246 and/or from leaking out of the syringe system

1200. The distal seal 1264 can prevent fluid from exiting the first passage 1224, 1246 and then entering the second passage 1250, 1254 and/or leaking out of the syringe system 1200. The adapter assembly 1208 can include a piercing member 1270.

Figure 27:
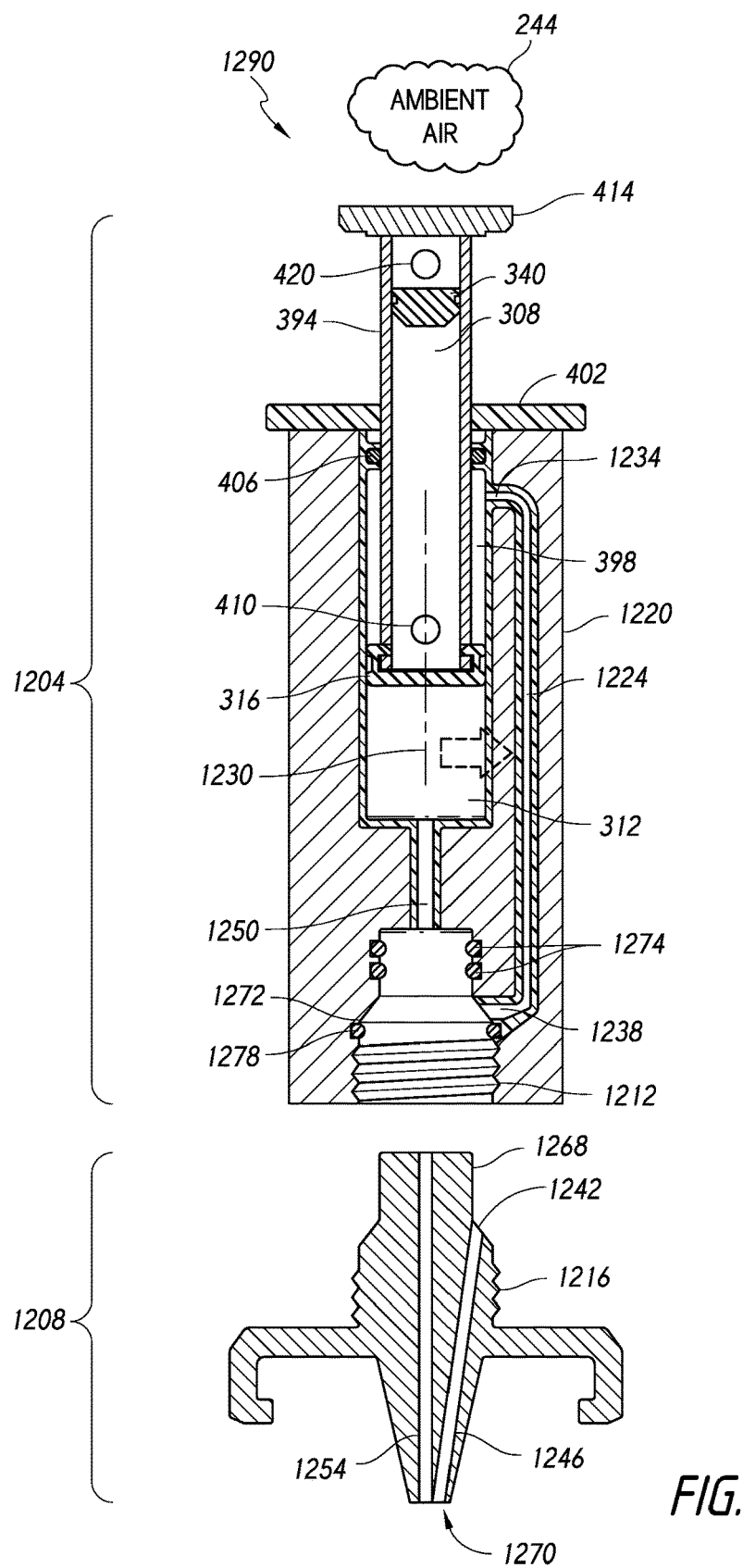
FIG. 27 illustrates a cross-sectional, side view of an embodiment of a pressure regulating syringe system wherein seals are located in a groove along an inner diameter.

FIG. 27 illustrates a side view of an embodiment of a pressure regulating syringe system 1290 wherein seals 1274, 1278 are located in a groove along an inner surface (e.g., diameter) rather than being located in a groove on an outer surface (e.g., diameter). The syringe system 1290 can include one or more proximal seals 1274 and/or distal seals 1278, which can serve the same function as described for the proximal seals 1260 and the distal seal 1264 in FIGS. 25 and 26. The system 1290 can be the same or identical to any of the other pressure-regulating syringe systems described herein and can include any of the features of those other systems.

Figure 28:
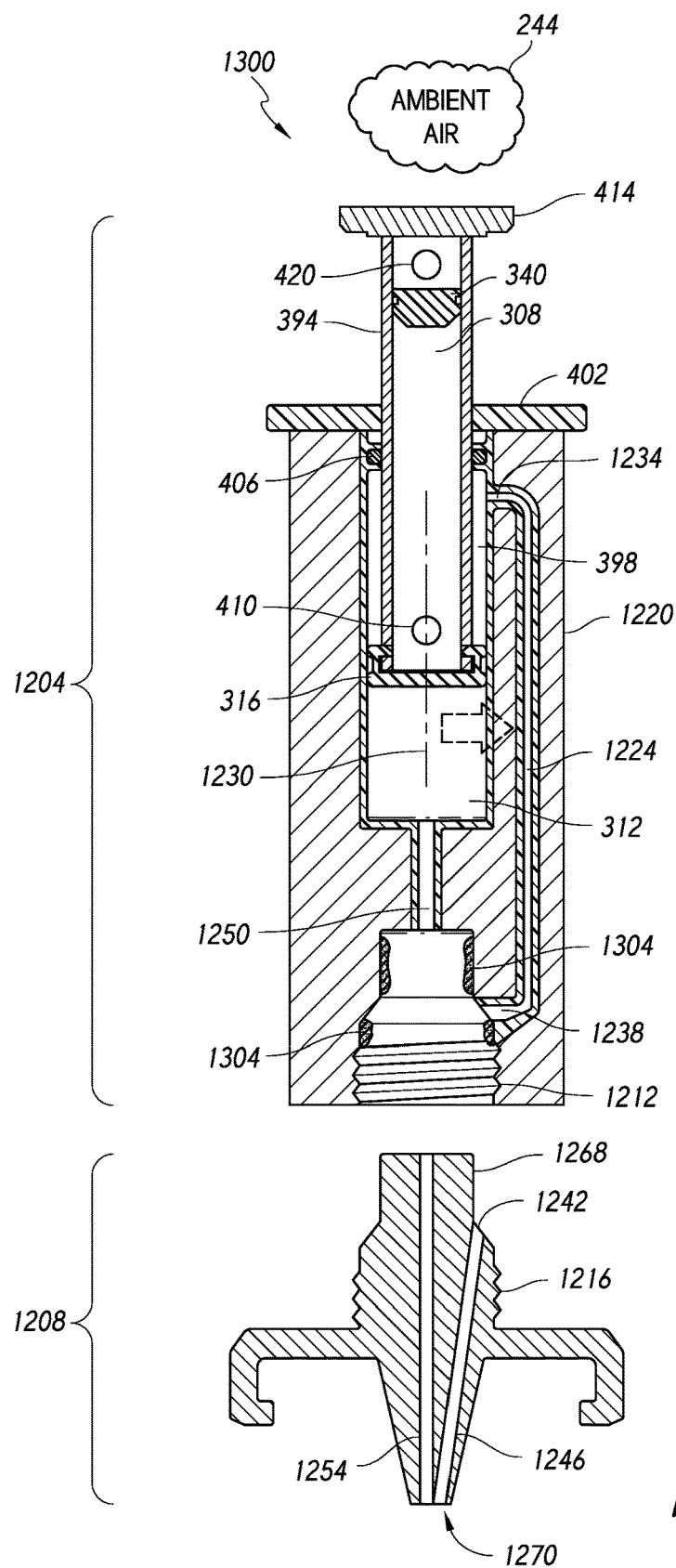
FIG. 28 illustrates a cross-sectional, side view of an embodiment of a pressure regulating syringe system that includes sealing gel.

FIG. 28 illustrates a side view of an embodiment of a pressure regulating syringe system 1300 that includes sealing gel 1304 and/or a resilient sealing material. The system 1300 can be the same or identical to any of the other pressure-regulating syringe systems described herein and can include any of the features of those other systems. The sealing gel can be located along a coupling interface between at least a portion of the syringe assembly 1204 and the adapter assembly 1208. In some embodiments, the gel 1304 is a silicone gel suitable for medical use.

Figure 29:
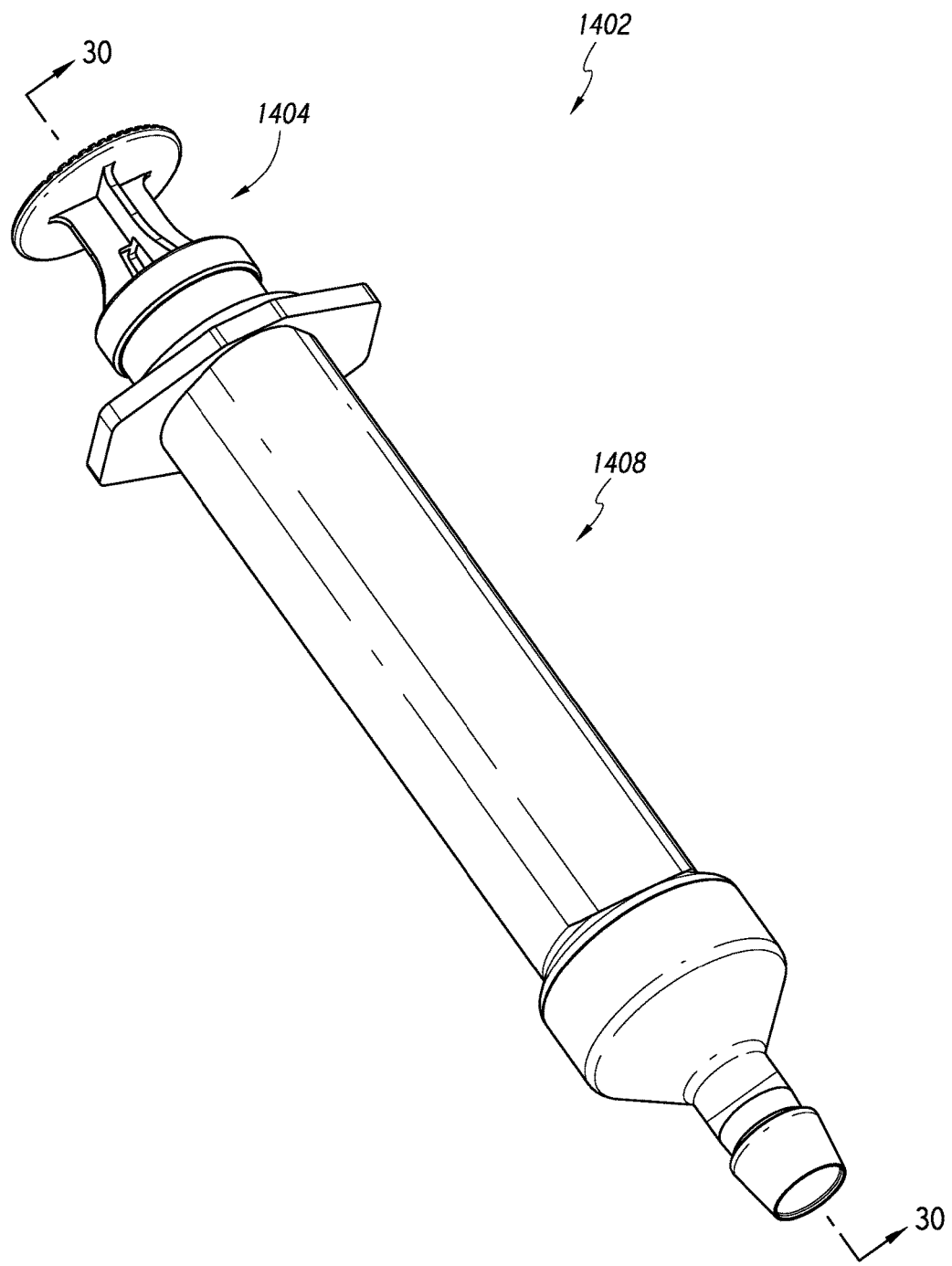
FIGS. 29 and 29A illustrate perspective views of a syringe assembly, including a plunger and barrel.
Figure 29A:
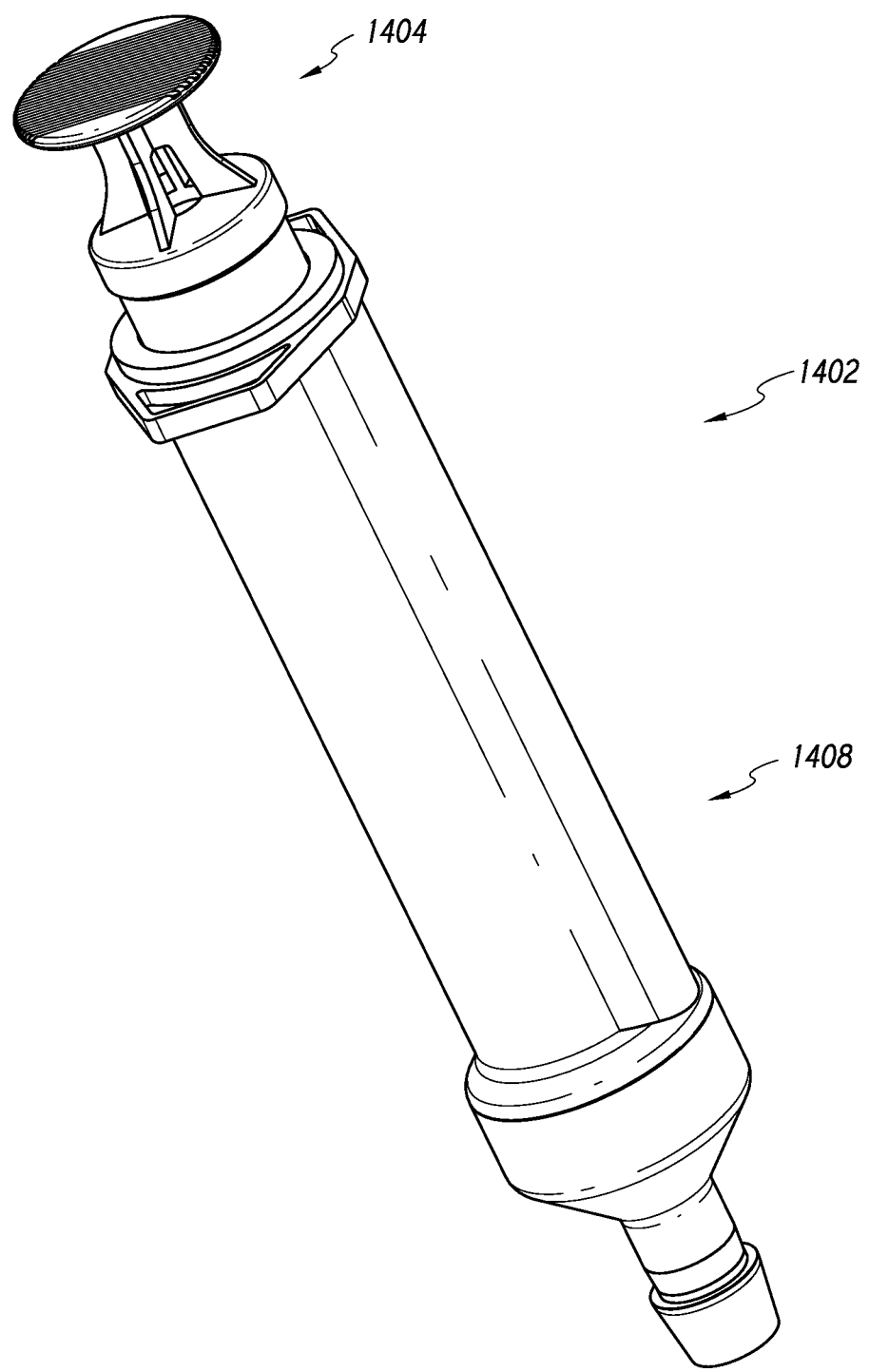
Figure 29D:
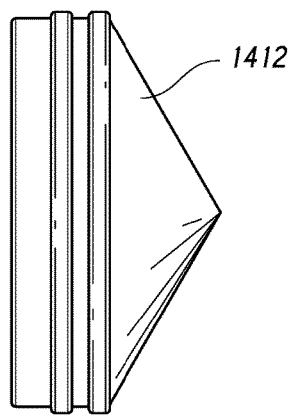
FIGS. 29D-G illustrate side, perspective, and front views of the proximal plunger seal of the plunger of FIG. 29B.
Figure 29E:
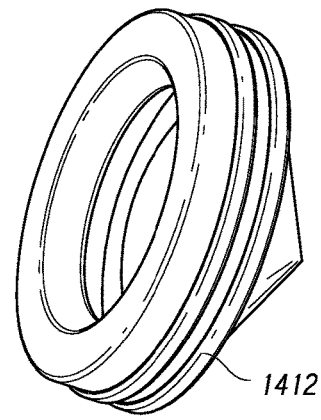
Figure 29F:
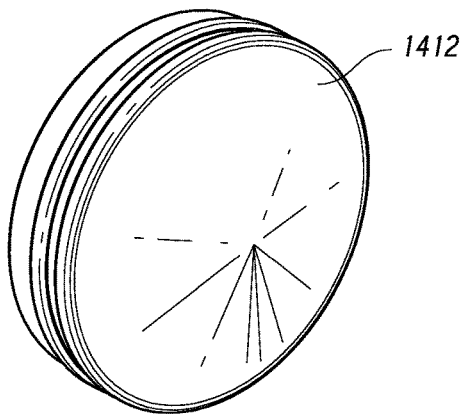
Figure 29G:
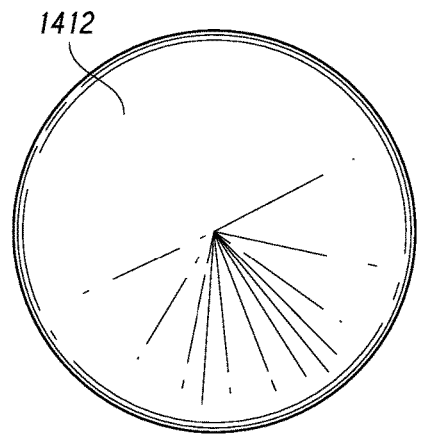
Figure 29H:
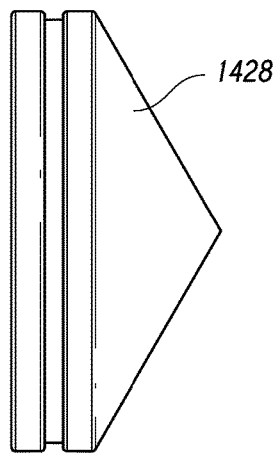
FIGS. 29H-K illustrate side, perspective, and front views of the distal plunger seal of the plunger of FIG. 29B.
Figure 29I:
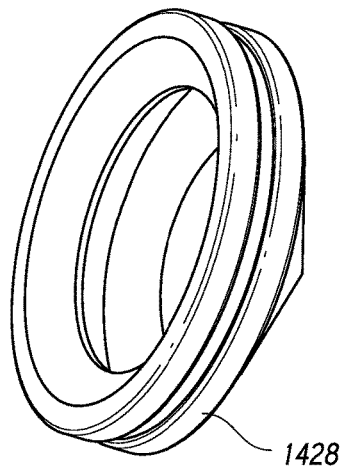
Figure 29J:
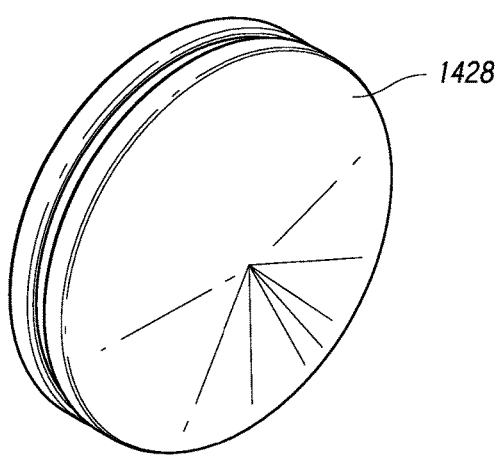
Figure 29K:
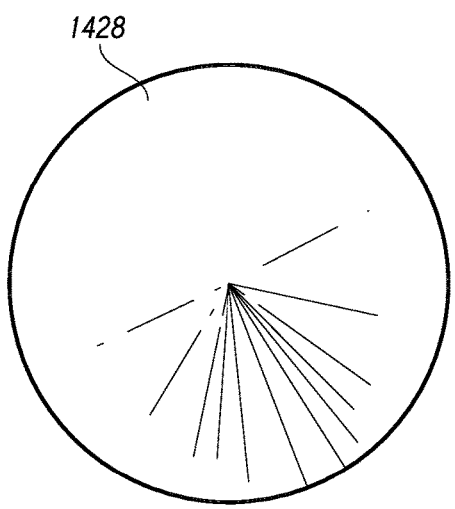

FIGS. 29 and 29A illustrate perspective views of an embodiment of a syringe assembly 1402. The syringe assembly 1402 can include a plunger 1404 (e.g., a tube, actuator, shaft, etc.) and a barrel 1408 (e.g., a housing, casing, enclosure, etc.). As discussed in more detail below, the syringe assembly 1402 can couple with a container of medical fluid, such as with an adaptor assembly 1450 (see FIG. 32), to facilitate pressure-regulated transfer of fluids.

FIGS. 29B and 29C illustrate side and exploded views of the plunger 1404. The plunger 1404 can include any of the features of the plunger 450 discussed above. As shown, the plunger 1404 can include a distal plunger seal 1428 coupled to a distal end of a plunger body 2800 by a seal coupler 2804. A proximal plunger seal 1412 can be inserted into an inner channel 1452 (shown in FIG. 29M) of the plunger body 2800. The proximal plunger seal 1412 can be pushed distally inside of the inner channel 1452 to form a first reservoir, such as a reservoir for regulating gas. A proximal end 2808 (e.g., a grip, handle, or end-cap) can be coupled to a proximal portion of the plunger body 2800. This can aid in retaining the proximal plunger seal 1412 inside of the plunger body 2800.

Figure 29L:
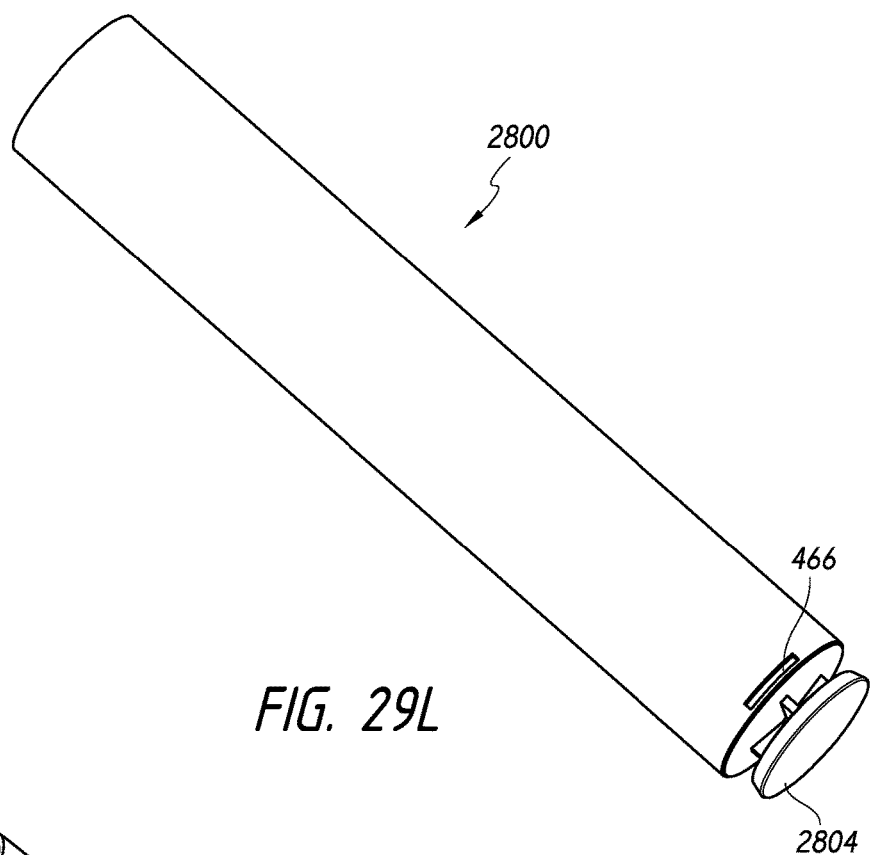
FIGS. 29L and 29M illustrate perspective views of the plunger body of the plunger of FIG. 29B.
Figure 29M:
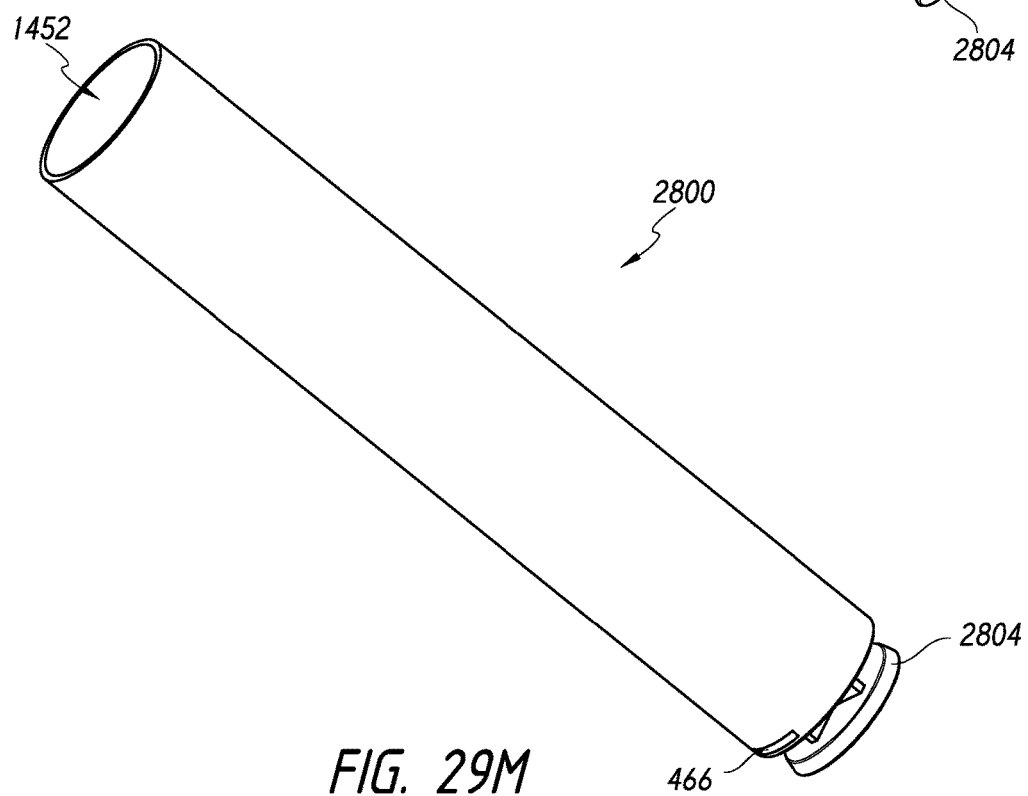
Figure 29N:
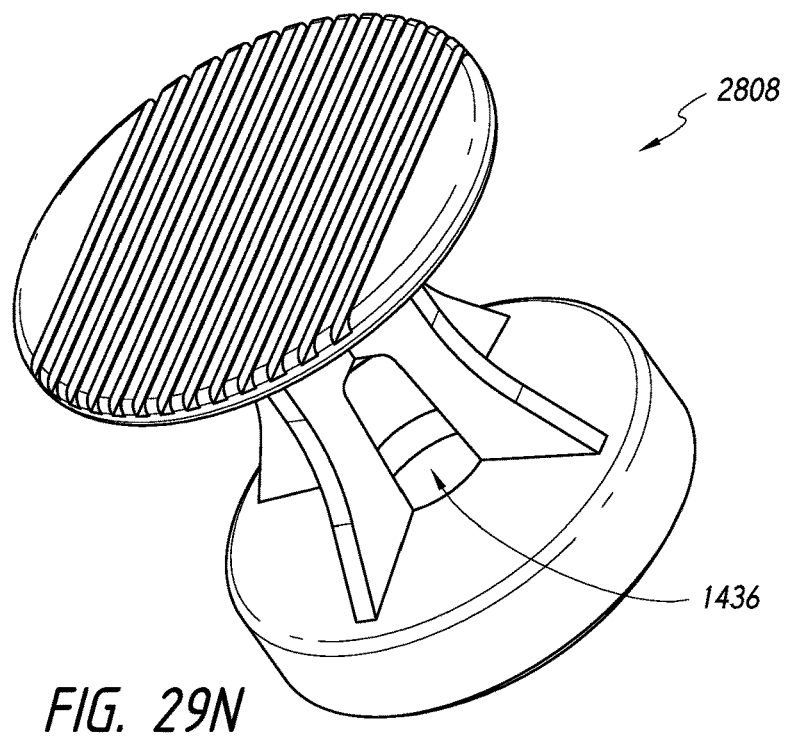
FIGS. 29N and 29O illustrate perspective views of the grip of the plunger of FIG. 29B.
Figure 29O:
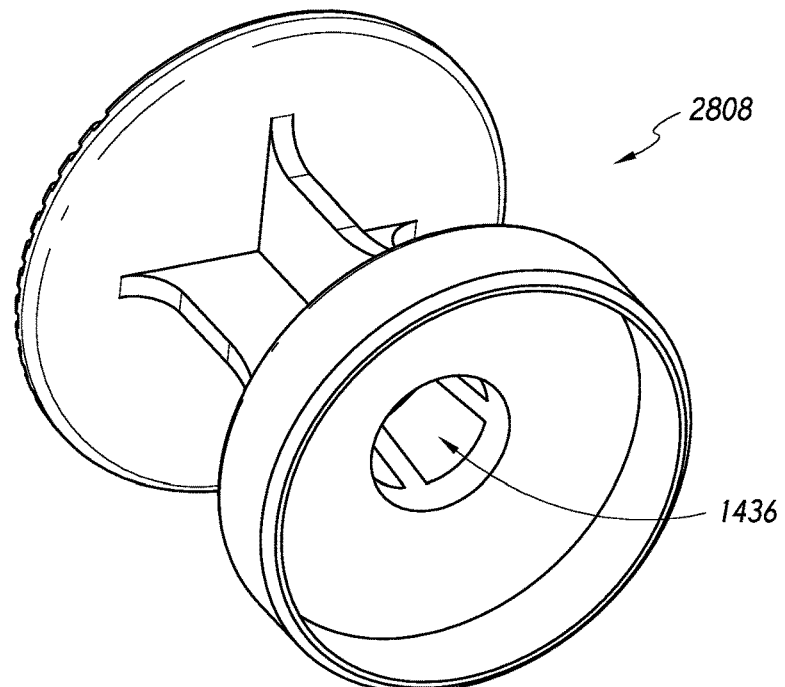

FIGS. 29D-G illustrate various views of the proximal plunger seal 1412. FIGS. 29H-K illustrate various views of the distal plunger seal 1428. FIGS. 29L and 29M illustrate perspective views of the plunger body 2800. As illustrated, the plunger body 2800 can be a hollow elongate member that is partially closed at one end. As shown, the plunger body 2800 can include one or more holes 466. FIGS. 29N and 29O illustrate perspective views of the handle.

Figure 29P:
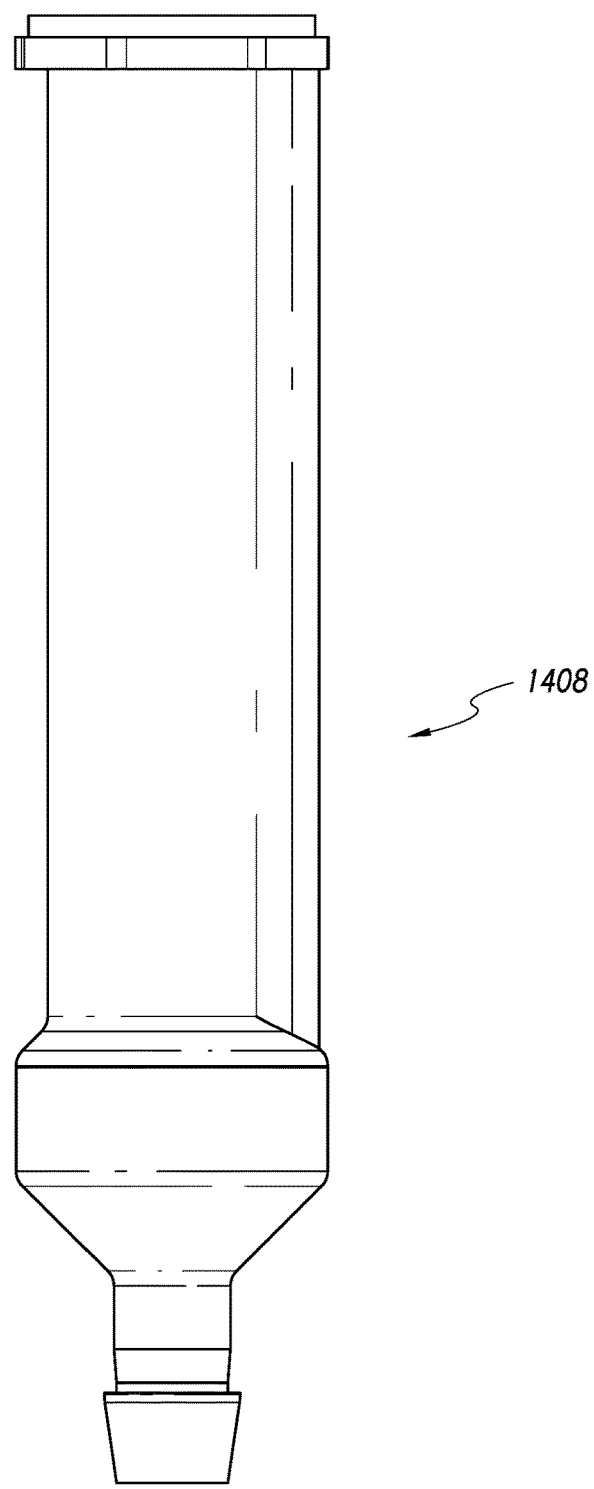
FIG. 29P illustrates a side view of the barrel of the syringe assembly of FIG. 29.

FIG. 29P illustrates a side view of the barrel 1408. The plunger 1404 (shown in FIG. 29B) can be inserted into (e.g., received in) an interior portion of the barrel 1408. Typically, the plunger 1404 can slide inside a portion of the barrel 1408. For example, in some embodiments, the plunger 1404 can slide distally and proximally relative to the barrel 1408.

Figure 29Q:
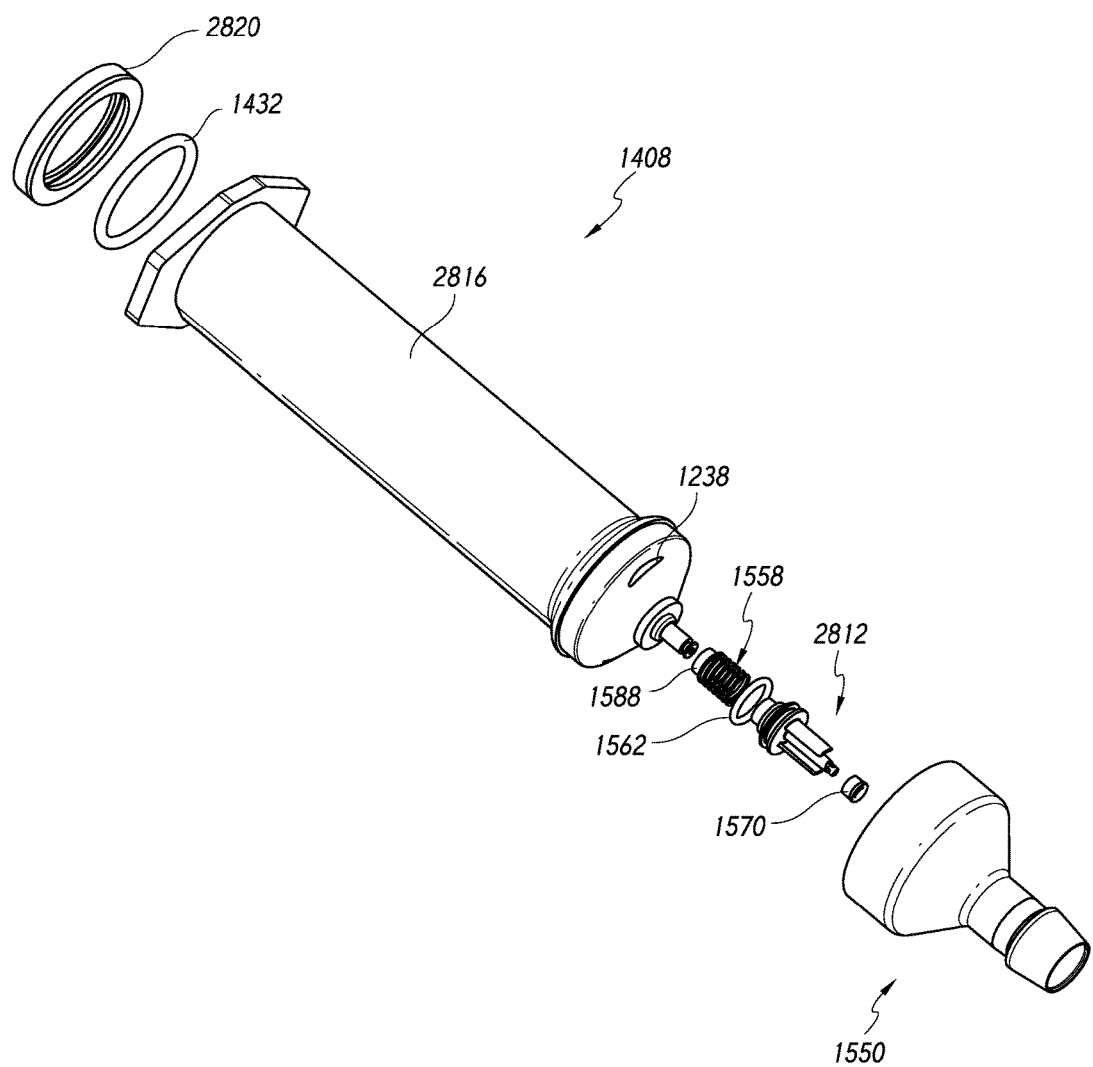
FIG. 29Q illustrates an exploded, perspective view of the barrel of FIG. 29P.

FIG. 29Q illustrates an exploded, perspective view of the barrel 1408. The barrel 1408 can include a barrel body 2816, which can be a hollow elongate member that is partially closed at an end. As shown, the barrel 1408 can include a proximal seal 1432, such as an O-ring, which can be held in place by a seal retainer 2820. A distal cap 1550 can be coupled to a distal end portion of the barrel body 2816. As shown, the barrel body 2816 can include one or more openings 1238.

Figure 29R:
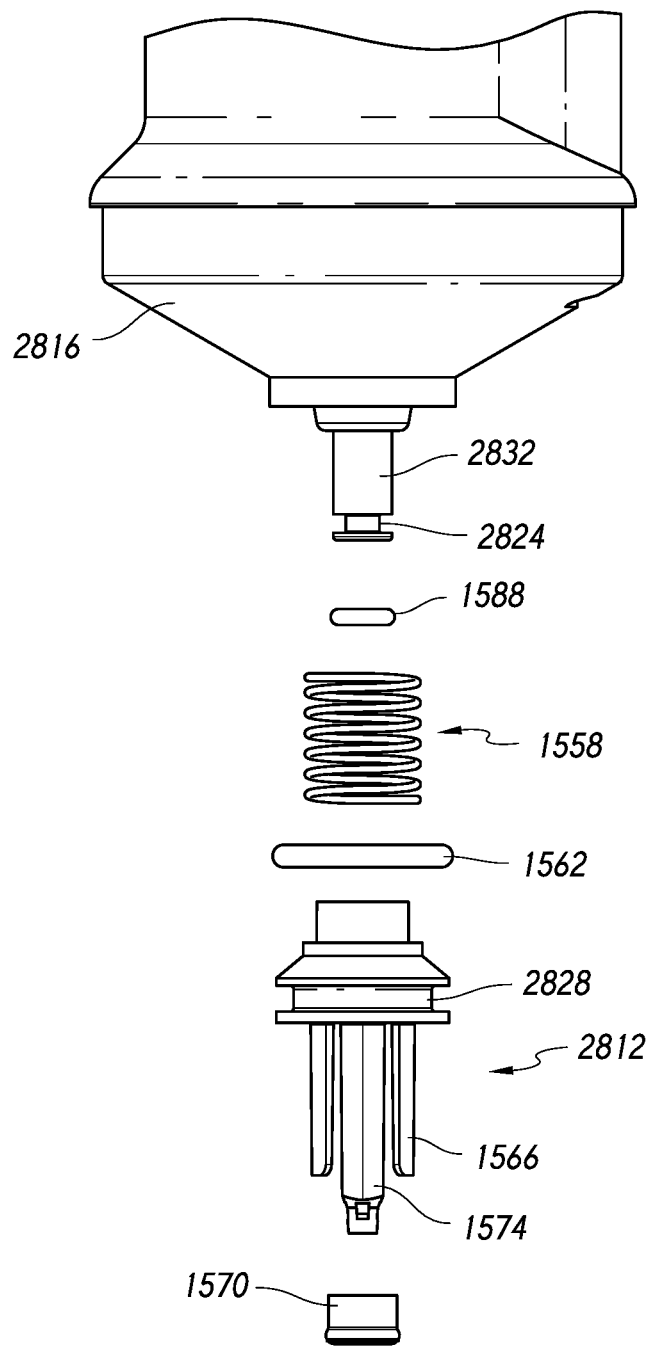
FIG. 29R illustrates an exploded, side view of a portion of the barrel of FIG. 29P.

FIG. 29R illustrates an exploded, side view of a portion of the barrel 1408. The barrel 1408 can include multiple seals. For example, the barrel 1408 can include a seal 1562 (called the third seal elsewhere herein), a seal 1570 (called a fourth seal elsewhere herein), and/or a seal 1588 (called the fifth seal elsewhere herein). As shown, the seal 1562 is positioned in a groove 2828 and/or secured by the groove 2828 of a movable member 2812. In some embodiments, the seal 1588 is located in a groove 2824 and/or secured by the groove 2824 of the barrel body 2816.

The barrel 1408 can include a movable member 2812, which can be configured to slide distally and/or proximally. In some embodiments, the movable member 2812 slides relative to a central axis of a distal shaft 2832 of the barrel body 2816. The distal shaft 2832 can be biased by a biasing member 1558, such as by a spring located around the distal shaft 2832. The spring 1558 can be configured to apply a force to the movable member 2812 in a distal direction. In some embodiments, the seal 1570 is positioned on the passage shaft 1574 of the movable member 2812. In certain embodiments, some or all of the items shown in FIG. 29S are formed by molding. In certain variants, the spring 1558 is shaped metal.

Figure 30:
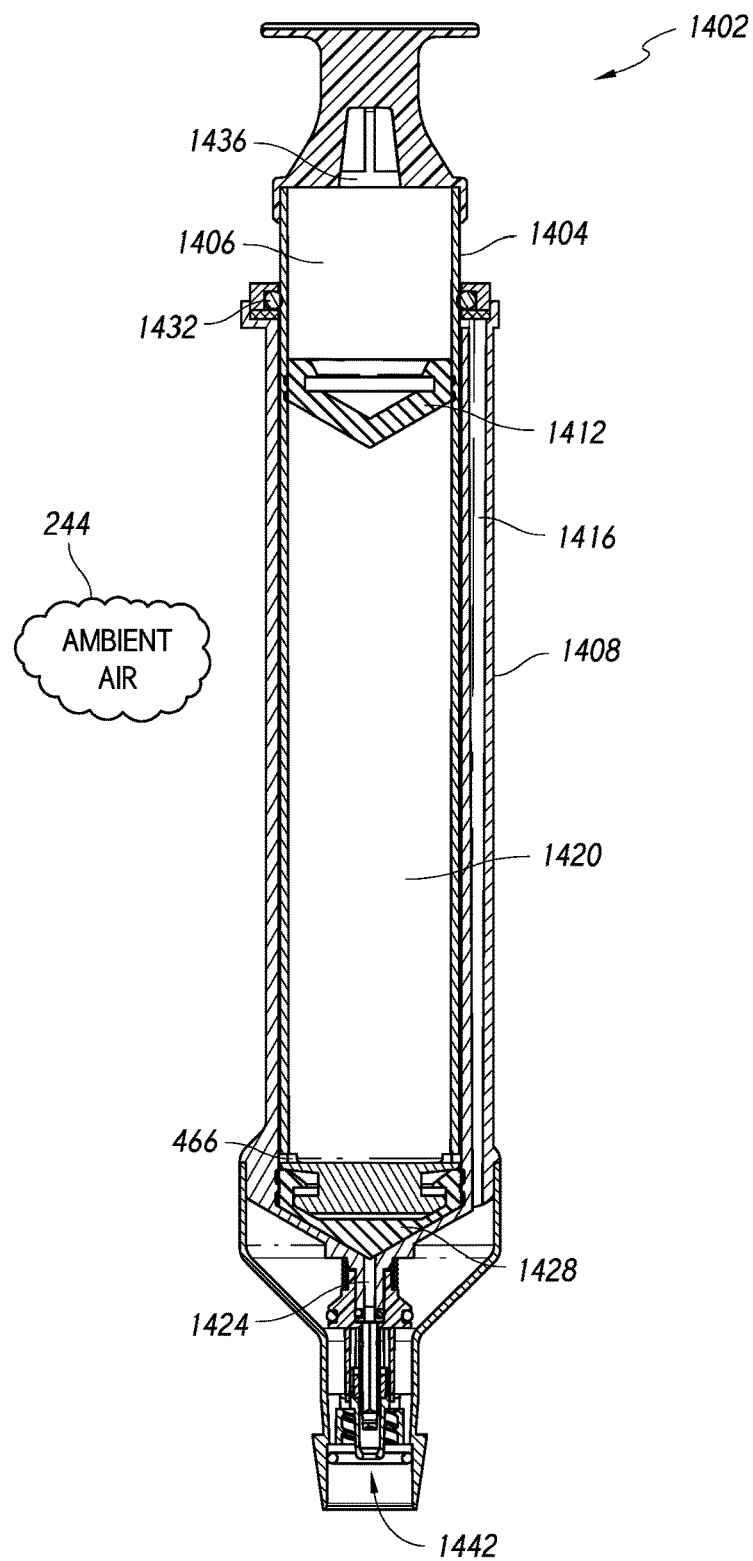
FIG. 30 illustrates a cross-sectional view along line 30-30 from FIG. 29.

FIG. 30 illustrates a cross-sectional view of the syringe assembly 1402 along line 30-30 of FIG. 29. As illustrated, the proximal plunger seal 1412 can be slidably located inside of the plunger 1404 such that ambient air can flow through a vent 1436 into a portion 1406 of the plunger 1404 located proximally relative to the proximal plunger seal 1412. The proximal seal 1432 can seal between an outer face, such as an outer diameter of the plunger 1404, and an inner face, such as an inner diameter of the barrel 1408. Fluid, such as gas, can exit the first reservoir 1420 through a hole 466, move through a proximal first passage 1416 and then exit a distal end of the syringe assembly 1402. A distal plunger seal 1428 can be coupled to a distal end of the plunger 1404.

Figure 31:
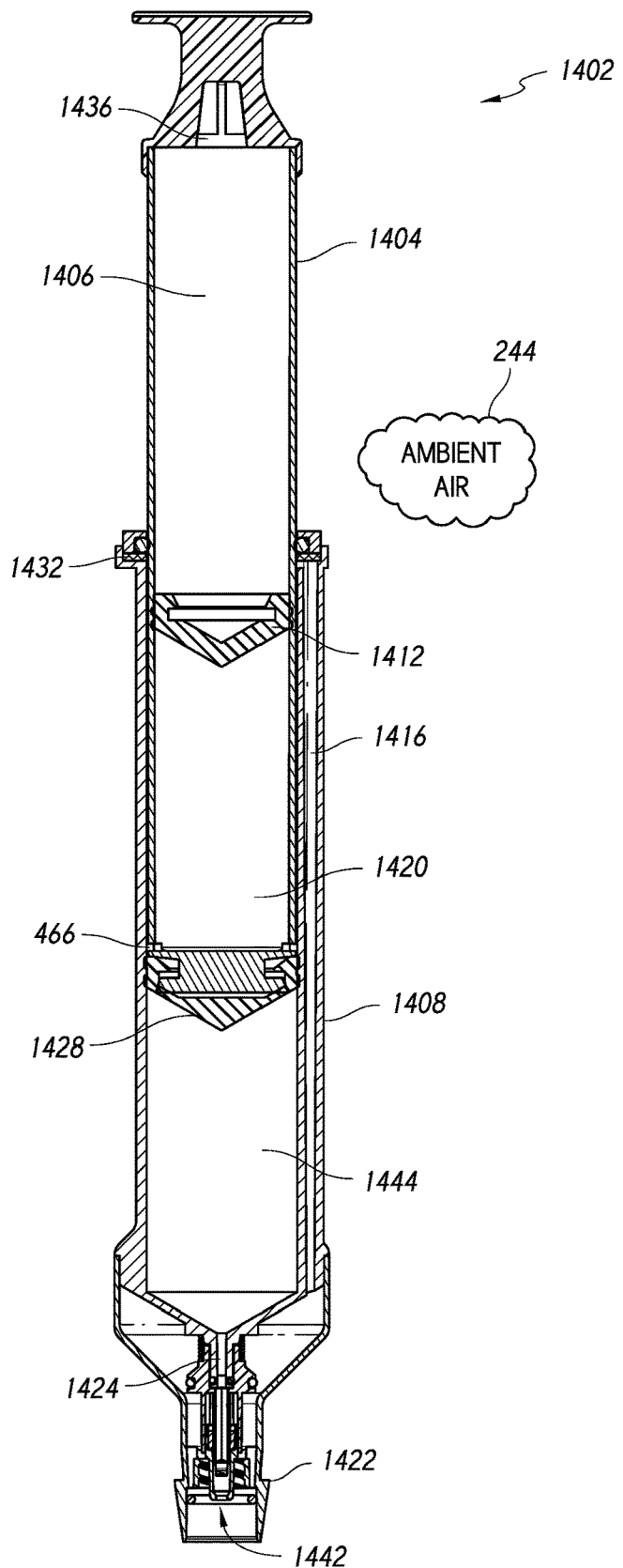
FIG. 31 illustrates a cross-sectional, side view of the syringe assembly from FIG. 30, wherein the plunger is in a more proximal location than illustrated in FIG. 30.

Referring now to FIGS. 29 and 31, a second reservoir 1444 can reside inside of the barrel 1408. For example, the second reservoir 1444 can be located between the distal plunger seal 1428 and the proximal second passage 1424. In several embodiments, at least a portion of the distal plunger seal 1428 is a movable proximal end of the second reservoir 1444, thereby allowing the second reservoir 1444 to change its volume (e.g., in proportion to the movement of the plunger seal 1428). The second reservoir 1444 can be in fluid communication with at least a portion of the proximal second passage 1424.

The syringe assembly 1402 can include an ambient portion 1406 that can be a third reservoir located inside a portion of the syringe assembly 1402. A vent 1436, or hole, can fluidly couple the ambient portion 1406 to ambient air 244 located outside of the syringe assembly 1402. In some embodiments, the third reservoir (e.g., the ambient portion 1406) can be located inside a portion of the plunger 1404. The proximal plunger seal 1412 can fluidly separate the third reservoir from the first reservoir 1420. The third reservoir can be located in a proximal portion of the plunger 1404 and the first reservoir 1420 can be located in a distal portion of the plunger 1404. In several embodiments, the ambient portion 1406 includes a reservoir in which a vacuum (e.g., relative to ambient) cannot form because the ambient portion 1406 is fluidly coupled to ambient air.

FIG. 31 illustrates a cross-sectional view of the syringe assembly 1402 from FIG. 30, wherein the plunger 1404 is in a more proximal location than illustrated in FIG. 30. In the configuration of FIG. 31, the second reservoir 1444 has a larger volume (e.g., at least ten times larger) than is the case when the plunger 1404 is pushed to its most distal location.

In some embodiments, a first reservoir and a second reservoir are located within a single outer housing such that reducing the volume of one of the reservoir increases the volume of the other reservoir. Referring to the embodiment illustrated in FIG. 31, the first reservoir 1420 and the second reservoir 1444 are in different housings (e.g., the barrel 1408 and the plunger 1404) such that changing the volume of one reservoir does not necessarily change the volume of the other reservoir. Thus, in some embodiments, the first reservoir 1420 and the second reservoir 1444 are "volumetrically independent". Volumetric independence can be advantageous in some embodiments, such as when changing the volume of one reservoir is beneficial (e.g., when fluid is injected into a container or removed from a container) but the volume of the other reservoir does not need to change (e.g., because the container is compliant such that gas does not need to be added or removed from the container). Volumetric independence can facilitate a syringe assembly being compatible with both rigid containers (e.g., glass vials) and compliant containers (e.g., IV bags). The lack of volumetric independence can create situations in which the pressure inside a first reservoir and/or inside a second reservoir is not approximately equal to atmospheric pressure (e.g., the pressure of the ambient air 244).

Figure 32:
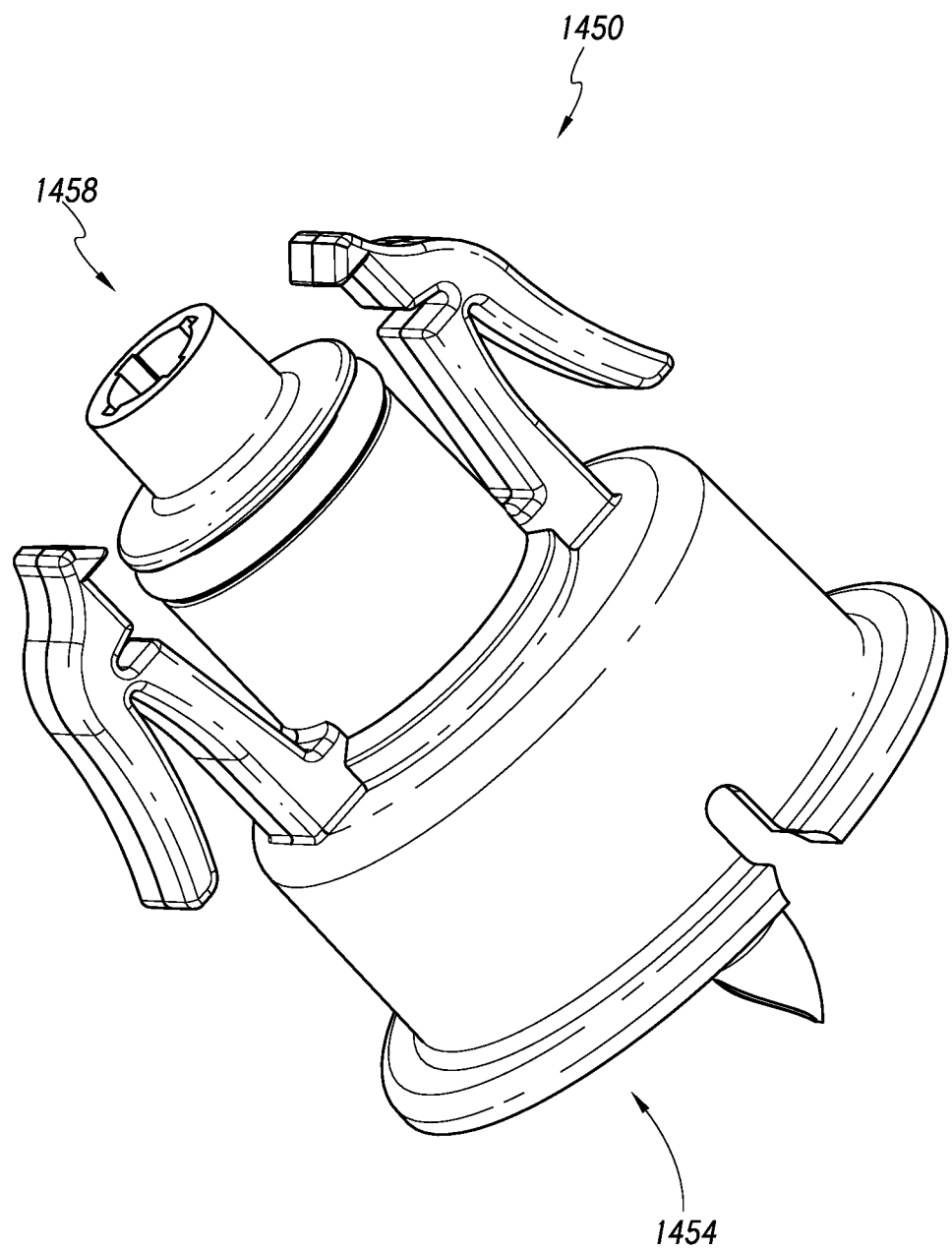
FIG. 32 illustrates a perspective view of an adapter assembly.

FIG. 32 illustrates a perspective view of an adapter assembly 1450. The distal end 1454 of the adapter assembly 1450 is configured to couple to containers. The proximal end 1458 of the adapter assembly 1450 is configured to couple to the syringe assembly 1402 illustrated in FIG. 29.

Figure 33:
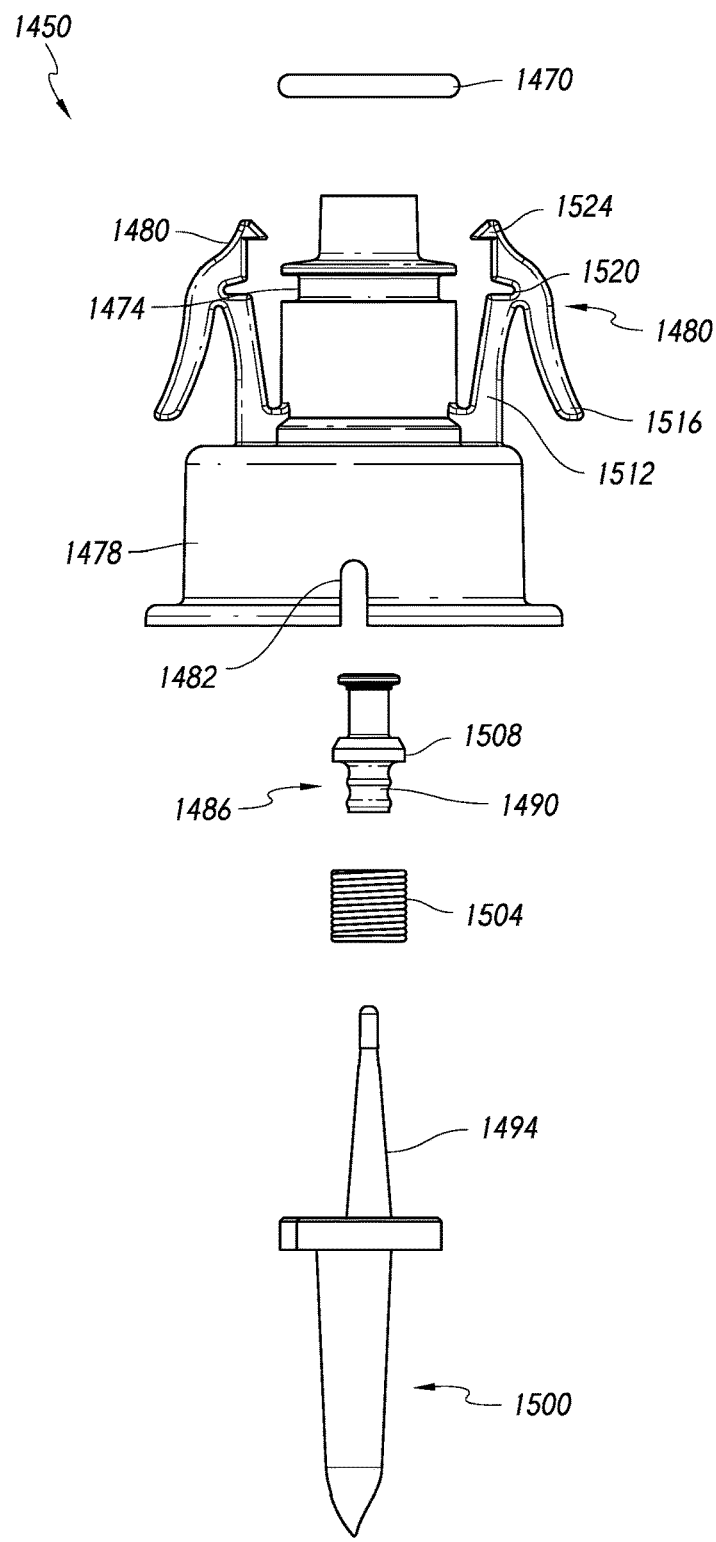
FIG. 33 illustrates an axially-exploded, side view of the adapter assembly from FIG. 32.

FIG. 33 illustrates an axially exploded, side view of the adapter assembly from FIG. 32. A first seal 1470, such as an O-ring, can be located in a groove 1474 of a skirt 1478. The skirt 1478 can be a plastic or metallic member configured to couple to the neck 358 of a container 304 (shown in FIG. 13). The skirt 1478 can include an engaging portion with an expansion facilitating feature, such as a slot 1482. In some embodiments, the skirt 1478 can include a cylindrical plastic protrusion with a slot 1482 to enable the cylindrical protrusion to expand (e.g., increase in diameter) as the protrusion moves over a lip 362 and then contract (e.g., decrease in diameter) as the protrusion couples to the neck 358 (see FIG. 13).

The skirt 1478 can include resilient latching members such as flexible arms 1480. The arms 1480 can be configured to flex outward to latch onto a shoulder or a protrusion 1422 of the syringe assembly 1402 (shown in FIG. 31). The flexible arm 1480 can include a stem that protrudes proximally from the skirt 1478, a lever 1516 that protrudes distally from the stem 1512, a notch 1520 configured to facilitate flexing of the lever 1516, and/or a protrusion 1524 that protrudes radially inward. In some embodiments, the syringe assembly 1402 (shown in FIG. 31) can include the latching members and the skirt 1478 can include the corresponding shoulder or protrusion 1422.

The adapter assembly 1450 can include a second seal 1486, such as a resilient boot. In some implementations, the second seal 1486 can move (e.g., resiliently collapse and/or expand) generally axially. Certain embodiments of the second seal 1486 have an inner lumen 1490 configured to seal against a proximal shaft 1494 of a piercing member 1500. The proximal shaft 1494 can pass through the center of a biasing member, such as a spring 1504. Some embodiments of the second seal 1486 are energized, biased, and/or compressed by the spring 1504. The spring 1504 can be configured to push the second seal 1486 in a proximal direction. The distal end of the spring 1504 can be coupled to, pressed against, and/or rest on the piercing member 1500 and the proximal end of the spring 1504 can be coupled to, pressed against, or rest on the second seal 1486. In some embodiments, a distal end of the second seal 1486 is located inside a portion of the spring 1504 (e.g., inside an interior space that includes the center axis formed by the helical nature of some springs) and the proximal end of the spring 1504 is coupled to and/or pressed against a radial protrusion 1508 of the second seal 1486. The spring 1504 is illustrated in a compressed state in FIG. 33, although in many embodiments, the spring 1504 can be in an uncompressed state unless compressed by external forces or structures.

Figure 34:
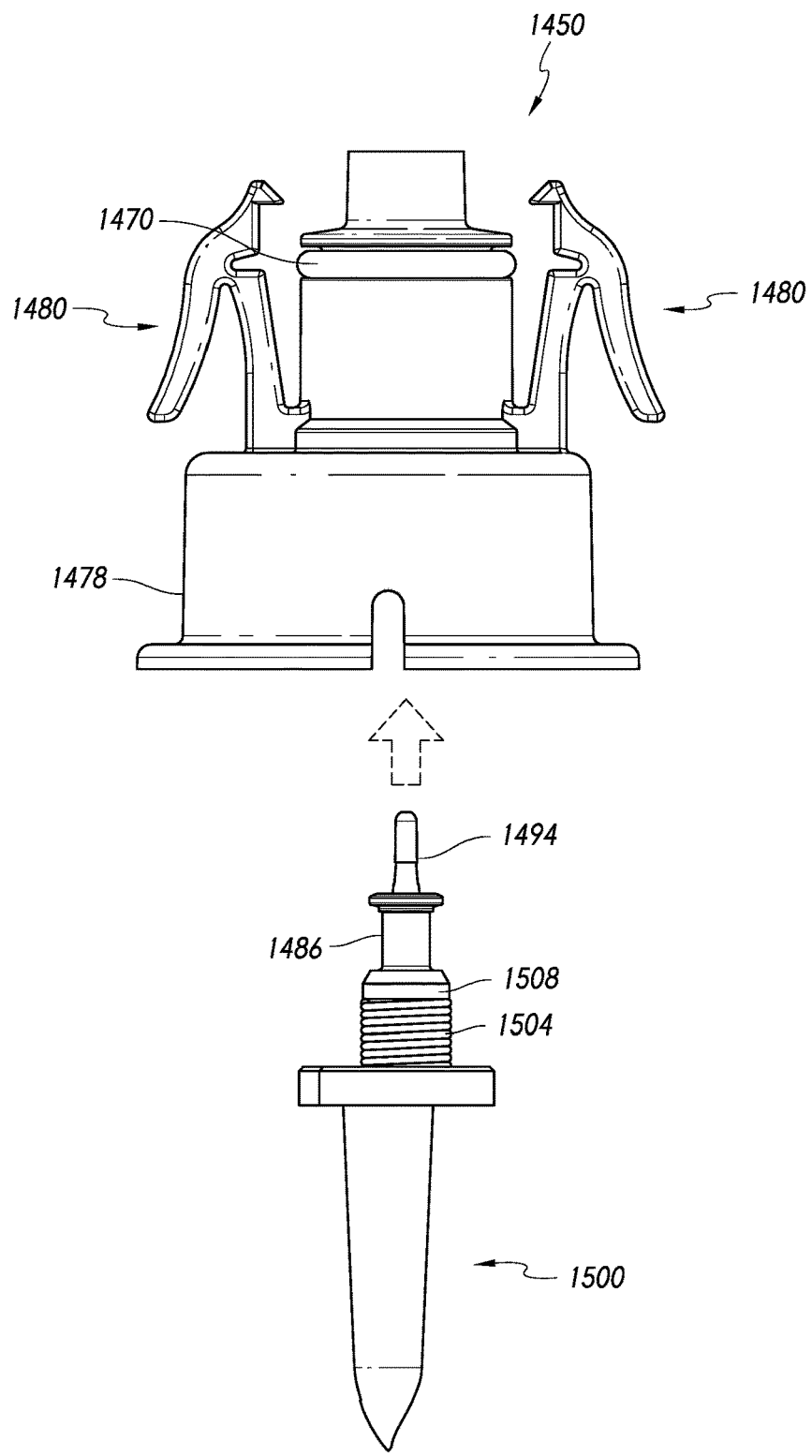
FIG. 34 illustrates a side view of the spring and the second seal coupled to the proximal shaft.

FIG. 34 illustrates the spring 1504 and the second seal 1486 located on the proximal shaft 1494. FIG. 34 also illustrates that the first seal 1470 can be located in the groove 1474 (shown in FIG. 33) of the skirt 1478. The piercing member 1500 (coupled to the spring 1504 and the second seal 1486) can be coupled to the skirt 1478 by sliding the piercing member 1500 proximally in the direction indicated by the dashed arrow.

Figure 35:
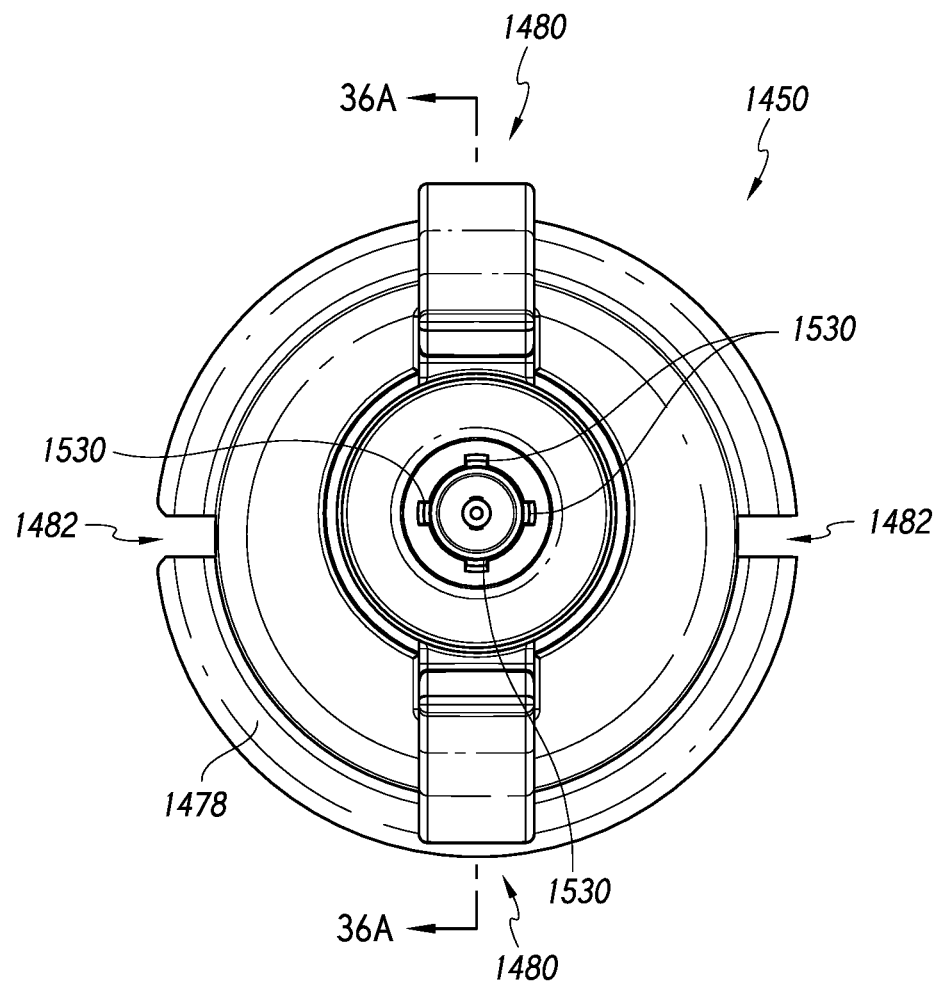
FIG. 35 illustrates a top view of the adapter assembly from FIG. 32.

FIG. 35 illustrates a top view of the adapter assembly 1450 from FIG. 32. The adapter assembly 1450 can include at least one channel 1530 (e.g., a slot), which can form a portion of a first passage (e.g., No. 220 in FIG. 7, No. 320 in FIG. 8, No. 612 in FIG. 14, No. 816 in FIG. 16, No. 1246 in FIG. 25). The channels 1530 can be configured to allow fluid, such as a gas, to bypass and/or flow around sealing members and/or out of a proximal portion of the adapter assembly 1450. Certain embodiments of the channels 1530 are configured to allow regulating fluid to pass between a distal cap 1550 of the syringe assembly 1402 (shown in FIG. 37) and a proximal sealing portion 1502 of the adapter assembly (shown in FIG. 36A). The channels 1530 can be located radially outward from a central axis of the adapter assembly 1450 and can be spaced apart from each other circumferentially and/or along an inner diameter.

Figure 36A:
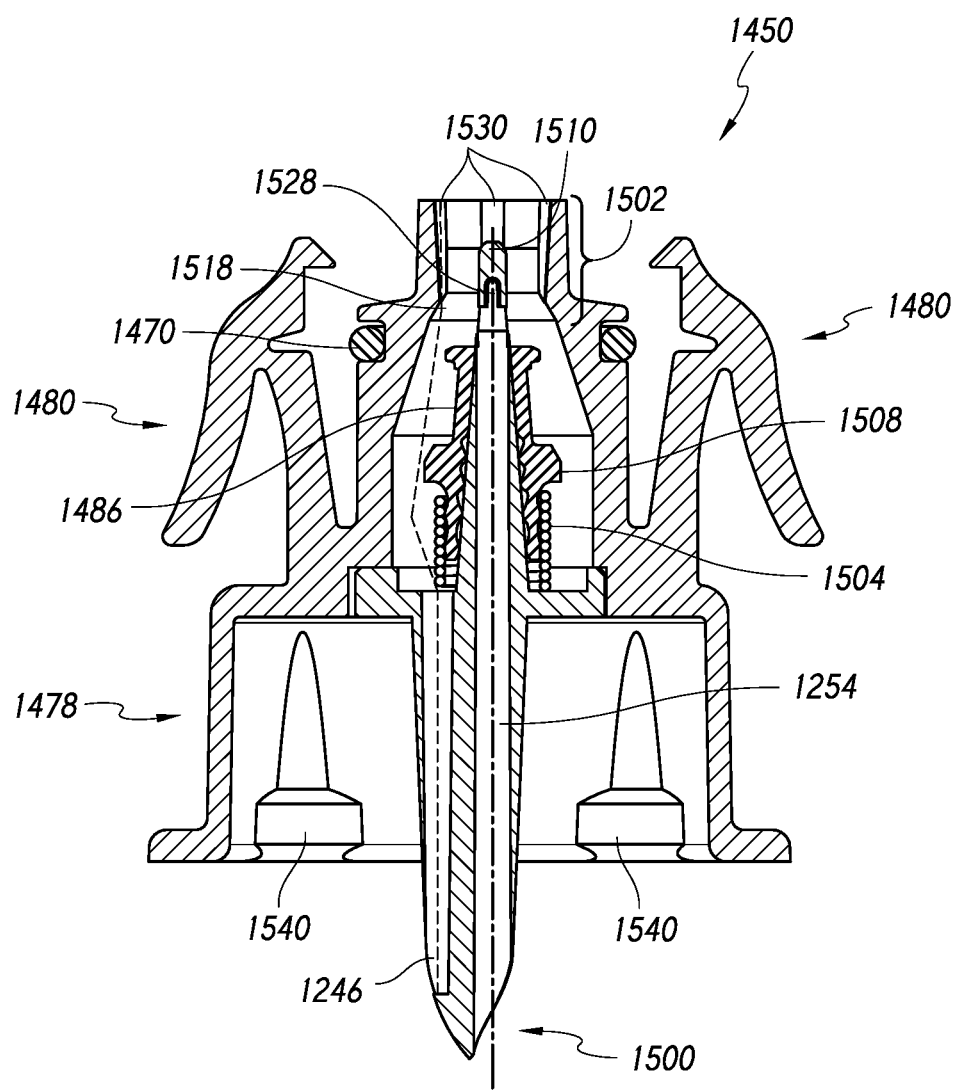
FIG. 36A illustrates a cross-sectional view along line 36A-36A from FIG. 35.

FIG. 36A illustrates a cross-sectional view along the line 36-36 from FIG. 35. The adapter assembly 1450 can include protrusions 1540 that extend radially inward towards a central axis of the adapter assembly 1450. The inward protrusions 1540 can be configured to protrude into a neck region (e.g., 358 in FIG. 13) of a container such that a lip (e.g., 362 in FIG. 13) is coupled between the inward protrusions 1540 and an internal region of the adapter assembly 1450.

Figure 40:
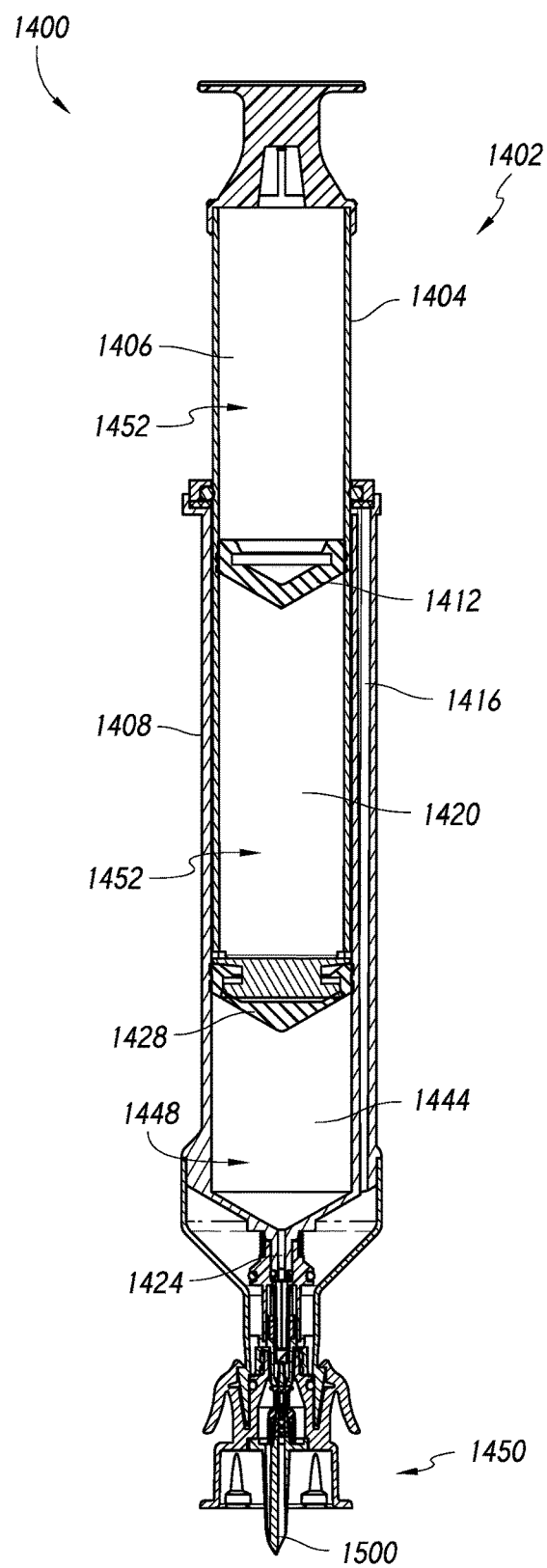
FIG. 40 illustrates a cross-sectional, side view of the syringe assembly from FIG. 29 coupled to the adapter assembly from FIG. 32.

For presentation purposes, the second seal 1486 is illustrated in a distal position in FIG. 36A. In some embodiments, when the second seal 1486 is in the distal position, one or more radial holes 1528 in the proximal shaft 1494 are in an open position (e.g., not occluded), and thus, the distal second passage 1254 can be open. In various embodiments, the second seal 1486 can be in such a position when, for example, the syringe assembly 1402 and adapter assembly 1450 are coupled (e.g., as illustrated in FIG. 40). As shown in FIG. 36A, when the second seal 1486 is in a distal position, the distal first passage 1246 can be open (e.g., in an open position).

Figure 36B:
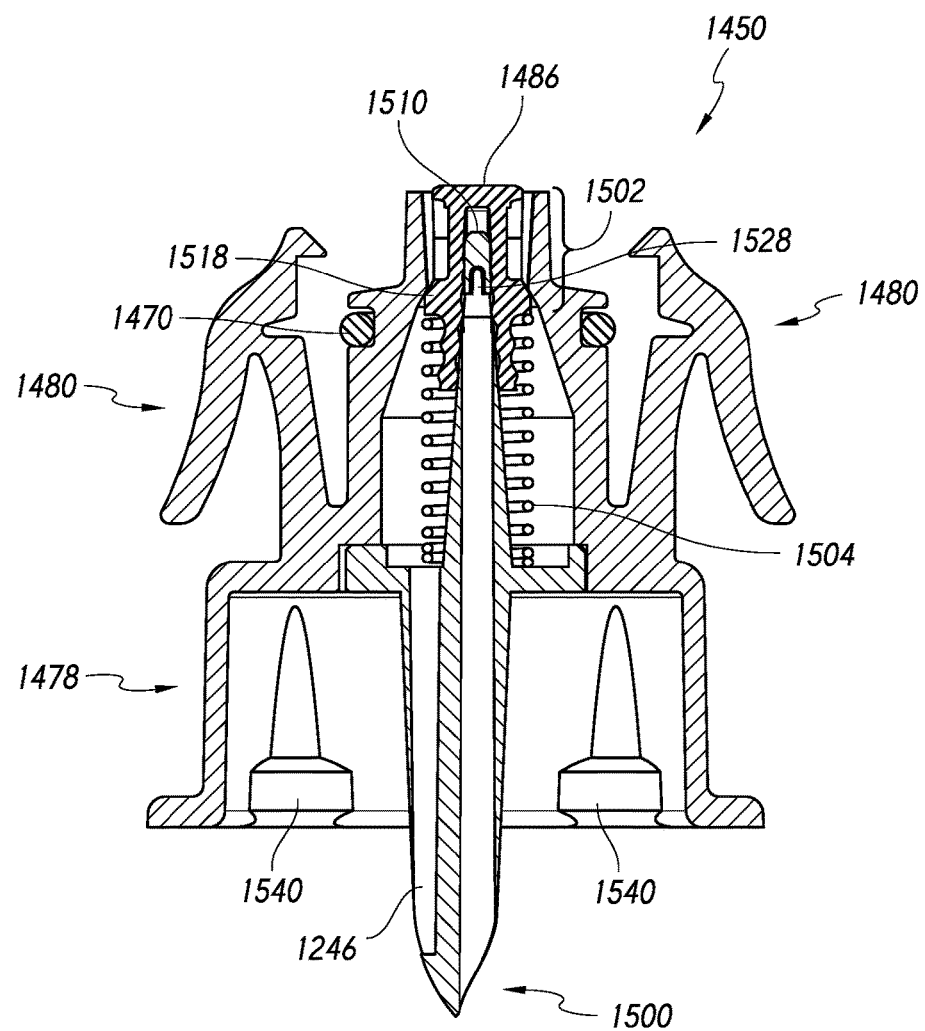
FIG. 36B illustrates a cross-sectional view with a second seal in a proximal position.

As shown in FIG. 36B, in some embodiments, the spring 1504 applies a force in a proximal direction to push the second seal 1486 to a proximal sealing location 1502. When the second seal 1486 is in the proximal sealing location 1502, the radial protrusion 1508 can fully or at least partially seal the distal first passage 1246 by sealing against an inner tapered region 1518. In some embodiments, the radial protrusion 1508 can partially or entirely interrupt fluid communication in the distal first passage 1246 (e.g., by sealing against the inner tapered region 1518).

In several embodiments, when the second seal 1486 is in the proximal sealing location 1502, the second seal 1486 can partially and/or completely occlude one or more radial holes 1528 to seal and/or close the distal second passage 1254. In several embodiments, if a syringe is not coupled to the adapter assembly 1450, the spring 1504 will force the second seal 1486 to the proximal sealing location 1502 to occlude, seal, and/or block the distal first passage 1246 and/or the distal second passage 1254. For presentation purposes, the spring 1504 is shown in a compressed state in FIG. 36A to illustrate how the distal first passage 1246 and the distal second passage 1254 can be in open states even though, in many embodiments, the spring 1504 would expand to push the second seal 1486 to the proximal sealing location 1502 unless a component (e.g., the axial sealing surface 1592 in FIG. 41) forced the spring 1504 to compress.

The piercing member can include at least a portion of the distal first passage 1246 and at least a portion of the distal second passage 1254. The skirt 1478 can include at least a portion of the distal first passage 1246 and at least a portion of the distal second passage 1254. The distal first passage 1246 and the distal second passage 1254 are indicated by dashed lines.

FIG. 36B illustrates a cross-sectional view with the second seal 1486 in a proximal position (e.g., in the proximal sealing location 1502). A biasing member (e.g., the spring 1504) can move (e.g., push) the second seal 1486 into the proximal sealing location 1502 such that the radial protrusion 1508 of the second seal 1486 contacts (e.g., seals against) an inner portion (e.g., the inner tapered portion 1518) of the adapter assembly 1450 to block and/or inhibit fluid flow through the distal second passage 1254 and/or through the distal first passage 1246. In the proximal sealing location 1502, the second seal 1486 can block and/or inhibit fluid flow through the radial hole 1528, which can be an exit channel of the distal second passage 1254. In the proximal sealing location 1502, the second seal 1486 can block and/or inhibit fluid flow along the paths illustrated by the dashed lines in FIG. 36A.

In FIG. 36B, the spring 1504 is illustrated in an expanded configuration. Coupling the syringe assembly 1402 (shown in FIG. 29) to the adapter assembly 1450 can compress the spring 1504 and force the second seal 1486 into a distal, non-sealing location. An example, distal, non-sealing location is illustrated in FIG. 36A.

Figure 37:
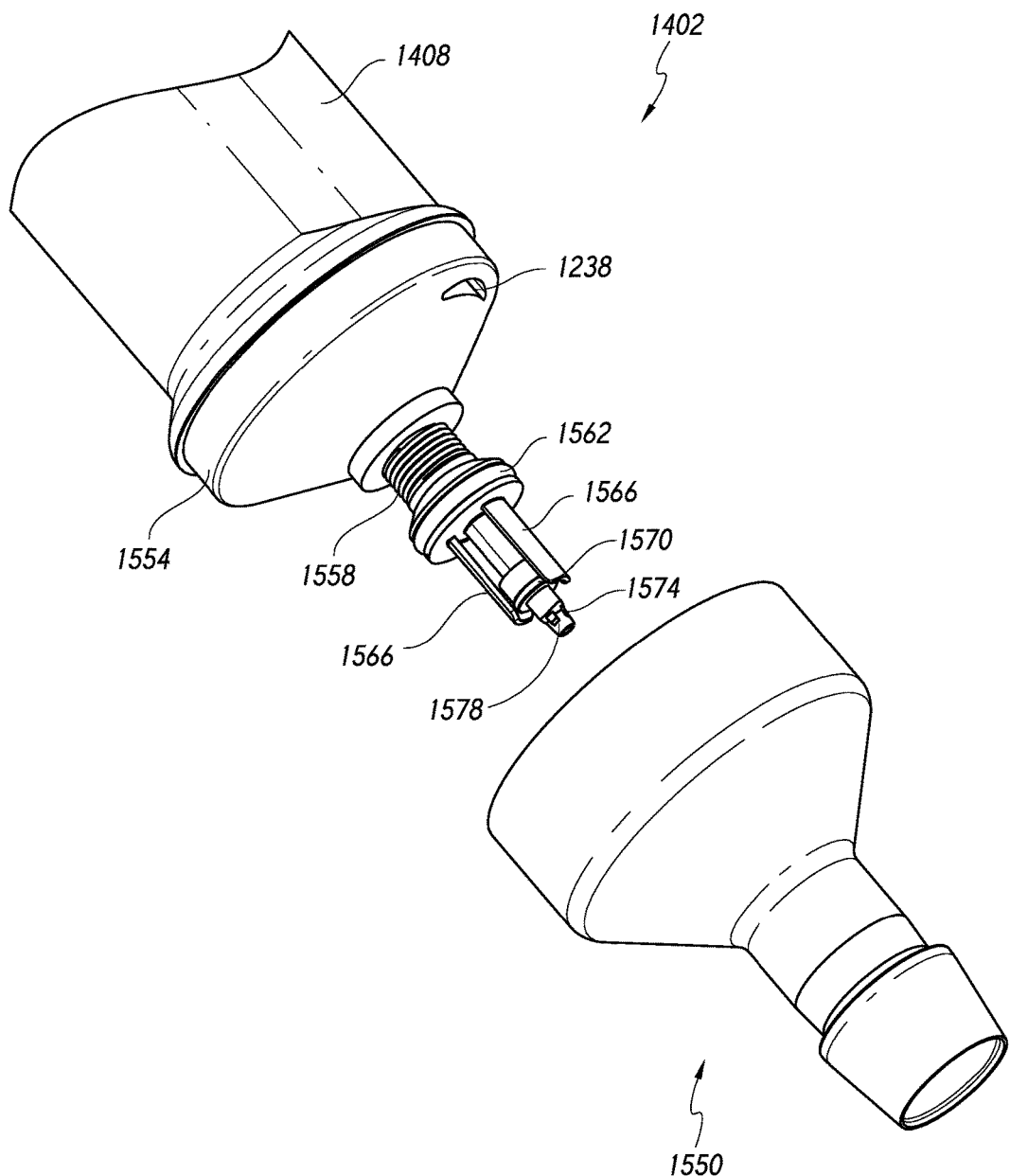
FIG. 37 illustrates a partially-exploded, perspective view of a distal portion of the syringe assembly illustrated in FIG. 29.

FIG. 37 illustrates a perspective view of a distal portion of the syringe assembly 1402 illustrated in FIG. 29. The syringe assembly 1402 can include a distal cap 1550 configured to be coupled with an attachment zone 1554 near the distal end of the barrel 1408. The distal cap 1550 can be coupled to the barrel 1408 via ultrasonic welding, adhesion, and/or a snap fit. FIG. 37 illustrates the syringe assembly 1402 before the distal cap 1550 is coupled to the barrel 1408.

The syringe assembly 1402 can include a biasing member, such as a spring 1558. The spring 1558 can apply a force in an axial direction (e.g., generally towards the distal end of the syringe assembly 1402 and/or generally towards the proximal end of the syringe assembly 1402). The spring 1558 can be configured to push one or more third seals 1562 (which can be an O-ring located in a groove) towards a tapered surface to close and/or seal a first passage (e.g., proximal first passage 1416 in FIG. 31). In some embodiments, the spring 1558 can push a support (e.g., a sliding member 1576) with the third seal 1562 towards the tapered surface. The tapered surface can be an inner surface 1580 of the distal cap 1550.

As described in more detail below, the sliding member 1576 can reciprocate proximally and distally. For example, the sliding member 1576 can slide up and down on the distal shaft 2832 of the barrel body 2816. As shown, the sliding member 1576 can include one or more axial protrusions 1566, such as flexible arms or rigid arms that extend distally. The axial protrusions 1566 can extend in a direction approximately parallel to the central axis of the syringe assembly 1402.

The syringe assembly 1402 can include a fourth seal 1570, which can be a generally cylindrical seal with a lumen and/or a seal with a cylindrical portion and a central lumen. A passage shaft 1574 can contain a second passage (e.g., proximal second passage 1424 in FIG. 31). The passage shaft 1574 can pass through the lumen of the fourth seal 1570, which can be made from rubber or any other suitable material. Any of the seals described herein can be made from rubber, such as medical-grade rubber, or any other suitable sealing material.

Figure 38:
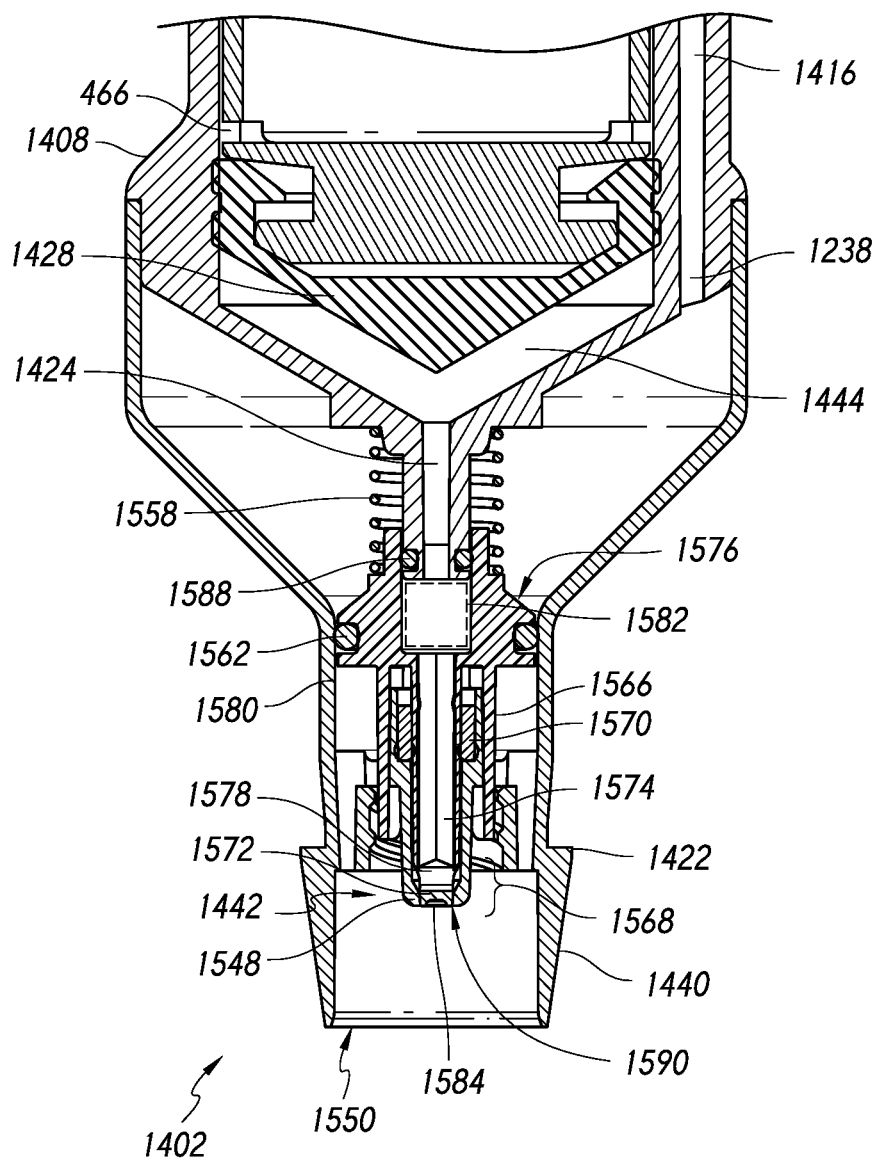
FIGS. 38 and 39 illustrate cross-sectional, side views of a distal portion of a syringe assembly.

The syringe assembly 1402 can include a fifth seal 1588, such as an O-ring (see FIG. 38). The fifth seal 1588 can be retained in a groove, such as in the distal shaft 2832. The fifth seal 1588 can provide a generally liquid-tight and/or gas-tight seal between the sliding member 1576 and the distal shaft 2832.

Figure 39:
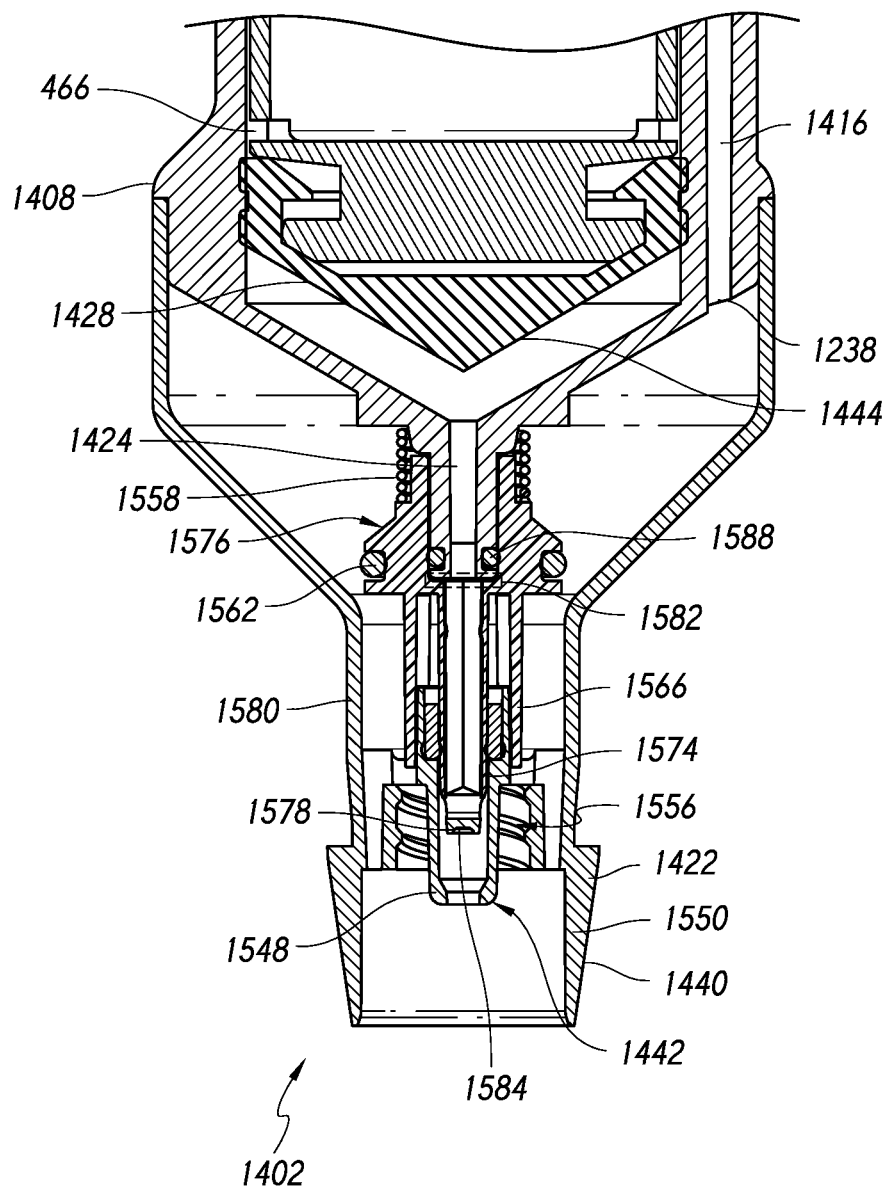

FIGS. 38 and 39 illustrate cross-sectional views of a distal portion of the syringe assembly 1402. An adapter assembly (e.g., No. 1450 in FIG. 40) is not shown in FIGS. 38 and 39 to increase the clarity of the illustrated features and components. In FIG. 38, the syringe assembly 1402 is shown in a configuration in which the syringe assembly 1402 is not coupled to an adapter assembly (e.g., No. 1450 in FIG. 40). In contrast, in FIG. 39, the syringe assembly 1402 is shown as coupled to the adapter assembly (e.g., No. 1450 in FIG. 40), although for presentation purposes the adapter assembly is not shown in FIG. 39. In FIG. 38, the syringe assembly 1402 can be said to "closed" and in FIG. 39, the syringe assembly 1402 can be said to "open."

As shown in FIG. 39, in the open position, the adapter assembly has pushed the distal portion 1584 of the passage shaft 1574 in a proximal direction to open the proximal second passage 1424. Such movement can be against the compressive force of the spring 1558. As illustrated, the sliding member 1576 and the distal portion 1584 of the passage shaft 1574 have been pushed in a proximal direction (relative to the configuration shown in FIG. 38) by the proximal shaft 1494 (not shown) of the adapter assembly 1450 (not shown). In some embodiments, the proximal movement of the sliding member 1576 separates, opens, and/or unseals the third seal 1562 from the inner surface 1580 (e.g., the tapered surface), thereby opening at least a distal portion of the proximal first passage 1416. In some embodiments, the proximal movement opens and/or unseals the proximal second passage 1424.

In some embodiments, a syringe assembly and/or an adapter assembly contain a residual volume of liquid after the syringe assembly is uncoupled from a container (e.g., uncoupled from the adapter assembly). The liquid can include a pharmaceutical, drug, and/or medicine. In several embodiments, the residual volume of an adapter assembly is less than about 0.2 milliliters, less than about 0.15 milliliters, less than about 0.11 milliliters, or less than about 0.05 milliliters. In several embodiments, the residual volume of a syringe assembly is less than about 0.18 milliliters, less than about 0.11 milliliters, less than about 0.07 milliliters, or less than about 0.01 milliliters.

Figure 41:
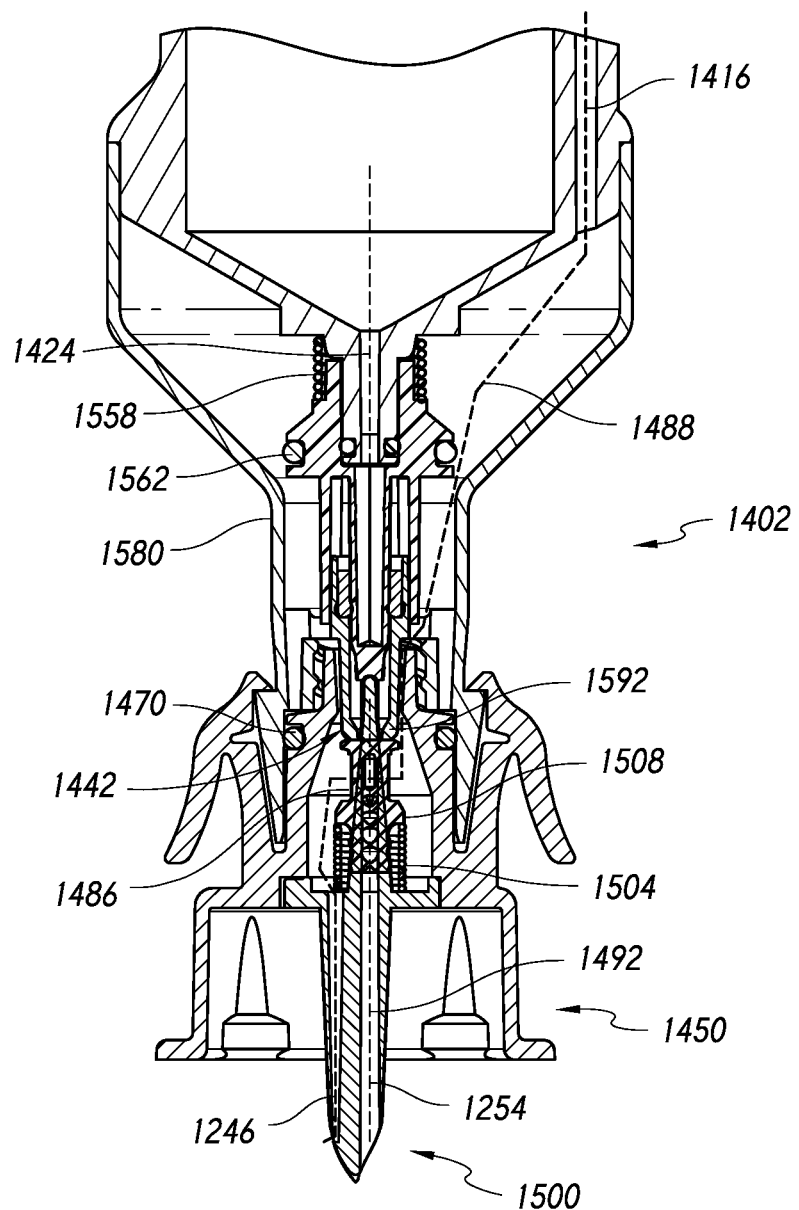
FIG. 41 illustrates a distal portion of the coupled assembly of FIG. 40.

The embodiment illustrated in FIGS. 38 and 39 includes a mechanism that increases the effective volume of the second reservoir 1444 and/or the proximal second passage 1424 when the syringe assembly 1402 is decoupled from the adapter assembly 1450 (shown in FIG. 41). Increasing the effective volume of the second reservoir 1444 and/or the proximal second passage 1424 can decrease local pressure, and thus, can "vacuum" or "suck" fluid into the second reservoir 1444 and/or into the proximal second passage 1424 (e.g., during decoupling), which can reduce or minimize the amount of potentially harmful liquid (e.g., medical fluid, extracted medicinal fluid) that may drip and/or escape from the syringe assembly 1402 and/or the adapter assembly 1450 (shown in FIG. 41). This safety feature can reduce medical professionals' exposure to the liquid.

In several embodiments, the sliding member 1576 is configured to move distally and proximally within the syringe assembly 1402, such as along the distal shaft 2832 of the barrel body 2816. When the syringe assembly 1402 is decoupled from the adapter assembly 1450 (shown in FIG. 41), the sliding member 1576 moves distally due to the force of the spring 1558. This distal movement enlarges an expansion chamber 1582, which can be located in the proximal second passage 1424, within the second reservoir 1444, within any portion of the syringe assembly 1402, and/or within any portion of the adapter assembly 1450 (shown in FIG. 41). In the embodiment illustrated in FIG. 38, the expansion chamber 1582 is located in the proximal second passage 1424. The expansion chamber 1582 is configured to expand from a first volume when the syringe assembly 1402 is coupled to the adapter assembly 1450 (shown in FIG. 41) to a second, larger volume when the syringe assembly 1402 is uncoupled from the adapter assembly 1450 (shown in FIG. 41). The increasing volume of the expansion chamber 1582 helps to "vacuum," "suck," or "pull" fluid into the syringe assembly 1402, which can prevent and/or reduce the occurrence of fluid escaping from the syringe assembly 1402 and/or from the adapter assembly 1450 (shown in FIG. 41).

FIG. 39 illustrates the first volume of the expansion chamber 1582. In FIG. 39, the expansion chamber 1582 is too small to easily see, so the expansion chamber is highlighted by a dashed box. FIG. 38 illustrates the second volume of the expansion chamber 1582. The expansion chamber 1582 is also highlighted by a dashed box in FIG. 38.

In some embodiments, the maximum volume of the expansion chamber 1582 is at least about 150% of the minimum volume of the expansion chamber 1582 or is at least about 300% of the minimum volume of the expansion chamber 1582. In some embodiments, the maximum volume of the expansion chamber 1582 is at least about 200% of the minimum volume of the expansion chamber 1582 and/or less than or equal to about 10,000% of the minimum volume of the expansion chamber. In some embodiments, the maximum volume of the expansion chamber 1582 is at least about 400% of the minimum volume of the expansion chamber 1582 and/or less than or equal to about 2,000% of the minimum volume of the expansion chamber 1582.

In several embodiments, the expansion chamber 1582 increases an internal volume of the syringe assembly 1402 (e.g., the volume of the second reservoir 1444, the volume of the proximal second passage 1424) by at least about 0.2 milliliters and/or less than or equal to about 25 milliliters; at least about 0.7 milliliters and/or less than or equal to about 10 milliliters; at least about 1 milliliter and/or less than or equal to about 3 milliliters; or at least about 2 milliliters and/or less than or equal to about 10 milliliters.

In FIG. 38, the third seal 1562 engages an inner surface 1580 of the syringe assembly 1402 (e.g., an inner surface of the distal cap 1550) to seal the proximal first passage 1416. In this configuration, fluid (such as gas) from a first reservoir (e.g., No. 1420 in FIG. 31) cannot pass through a first passage and then out of a syringe. The third seal 1562, the inner surface 1580, and the spring 1558 can form a flow controller such as a valve (e.g., No. 228 in FIG. 7) to close and/or seal a first passage. Pressing axially on the distal portion 1584 of the passage shaft 1574 can overcome the axial spring force of the spring 1558. Overcoming the spring force causes the valve to open to allow fluid, liquid, and/or gas flow.

FIG. 39 illustrates the valve in an open position. The third seal 1562 is positioned away from the inner surface 1580 such that the third seal 1562 no longer seals against the inner surface 1580. In some embodiments, a proximal end 1510 of the proximal shaft 1491 of the adapter assembly 1450 (shown in FIG. 33) engages (e.g., contact, pushes against, or otherwise) the distal portion 1584 of the passage shaft 1574 of the syringe assembly 1402. This can move (e.g., compress) the spring 1558 such that the third seal 1562 no longer seals against the inner surface 1580.

FIG. 40 illustrates a cross-sectional view of a pressure-regulating syringe system comprising the syringe assembly 1402 from FIG. 29 and the adapter assembly 1450 from FIG. 32. The system shown in FIG. 40 can be the same or identical to any of the other pressure-regulating syringe systems described herein and can include any of the features of those other systems.

FIG. 41 illustrates a distal portion of the system of FIG. 40. Not all of the elements have been labeled in the interest of clarity. The spring 1504 can be configured to push the second seal 1486 in a proximal direction. The proximal end of the spring 1504 can be coupled to and/or pressed against the radial protrusion 1508 of the second seal 1486. The spring 1504 can be configured to press the second seal 1486 towards a sealing surface of the syringe assembly 1402. The sealing surface can be a surface that faces in an axial direction rather than in a radial direction (although some embodiments include additional or alternative sealing surfaces that face in a radial direction).

In FIG. 41, the second seal 1486 is coupled between the spring 1504 and an axial sealing surface 1592. The second seal 1486 can provide generally gas-tight sealing and/or can fluidly seal the proximal second passage 1424 and the distal second passage 1254 (shown in FIG. 28) to facilitate fluid flow between the proximal second passage 1424 and the distal second passage 1254. Thus, fluid can flow between the second passages 1424, 1254, and the second passages 1424, 1254 can be fluidly isolated from the first passages 1416, 1246.

The barrel 1408 (which is one type of housing) can include an inner channel 1448 with a diameter. The second reservoir 1444 can be located in a portion of the inner channel 1448. The plunger 1404 can include an inner channel 1452. The first reservoir 1420 and the ambient portion 1406 (which can be a third reservoir) can be located in the inner channel 1452 of the plunger 1404. The inner channel 1452 of the plunger 1404 can include a diameter. The proximal plunger seal 1412 can separate the inner channel 1452 into the first reservoir 1420 and the ambient portion 1406. The first reservoir 1420 and the ambient portion 1406 can be isodiametric. The second reservoir 1444 can have a larger outer diameter than the first reservoir 1420 and the ambient portion 1406.

FIG. 41 illustrates example fluid paths via dashed lines. A first dashed line 1488 illustrates a first fluid path that fluidly couples the proximal first passage 1416 and the distal first passage 1246. The first dashed line 1488 passes behind (e.g., around a circumferential rear portion of) the second seal 1486 in FIG. 41. A second dashed line 1492 illustrates a second fluid path that fluidly couples the proximal second passage 1424 and the distal second passage 1254.

Various embodiments of the syringe assembly 1402 can be coupled to the adapter assembly 1450 in any angular orientation around the longitudinal axis of the system 1400. For example, the syringe assembly 1402 can be rotated around the longitudinal axis of the system 1400 and relative to the adapter assembly 1450 (e.g., at least about: 90 degrees, 135 degrees, 180 degrees, 210 degrees, 650 degrees, or any other number of degrees) without impeding the ability of the system to transmit fluid (e.g., gas, liquid) between the proximal first passage 1416 and the distal first passage 1246. In some embodiments, the syringe assembly 1402 can be rotated (e.g., at least about: 45 degrees, 110 degrees, 290 degrees, 500 degrees, 1,000 degrees, values between the aforementioned values, or any other number of degrees) without impeding the ability of the system to transmit fluid (e.g., gas, liquid) between the proximal second passage 1424 and the distal second passage 1254.

The ability of the syringe assembly 1402 to be rotated around its central axis relative to the adapter assembly 1450 can simplify coupling the syringe assembly 1402 to the adapter assembly 1450 and/or can facilitate embodiments that use threads to couple (e.g., tighten) the syringe assembly 1402 to the adapter assembly 1450. In some threaded embodiments, the syringe assembly 1402 cannot be rotated indefinitely relative to the adapter assembly 1450, but can be rotated until the syringe assembly 1402 is fully coupled to the adapter assembly 1450 (e.g., the threads are fully or substantially fully engaged). In several threaded embodiments, the syringe assembly 1402 can be rotated indefinitely relative to the adapter assembly 1450.

As shown in FIG. 41, the syringe assembly 1402 can include a penetrating member 1442. The penetrating member 1442 can pass into at least a portion of the adapter assembly 1450. In some embodiments, the penetrating member 1442 does not pierce as it passes into the adapter assembly 1450. In several embodiments, the penetrating member 1442 is dull (e.g., not sharp) such that it would not cut a person in normal use even if the penetrating member 1442 was exposed. In some embodiments, the penetrating member 1442 is recessed within an outer covering 1440 (labeled in FIG. 39) such that the penetrating member 1442 is inaccessible by a person or at least is generally inaccessible (during normal operating use). The outer covering 1440 can be a portion of the distal cap 1550, as shown in FIG. 39.

In some embodiments, the distal end of the penetrating member is recessed at least about 0.2 centimeters and/or less than or equal to about 11 centimeters from the distal end of the outer covering 1440. In some embodiments, the distal end of the penetrating member is recessed at least about 0.5 centimeters and/or less than or equal to about 6 centimeters from the distal end of the outer covering 1440. In some embodiments, the distal end of the penetrating member is recessed at least about 0.8 centimeters and/or less than or equal to about 3 centimeters from the distal end of the outer covering 1440.

In some embodiments, a component (e.g., the penetrating member 1442) is configured to penetrate into a portion of the adapter assembly 1450 and/or into a portion of a container. The component (e.g., penetrating member 1442) can remain recessed, covered, or otherwise shielded by the syringe assembly 1402 throughout the use of the system 1400 and/or when the syringe assembly 1402 is in a pre-use state (e.g., upon removal from packaging), in a post-use state (e.g., having been coupled and decoupled from the adapter 1450), initially disposed, thrown away, and/or discarded.

The proximal first passage 1416 can be a regulating channel to convey or otherwise transmit fluid that regulates pressure inside of a container. The distal first passage 1246 can be a regulating channel to convey or otherwise transmit fluid that regulates pressure inside of a container. The proximal second passage 1424 and the distal second passage 1254 can be extraction channels configured to remove fluid from a container and/or deliver fluid to a container.

As illustrated in FIG. 41, the syringe assembly 1402 can include a first biasing member (e.g., a spring 1558) and/or a regulating channel seal (e.g., third seal 1562). The first spring 1558 can be configured to apply an axial force to press the regulating channel seal against a sealing surface (e.g., inner surface 1580) to seal the regulating channel.

The adapter assembly 1450 can include a distally protruding piercing member (e.g., the distal portion of the piercing member 1500 in FIG. 36A). The distally protruding piercing member can be configured to enable fluid communication with an internal portion of a container (e.g., a vial). The adapter assembly 1450 can include a proximally protruding member (e.g., the proximal end 1510 in FIG. 36A), which can be configured to compress the first spring (e.g., spring 1558 in FIG. 41) to unseal the regulating channel (e.g., the proximal first passage 1416 in FIG. 41).

The adapter assembly 1450 can include a passage (e.g., the distal first passage 1246 and/or the distal second passage 1254 in FIG. 41). The passage can be capable of fluid communication with an internal portion of a container, such as a vial. The adapter assembly 1450 can include a second spring (e.g., spring 1504 in FIG. 41) axially coupled to an adapter seal (e.g., the second seal 1486 in FIG. 41). The second spring can be configured to move the adapter seal to seal the passage of the adapter.

Figure 44:
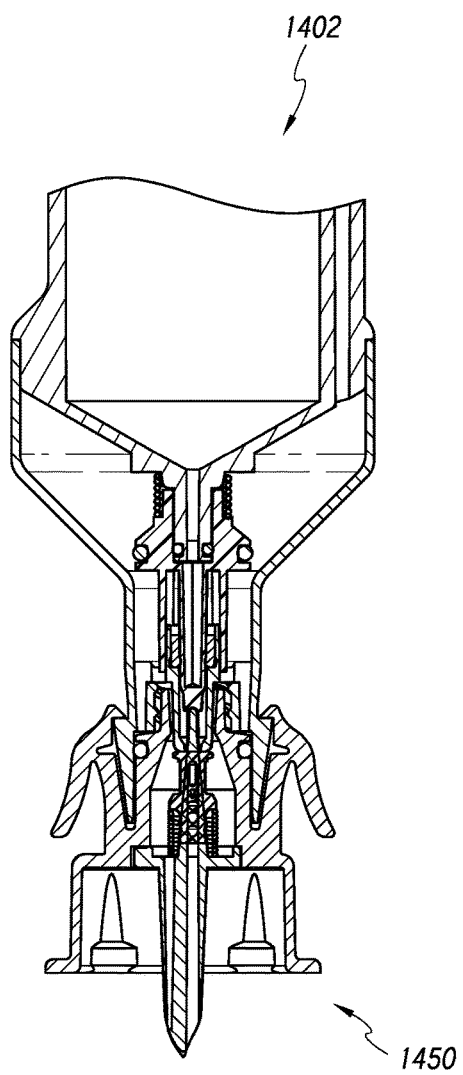
FIG. 44 illustrates a close-up, side view of the syringe assembly of FIG. 41 mechanically and fluidly coupled to the adapter assembly.
Figure 45:
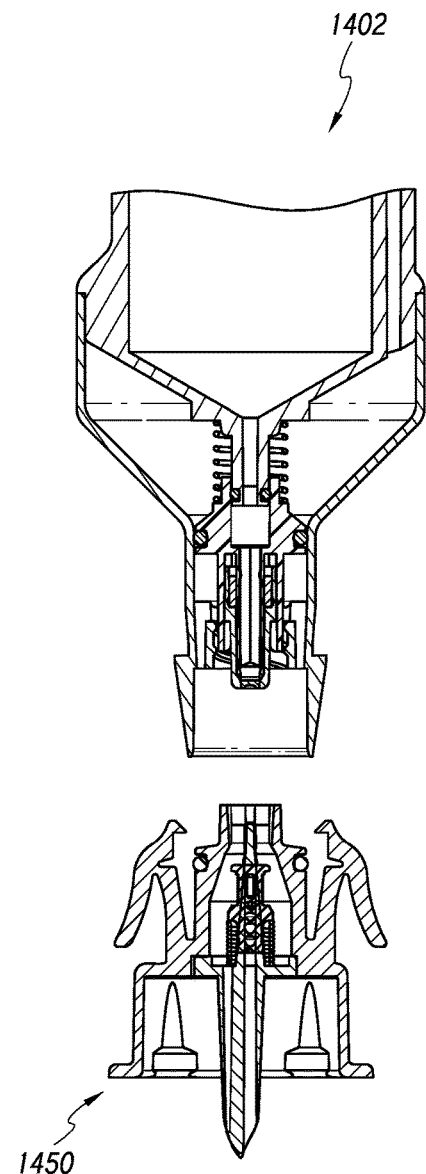
FIG. 45 illustrates a close-up, side view of the syringe assembly of FIG. 41 mechanically and fluidly uncoupled from the adapter assembly.

FIGS. 42-45 illustrate various configurations and views of the syringe assembly 1402 and the adapter assembly 1450. FIG. 42 illustrates the syringe assembly 1402 of FIG. 41 mechanically and fluidly coupled to the adapter assembly 1450 of FIG. 41. FIG. 43 illustrates the syringe assembly 1402 of FIG. 41 mechanically and fluidly uncoupled from the adapter assembly 1450 of FIG. 41. FIG. 44 illustrates a close-up view of the syringe assembly 1402 mechanically and fluidly coupled to the adapter assembly 1450. FIG. 45 illustrates a close-up view of the syringe assembly 1402 mechanically and fluidly uncoupled from the adapter assembly 1450. Not all of the features, components, and assemblies are labeled in FIGS. 42-45 to increase the clarity of the syringe assembly 1402 and adapter assembly 1450.

Figure 46:
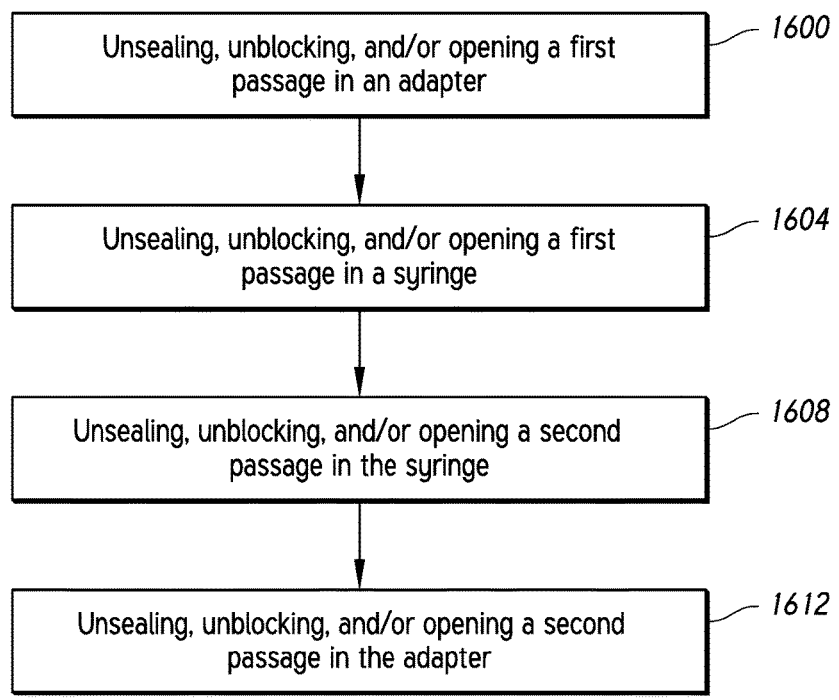
FIG. 46 illustrates a method of fluidly coupling a syringe to an adapter.

FIG. 46 illustrates a method of fluidly coupling a syringe to an adapter, according to several embodiments. This method can be used with any of the syringe systems and adapters described herein. Block 1600 can include unsealing, unblocking, and/or opening a first passage in an adapter. The first passage can be configured to fluidly communicate gas between a first reservoir and a container. The first passage can be a gas passage. Referring now to FIG. 36A, the first passage in the adapter can be the distal first passage 1246, which can be unsealed, unblocked, and/or opened by moving the radial protrusion 1508 distally such that the radial protrusion 1508 of the second seal 1486 no longer contacts the inner tapered region 1518 of the adapter assembly 1450.

Block 1604 of FIG. 46 can include unsealing, unblocking, and/or opening a first passage in a syringe. The first passage in the syringe can be configured to fluidly communicate with the first passage in the adapter to form a first passage (e.g., 220 in FIG. 7) between a first reservoir and a container. Referring now to FIG. 39, the first passage in the syringe can be the proximal first passage 1416, which can be sealed, blocked, and/or closed by moving the third seal 1562 in a distal direction such that the third seal 1562 seals against the inner surface 1580 (as shown in FIG. 38). The proximal first passage 1416 can be unsealed, unblocked, and/or opened when the syringe assembly 1402 is coupled to an adapter such that the adapter presses the distal portion 1584 of the passage shaft 1574 in a proximal direction, which moves the third seal 1562 from a sealing, blocking, and/or closing position to an unsealing, unblocking, and/or opening position.

Block 1608 of FIG. 46 can include unsealing, unblocking, and/or opening a second passage in the syringe. The second passage can be configured to fluidly communicate a liquid between a second reservoir and the container. The second passage can be a liquid passage and/or can be configured to fluidly communicate medicine from a container, such as a vial. Referring now to FIGS. 38 and 39, the second passage in the syringe can be the proximal second passage 1424. FIG. 38 illustrates the proximal second passage 1424 in a sealed, blocked, and/or closed position. FIG. 39 illustrates the proximal second passage 1424 in an unsealed, unblocked, and/or open position. The distal portion 1584 of the passage shaft 1574 can include a tapered portion that seals, blocks, and/or closes against a tapered portion 1548 of the distal cap 1550 in a seal zone 1590.

In some embodiments, the proximal second passage 1424 includes a "self-engaging" sealing system 1568. In several self-engaging embodiments, greater pressure inside the proximal second passage 1424 increases the sealing force of the sealing system, flow controller, and/or valve that controls flow through the proximal second passage 1424. The self-engaging sealing system 1568 can include a surface against which pressure drives two sealing surfaces together to tighten a seal. In several embodiments, the surface can be perpendicular to the direction of travel that causes the sealing surfaces to tighten together. In some embodiments, greater pressure against an actuation surface 1572 pushes a distal portion 1584 of the passage shaft 1574 towards a tapered portion 1584 to increase the seal strength.

Block 1612 of FIG. 46 can include unsealing, unblocking, and/or opening a second passage in the adapter. The second passage in the adapter can be configured to fluidly communicate with the second passage in the syringe to form a second passage (e.g., 224 in FIG. 7) between a second reservoir and a container. Referring now to FIG. 36A, the second passage in the adapter can be the distal second passage 1254. FIG. 36A illustrates the distal second passage 1254 in an unsealed, unblocked, and/or open position because the second seal 1486 is in a distal location (rather than in a proximal sealing location 1502) so the second seal 1486 does not cover, seal, occlude, and/or block the radial hole 1528. As a result, fluid (such as a medical liquid) can flow through the distal second passage 1254, through the radial hole 1528, and into the proximal second passage 1424 (shown in FIG. 39).

As shown in FIG. 46, Blocks 1600, 1604, 1608, and 1612 can be performed in any order. Some embodiments perform these Blocks in specific orders. In some embodiments, Block 1600 is performed first, Block 1604 is performed second, Block 1608 is performed third, and Block 1612 is performed fourth. Several embodiments include opening a first passage in an adapter; then opening a first passage in a syringe; then opening a second passage in the syringe; and then opening a second passage in the adapter. Some embodiments include unsealing, unblocking, and/or opening a first passage before unsealing, unblocking, and/or opening a second passage, wherein the first passage is configured to communicate gas and the second passage is configured to communicate liquid.

Several embodiments include fluidly coupling a container, such as a vial, to a gas reservoir before fluidly coupling the container to a reservoir configured to hold liquid, such as a medicinal fluid. Several embodiments include fluidly coupling a container, such as a vial, to a pressure equalization reservoir before fluidly coupling the container to a reservoir configured to hold medicinal fluid.

Some embodiments include fluidly sealing an internal portion of an adapter to an internal portion of a syringe prior to performing at least one of or all of Blocks 1600, 1604, 1608, and 1612. Referring now to FIG. 41, the first seal 1470 can fluidly seal an internal portion of the adapter assembly 1450 to an internal portion of the syringe assembly 1402. Thus, the syringe system can create an internally isolated area prior to opening the proximal first passage 1416, the proximal second passage 1424, the distal first passage 1246, and/or the distal second passage 1254 (as shown in FIGS. 36A and 39).

Figure 47:
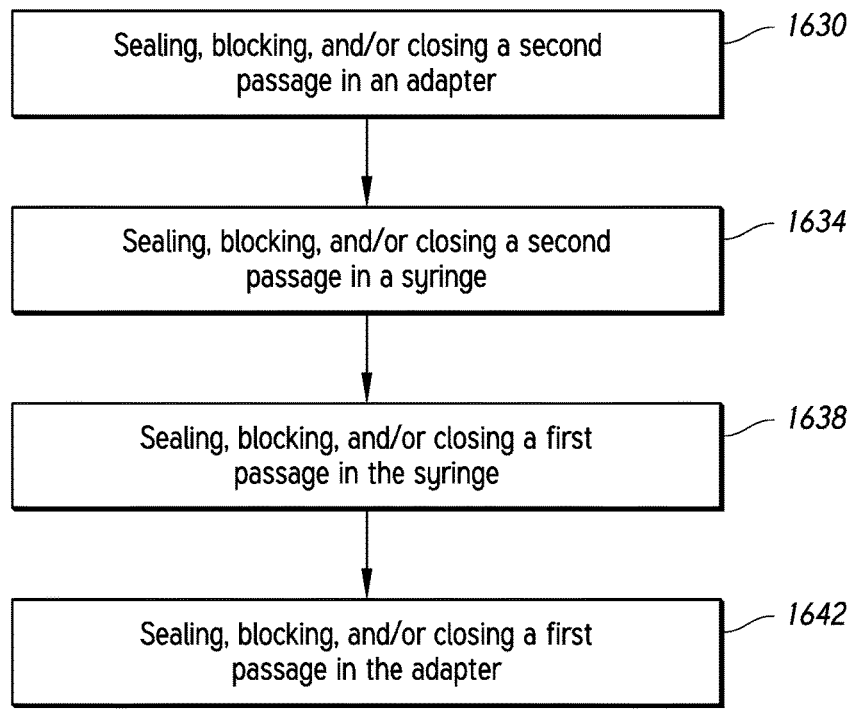
FIG. 47 illustrates a method of fluidly uncoupling a syringe from an adapter.

FIG. 47 illustrates a method of fluidly uncoupling a syringe from an adapter, according to several embodiments. This method can be used with any of the syringe systems and adapters described herein. Block 1630 can include sealing, blocking, and/or closing a second passage in an adapter. Block 1634 can include sealing, blocking, and/or closing a second passage in a syringe. Block 1638 can include sealing, blocking, and/or closing a first passage in the syringe. Block 1642 can include sealing, blocking, and/or closing a first passage in the adapter.

Blocks 1630, 1634, 1638, and 1642 can be performed in any order. Some embodiments perform these Blocks in specific orders. In some embodiments, Block 1630 is performed first, Block 1634 is performed second, Block 1638 is performed third, and Block 1642 is performed fourth. Some embodiments include sealing, blocking, and/or closing a second passage in an adapter; then sealing, blocking, and/or closing a second passage in a syringe; then sealing, blocking, and/or closing a first passage in the syringe; and then sealing, blocking, and/or closing a first passage in the adapter. Some embodiments include sealing, blocking, and/or closing a second passage (which can be a passage configured to communicate medicinal fluid) before sealing, blocking, and/or closing a first passage (which can be a passage configured to communicate gas and/or equalize pressure inside of the container). Some embodiments include sealing, blocking, and/or closing the first passage before sealing, blocking, and/or closing the second passage.

Some embodiments include fluidly unsealing an internal portion of an adapter from an internal portion of a syringe after performing at least one of or all of Blocks 1630, 1634, 1638, and 1642. Referring now to FIG. 41, the first seal 1470 can fluidly unseal an internal portion of the adapter assembly 1450 from an internal portion of the syringe assembly 1402. Thus, the syringe system can open, unblock, and/or unseal an internally isolated area after closing the proximal first passage 1416, the proximal second passage 1424, the distal first passage 1246, and/or the distal second passage 1254 (as shown in FIGS. 36A and 39).

Figure 48:
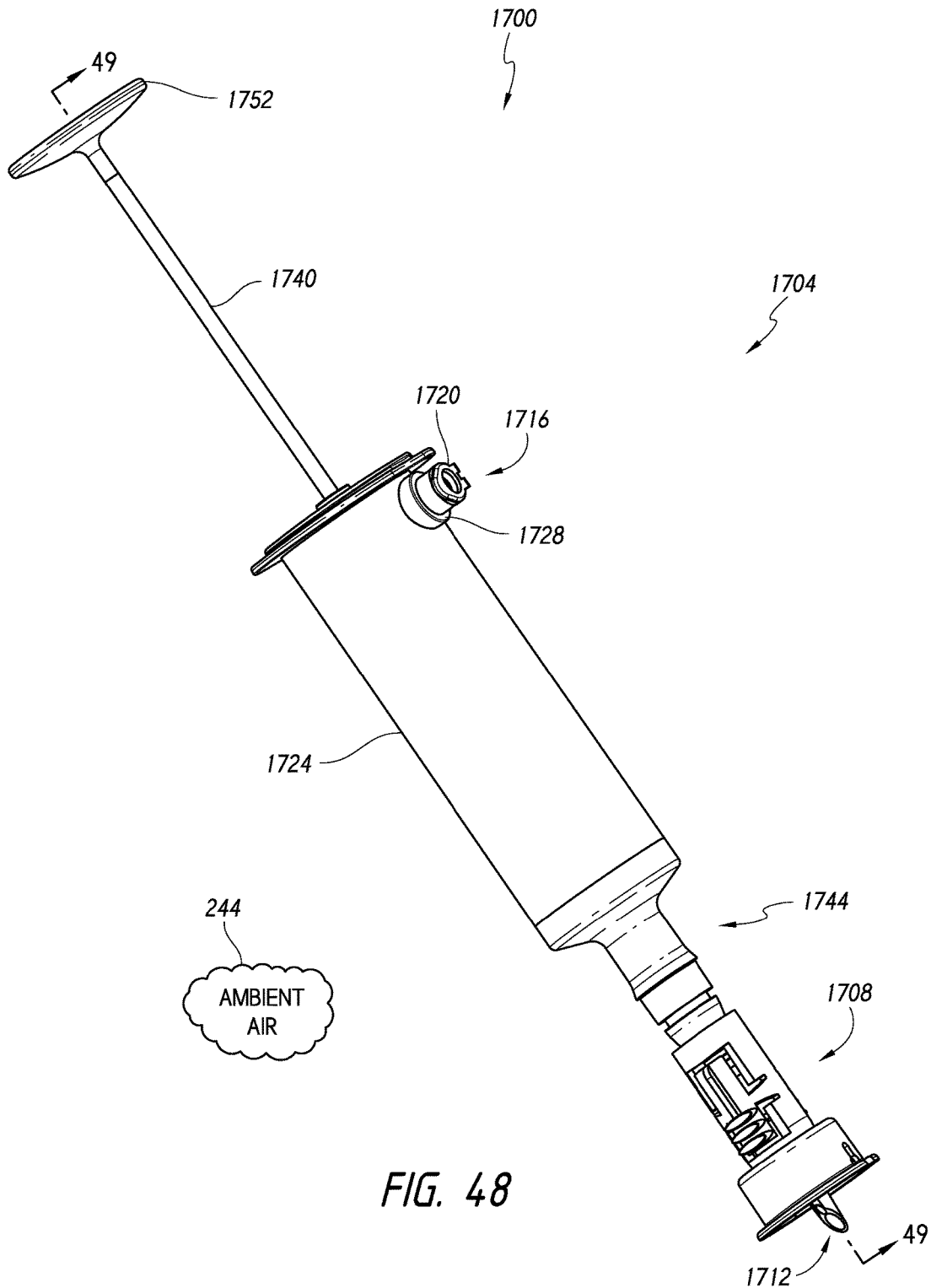
FIG. 48 illustrates a perspective view of a pressure regulating syringe system just before a syringe assembly couples to an adapter assembly.

FIG. 48 illustrates a perspective view of another embodiment of a pressure regulating syringe system 1700 just before a syringe assembly 1704 couples to an adapter assembly 1708. The adapter assembly 1708 can include a piercing member 1712. The system 1700 can be the same or identical to any of the other pressure-regulating syringe systems described herein and can include any of the features of those other systems. As shown, the syringe assembly 1704 can include a plunger 1740 and a distal cap 1744. The plunger 1740 can include finger grips 1752. Although some embodiments described herein use manual plungers, embodiments can use pneumatic syringes and/or pneumatic plungers.

The syringe system 1700 can include an outside fluid access port, such as a valve 1716. The valve 1716 can have an open position and a closed position. When in the open position, the valve 1716 can permit gas located outside of the syringe system 1700 (such as ambient air 244) to enter a first passage and/or a first reservoir to help equalize the pressure inside of a container with ambient pressure. The valve 1716 can include a cap 1720 that covers an entrance to the first passage. In some embodiments, a user can open the cap 1720 with a finger by pulling one side of the cap 1720 away from the barrel 1724. The valve 1716 can include a filter 1728 to filter gas flowing into or out of the valve 1716. The valve 1716 can include a cap configured to enable a user to "flip" the cap to an open position using a thumb. The valve 1716 can include a pinch valve, a duckbill valve, a check valve, a clack valve, a one-way valve, a ball valve, a diaphragm check valve, a swing check valve, a tilting disc check valve, a stop check valve, a lift check valve, an in-line check valve, and/or a two-way valve.

Certain other embodiments do not include the outside fluid access port. For example, as illustrated, numerous other embodiments disclosed in this specification do not include the outside fluid access port. Several embodiments that do not include the outside fluid access port are configured such that no external (e.g., ambient) fluid is used as regulating fluid. For example, in various embodiments that do not include the outside fluid access port, even after liquid has been injected into and/or withdrawn from a flexible container (e.g., an IV bag), no outside fluid is used as regulating fluid.

Figure 49:
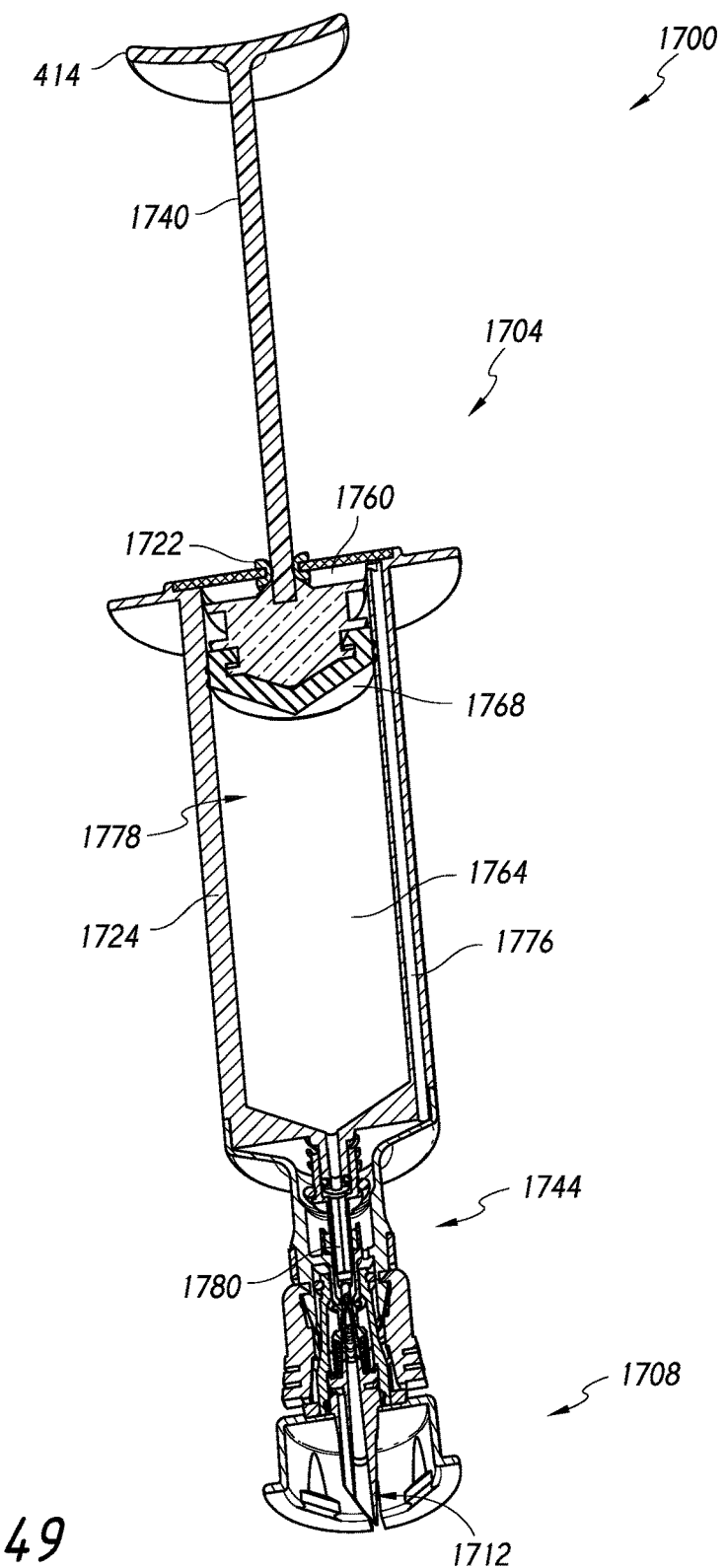
FIG. 49 illustrates a perspective, cross-sectional view along line 49-49 from FIG. 48 when the syringe assembly is secured to the adapter assembly.

FIG. 49 illustrates a perspective, cross-sectional view along the line 49-49 from FIG. 48 when the syringe assembly 1704 is coupled to the adapter assembly 1708. The syringe assembly 1704 can include a first reservoir 1760 separated from a second reservoir 1764 by a distal plunger seal 1768. The distal plunger seal 1768 can be coupled to a distal end of the plunger 1740. A proximal end of the first reservoir 1760 can be sealed by a proximal seal 1772. The plunger 1740 can slidably pass through a central lumen of the proximal seal 1772. A first passage 1776 can be configured to place the first reservoir 1760 in fluid communication with a container, such as a container configured to hold medicine. A second passage 1780 can be configured to place the second reservoir 1764 in fluid communication with the container. The barrel 1724 (which can be a housing) can include an inner channel 1778 with a diameter.

Figure 50:
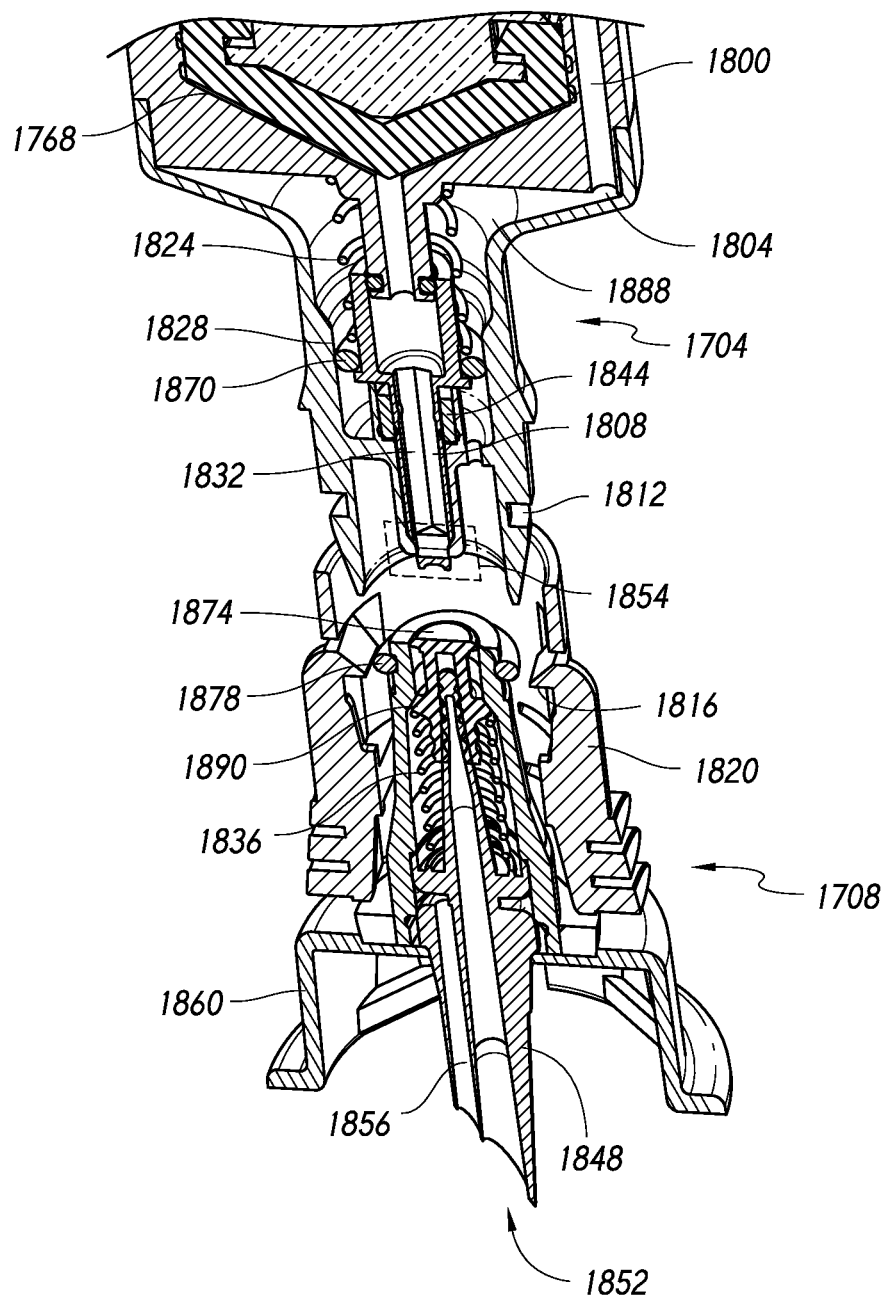
FIG. 50 illustrates a perspective, cross-sectional view of the adapter assembly from FIG. 48 when the adapter assembly is not secured to the syringe assembly and when a distal plunger seal has been moved to a distal position.

FIG. 50 illustrates a perspective, cross-sectional view of the adapter assembly 1708 of FIG. 48 with the plunger 1740 and distal plunger seal 1768 moved to a distal position. In this view, the adapter assembly 1708 is in close proximity to the syringe assembly 1704, but not coupled to the syringe assembly 1704.

The syringe assembly 1704 can include a proximal first passage 1800 configured to be fluidly coupled with a distal first passage 1856 of the adapter assembly 1708. A distal opening 1804 can allow fluid to flow from a portion of the proximal first passage 1800 into an open area 1888 inside a distal portion of the syringe assembly 1704. The open area 1888 can be sealed, blocked, and/or closed by a third seal 1870, which can be an O-ring. The syringe assembly 1704 is disconnected from the adapter assembly 1708 so the third seal 1870 seals against an inner surface 1828 to seal, block, and/or close the proximal first passage 1800 to prevent air located inside of a first reservoir from leaking outside of the syringe assembly 1704.

A fourth seal 1844 can allow a passage shaft 1808 to slide within a lumen of the fourth seal 1844 such that the passage shaft 1808 can move distally and/or proximally. A biasing member, such as a spring 1824, pushes the passage shaft 1808 in a distal direction. The adapter assembly 1708 can overcome the spring force of the spring 1824 when the syringe assembly 1704 is coupled to the adapter assembly 1708 to force the passage shaft 1808 to a proximal position, which disengages the third seal 1870 to open, unseal, and/or unblock the proximal first passage 1800 and/or disengages a seal zone 1854 (indicated by a dashed rectangle) between the passage shaft 1808 and a distal portion of the syringe assembly 1704 to open, unseal, and/or unblock the proximal second passage 1832.

In some embodiments, when the syringe assembly 1704 is coupled to the adapter assembly 1708, a protrusion 1816 that protrudes radially inward from a flexible arm 1820 is located inside of a groove 1812 to help secure the syringe assembly 1704 to the adapter assembly 1708. Some embodiments include threads to mechanically couple the syringe assembly 1704 to the adapter assembly 1708 (see, e.g., FIGS. 25 and 26).

As illustrated in FIG. 50, the adapter assembly 1708 can include a distal second passage 1848 and a distal first passage 1856. A portion of the distal second passage 1848 and a portion of the distal first passage 1856 can be located inside of the piercing member 1852. The distal second passage 1848 can be configured to fluidly couple with the proximal second passage 1832 when the syringe assembly 1704 is mechanically and/or fluidly coupled to the adapter assembly 1708. The distal first passage 1856 can be configured to fluidly couple with the proximal first passage 1800 when the syringe assembly 1704 is mechanically and/or fluidly coupled to the adapter assembly 1708. The first passage can be fluidly isolated and/or sealed from the second passage when the syringe assembly 1704 is not coupled to the adapter assembly 1708 and/or when the syringe assembly 1704 is coupled to the adapter assembly 1708.

A second seal 1874 can be configured to seal against an inner tapered region 1890. A biasing member, such as a spring 1836, can push the second seal 1874 in a proximal direction. Coupling the syringe assembly 1704 to the adapter assembly 1708 can compact the spring 1836 to unseal, unblock, and/or open the distal first passage 1856 and the distal second passage 1848.

As shown in FIG. 50, when the syringe assembly 1704 is not coupled to the adapter assembly 1708 (e.g., is spaced apart from), according to some embodiments, the first seal 1878 is in an unsealed, unblocked, and/or open position. In some embodiments, when the syringe assembly 1704 is not coupled to the adapter assembly 1708, the second seal 1874 seals, blocks, and/or closes the distal second passage 1848 and/or the distal first passage 1856.

Figure 51:
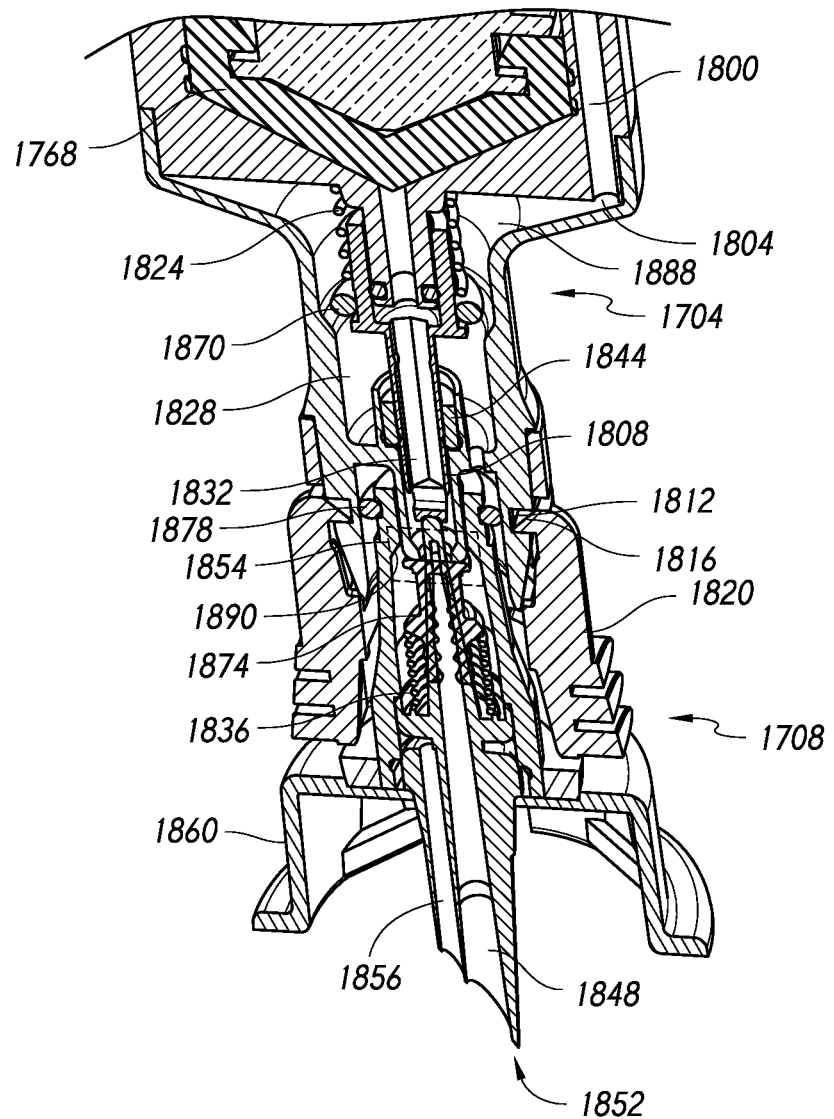
FIG. 51 illustrates a perspective, cross-sectional view of the adapter assembly from FIG. 50 when the adapter assembly is secured to the syringe assembly.

FIG. 51 illustrates a perspective, cross-sectional view of the adapter assembly 1708 along the line 49-49 from FIG. 48, when the adapter assembly 1708 is coupled to the syringe assembly 1704. As shown, according to some embodiments, the seal zone 1854 is open, unblocked, and/or unsealed when the syringe assembly 1704 is coupled to the adapter assembly 1708. The first seal 1878 is in a sealed, blocked, and/or closed position in FIG. 51.

As shown in FIG. 51, the second seal 1874 can seal the transition between the proximal second passage 1832 and the distal second passage 1848. In some embodiments, the second seal can also permit the proximal second passage 1832 and the distal second passage 1848 to be in fluid communication. In some embodiments, the second seal 1874 can permit the proximal first passage 1800 and the distal first passage 1856 to be in fluid communication. In FIG. 51, the second seal 1874 seals and/or blocks fluid communication between the first passage and the second passage.

Figure 52:
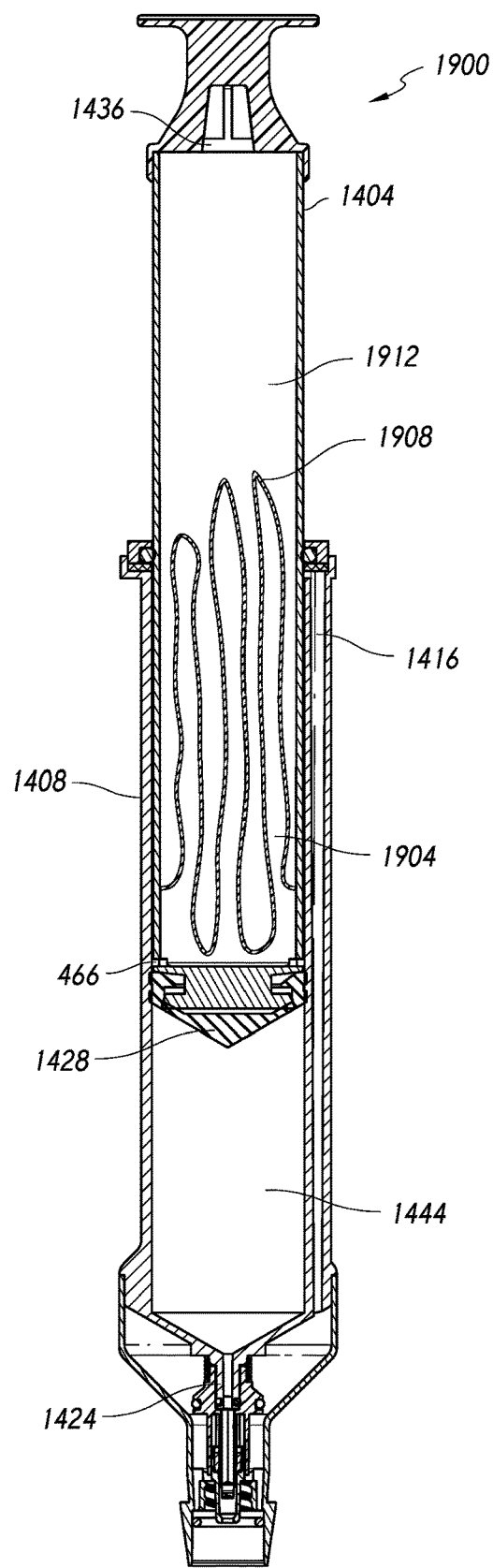
FIGS. 52 and 53 illustrate cross-sectional, side views of a syringe assembly with a bag.
Figure 53:
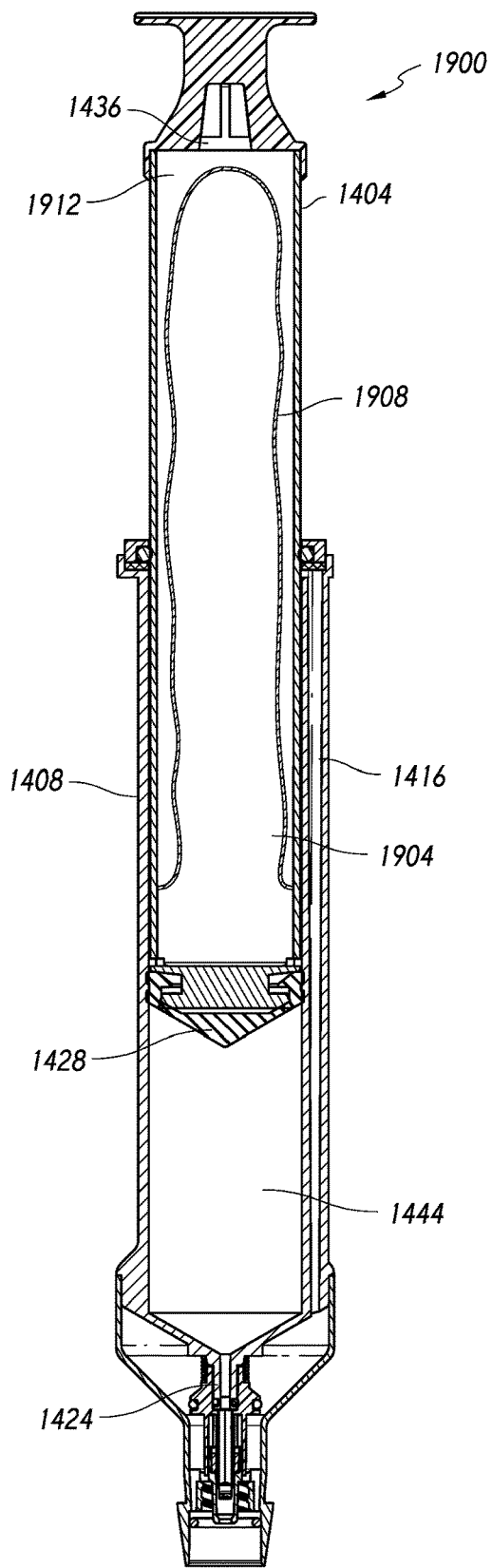

FIGS. 52 and 53 illustrate cross-sectional, side views of another embodiment of a syringe assembly 1900 with a bag 1908 located inside of a housing. The system shown in FIGS. 52 and 53 can be the same or identical to any of the other pressure-regulating syringe systems described herein and can include any of the features of those other systems. Referring now to FIG. 52, the syringe assembly 1900 can include a bag 1908, which is illustrated in a collapsed and folded configuration. An internal portion of the bag 1908 includes a first reservoir 1904 configured to be fluidly coupled with an internal portion of a container via the proximal first passage 1416. The bag 1908 can be located inside of the syringe assembly 1900 and inside of a plunger 1404. The bag 1908 can fluidly separate the first reservoir 1904 from a third reservoir 1912 (e.g., ambient portion). The third reservoir 1912 can be placed in fluid communication with ambient air via a vent 1436, hole, valve, and/or filter. In some embodiments, the vent 1436 is located in a proximal portion of the plunger 1404.

FIG. 53 illustrates the bag 1908 in an expanded and unfolded configuration. In some embodiments, the bag 1908 does not stretch when it expands, but the internal volume of the bag 1908 increases as the bag expands (e.g., unfolds). The internal volume of the bag 1908 is larger in FIG. 53 than in FIG. 52. The volume of the third reservoir 1912 is smaller in FIG. 53 than in FIG. 52. The surface area of the bag 1908 in FIG. 53 is equal (or at least approximately equal) to the surface area of the bag 1908 in FIG. 52. In some embodiments, the surface area of an expanded bag is within +/−5%, +/−10%, or +/−20% of the surface area of a collapsed bag such that the bag is configured not to substantially stretch during expansion and/or inflation (during normal operating conditions). In some embodiments, the bag's material does not cause the bag to have a restoring force. In some implementations, when the bag 1908 expands (e.g., increases in internal volume) the bag 1908 stretches and/or imparts a restoring force on the fluid in the bag 1908.

Figure 54:
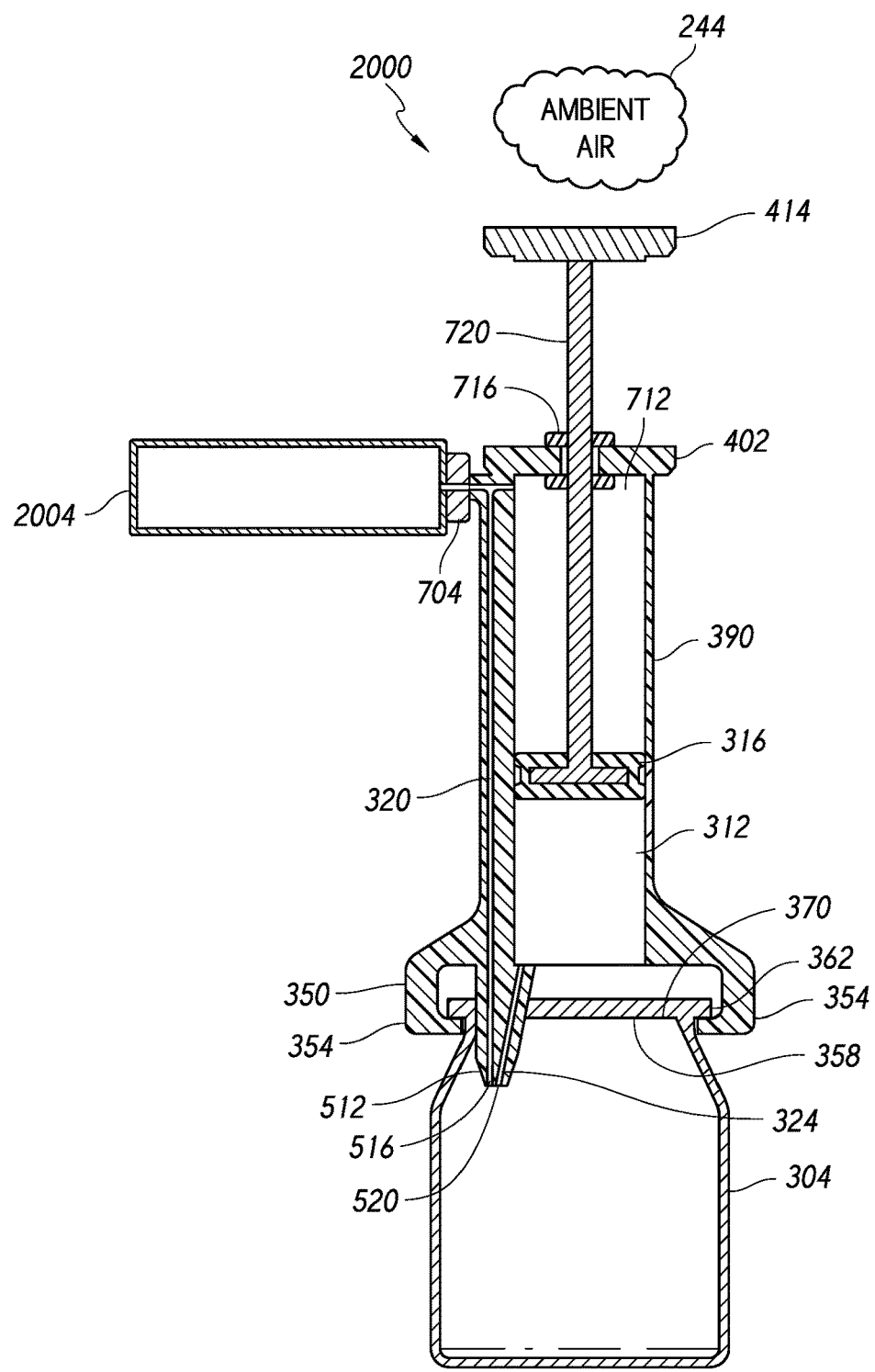
FIG. 54 illustrates a cross-sectional, side view of a pressure regulating syringe system with a supplemental reservoir.

FIG. 54 illustrates a cross-sectional view of an embodiment of a pressure regulating syringe system 2000 with a supplemental reservoir 2004, which can be configured to provide additional volume to a first reservoir 712. The system 2000 can be the same or identical to any of the other pressure-regulating syringe systems described herein and can include any of the features of those other systems. The supplemental reservoir 2004 can have rigid walls and can be located outside of the barrel 390 and/or plunger 720. The supplemental reservoir 2004 can have an internal volume that is at least 50% of the volume of the first reservoir 712 and/or less than 300% of the volume of the first reservoir 712 (as measured at the largest potential volume of the first reservoir 712 under normal operating conditions). The supplemental reservoir 2004 can have an internal volume that is at least 110% of the volume of the first reservoir 712 and/or less than 500% of the volume of the first reservoir 712. The supplemental reservoir 2004 can have an internal volume that is at least 200% of the volume of the first reservoir 712 and/or less than 900% of the volume of the first reservoir 712. As illustrated in various embodiments, the sum of the maximum volumes of the supplement reservoir and the first reservoir can be larger than the maximum volume of the second reservoir.

A valve 704 can control (e.g., block) fluid communication between the first reservoir 712 and the supplemental reservoir 2004. The supplemental reservoir 2004 can be used when a medical professional determines that additional gas and/or volume is necessary, desirable, and/or beneficial to regulate pressure inside the container 304. The supplemental reservoir 2004 can couple to the pressure regulating syringe system 2000, to the barrel 390, and/or to the plunger 720 via threads. In several embodiments, the supplemental reservoir 2004 can be in fluid communication with the first reservoir 712. Some embodiments include moving fluid from the second reservoir 312 to the container 304 and/or moving fluid from the container 304 to the second reservoir 312 before placing the supplemental reservoir 2004 in fluid communication with the first reservoir 712 and/or container 304.

Figure 55:
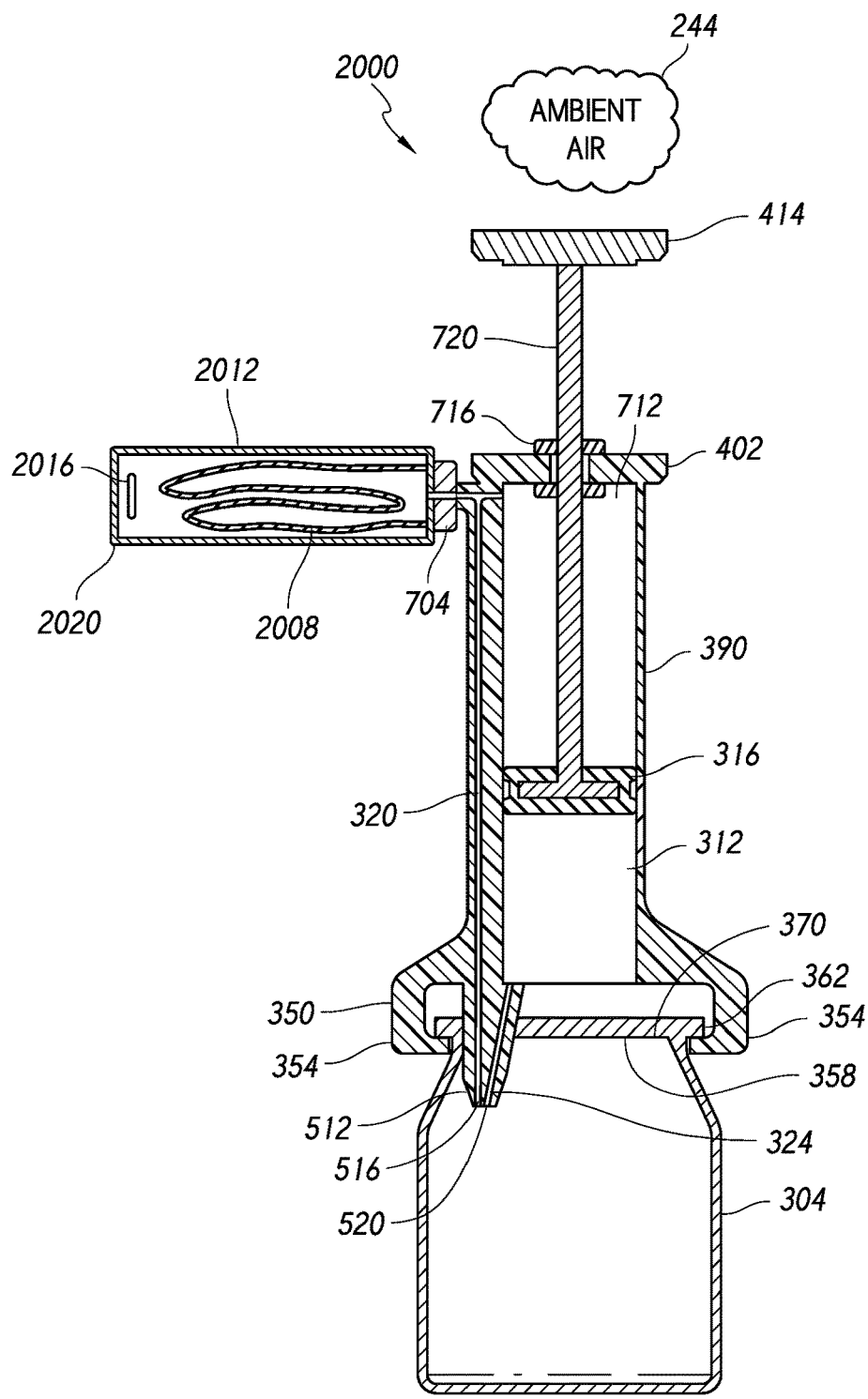
FIG. 55 illustrates a cross-sectional, side view of a supplemental reservoir that includes a bag inside of rigid walls.

FIG. 55 illustrates a cross-sectional view of an embodiment in which a supplemental reservoir 2020 includes a bag 2008, which can be located inside of walls 2012. The system illustrated in FIG. 55 can be the same or identical to any of the other pressure-regulating syringe systems described herein and can include any of the features of those other systems. The walls 2012 can be rigid. A vent 2016 can allow ambient air to enter the supplemental reservoir 2020. The bag 2008 can fluidly seal the first reservoir 712 from the ambient air such that ambient air does not contact the interior surface of the bag 2008. In various embodiments, ambient air can contact an exterior surface of the bag 2008.

Figure 56:
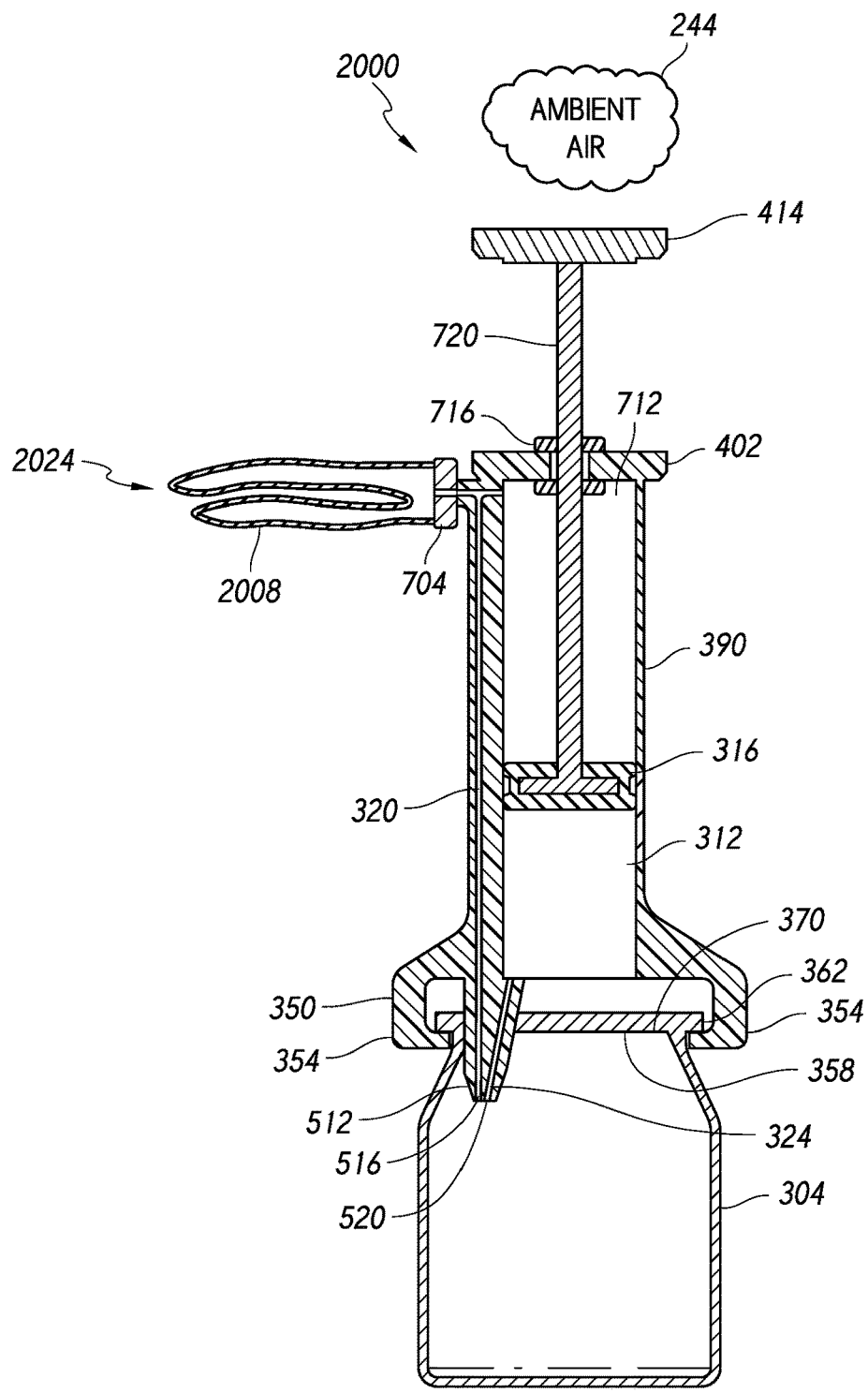
FIG. 56 illustrates a cross-sectional, side view of a supplemental reservoir, which includes a bag that is not encased by walls.

FIG. 56 illustrates a cross-sectional view of an embodiment in which a supplemental reservoir 2024 includes a bag 2008 coupled to the barrel 390. In some embodiments, the bag 2008 is not surrounded and/or encased by rigid walls.

Figure 57:
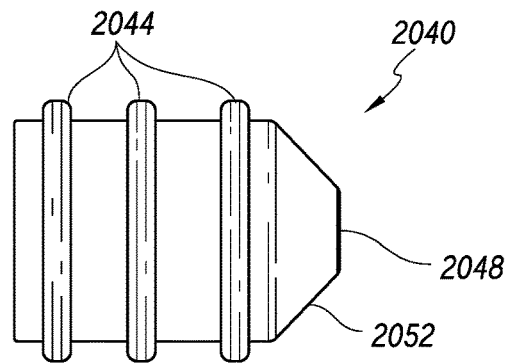
FIGS. 57-59 illustrate side views of seals with a rigid inner body and a compliant sealing member configured to fluidly seal against an inner surface of a plunger.
Figure 58:
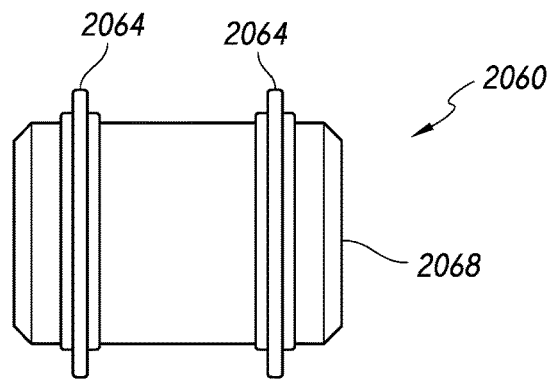
Figure 59:
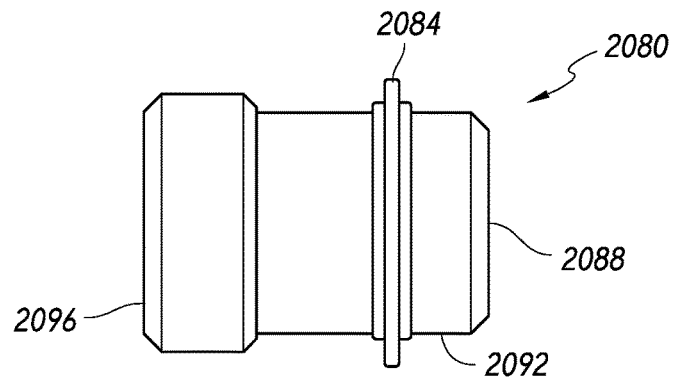

FIGS. 57-59 illustrate seals with a rigid inner body and a compliant sealing member configured to fluidly seal against an inner surface of a plunger. The compliant sealing member can be positioned around at least a portion of the rigid inner body. The seals of FIGS. 57-59 can be used with any of the systems or components described herein. The seals of FIGS. 57-59 can be used in place of other proximal plunger seals described and/or illustrated herein.

FIG. 57 illustrates a side view of a proximal plunger seal 2040 with seals, such as gaskets, rubber protrusions, or O-rings 2044, placed partially within grooves around the outer diameter of the proximal plunger seal 2040. The O-rings 2044 can be made from a compliant, rubber material. Some embodiments include O-rings 2044 made of medical-grade silicone or neoprene. Several embodiments include at least two O-rings coupled to a rigid carrier 2048, which can be made of molded plastic and/or machined. In some embodiments, the carrier 2048 is molded and then machined (e.g., deflashed, on a lathe, on a grinder) to remove parting lines to facilitate the O-rings 2044 sealing against the outer surface of the carrier 2048.

A distal portion can include a seal (e.g., an O-ring 2044) and a proximal portion can include a seal (e.g., an O-ring 2044). Some embodiments include three or more seals. One or both ends of the carrier 2048 can include a rounded or chamfered edge 2052 to avoid catching (e.g., snagging) an interior surface of a plunger (e.g., 1404 in FIG. 30). The carrier can be configured to prevent the proximal plunger seal 2040 from canting.

In some embodiments, a first seal (e.g., O-ring 2044) is spaced at least 0.5 cm, 0.75 cm, or 1 cm from a second seal (e.g., O-ring 2044). In some embodiments, the outer diameter of the carrier 2048 is at least 80% and/or less than 99% of the inner diameter of the plunger in which the carrier 2048 is located. In some embodiments, the outer diameter of the carrier 2048 is at least 90% and/or less than 98% of the inner diameter of the plunger in which the carrier 2048 is located.

FIG. 58 illustrates a side view of a proximal plunger seal 2060 with wiper seals 2064 placed partially within grooves around the outer diameter of the proximal plunger seal 2060. The wiper seals 2064 can be made from medical-grade silicone or neoprene. The wiper portion of the wiper seals 2064 can extend radially outward from a carrier 2068. A wiper seal 2064 can be placed on a distal portion of the carrier 2068 and a wiper seal 2064 can be placed on a proximal portion of the carrier 2068. In some embodiments, a first wiper seal 2064 is spaced at least 0.5 cm, 0.75 cm, or 1 cm from a second wiper seal 2064. In some embodiments, the outer diameter of the carrier 2068 is at least 80% and/or less than 99% of the inner diameter of the plunger in which the carrier 2068 is located. In some embodiments, the outer diameter of the carrier 2068 is at least 90% and/or less than 98% of the inner diameter of the plunger in which the carrier 2068 is located.

FIG. 59 illustrates a side view of a proximal plunger seal 2080 with a wiper seal 2084 placed partially within a groove around the outer diameter of the proximal plunger seal 2080. The groove can be part of the carrier 2088, which can be configured to secure and/or hold a seal, such as a wiper seal 2084. The carrier 2088 can include a first diameter and a second diameter. A seal (e.g., wiper seal 2084, an O-ring) can protrude radially outward from a portion of the carrier 2088 that includes the first diameter 2092. The second diameter 2096 can be larger than the first diameter 2092 and can be spaced apart from a portion of the proximal plunger seal 2080 that includes a seal (e.g., the wiper seal 2084). The second diameter 2096 can be a support surface configured to limit the degree to which the proximal plunger seal 2080 is able to cant within a plunger. The second diameter 2096 can be smaller than the outer diameter of the seal (e.g., wiper seal 2084). The second diameter 2096 can be made from a rigid material, such that it can form a rigid support surface configured to limit the degree to which the proximal plunger seal 2080 is able to cant within a plunger. In several embodiments, the outer diameter of the seal is larger than the second diameter, which is larger than the first diameter.

Figure 60:
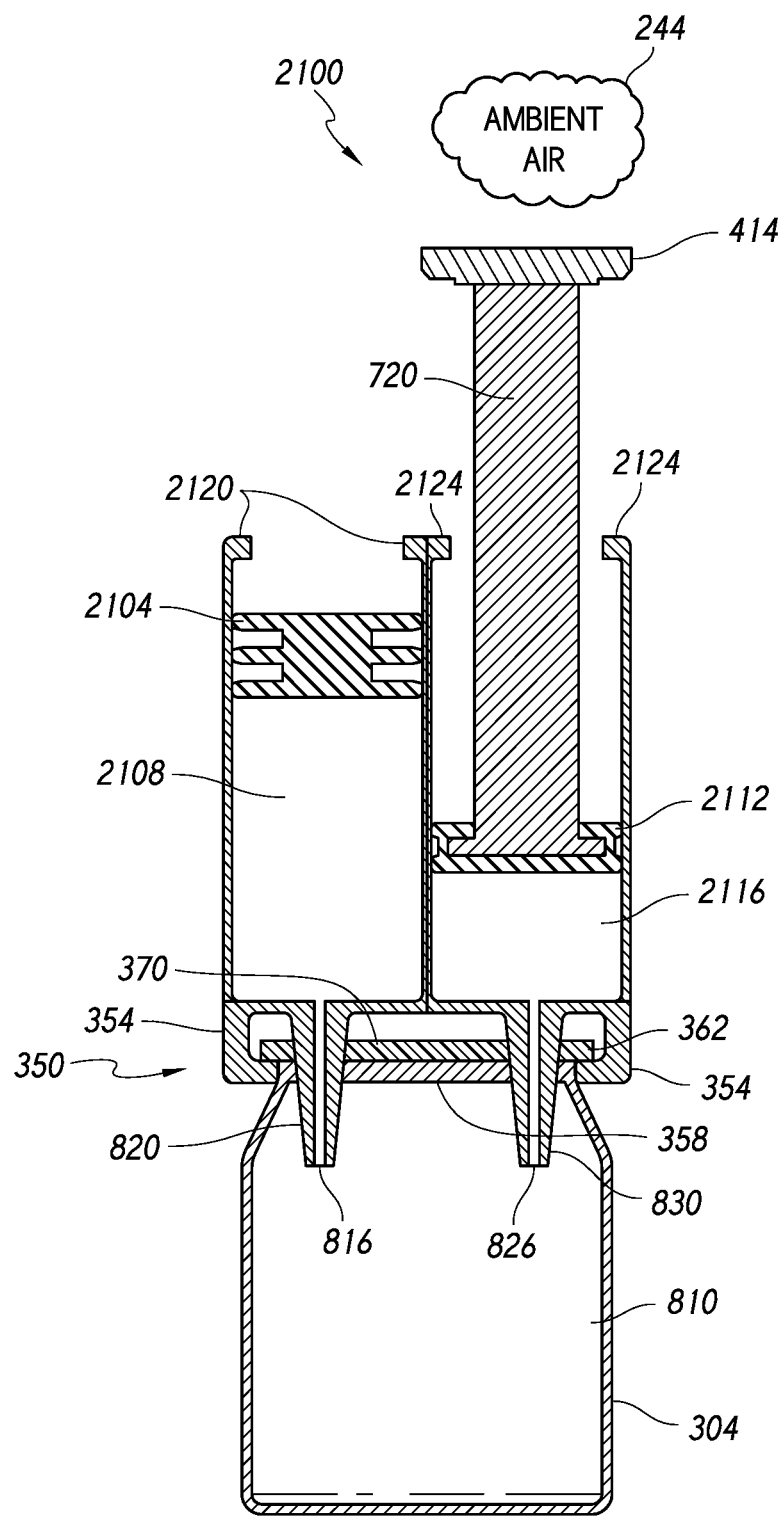
FIG. 60 illustrates a cross-sectional, side view of a pressure regulating syringe system.

FIG. 60 illustrates a cross-sectional, side view of a pressure regulating syringe system 2100. The system 2100 can be the same or identical to any of the other pressure-regulating syringe systems described herein and can include any of the features of those other systems. The pressure regulating syringe system 2100 includes a seal 2104, which can be a wiper seal with multiple wipers. The seal 2104 can form a proximal boundary of a first reservoir 2108 configured to communicate fluid, such as a gas, via a first passage 816 to and/or from an internal portion 810 of a container 304. The seal 2104 can be slidably coupled within the pressure regulating syringe system 2100 such that the seal 2104 can slide within a portion of the pressure regulating syringe system 2100 to change the volume of the first reservoir 2108.

Figure 61:
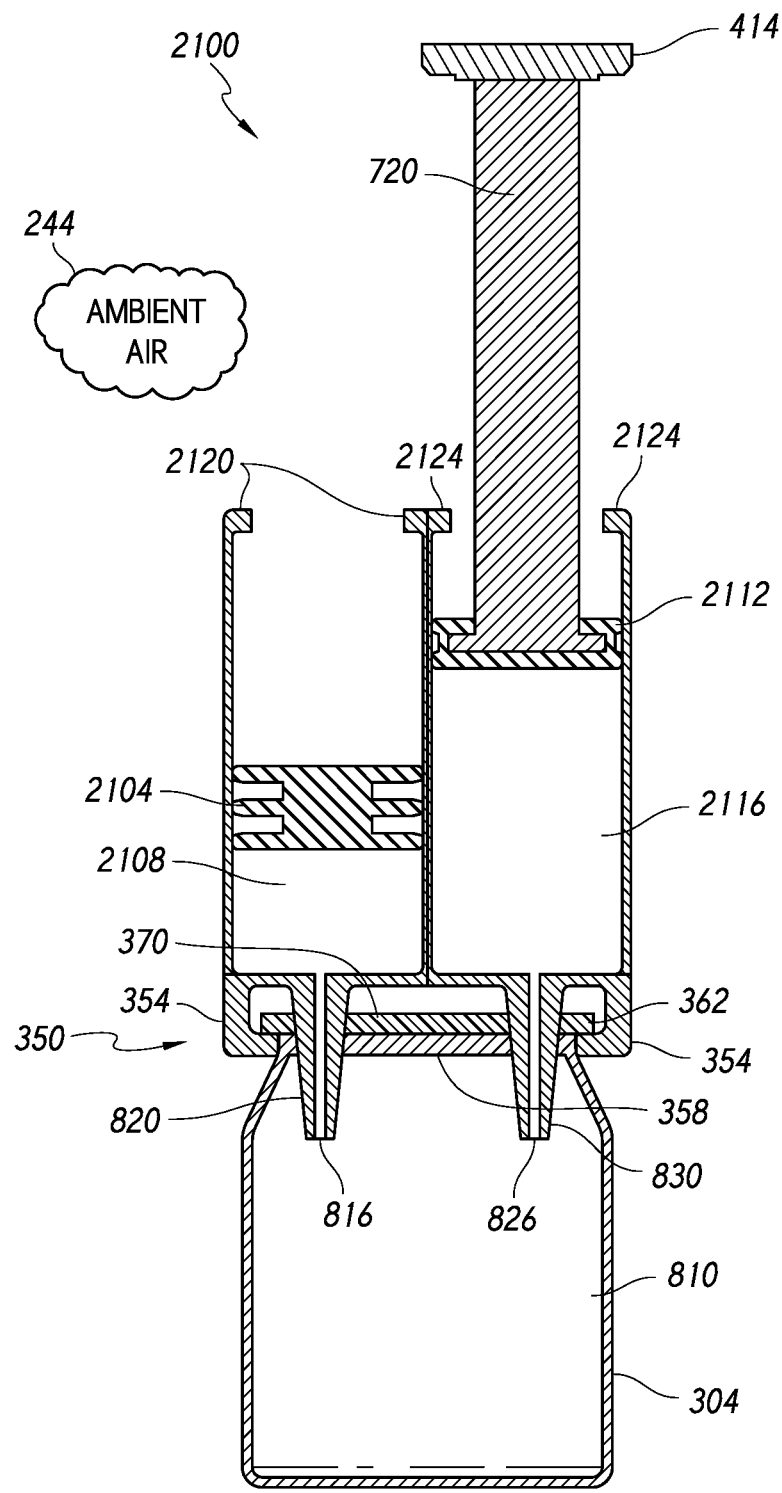
FIG. 61 illustrates the pressure regulating syringe system from FIG. 60 after the seal has moved distally and the plunger has moved proximally.

The pressure regulating syringe system 2100 can include a second reservoir 2116 configured to communicate fluid, such as a liquid, via a second passage 826 to and/or from an internal portion 810 of a container 304. As illustrated in FIGS. 60 and 61, the longitudinal axes of the first and second reservoirs can be offset and non-colinear in some embodiments. Also, as illustrated, the longitudinal axes of the first and second reservoirs can be generally parallel. A plunger seal 2112 can form a proximal boundary of the second reservoir 2116. The plunger seal 2112 can be coupled to a plunger 720 configured to enable and/or allow a user to alter the volume of the second reservoir 2116 by pushing the plunger 720 into and/or out of the pressure regulating syringe system 2100. The first reservoir 2108 and the second reservoir 2116 can be side by side. In some embodiments, a first side of the pressure regulating syringe system 2100 includes the first reservoir 2108 and second side of the pressure regulating syringe system 2100 includes the second reservoir 2116. The first reservoir 2108 and/or the second reservoir 2116 can be cylindrical and/or generally cylindrical.

Stops 2120, 2124 can limit the travel of the seal 2104 and the plunger 720 to prevent and/or reduce the likelihood of the seal 2104 and the plunger 720 to inadvertently decouple from the pressure regulating syringe system 2100. The stops 2120, 2124 can be protrusions that protrude radially inward to interfere with the seal 2104 and/or a portion of the plunger 720 when the seal 2014 and/or the plunger 720 reaches a proximal travel termination point. The stops 2120, 2124 can be located proximally relative to the seal 2104 and/or the plunger seal 2112.

FIG. 61 illustrates the pressure regulating syringe system 2100 after the seal 2104 has moved distally and the plunger 720 has moved proximally. The seal 2104 and the plunger 720 (e.g., including the plunger seal 2112) can slide within the pressure regulating syringe system 2100. In some embodiments, the seal 2104 and the plunger 720 are configured to slide distally and proximally within the pressure regulating syringe system 2100.

Syringe assemblies can be coupled to vial adapters and/or can be coupled to other fluid transfer connectors. For example, medical professionals can connect syringe assemblies to containers that are not vials. In some cases, syringe assemblies are used to remove a pharmaceutical substance from a container such as a vial and then are used to inject the pharmaceutical substance into peripheral, arterial, and/or central venous catheters. Syringe assemblies can be used to deliver pharmaceutical substances to an intravenous therapy ("IV") bag or IV line. In some embodiments, syringe assemblies are mechanically and fluidly coupled to a Clave® needle-free connector commercially available from ICU Medical, Inc.

Figure 62:
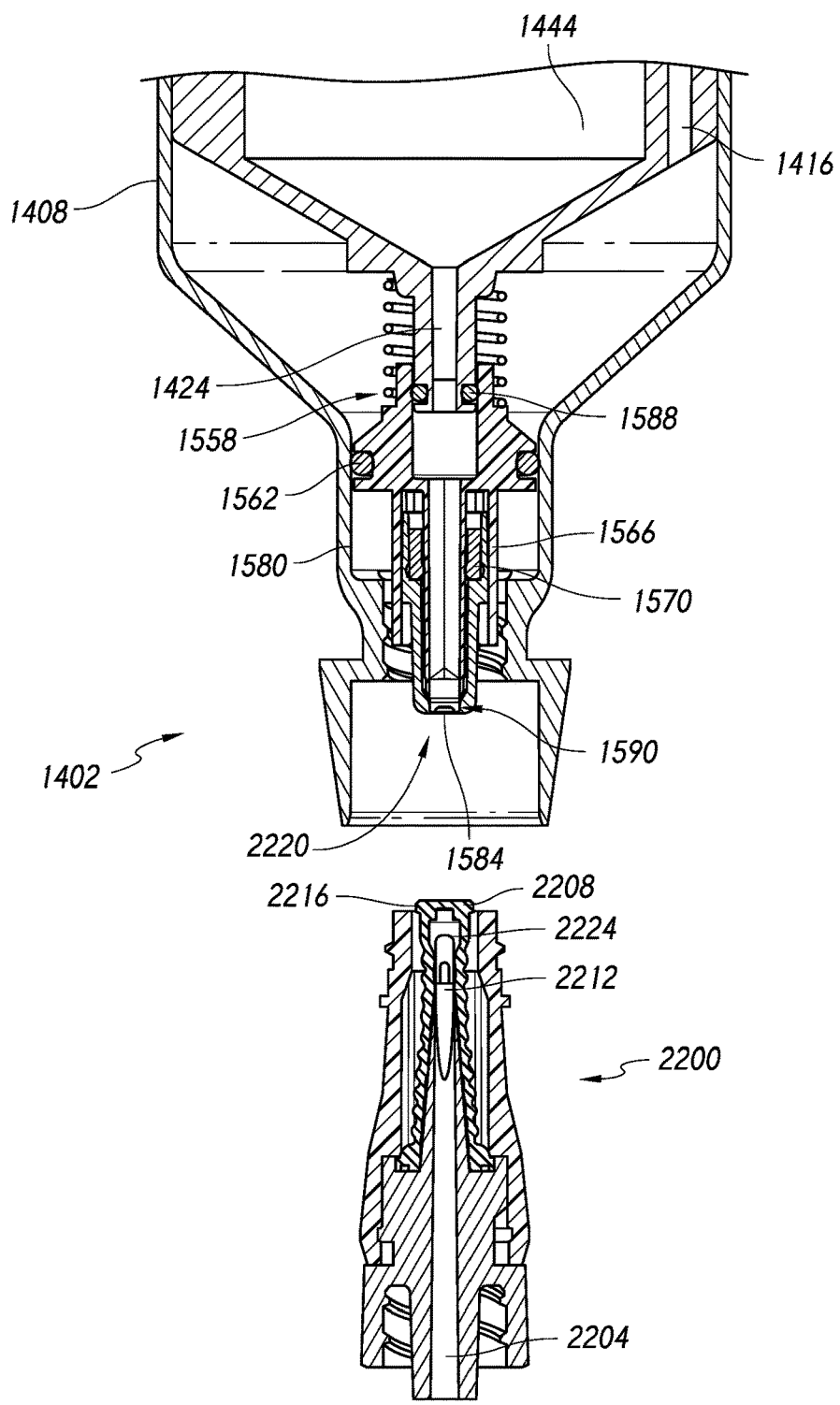
FIG. 62 illustrates a cross-sectional, side view of the syringe assembly from FIG. 38 and a connector.

FIG. 62 illustrates a cross-sectional view of the syringe assembly 1402 from FIG. 38 and a connector 2200. In FIG. 62, the syringe assembly 1402 is not coupled to the connector 2200. The connector 2200 can be configured to mechanically and fluidly couple with a tube, cannula, container, and/or bag.

The connector 2200 can include a distal second passage 2204 configured to and/or capable of being placed in fluid communication with the proximal second passage 1424 of the syringe assembly 1402. A proximal portion of the distal second passage 2204 can be sealed by a second seal 2208, which can be configured to cover a connector proximal aperture 2212 from the distal second passage 2004 and can be configured to provide substantially fluid-tight sealing of the connector proximal aperture 2212. In some embodiments, the connector proximal aperture 2212 can be oriented radially outward from the central axis of the distal second passage 2204. In several embodiments, the connector proximal aperture 2212 can be an aperture, a hole, and/or an exit of a passage (e.g., the distal second passage 2204).

The second seal 2208 can include a sealing surface 2216 facing proximally. In some embodiments, during coupling of the syringe assembly 1402 and the connector 2200, the sealing surface 2216 is oriented towards a distal end 2220 of the syringe assembly 1402 and/or of the proximal second passage 1424. The sealing surface 2216 can also be oriented in a proximal direction relative to the connector 2200. In some embodiments, the second seal 2208 is a boot seal. The second seal 2208 can be made from rubber or medical-grade silicone. In various implementations, the second seal 2208 can resiliently and axially collapse (e.g., in a distal direction).

In FIG. 62, the second seal 2208 is shown in a fully extended position. As discussed in more detail below, the syringe assembly 1402 is configured to compress the second seal 2208 in a distal direction to expose the connector proximal aperture 2212, to open the distal second passage 2204, and/or to place the distal second passage 2204 in fluid communication with the proximal second passage 1424.

Figure 63:
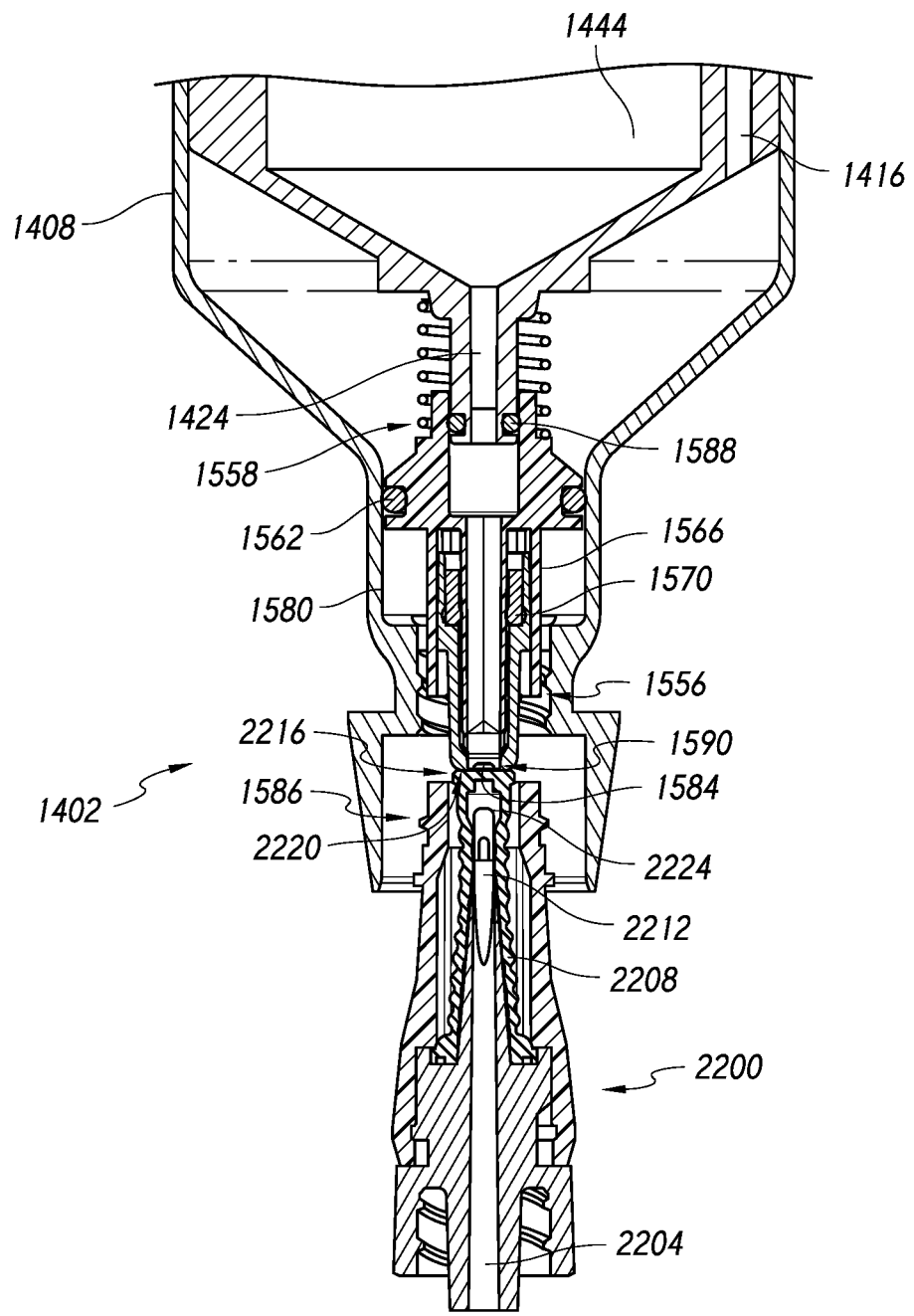
FIG. 63 illustrates the connector from FIG. 62 during an initial contact stage with the syringe assembly.

FIG. 63 illustrates the connector 2200 during a stage of initial contact with the syringe assembly 1402. In some embodiments, during the initial contact stage (and in subsequent contact stages), the sealing surface 2216 seals against at least a portion of the distal end 2220 of the syringe assembly 1402. The seal zone 1590 is still in a closed, sealed configuration in FIG. 63.

The syringe assembly 1402 can include threads 1556. The threads 1556 can couple with threads 1586 of the connector 2200 so as to provide threaded engagement. The threads 1556, 1586 can transmit rotational movement into axial movement, such as distal movement or proximal movement.

Figure 64:
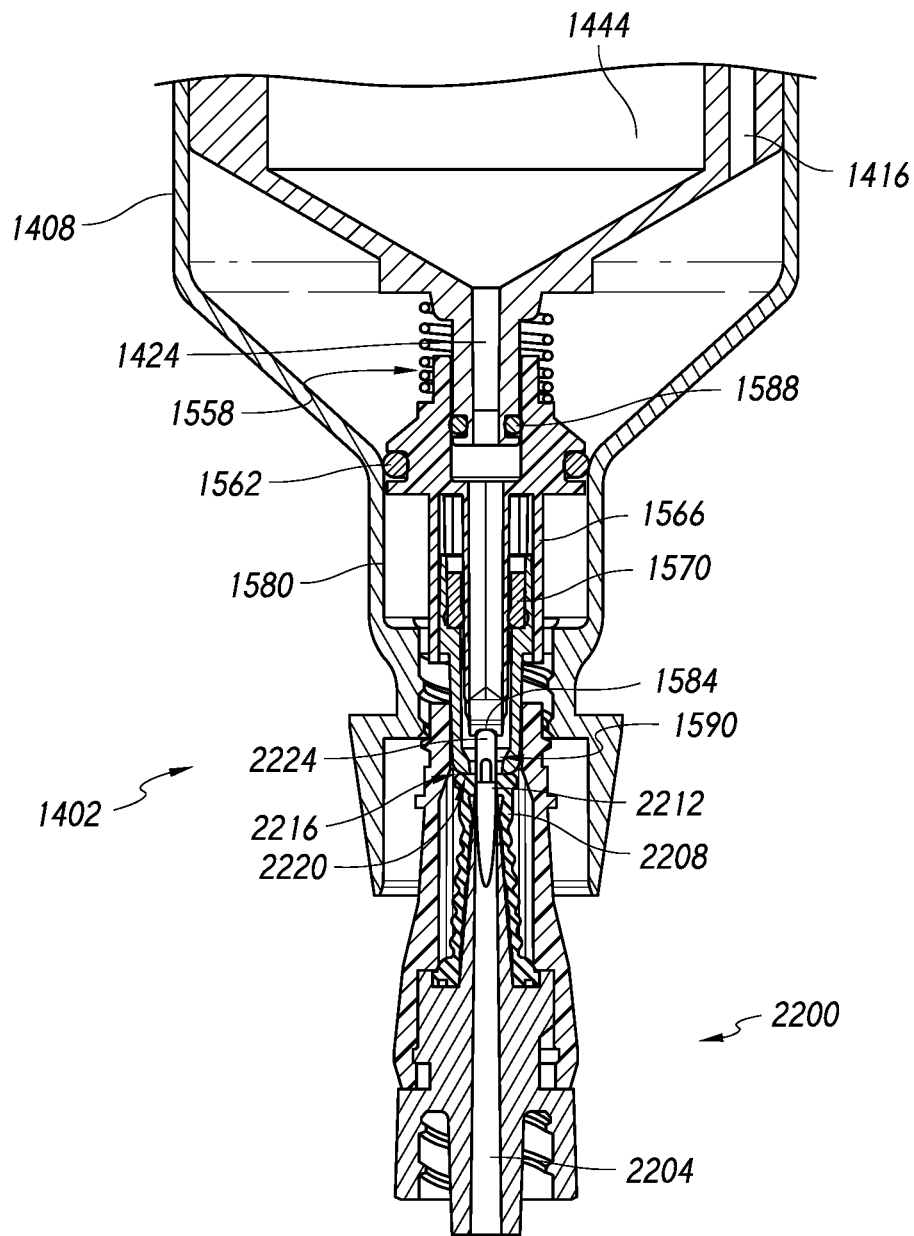
FIG. 64 illustrates the connector from FIG. 62 partially coupled to the syringe assembly.

FIG. 64 illustrates the connector 2200 partially coupled to the syringe assembly 1402. In some embodiments, the connector 2200 and the syringe assembly 1402 are coupled. For example, the connector 2200 and the syringe assembly 1402 can include corresponding threads, which can facilitate mechanical coupling. In several embodiments, as the connector 2200 is advanced into the syringe assembly 1402, a proximal end 2224 of a pushing member (such as a shaft or protrusion) engages (e.g., presses against) the distal portion 1584. This can result in a proximally directed force, which can compress the spring 1558. This movement can open the seal zone 1590 (as shown in FIG. 64). Although the seal zone 1590 can be in an open position and the distal second passage 2204 can be in fluid communication with the proximal second passage 1424, the third seal 1562 can still be in a closed position (as illustrated in FIG. 64). The closed position of the third seal 1562 can block and/or inhibit fluid communication between the proximal first passage 1416 and the connector 2200.

Figure 65:
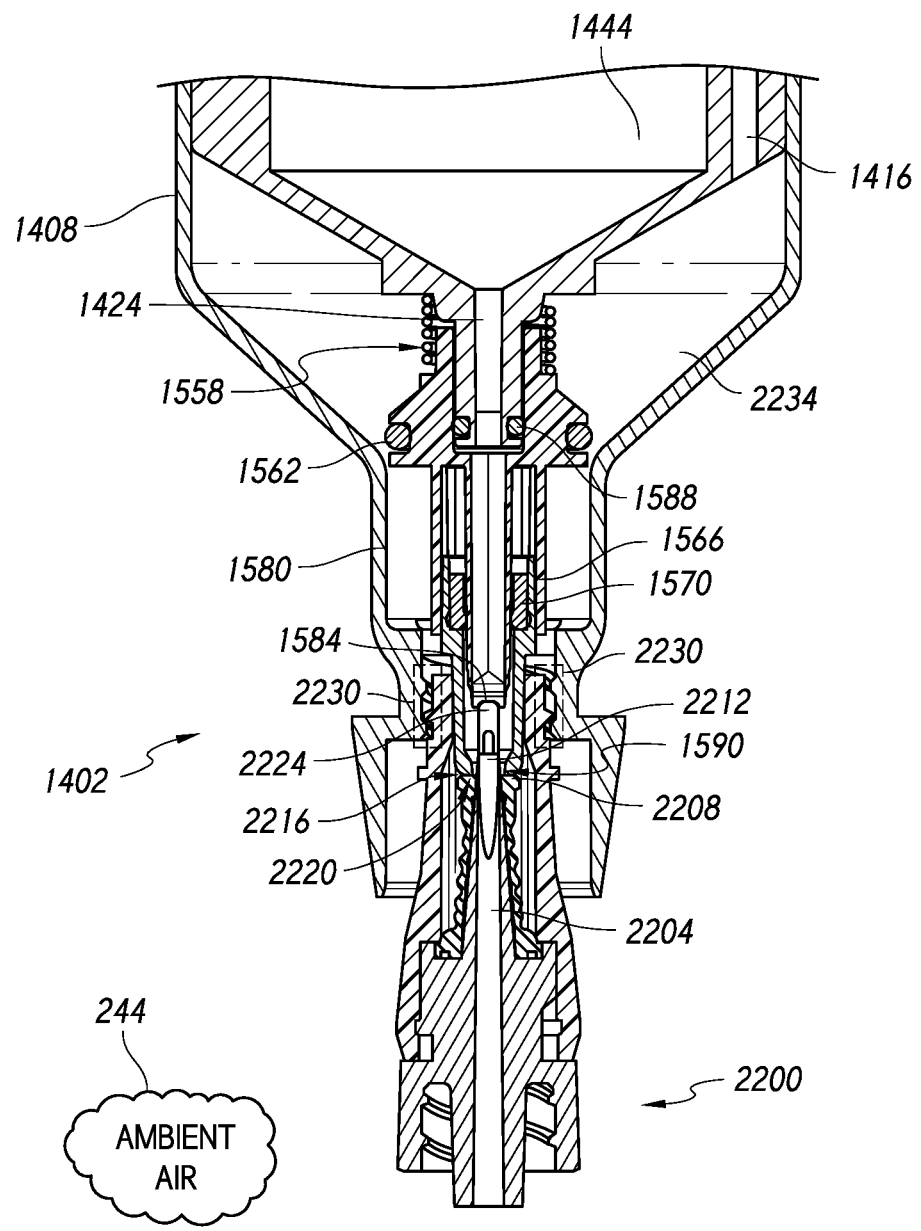
FIG. 65 illustrates the connector from FIG. 62 coupled to the syringe assembly.

FIG. 65 illustrates the connector 2200 coupled to the syringe assembly 1402. As the proximal end 2224 continues to engage (e.g., push) the distal portion 1584, (which compresses the spring 1558) the second seal 2208 is compressed, which opens the connector proximal aperture 2212 by moving the second seal 2208 to a position in which the second seal 2208 is no longer sealing (e.g., covering) the connector proximal aperture 2212. Opening the connector proximal aperture 2212 places the distal second passage 2204 in fluid communication with the proximal second passage 1424 and/or the second reservoir 1444. Thus, in some embodiments, fluid can flow between the second reservoir 1444 and the connector 2200 (e.g., an internal portion of the connector such as the distal second passage 2204). The sealing surface 2216 is configured to prevent fluid flowing between the proximal second passage 1424 and the distal second passage 2204 from leaking out.

In several embodiments, the aforementioned proximal movement of the sliding member 1576 and/or the compression of the spring 1558, which can be any type of spring or compressible member, moves the third seal 1562 proximally. This proximal movement can result in the third seal 1562 no longer contacting (or otherwise sealing with) the inner surface 1580. After the third seal 1562 no longer contacts the inner surface 1580, the third seal 1562 no longer seals the proximal first passage 1416 (e.g., is in an open position).

In certain implementations, after the third seal 1562 is in an open position, the proximal first passage 1416 is open. For example, as shown in FIG. 65, the seal 1562 is spaced apart from the inner surface 1580, thereby allowing fluid to flow between seal 1562 and the inner surface 1580. This can open access to the proximal first passage 1416 and thus allow fluid to flow to and/or from that passage 1416.

In some embodiments, coupling the syringe assembly 1402 to a connector 2200 does not unseal the proximal first passage 1416, but connecting the syringe assembly 1402 to a vial adapter unseals the proximal first passage 1416. This can permit the syringe assembly 1402 to fluidly communicate gas into and out of a container such as a vial. In some embodiments, if the connector 2200 does not have a distal first passage (e.g., 1246 in FIG. 41) configured to transmit fluid from a container to and/or from the syringe assembly 1402, coupling the connector 2200 to the syringe assembly 1402 will not unseal and/or open the proximal first passage.

Coupling the connector 2200 to the syringe assembly 1402 can create a seal zone 2230 that seals and/or blocks the proximal first passage 1416 such that fluid (e.g., gas) from the first reservoir 1420 (shown in FIG. 40) does not escape from the syringe assembly 1402 and/or escape into the ambient air 244, which is located outside of the syringe assembly 1402 and outside of the connector 2200. The seal zone 2230 can be formed by any suitable seal, including mating threads of the connector 2200 and the syringe assembly 1402. In the embodiment illustrated in FIG. 65, boxes formed by dashed lines indicate the area in which there are mating threads that inhibit or prevent fluid from exiting the proximal first passage 1416. Some embodiments include seal zones 2230 that block fluid transfer via seals (e.g., O-rings, gaskets or otherwise) in addition to, or instead of, mating threads. Some mating thread embodiments use plastics that provide enough compliance to form a gas seal and/or a generally gas-tight seal between the mating threads. The proximal first passage 1416 in FIG. 65 includes a relatively large open area 2234 that can be sealed by the third seal 1562 and/or by the seal zone 2230.

In several embodiments, the connector 2200 does not include a distal first passage 1246 (shown in FIG. 41) configured to transmit fluid (e.g., gas) from a first reservoir 1420 (shown in FIG. 40) through the connector 2200 (e.g., to a container that can be located distally relative to the connector 2200). Some connectors 2200 include a passage to transmit fluid (e.g., a liquid) from a second reservoir but do not include a passage to transmit fluid (e.g., a gas) from a first reservoir. In some embodiments in which the connector includes a passage to transmit fluid from a second reservoir but does not include a passage to transmit fluid from a first reservoir, the syringe assembly 1402 can be configured such that the volume of the second reservoir can change without requiring the volume of the first reservoir to change. As described above, this can be called volumetric independence. Volumetric independence of the first reservoir from the second reservoir can reduce or prevent substantial pressure deviations from atmospheric pressure.

For example, in some embodiments, if the first reservoir is not volumetrically independent from the second reservoir and the proximal first passage 1416 is sealed (e.g., when the syringe assembly 1402 is coupled to the connector 2200), then transmitting fluid from the second reservoir 1444 through the connector 2200 could increase the volume of the first reservoir without permitting the proximal first passage 1416 to transmit fluid into the first reservoir to regulate the pressure inside of the first reservoir. As a result, the pressure inside of the first reservoir could drop below atmospheric pressure (e.g., create a "vacuum"). In another example, if the first reservoir is not volumetrically independent from the second reservoir and the proximal first passage 1416 is sealed (e.g., when the syringe assembly 1402 is coupled to the connector 2200) then transmitting fluid through the connector 2200 to the second reservoir 1444 could decrease the volume of the first reservoir without enabling the proximal first passage 1416 to transmit fluid out of the first reservoir to regulate the pressure inside of the first reservoir. As a result, the pressure inside of the first reservoir could rise above atmospheric pressure (e.g., create an "over pressure").

Referring back to FIG. 40, in several embodiments, the first reservoir 1420 and the second reservoir 1444 are volumetrically independent for at least one of several reasons. The first reservoir 1420 and the second reservoir 1444 are located in separate housings (e.g., separate cylinders). Moving the plunger distally or proximally can change the volume of the second reservoir 1444, but does not necessarily change the volume of the first reservoir 1420. As discussed above, in some embodiments, the volume of the first reservoir 1420 can change when a pressure gradient causes the proximal plunger seal 1412 to move (e.g., slide) within the plunger 1404. Thus, in several embodiments, the volume of the first reservoir 1420 changes in response to pressure gradients rather than in response to changing the volume of the second reservoir 1444.

Fluidly coupling the syringe assembly 1402 to an adapter assembly 1450 and to a container can create a closed volume system. In a closed volume system, the system is sealed from ambient air such that the volume of the system is generally constant during normal operation and/or does not change (at least until the seals start leaking). In some embodiments, if the container has a fixed volume (e.g., due to rigid walls) then reducing the volume of the second reservoir 1444 will typically cause the volume of the first reservoir 1420 to increase because transmitting fluid from the second reservoir 1444 to the container can displace fluid inside the container and the displaced fluid can be transmitted into the first reservoir 1420. Similarly, if the container has a fixed volume (e.g., due to rigid walls) then increasing the volume of the second reservoir 1444 will typically cause the volume of the first reservoir 1420 to decrease because transmitting fluid from the container to the second reservoir 1444 can reduce the pressure inside the container, which can cause fluid inside the first reservoir 1420 to flow into the container to regulate pressure.

A closed volume system with a container that has a variable volume (e.g., due to flexible walls) can behave differently than a closed volume system with a container that has a fixed volume. A glass vial is an example of a container with rigid walls and a fixed volume. An IV bag is an example of a container with flexible walls and a variable volume. The volume of an IV bag can vary depending on how much fluid is transmitted into or out of the IV bag.

In some embodiments, if the container has a variable volume (e.g., due to flexible and/or compliant walls) then reducing the volume of the second reservoir 1444 will not typically cause the volume of the first reservoir 1420 to increase. This is because reducing the volume of the second reservoir 1444 does not necessarily increase the pressure inside of the first reservoir 1420. The pressure inside the first reservoir 1420 may remain generally constant (e.g., not increase)—aside from a restoring force provided by the container itself, such as the compressive restoring force of an inflated latex balloon. This is because transmitting fluid from the second reservoir 1444 to the variable volume container typically results in the volume of the container increasing, rather the pressure in the container increasing (which would tend to drive fluid from the container to the first reservoir 1420). Typically, if the pressure inside the first reservoir 1420 does not increase, then the proximal plunger seal 1412 does not need to move to regulate pressure. Accordingly, the plunger seal 1412 can remain substantially stationary (e.g., relative to the plunger body).

Similarly, if the container has a variable volume (e.g., due to flexible and/or compliant walls) then increasing the volume of the second reservoir 1444 typically will not cause the volume of the first reservoir 1420 to decrease. This is because transmitting fluid from the variable volume container to the second reservoir 1444 typically reduces the volume inside the container, not the pressure inside the container. As a result, a pressure gradient (that would otherwise drive fluid from the first reservoir 1420 to the container) is reduced or avoided.

A container with a fixed volume is configured to change in volume by 0% to 15% under normal operating conditions. For example, a glass or plastic vial does not change substantially in volume. A container with a variable volume is configured to change in volume by at least 50% under normal operating conditions. For example, an IV bag can start with a volume of approximately 10 milliliters but can expand to a volume of approximately 100 milliliters. Other IV bags have different typical expansion ranges.

A container with a fixed volume can be a variable pressure container. In other words, if the volume of the container is fixed, removing fluid from the container and adding fluid to the container can vary the gas pressure inside the container. A container with a variable volume can be a constant pressure container. In other words, if the volume of the container is variable, removing fluid from the container and adding fluid to the container typically does not substantially vary the gas pressure inside the container (unless the volume of the container reaches the container's minimum volume or maximum volume). An IV bag is an example of a constant pressure container. Although adding fluid to an IV bag can increase pressure imparted on the bag due to the fluid, adding fluid typically does not alter the pressure inside the IV bag. This is because the volume of the IV bag can increase and decrease to reach an equilibrium with atmospheric pressure.

Figure 66:
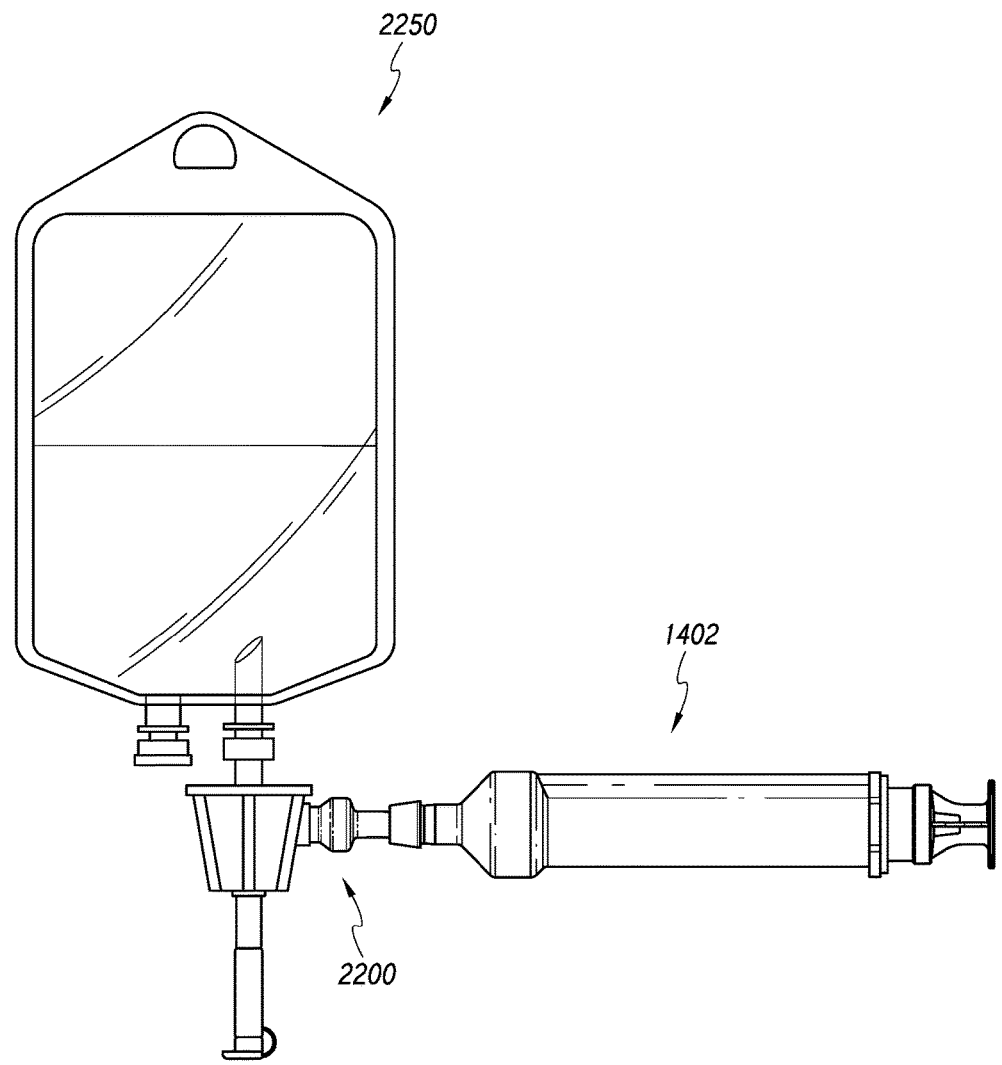
FIG. 66 illustrates a side view of a syringe assembly coupled to an IV bag.

FIG. 66 illustrates a side view of a syringe assembly 1402 coupled to an IV bag 2250. A connector 2200 can fluidly and mechanically couple the syringe assembly 1402 to the IV bag 2250. The syringe assembly 1402 can transmit fluid to and/or from the IV bag 2250. In several embodiments, the IV bag 2250 is a compliant container. The compliance of the IV bag 2250 can enable the internal pressure of at least a portion of the IV bag 2250 to be approximately equal to atmospheric pressure. In several embodiments, the syringe assembly 1402 can be configured to deliver a fluid (e.g., a liquid) from the second reservoir to an internal portion of the IV bag without reducing the pressure inside the first reservoir below atmospheric pressure, more than 5% below atmospheric pressure, more than 10% below atmospheric pressure, more than 20% below atmospheric pressure, or more than 35% below atmospheric pressure.

Some embodiments include reducing the volume of the second reservoir without reducing the volume of the first reservoir. Several embodiments include reducing the volume of the second reservoir by at least 50% without reducing the volume of the first reservoir by more than 10%. Some embodiments include reducing the volume of a liquid reservoir by at least 50% without reducing the volume of a gas reservoir by more than 10%. Several embodiments include transmitting a liquid from a syringe assembly to an IV bag without reducing (e.g., without any reduction, without substantial reduction, without more than a 10% reduction) the volume of a gas reservoir located inside of the syringe assembly. Several embodiments include transmitting a liquid to a syringe assembly from an IV bag without reducing (e.g., without any reduction, without substantial reduction, without more than a 10% reduction) the volume of a gas reservoir located inside of the syringe assembly.

Several embodiments include removing a liquid from a rigid container (e.g., a vial) and placing a gas inside of the rigid container to reduce the pressure difference between the pressure inside of the container and ambient pressure. Some embodiments include placing the liquid inside of a compliant container (e.g., a bag, an IV bag) without removing gas from inside of the compliant container.

Figure 67:
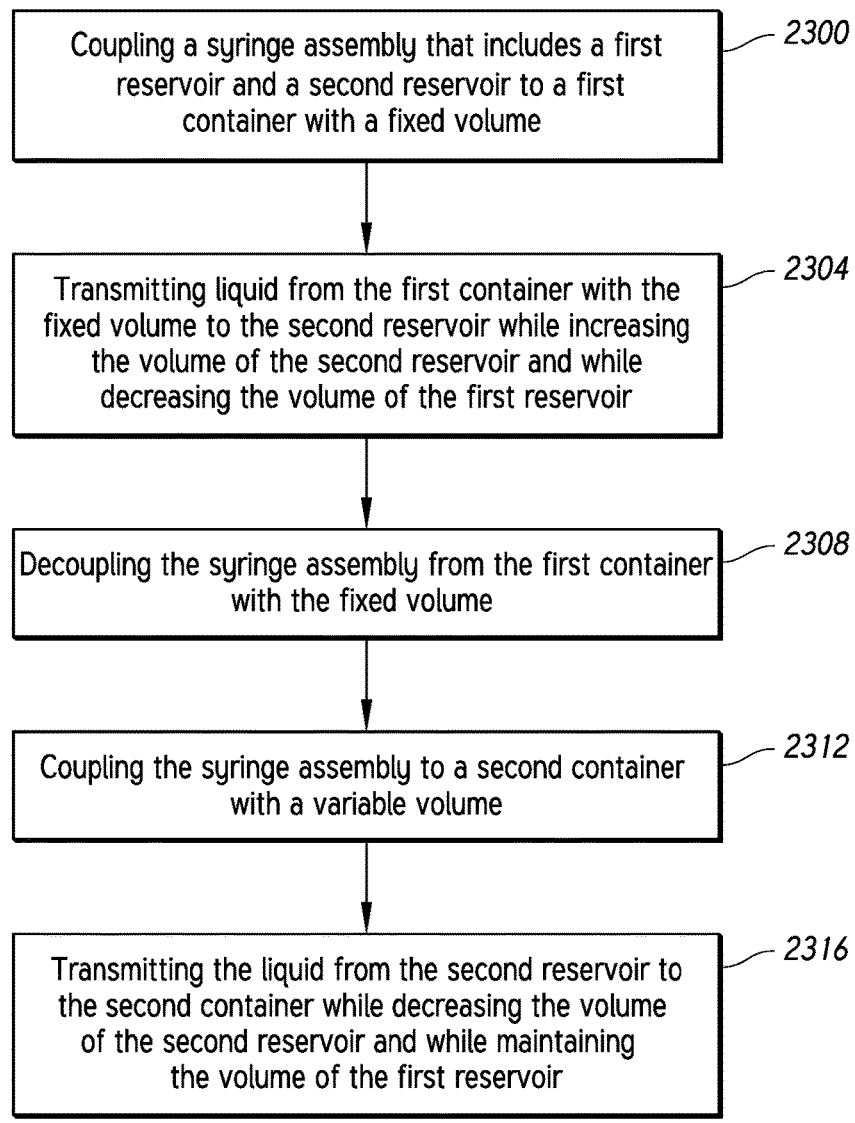
FIG. 67 illustrates a method of transferring a liquid from a first container to a second container.

FIG. 67 illustrates a method of transferring a liquid from a first container to a second container, according to several embodiments. This method can be used with any of the syringe systems, syringe assemblies, and adapter assemblies described herein. The method can include obtaining a syringe assembly with a first reservoir and a second reservoir. Block 2300 can include coupling the syringe assembly to a first container with a fixed volume. Block 2304 can include transmitting liquid from the first container with the fixed volume to the second reservoir while increasing the volume of the second reservoir and while decreasing the volume of the first reservoir. Decreasing the volume of the first reservoir can include transmitting gas from the first reservoir to the first container to regulate pressure inside the container.

Block 2308 can include decoupling the syringe assembly from the first container with the fixed volume. Decoupling can include mechanically and/or fluidly decoupling. Decoupling can include sealing a first passage in the syringe assembly that leads to the first reservoir. Decoupling can include sealing a second passage in the syringe assembly that leads to the second reservoir. Decoupling can include sealing the first passage (e.g., the gas passage) prior to sealing the second passage (e.g., the liquid passage). Decoupling can include sealing the second passage (e.g., the liquid passage) prior to sealing the first passage (e.g., the gas passage). In some embodiments, the liquid reservoir is located distally relative to the gas reservoir. In several embodiments, reservoirs can hold gas and/or liquid.

Block 2312 can include coupling the syringe assembly to a second container with a variable volume. The second container can be a bag. The first container can be a vial, such as a glass vial. Block 2316 can include transmitting the liquid from the second reservoir to the second container while decreasing the volume of the second reservoir and while maintaining the volume of the first reservoir. In several embodiments, Block 2316 is replaced with transmitting the liquid from the second reservoir to the second container while decreasing the volume of the second reservoir by at least 50% and while reducing the volume of the first reservoir by less than 10%, 20%, or 30%. In the context of replacing Block 2316, reducing the volume by less than 10%, 20%, or 30% includes not reducing the volume. In several embodiments, Block 2316 is replaced with transmitting the liquid from the second reservoir to the second container while decreasing the volume of the second reservoir by at least about 50% and/or less than or equal to about 100%; at least about 20% and/or less than or equal to about 90%; at least about 70% and/or less than or equal to about 100%; and while reducing the volume of the first reservoir by 0% and/or less than or equal to about 10%; at least about 5% and/or less than or equal to about 20%; at least about 10% and/or less than or equal to about 35%.

Figure 68:
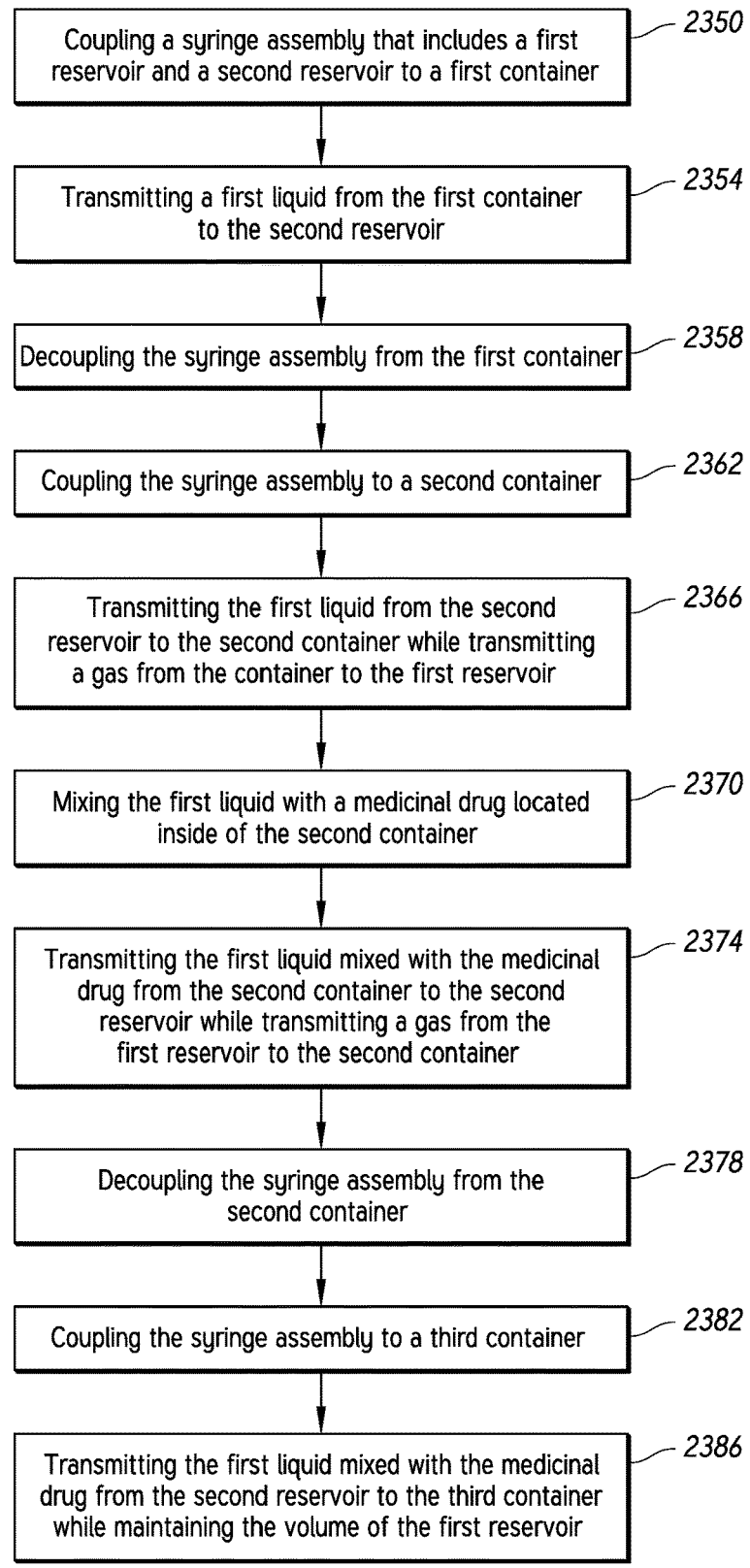
FIG. 68 illustrates a method of using a syringe assembly.

FIG. 68 illustrates a method of using a syringe assembly, according to several embodiments. This method can be used with any of the syringe systems, syringe assemblies, and adapter assemblies described herein. The method can include obtaining a syringe assembly with a first reservoir and a second reservoir. Block 2350 can include coupling a syringe assembly to a first container. Coupling can include mechanically and/or fluidly coupling.

Block 2354 can include transmitting (e.g., withdrawing) a first liquid from the first container to the second reservoir. The first liquid can be, for example, a saline solution, a sodium chloride solution, and/or sterile water. Some embodiments include transmitting a first liquid from the first container to the second reservoir while maintaining the volume of the first reservoir (e.g., in embodiments where the first container has a variable volume). Some embodiments include transmitting a first liquid from the first container to the second reservoir while reducing the volume of the first reservoir (e.g., in embodiments where the first container has a fixed volume).

Block 2358 can include decoupling the syringe assembly from the first container. Decoupling can include mechanically and/or fluidly decoupling. Block 2362 can include coupling the syringe assembly to a second container. The second container can contain a drug, a pharmaceutical, a pharmaceutical agent, and/or medicine. The drug, pharmaceutical, pharmaceutical agent, and/or medicine can be in powder form such that it can be reconstituted with a diluent prior to being administered to a patient. The diluent can be a saline solution and/or sterile water. The drug can be in a dry, freeze-dried, dehydrated, and/or lyophilized form.

As shown in FIG. 68, Block 2366 can include transmitting (e.g., introducing) the first liquid from the second reservoir to the second container. In some embodiments, (e.g., where the second container has a fixed volume) Block 2366 can include transmitting the first liquid from the second reservoir to the second container while transmitting a gas from the container to the first reservoir. In some embodiments, (e.g., where the second container has a variable volume) Block 2366 can include transmitting the first liquid from the second reservoir to the second container while maintaining the volume of the first reservoir (e.g., without changing the volume of the first reservoir).

Block 2370 can include mixing at least a portion of the first liquid with at least a portion of a drug, a pharmaceutical, a pharmaceutical agent, and/or medicine located inside of the second container. Block 2374 can include transmitting (e.g., withdrawing) at least a portion of the first liquid mixed with at least a portion of the medicinal drug from the second container to the second reservoir while transmitting a gas from the first reservoir to the second container. Block 2378 can include decoupling the syringe assembly from the second container. Block 2382 can include coupling the syringe assembly to a third container, which can be a container with a fixed volume or a variable volume. In several embodiments, the third container is a bag, such as an IV bag.

Block 2386 can include transmitting (e.g., introducing) at least a portion of the first liquid mixed with at least a portion of the medicinal drug from the second reservoir to the third container while maintaining the volume of the first reservoir. In some embodiments, Block 2386 is replaced with transmitting the first liquid mixed with the medicinal drug from the second reservoir to the third container while reducing the volume of the second reservoir by at least 50% and while reducing the volume of the first reservoir by less than 10%. In some embodiments, Block 2386 is replaced with transmitting the first liquid mixed with the medicinal drug from the second reservoir to the third container while reducing the volume of the second reservoir by at least 90% and while reducing the volume of the first reservoir by less than 5%. In some embodiments, Block 2386 is replaced with transmitting the first liquid mixed with the medicinal drug from the second reservoir to the third container without transmitting gas from the third container to the first reservoir. In some embodiments, Block 2386 is replaced with transmitting the first liquid mixed with the medicinal drug from the second reservoir to the third container without creating a vacuum in the first reservoir. In some embodiments, Block 2386 is replaced with transmitting the first liquid mixed with the medicinal drug from the second reservoir to the third container without reducing the pressure inside of the first reservoir to less than 90% of atmospheric pressure, to less than 80% of atmospheric pressure, or to less than 70% of atmospheric pressure.

FIGS. 69-74 illustrate the syringe assembly 1402 and the adapter assembly 1450 described previously in the context of FIGS. 29-41. The steps, methods, benefits, and features described in the context of FIGS. 69-74 can apply to any other syringe assemblies, adapter assemblies, and pressure regulating syringe systems described herein. Some items are not labeled in FIGS. 69-74 to the interest of clarifying certain items. Many structures, steps, and/or methods illustrated and/or described in connection with other embodiments herein are the same as or similar to those in the embodiment of FIGS. 69-74 (e.g., the adapter assembly 1450 and barrel passage 1416), and any structure, step, and/or method illustrated and/or described in other embodiments herein can be used in addition to or instead of those shown in FIGS. 69-74. As shown in various of these figures, the syringe assembly 1402 and the adapter assembly 1450, as well as a container, can be inverted to facilitate fluid transfer.

Figure 69:
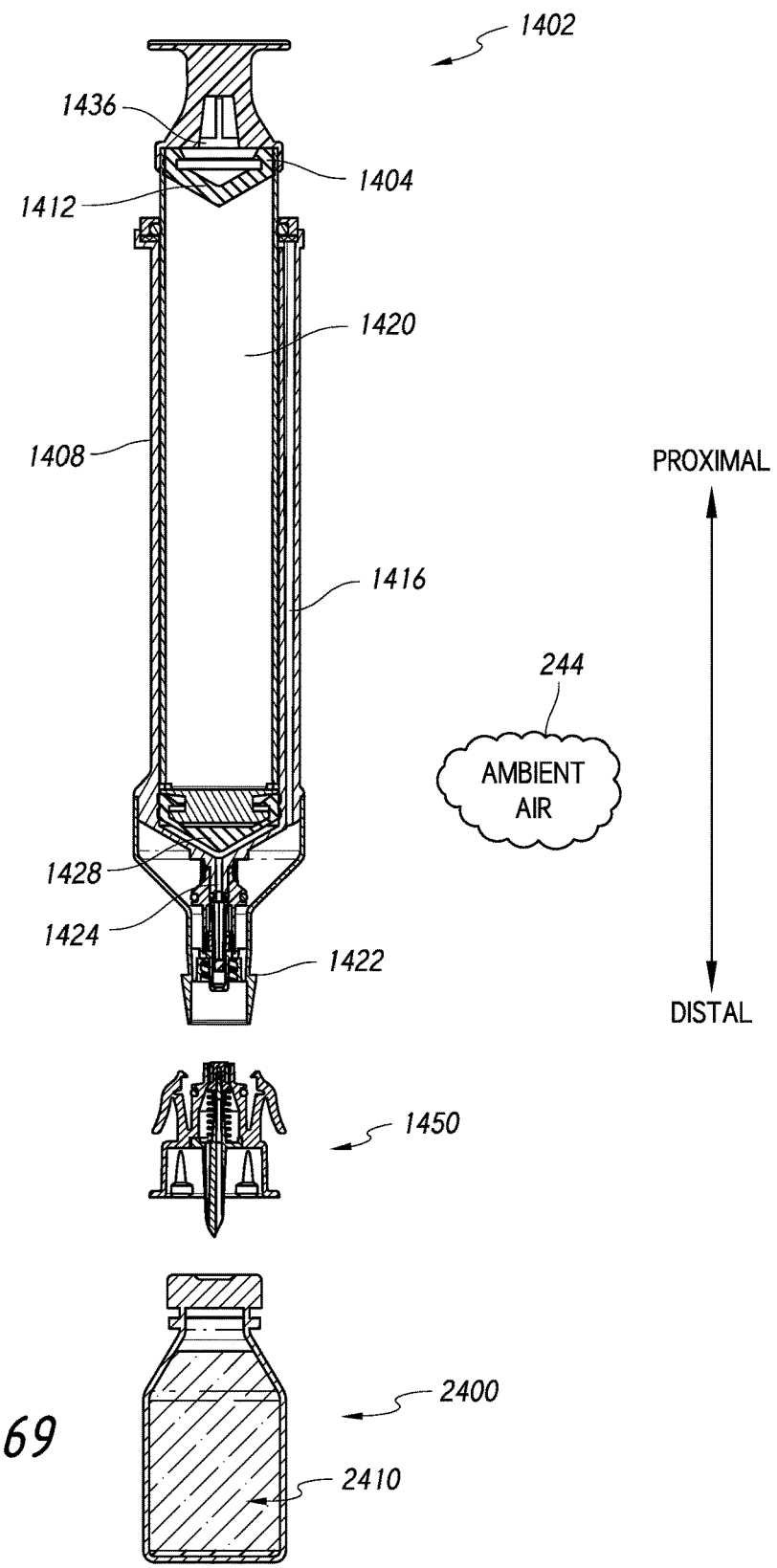
FIG. 69 illustrates a cross-sectional, side view of a syringe assembly, an adapter assembly, and a first container in an uncoupled configuration.

FIG. 69 illustrates a cross-sectional view of the syringe assembly 1402, the adapter assembly 1450, and a first container 2400. For purposes of presentation, the syringe assembly 1402, the adapter assembly 1450, and the first container 2400 are not coupled to each other in FIG. 69. In some embodiments, as illustrated, the system for transferring fluids to or from a container includes only two components: the syringe assembly 1402 and the adapter assembly 1450, and no other additional or intervening adapters or connectors are required. In some embodiments, the fluid connection between the syringe assembly and the adapter assembly 1450 can be accomplished by way of an industry standard connection. For example, the syringe can includes an ISO-594 fluid-transferring male luer and the adapter assembly 1450 can include an ISO-594 fluid transferring female luer-receiver. In some embodiments, the fluid connection between the syringe assembly and the adapter assembly 1450 can be accomplished by a non-standard fluid connection, such as when it is desirable to avoid unintentionally infusing fluid into a fluid line on a patient that is not suited for the type of therapeutic fluid within the syringe assembly.

The first container 2400 can contain a liquid 2410, such as a diluent, a reconstitution liquid, a saline solution, water, sterilized water, a liquid medication, and/or a liquid configured to be mixed with a drug, such as a powdered or lyophilized drug. In some embodiments, the first container 2400 is a vial or a bag with a liquid. The first container 2400 can have a fixed volume or a variable volume.

The syringe assembly 1402 can include a plurality of different stages, which the syringe assembly 1402 can transition between or among. For example, the syringe assembly can be in a first stage, such as an initial stage. In some embodiments, in the first stage, the syringe assembly contains gas (e.g., sterilized gas) but essentially no liquid (little or no liquid). The syringe assembly can be in a second stage. The second stage can be a diluents-filling stage. The syringe assembly can be in a third stage, such as a diluents-expelling stage. The syringe assembly can be in a fourth stage, such as a drug-filling stage. The syringe assembly can be in a fifth stage, such as a drug-expelling stage. Any of the stages can be omitted and/or other stages can be included. For example, one or more stages can be omitted and/or modified if the drug to be administered to the patient need not be diluted or mixed during these stages. In some embodiments, the stages can be numbered different and/or performed in a different order.

In FIG. 69, the proximal plunger seal 1412 is located in the first stage. In the example shown, the ambient portion 1406 (see FIG. 70) has a de minimis volume (e.g., essentially zero or close to zero) that is too small to easily see in the example of FIG. 69. As illustrated, the first and second reservoirs 1420, 1444, and the ambient portion 1406 are bounded on one or more sides by the plunger seals 1412, 1428. In some embodiments (e.g., those without a proximal plunger seal 1412), the first and second reservoirs 1420, 1444, and/or the ambient portion 1406 can be structured, formed, and/or bounded in many other ways. For example, the reservoirs 1420, 1444 can be bounded with one or more bags, balloons, enclosures, selectively accessible chambers, expanding or contracting chambers, and/or sliding chambers, etc.

The first reservoir 1420 can extend inside the plunger between the proximal plunger seal 1412 and the distal plunger seal 1428. In some implementations, the first reservoir 1420 contains a gas, such as sterilized gas or sterilized air. In some embodiments, during manufacturing, the proximal plunger seal 1412 is located distal of its most proximal position. This can provide room for the gas inside the first reservoir 1420 to expand, such as during shipping. The proximal plunger seal 1412 is configured to slide within an inner channel of the plunger 1404 while maintaining a seal against an inner wall of the inner channel. In some embodiments, the first reservoir 1420 in the first stage can include the volume of the inner channel from a distal end of the inner channel to the distal side of the proximal plunger seal 1412.

FIGS. 69-74 depict, among other things, how the proximal plunger seal 1412 can slide to different positions inside of the inner channel of the plunger 1404. The proximal plunger seal 1412 can seal against the walls of the inner channel. For example, the proximal plunger seal 1412 can slidingly seal against the inner diameter of the interior wall of the plunger 1404. In certain circumstances, the proximal plunger seal 1412 moves relative to the plunger 1404 and/or is substantially stationary relative to the barrel 1408. For example, this can occur when fluid is exchanged between the syringe assembly 1402 and a rigid container, such as a glass vial. In certain circumstances, the proximal plunger seal 1412 moves relative to the barrel 1408 and/or is substantially stationary relative to the plunger 1404. For example, this can occur during a fluid transfer operation when the syringe assembly 1402 is connected with a flexible container, such as an IV bag. These circumstances are discussed in more detail further below.

In FIG. 69, the plunger 1404 is located in the first stage, such as its most distal position or distal region of the barrel 1408. In the example shown, the second reservoir 1444 (see FIG. 70) has a de minimis volume (essentially zero or close to zero) that is too small to easily see in the example of FIG. 69 because the distal plunger seal 1428 is in contact with a distal portion of the barrel 1408. The distal plunger seal 1428 need not be in contact with the distal portion of the barrel 1408 in the first stage. The barrel 1408 can include an inner channel in which the plunger 1404 is configured to slide. In some embodiments, the second reservoir 1444 can include the distal portion of the inner channel of the barrel 1408, distal from the distal plunger seal 1428 (see FIG. 70).

Figure 70:
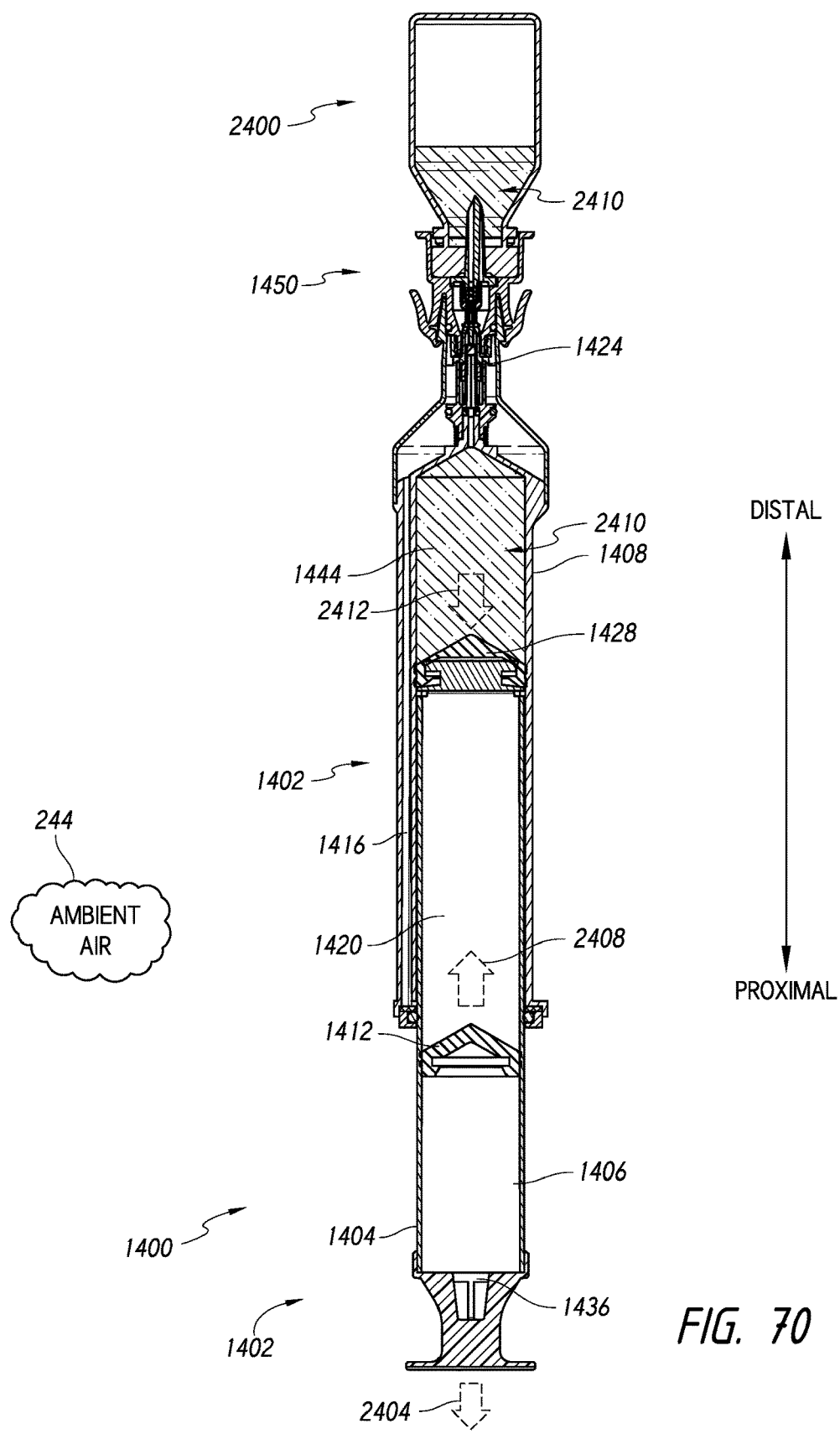
FIG. 70 illustrates a cross-sectional, side view of the adapter assembly coupled to the syringe assembly and coupled to the first container from FIG. 69.

FIG. 70 illustrates a cross-sectional view of the adapter assembly 1450 coupled to the syringe assembly 1402 and coupled to the first container 2400. For example, the first container can include a diluent, such as saline. The second reservoir 1444 can be the portion of the inner channel of the barrel 1408 located between the distal plunger seal 1428 and the distal end of the inner channel.

In the second stage, the plunger 1404 is moved in a proximal direction, as indicated by a dashed arrow 2404. Moving the plunger 1404 proximally causes the distal plunger seal 1428 to move proximally, as indicated by a dashed arrow 2412. The second reservoir 1444 expands in volume, which causes fluid (e.g., the liquid 2410) from the first container 2400 to move through a second passage of the adapter assembly 1450 and into the second reservoir 1444, and generally simultaneously, the proximal plunger seal 1412 moves distally, the first reservoir 1416 contracts in volume, and/or the ambient portion 1406 expands in volume, which in some embodiments all occurs automatically, without any further adjustment or movement by the user. As illustrated, the apparatus can be inverted to facilitate movement of the liquid 2410 into the second reservoir 1444.

If the first container 2400 has a fixed volume, removing fluid from the first container 2400 reduces the pressure inside of the first container 2400 and causes gas located inside of the first reservoir 1420 to regulate pressure inside of the first container 2400. The system can regulate pressure by transmitting gas from the first reservoir 1420 through a first passage via the adapter assembly 1450 and into the first container 2400 until the difference between atmospheric pressure and the pressure inside of the first container 2400 is reduced and/or eliminated. Transmitting gas from the first reservoir 1420 to the first container 2400 can make the proximal plunger seal move in a distal direction, as indicated by a dashed arrow 2408. The volume of the first reservoir 1420 can be reduced when the proximal plunger seal 1412 moves distally. In some embodiments, as illustrated, the first fluid reservoir 1420 and the second fluid reservoir 1444 are fluidly separated from each other, and not in fluid communication with each other, at least not by way of the syringe 1402. The contents of each reservoir 1420, 1444 may be in fluid communication with each other by way of a container to which the syringe is attached.

In some embodiments, the system can regulate pressure by transmitting gas from the first reservoir 1420 and/or to the first reservoir 1420 until the pressure inside of the first container 2400 is within about +/−3% of atmospheric pressure, within about +/−5% of atmospheric pressure, within about +/−10% of atmospheric pressure, within about +/−25% of atmospheric pressure, or within about +/−50% of atmospheric pressure. In several embodiments, the system will regulate pressure inside of the container when the pressure inside of the container is more than about 105% of atmospheric pressure, more than about 115% of atmospheric pressure, more than about 125% of atmospheric pressure, or more than about 150% of atmospheric pressure; and/or will stop regulating pressure when the pressure inside of the container is less than about 135% of atmospheric pressure, less than about 120% of atmospheric pressure, less than about 110% of atmospheric pressure, or less than about 105% of atmospheric pressure. In several embodiments, the system will regulate pressure inside of the container when the pressure inside of the container is less than about 95% of atmospheric pressure, less than about 85% of atmospheric pressure, less than about 75% of atmospheric pressure, or less than about 50% of atmospheric pressure; and/or will stop regulating pressure when the pressure inside of the container is less than about 65% of atmospheric pressure, less than about 80% of atmospheric pressure, less than about 90% of atmospheric pressure, or less than about 95% of atmospheric pressure. In several embodiments, the pressure threshold that starts pressure regulation is different than the pressure threshold that stops pressure regulation.

In some embodiments, the difference between the pressure inside of the container and atmospheric pressure (e.g., the pressure of the ambient air) can be greater to start pressure regulation than to stop pressure regulation. For example, a pressure difference of 3 pounds per square inch ("psi") can be necessary to start pressure regulation and pressure regulation can stop when there is a pressure difference of 1 psi.

If the first container 2400 has a variable volume, removing fluid from the first container 2400 will not necessarily reduce the pressure inside of the first container 2400. For example, the first container 2400 could be a compliant bag that can increase and reduce its volume as necessary to regulate pressure inside of the first container 2400. Thus, if the first container 2400 has a variable volume, then removing fluid from the first container 2400 does not necessarily cause gas located inside of the first reservoir 1420 to regulate pressure inside of the first container 2400. As a result, the proximal plunger seal 1412 might not move and the volume of the first reservoir 1420 might not change. In some embodiments, the configuration and ordering of one or more of these steps could be different or omitted.

The adapter assembly 1450 can be mechanically and fluidly decoupled from the first container 2400 while the second reservoir 1444 holds a liquid. The adapter assembly 1450 can then be coupled to another container, such as a container with a drug that needs to be mixed with the liquid that was drawn into the syringe assembly 1402 in the first stage, such as concentrated liquid drug, a powdered drug, a lyophilized drug, and/or a lyophilized pharmaceutical.

Figure 71:
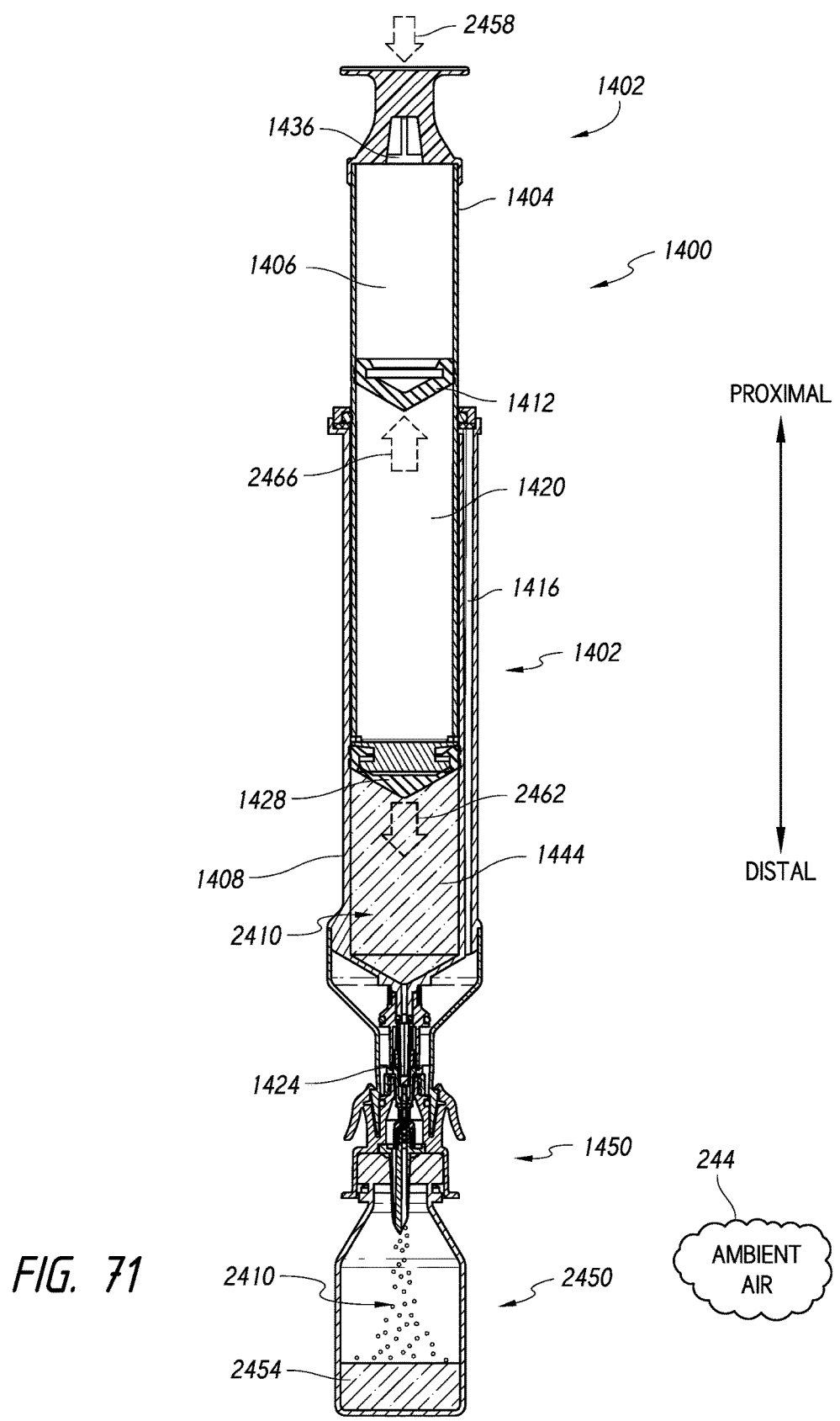
FIG. 71 illustrates a cross-sectional, side view of the adapter assembly coupled to the syringe assembly and coupled to a second container.

FIG. 71 illustrates a cross-sectional view of the adapter assembly 1450 coupled to the syringe assembly 1402 and coupled to a second container 2450. As shown, the second container 2450A can include a concentrated or reconstitutable medication 2454, such as a liquid drug concentrate, powdered drug, lyophilized drug, and/or a lyophilized pharmaceutical. In a third stage, the plunger 1404 is moved in a distal direction (as indicated by an arrow 2458). This can push the distal plunger seal 1428 in a distal direction (as indicated by an arrow 2462), which can push (e.g., transmit or expel) the liquid 2410 located inside of the second reservoir 1444 through a second passage via the adapter assembly 1450 and into the second container 2450. This can facilitate mixing of the some or all of the liquid 2410 and the concentrated or reconstitutable medication 2454. The liquid 2410 transmitted or expelled from the syringe assembly 1402 can be used to dilute or reconstitute the concentrated or reconstitutable medication 2454 to form a pharmaceutical liquid that can be administered to a patient, either directly (e.g., via an venous access port) or indirectly (e.g., via an IV bag of saline connected with a patient). For example, the transmitted or expelled liquid 2410 can reconstitute a powdered drug or lyophilized pharmaceutical, or can dilute a concentrated drug in the second container 2450. In some embodiments, as the distal plunger seal 1428 moves distally, the second reservoir 1444 decreases or contracts in volume, the first reservoir 1420 increases or expands in volume, and/or the ambient portion 1406 decreases or contracts in volume, all generally simultaneously, and all automatically, without any further adjustment or movement by the user.

Several embodiments include injecting and/or transmitting a liquid from the syringe assembly 1402 into the second container 2450. In some embodiments (e.g., where the second container 2450 has a fixed volume), "overpressure" could result inside of the second container 2450 (because additional matter is added to the second container 2450) unless the syringe system 1402 and/or adapter assembly 1450 regulates pressure inside of the second container 2450, such as by permitting gas (e.g., air and/or vapors) to escape. If the pressure inside of the second container rises above a certain threshold (e.g., relative to atmospheric pressure), gas from the second container 2450 can flow through a first passage (via the adapter assembly 1450) and into the first reservoir 1420. The gas from the second container 2450 can contain harmful drug vapors and/or fumes. In some embodiments, the first reservoir 1420, the syringe assembly 1402, the adapter assembly 1450, and/or the second container 2450 can form a closed system that prevents gas from the second container 2450 from mixing with the ambient air 244. Gas flowing into the first reservoir 1420 can cause the proximal plunger seal 1412 to move (e.g., slide) proximally relative to the plunger 1404 to enlarge the volume of the first reservoir 1420. This movement (indicated by an arrow 2466) of the proximal plunger seal 1412 can reduce the volume of the ambient portion 1406 (which can be a third reservoir fluidly coupled to ambient air via a vent 1436). In some embodiments, the ambient portion 1406 can be at least partially bounded by a vent 1436 and plunger seal 1412. In some embodiments, the ambient portion 1406 can be further bounded by an inner surface of the plunger 1404.

Figure 72:
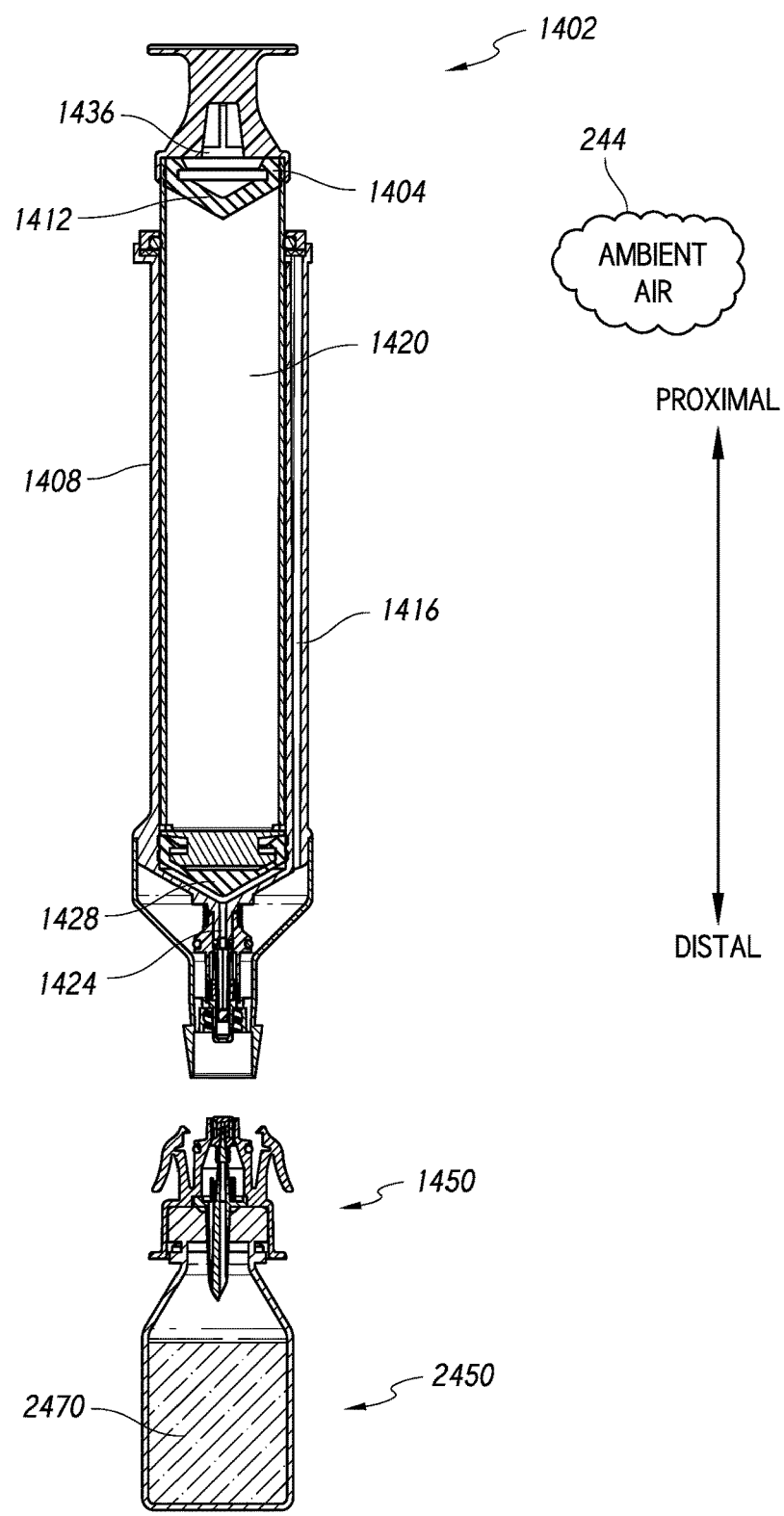
FIG. 72 illustrates a cross-sectional, side view of the adapter assembly disconnected from the syringe assembly after the syringe assembly has injected liquid into the second container.

FIG. 72 illustrates a cross-sectional view of the adapter assembly 1450 disconnected from the syringe assembly 1402 after the syringe assembly 1402 has injected liquid into the second container 2450. The adapter assembly 1450 is coupled to the second container 2450, although in some embodiments, the adapter assembly 1450 is disconnected from the second container 2450.

As shown, the second container 2450 can be at least partially filled with a liquid pharmaceutical, liquid drug, and/or liquid medicine 2470. The medicine 2470 can have been formed by combining the concentrated or reconstitutable medication 2454 with the liquid 2410 that was transmitted or expelled from the second reservoir 1444. Some embodiments include shaking, moving, and/or agitating the second container 2450 to facilitate dilution, reconstitution, and/or mixing of the medication 2454 with the liquid 2410. The second container 2450 can be coupled to or uncoupled from the adapter assembly 1450 and/or the syringe assembly 1402 during the shaking, moving, agitating, reconstituting, and/or mixing. For example, as shown, the syringe assembly 1402 can be decoupled from the vial adaptor 1450, thereby facilitating shaking of the vial adaptor 1450 and the second container 2400.

In some embodiments, at or near the end of the third stage, the volumes inside the ambient portion 1406 and/or the second reservoir 1444 are de minimis (e.g., essentially zero or close to zero). For example, in some embodiments such as the embodiment illustrated in FIG. 72, either or both of these volumes are too small to easily see in FIG. 72 (and thus are not shown). Essentially all of the liquid in the second reservoir 1444 has been transferred to an internal portion of the second container 1450 and the first reservoir 1420 was filled with gas (e.g., from the second container 2450). In some embodiments, depending on the relative volumes of the syringe assembly 1402 and the container 2450, the volumes of either or both of the ambient portion 1406 and the second reservoir 1444 may still be substantial at the end of the third stage.

Figure 73:
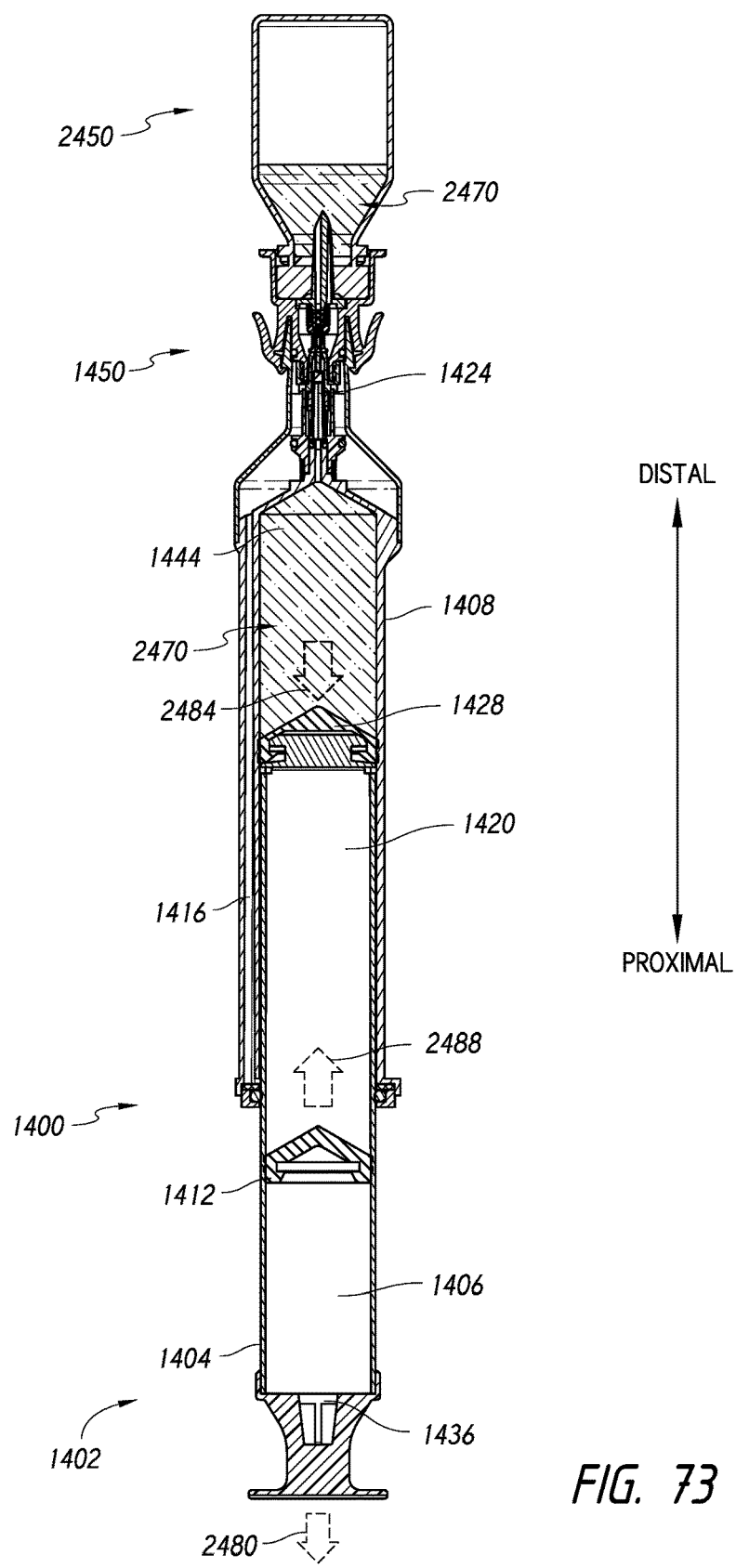
FIG. 73 illustrates a cross-sectional, side view of withdrawing the liquid pharmaceutical from the second container into the second reservoir.

As shown in FIG. 73, the syringe assembly 1402 can be in fluid communication with the second container 2450. For example, if the syringe assembly 1402 had been decoupled from the vial adaptor 1450 (see FIG. 72), it can be recoupled with the vial adaptor 1450, as illustrated. As also shown, during a fourth stage, the liquid pharmaceutical 2470 can be transferred (e.g., withdrawn) from the second container 2450 to the second reservoir 1444 of the syringe assembly 1402. For example, in certain variants, pulling or otherwise moving the plunger 1404 in a proximal direction (as indicated by an arrow 2480) causes the distal plunger seal 1428 to move (e.g., slide) in a proximal direction (as indicated by an arrow 2484). Such movement of the distal plunger seal 1428 can enlarge the volume of the second reservoir 1444, thereby decreasing the pressure in that space. This can draw at least a portion of the liquid pharmaceutical 2470 in the second container 2450 (e.g., vial) into the second reservoir 1444. In several implementations, the liquid pharmaceutical 2470 includes a liquid drug and/or a liquid medicine. As illustrated, the apparatus can be inverted to facilitate transfer of the liquid pharmaceutical 2470 into the second reservoir 1444.

In several implementations, gas from the first reservoir 1420 can flow through the proximal first passage 1416, through a portion of the adapter assembly 1450, and into an internal portion of the second container 2450. This can facilitate regulating and/or generally equalizing the pressure inside of the second container 2450 (e.g., reducing the difference between atmospheric pressure and the gas pressure inside of the second container 2450). In some embodiments, the volume amount of gas that flows from the first reservoir 1420 to the second container 2450 is proportional (e.g., substantially equal) to the amount of volume change of the second reservoir 1444. In various embodiments, as gas flows from the first reservoir 1420 to the second container 2450, the volume of the first reservoir 1420 decreases. This can reduce or substantially eliminate any pressure differential between the first reservoir 1420 and the surrounding atmospheric pressure. In some embodiments, the volume of the first reservoir 1420 is reduced by moving (e.g., sliding) the distal plunger seal 1412 proximally (as indicated by an arrow 2484). In certain variants, the volume of the first reservoir 1420 is reduced by moving (e.g., sliding) the proximal plunger seal 1412 distally (as indicated by an arrow 2488) with respect to the plunger 1404. In some embodiments, reducing the volume of the first reservoir can include reducing the volume of a bag in which the first reservoir is located.

As shown in FIG. 73, in some implementations, the plunger 1404 can be pulled or otherwise moved proximally. This can allow the second reservoir 1444 to expand to and/or contain a volume that is equal to substantially the inside volume of the barrel 1408. In some implementations, the plunger 1404 is moved proximally until the distal plunger seal 1428 is at or near a proximal end of the barrel 1408 and/or near or in abutment with the proximal plunger seal 1412. This can result in a maximum volume for the second reservoir 1444. In certain variants, when fluid is transferred between the second container 2450 (e.g., a generally constant volume container) and the second reservoir 1444, the proximal plunger seal 1412 remains substantially stationary relative to the barrel 1408.

In various embodiments, the syringe assembly 1402 can be decoupled from the adapter assembly 1450 and/or the second container 2450. In some implementations, the syringe assembly 1402 can be coupled to a medical connector, such as the connector 2200 shown in FIGS. 62-65. The connector 2200 can be coupled with a container (not shown), such as a bag (e.g., the IV bag 2250 shown in FIG. 66), port, or other medical fluid access location. In certain variants, the container is flexible or resilient, has a variable volume, and/or is not a rigid container. In some implementations, the pressure of the inside and/or outside of the container is at about ambient pressure (or atmospheric pressure). In several embodiments, the container can expand and contract as fluid is added into and withdrawn from the container. In certain embodiments, the medical connector or the container is in fluid communication with a patient's bloodstream.

In various implementations, in a fifth stage, the syringe assembly 1402 can transfer some or substantially all of the fluid (e.g., the liquid pharmaceutical 2470) in the second reservoir 1444 to the container. In certain variants, the plunger 1404 can be moved distally, thereby moving the distal plunger seal 1428 distally as well. This can decrease the volume of the second reservoir 1444, thereby increasing the pressure therein. This can encourage fluid (e.g., the liquid pharmaceutical 2470) from the second reservoir 1444 to flow through the connector 2200 and into the container.

When the connector 2220 is connected to a container that is rigid and/or has a constant volume (e.g., a glass vial), then the flow of liquid from the second reservoir 1444 can tend to increase the pressure of the container, since the flow of liquid into the container has added material to the contents to the rigid container, but the volume of the rigid container has not changed. As previously described, some embodiments are configured to reduce or avoid such a pressure increase by allowing some of the contents of the container (e.g., regulating fluid, such as gas) to flow from the container into the first reservoir 1420. In some embodiments, such a transfer of regulating fluid approximately offsets the amount of liquid added to the container, which can result in the pressure of the rigid container being substantially unchanged.

In various embodiments, the transfer of fluid into and out of the syringe assembly (regulating gas into or out of first reservoir and liquid out of or into the second reservoir) maintains a substantially equal volume between the first and second reservoirs. In some embodiments, such transfer of fluid maintains a substantially equal pressure in the reservoirs. For example, the pressure can be maintained as substantially ambient pressure. This can reduce or avoid a pressure gradient between ambient and the first reservoir during the fluid transfer operation. Thus, as the plunger 1404 is moved relative to the barrel 1408 during a fluid transfer operation between the syringe assembly 1404 and a rigid container 2400, the proximal plunger seal 1412 can slide within (e.g., move relative) to the plunger 1404 and/or be substantially stationary relative to the barrel 1408.

When the connector 2220 is connected to a flexible or resilient container (e.g., a container with a non-constant volume, such as an IV bag), or to a medical connector in fluid communication with a patient's bloodstream, then the flow of liquid from the second reservoir 1444 may tend to not significantly affect the pressure in the container, at least not until the container reaches an expansion limit. This is because the volume of the container, or of the patient's bloodstream, can change as fluid is added or removed. In some implementations, when liquid is added into the flexible container from the second reservoir 1444, the flexible container can expand an amount to substantially offset the addition, thereby keeping the pressure in the container substantially unchanged. In some implementations, the total volume of the second reservoir 1444 and the flexible container is about constant.

As discussed above (e.g., in connection with FIGS. 69-73), in one or more previous stages, the liquid pharmaceutical 2470 can be loaded into the second reservoir 1444. In some embodiments, during such loading, the plunger 1404 is moved proximally until the distal plunger seal 1428 is at or near a proximal end or proximal region of the barrel 1408 and/or near or in abutment with the proximal plunger seal 1412. After the syringe assembly 1402 is coupled with the connector 2220 and the connector 2200 is coupled with a variable-volume container (e.g., an IV bag), the plunger 1404 can be pushed distally in the fifth stage. The fifth stage can also be performed to transfer liquid from the second reservoir to a container that has a fixed or substantially fixed volume. The liquid transfer during the fifth stage can move the distal plunger seal 1428 distally as well, thereby encouraging the liquid pharmaceutical 2470 from the second reservoir 1444 to flow through the connector 2200 and into the flexible container. In some embodiments, distal movement of the plunger 1404 and/or the distal plunger seal 1428 tends to increase the volume of the first reservoir 1420. This can decrease the pressure in the first reservoir 1420, generally simultaneously and without further adjustment or movement by the user.

In some instances, the decrease in pressure in the first reservoir 1420 is generally offset by transferring a corresponding amount of regulating fluid from the container to the first reservoir 1420. However, in certain instances, the flexible container may not include a sufficient amount of (or any) regulating fluid (e.g., air or other gas). For example, some IV bags are formed from substantially flat, multilayer sheets that are attached along their peripheral edges, and such IV bags may include little or no internal volume in an initial empty, flat state (with essentially no gas inside or less gas than the amount of liquid desired to be added into the IV bag). The IV bag may be configured to expand its internal volume in a later state. In some configurations, the orientation of the syringe assembly 1402 and the flexible container may inhibit or prevent regulating fluid from being transferred to the first reservoir 1420. For example, in orientations in which the syringe assembly 1402 is generally inverted and/or positioned below the container, gas (that could serve as regulating fluid) in the container may rise toward the top of the container, and thus away from the syringe assembly 1402.

In certain embodiments, the syringe assembly 1402 can be configured to allow the plunger 1404 to be depressed and/or liquid to be transferred from the second reservoir 1444 to the flexible container with none or substantially no regulating fluid being transferred from the flexible container into the first reservoir 1420. This can reduce the likelihood of a pressure differential forming (e.g., between the first and second reservoirs 1420, 1444 and/or between one or both of the reservoirs 1420, 1444 and the surrounding environment). Such a pressure differential could otherwise inhibit a user's ability to further depress the plunger and/or to transfer liquid to the flexible container. Such a pressure differential could produce a proximally directed force on the plunger as the liquid in the second reservoir 1444 is being expelled. This could require a user to restrain the plunger to avoid sucking back into the second reservoir 1444 the liquid that was just expelled, or it could even require an ambient air inlet leading into the first reservoir 1420, which could possibly introduce ambient contaminants into the system and/or permit the escape of harmful liquid or vapors from the system into ambient.

In certain embodiments, as illustrated, the total combined volume of the first and second reservoirs 1420, 1444 is variable, and is not required to be constant during use. This can facilitate maintaining approximately equal pressure in the first and second reservoirs 1420, 1444 without requiring a flow of regulating fluid in the container. In some embodiments, when the plunger 1404 is moved distally, the volume of the second reservoir 1444 decreases. As discussed in more detail below, in some embodiments, the volume of the first reservoir 1420 can remain substantially constant when the syringe assembly 1402 is transferring fluid to a flexible container. Thus, the total volume of the first and second reservoirs 1420, 1444 can change (e.g., decrease). In various embodiments, the volume of the first reservoir 1420 changes as a function of the amount of longitudinal movement of the proximal plunger seal 1412 relative to the plunger 1404. The change can be linear, exponential, or otherwise.

As noted above, the first reservoir 1420 can be configured to have a generally constant volume in one or more stages, such as in a stage when regulating fluid is not transferred into the first reservoir 1420. In certain embodiments, the proximal plunger seal 1412 and the distal plunger seal 1428 are the respective proximal and distal ends of the first reservoir 1420. When the plunger 1404 and the distal plunger seal 1428 are moved distally, but the proximal plunger seal 1412 remains generally static (at least with respect to the syringe barrel 1408), the volume of the first reservoir 1420 is increased. In such situations, when regulating fluid is not transferred into the first reservoir 1420, the pressure in the first reservoir 1420 decreases. This pressure gradient can cause the proximal plunger seal 1412 to move distally by the pressure of the atmosphere acting on an external surface of the proximal plunger seal 1412 (e.g., via the vent 1436).

In certain implementations, the proximal plunger seal 1412 moves a sufficient distal distance to offset the distal movement of the distal plunger seal 1428. In some variants, the proximal plunger seal 1412 moves a sufficient distance to maintain a generally constant volume of the first reservoir 1420, while the total combined volume of the first and second reservoirs 1420, 1444 decreases (e.g., because the volume of the second reservoir 1444 decreases). In various embodiments, when the syringe assembly 1404 is connected with a flexible container 2400 and the plunger 1404 is moved relative to the barrel 1408, the proximal plunger seal 1412 moves relative to the barrel 1408 and/or is substantially stationary relative to the plunger 1404. In some implementations, the proximal plunger seal 1412 moves relative to both the plunger 1404 and the barrel 1408.

Typically, the first reservoir 1420, the second reservoir 1444, the inside of the flexible container (e.g., an IV bag), and/or the surrounding environment are each at about atmospheric pressure, or each at about the same pressure, without requiring ambient air to be introduced into the first reservoir 1420 and/or without requiring ambient air to be in fluid communication with the first reservoir 1420. In some embodiments, when the plunger 1404 is moved distally, liquid is transferred from the second reservoir 1444 into the flexible container, which causes the flexible container to expand, thereby maintaining about atmospheric pressure in the second reservoir 1444 and the flexible container. In some embodiments, when the plunger 1404 is moved distally, the pressure of the surrounding environment causes the proximal plunger seal 1412 to move distally as well, thereby maintaining about atmospheric pressure in the first reservoir 1420, while the first reservoir 1420 is sealed from ambient air.

In various embodiments, during transfer of liquid from the second reservoir 1444 into the flexible container, the proximal plunger seal 1412 moves with the plunger 1404, generally in tandem at about the same time. For example, the position of the proximal plunger seal 1412 with respect to the plunger 1404 and/or the distal plunger seal 1428 can be substantially constant during such liquid transfer.

Figure 74:
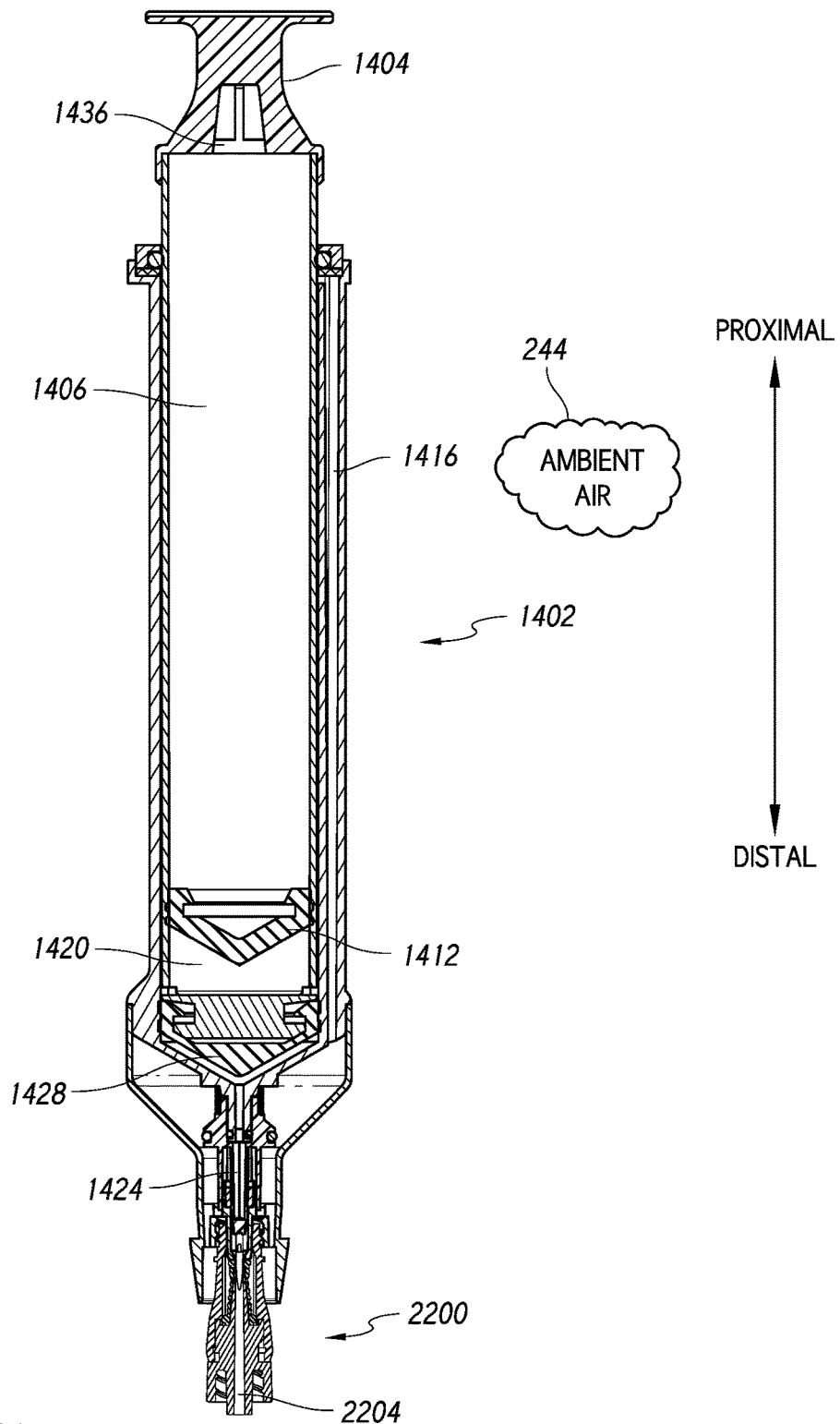
FIG. 74 illustrates a cross-sectional, side view of the syringe assembly coupled to a connector.

FIG. 74 illustrates an embodiment of the syringe assembly 1402 after the plunger 1404 has been moved proximally to its substantially proximal-most position (thereby transferring fluid into the second reservoir 1444), and then moved distally to its substantially distal-most position, thereby transferring fluid from the second reservoir 1444 through the connector 2200 and into a flexible container (not shown) or to a medical connector in fluid communication with a patient's bloodstream. As previously discussed, such transfer can cause the flexible container to expand. As shown, the proximal plunger seal 1412 has moved with (e.g., remained substantially stationary relative to) the plunger 1404 during the distal movement of the plunger 1404. In some embodiments, this can maintain the first reservoir 1420 at a generally constant volume. In various implementations, a proximal side of the proximal plunger seal 1412 is in fluid communication with ambient air, such as via the vent 1436.

In various embodiments, when the second reservoir 1444 is at or near its minimum volume, the first reservoir 1420 can have a volume of at least about 0.5 milliliters and/or less than or equal to about 100 milliliters; at least about 1 milliliters and/or less than or equal to about 20 milliliters; or at least about 3 milliliters and/or less than or equal to about 10 milliliters. In some embodiments, when the second reservoir 1444 reaches its minimum volume, the first reservoir 1420 can have a volume of at least about 2% of the maximum volume of the second reservoir 1444 and/or less than or equal to about 50% of the maximum volume of the second reservoir 1444. In some embodiments, when the second reservoir 1444 reaches its minimum volume, the first reservoir 1420 can have a volume of at least about 5% of the maximum volume of the second reservoir 1444 and/or less than or equal to about 20% of the maximum volume of the second reservoir 1444. In embodiments with volumetric independence of the first reservoir 1420 and the second reservoir 1444, changing the volume of the second reservoir 1444 does not necessarily change the volume of the first reservoir 1420, but changing the volume of the second reservoir 1444 can change the volume of the first reservoir 1420 if the reservoirs are fluidly coupled via a container with a fixed volume.

Figure 75A:
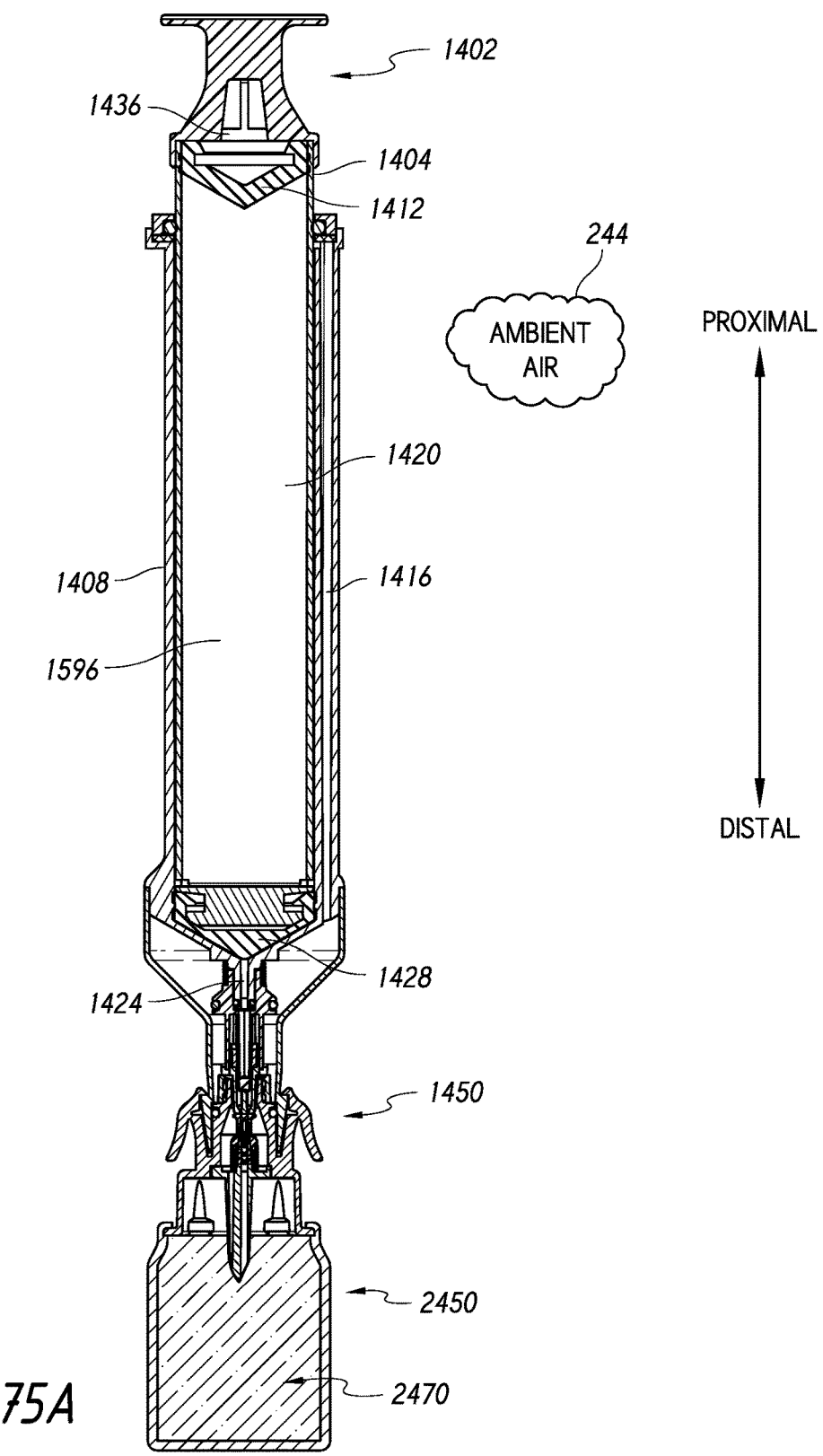
FIGS. 75A, 75B, and 75C illustrate cross-sectional, side views of a syringe assembly extracting fluid from a container.
Figure 75B:
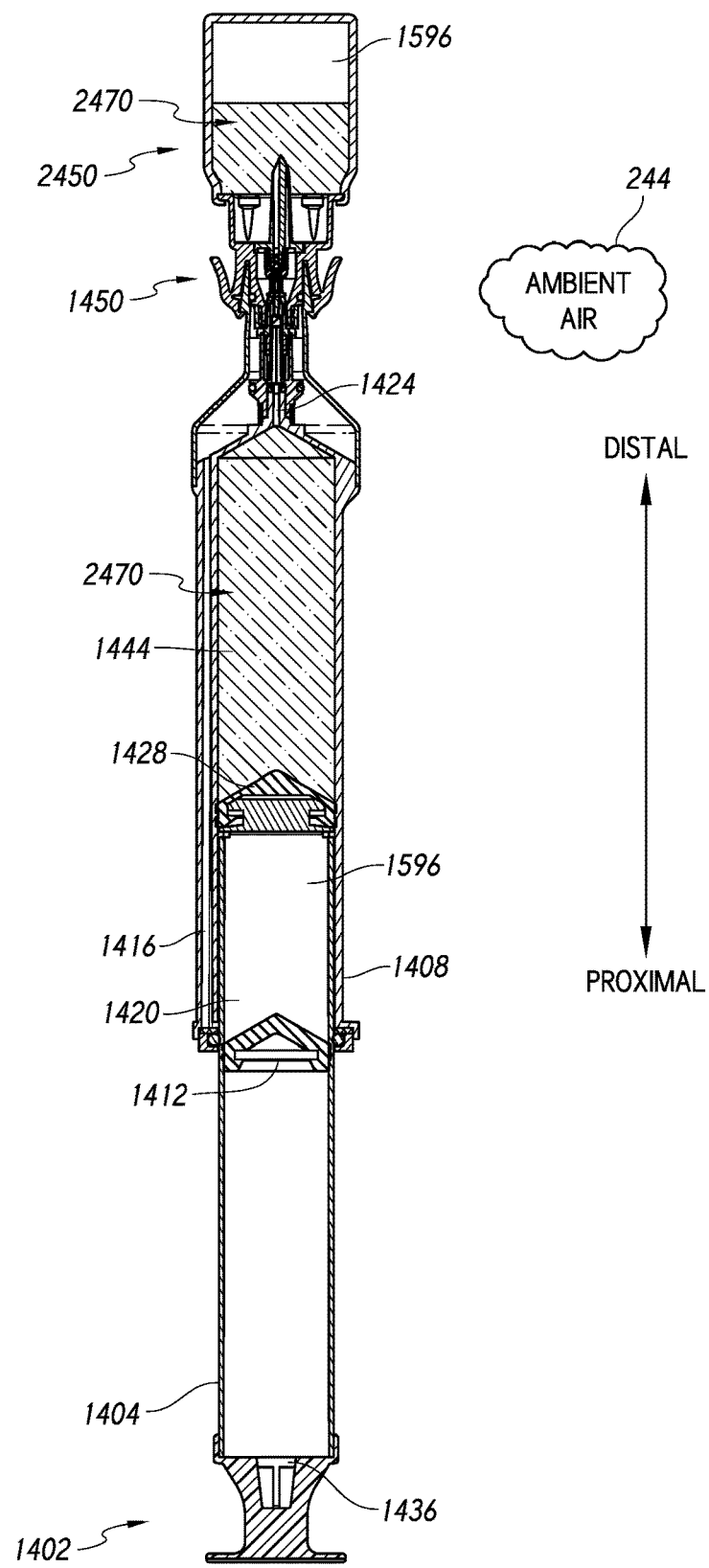
Figure 75C:
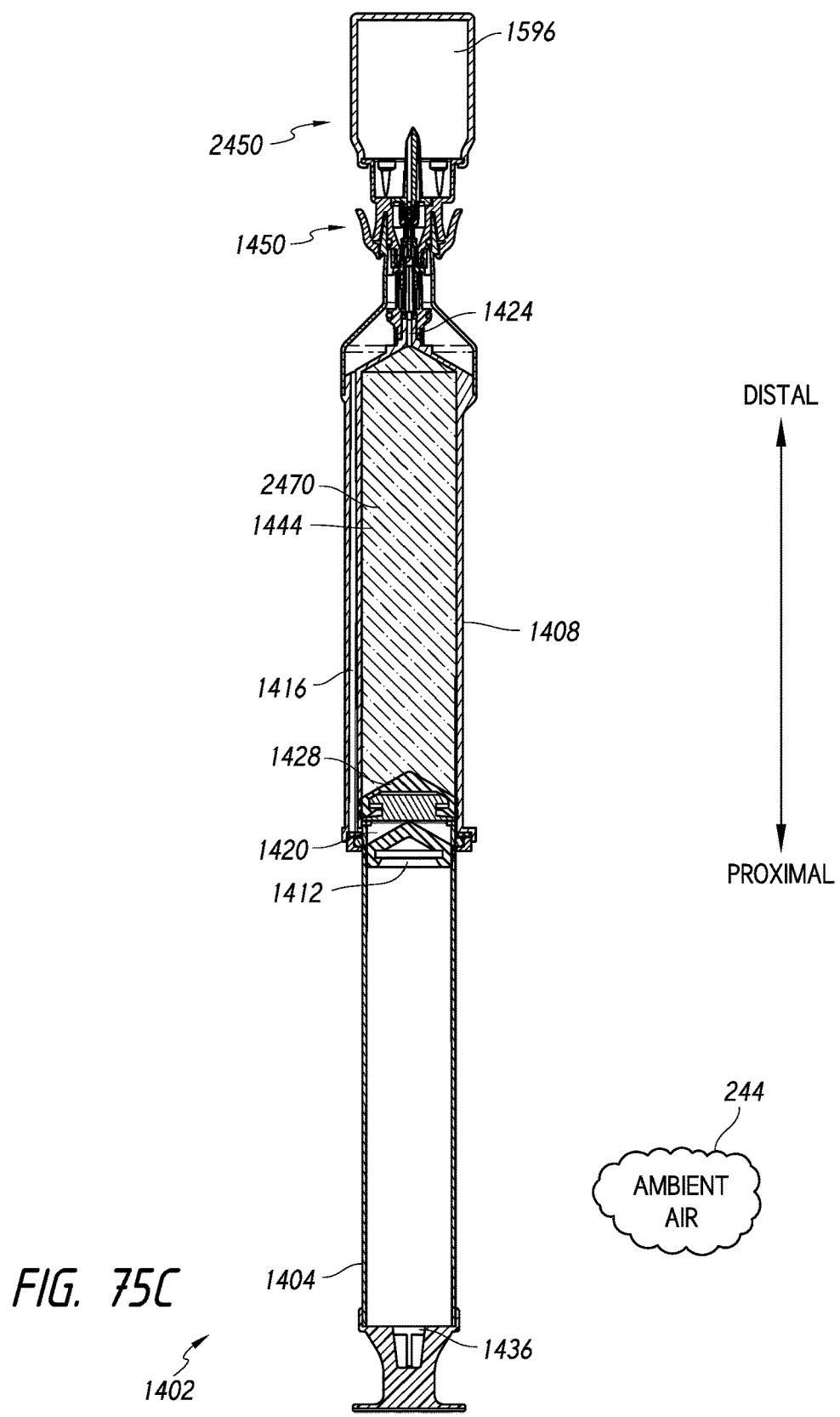

FIGS. 75A-75C illustrate cross-sectional, side views of the syringe assembly 1402 extracting fluid from the second container 2450. In FIG. 75A, the distal plunger seal 1428 is in its distal-most position. This can result in the second reservoir 1444 being at a minimum volume (e.g., substantially no volume). As is also shown in FIG. 75A, the proximal plunger seal 1412 is in its proximal-most position. In some embodiments, when the distal plunger seal 1428 is in its distal-most position and the proximal plunger seal 1412 is in its proximal-most position, the first reservoir 1420 is at its maximum volume. In certain implementations, when the plunger 1404 is moved proximally with respect to the barrel 1408, extraction fluid (e.g., the liquid pharmaceutical 2470) can be extracted (e.g., pulled, removed, or otherwise withdrawn) from the second container 2450. For example, the fluid can travel through the adapter assembly 1450, through the proximal second passage 1424, and/or into the second reservoir 1444 (as shown in FIG. 75B). In some embodiments, during proximal movement of the plunger 1404, the position of the proximal plunger seal 1412 remains generally constant (e.g., substantially does not move) with respect to the barrel 1408. In some embodiments, during proximal movement of the plunger 1404, the position of the distal plunger seal 1428 remains generally constant (e.g., substantially does not move) with respect to the vent 1436. To facilitate transferring the liquid pharmaceutical 2470 into the second reservoir 1444, the syringe assembly 1402, adaptor assembly 1450, and second container 2450 can be inverted as a group, as shown in FIG. 75B.

In some variants, regulating fluid 1596 (e.g., gas) from the first reservoir 1420 can flow into (e.g., backfill) the second container 2450 to regulate the pressure inside of the second container 2450 as the liquid pharmaceutical 2470 is extracted from the second container 2450. In some embodiments, the regulating fluid 1596 flows through the liquid pharmaceutical 2470 in the second container 2450, such when the apparatus is in an inverted position as shown in FIG. 75B. The first reservoir 1420 has a smaller volume in FIG. 75B than in FIG. 75A due to the fluid 1596 from the first reservoir 1420 flowing into the second container 2450.

In FIG. 75C, substantially all (e.g., at least about 90%) of the liquid pharmaceutical 2470 has been transferred from the second container 2450 to the second reservoir 1444 and/or the second reservoir 1444 has been substantially filled (e.g., to at least 90% capacity) with the liquid pharmaceutical 2470. In some embodiments, the second container 2450 is filled with the fluid 1596 from the first reservoir 1420.

In FIG. 75C, the distal plunger seal 1428 is in its proximal-most position and the proximal plunger seal 1412 is in its distal-most position. Some embodiments include moving the distal plunger seal proximally (e.g., relative to the second container 2450) while moving the proximal plunger seal 1412 distally (e.g., relative to the second container 2450, relative to the plunger 1404), and while removing a first fluid (e.g., the liquid pharmaceutical 2470) from the second container 2450 and/or while injecting a second fluid (e.g., the fluid 1596) into the second container 2450. Several embodiments include moving the distal plunger seal 1428 distally (e.g., relative to the second container 2450) while moving the proximal plunger seal 1412 proximally relative to the plunger 1404 (e.g., transferring gas from the second container 2450 to the syringe assembly 1402), and while injecting fluid (e.g., water, saline, the liquid pharmaceutical 2470) into the second container 2450.

The order in which flow controllers can open and close in some embodiments is addressed above in the context of FIGS. 46 and 47. Flow controllers include means to open and close passages, such first passages and second passages described in the context of many diverse embodiments. In some embodiments, the flow controllers can open and/or close in any possible order. Some embodiments include flow controllers configured to open and close in particular orders. The geometry of various components can be configured to make one flow controller open and/or close before another flow controller. A flow controller can include a valve and/or seal configured to block, seal, and/or prevent flow in a passage when the flow controller is in a closed position. A flow controller can include a valve and/or seal configured to allow and/or permit flow in a passage when the flow controller is in an open position.

Figure 76A:
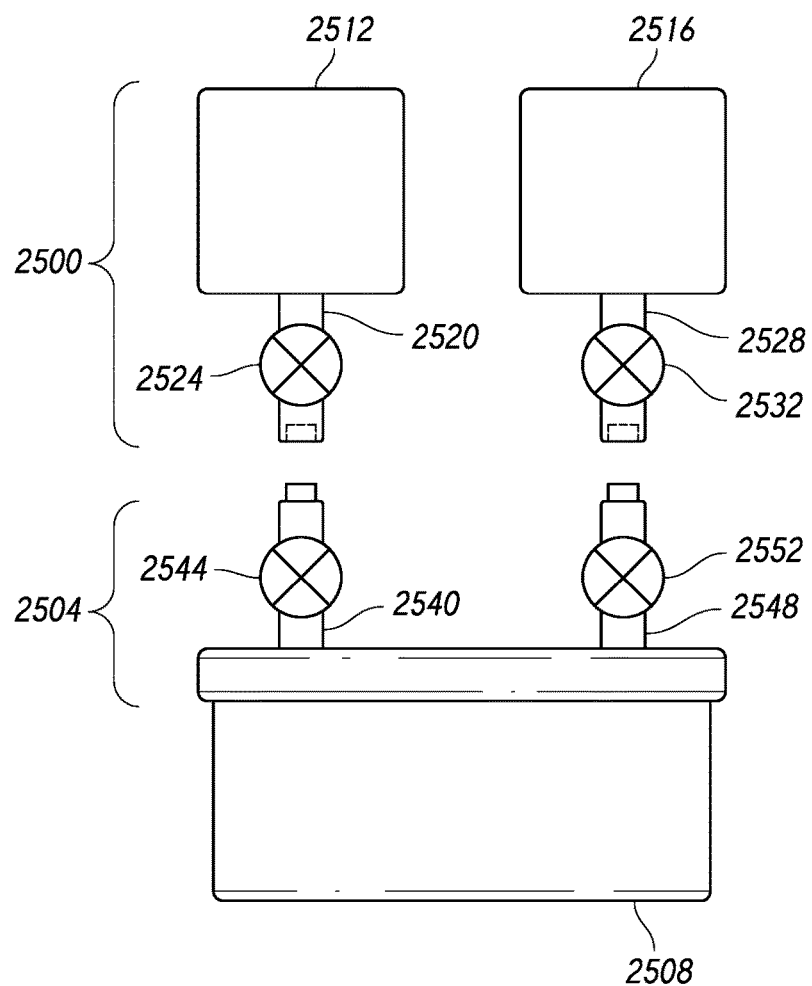
FIGS. 76A and 76B illustrate schematic views of a fluid transfer assembly and an adapter assembly, which is coupled to a container assembly.
Figure 76B:
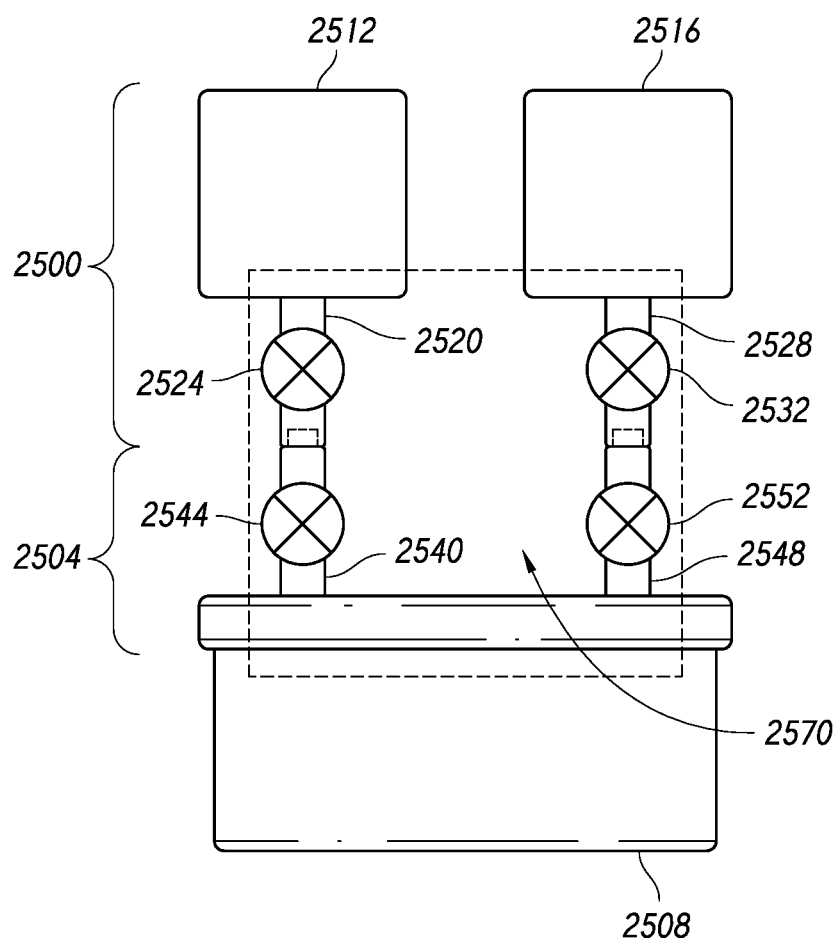

FIGS. 76A and 76B illustrate schematic views of a fluid transfer assembly 2500 and an adapter assembly 2504, which is coupled to a container assembly 2508. In FIG. 76A, the fluid transfer assembly 2500 is not coupled to the adapter assembly 2504, but the adapter assembly 2504 is coupled to the container assembly 2508. In FIG. 76B, the adapter assembly 2504 is coupled to the fluid transfer assembly 2500 and to the container assembly 2508.

The fluid transfer assembly 2500 can include a first reservoir 2512 and a second reservoir 2516. The first reservoir 2512 can include a first passage 2520. A first flow controller 2524 can be configured to open and close the first passage 2520. The second reservoir 2516 can include a second passage 2528. A second flow controller 2532 can be configured to open and close the second passage 2528.

The adapter assembly 2504 can include a third passage 2540. A third flow controller 2544 can be configured to open and close the third passage 2540. The adapter assembly 2504 can include a fourth passage 2548. A fourth flow controller 2552 can be configured to open and close the fourth passage 2548.

Referring now to FIG. 76B, the first passage 2520 can be fluidly and/or mechanically coupled to the third passage 2540. In some embodiments, mechanically coupling the first passage 2520 to the third passage 2540 automatically fluidly couples the first passage 2520 to the third passage 2540 by moving the first flow controller 2524 and the third flow controller 2544 to open positions such that fluid can flow between the first reservoir 2512 and an internal portion of the container assembly 2508.

In some embodiments, placing the container assembly 2508 in fluid communication with the first reservoir 2512 via the first passage 2520 and the third passage 2540 requires both the first flow controller 2524 and the third flow controller 2544 to be in open positions (e.g., fluid transmission positions). In several embodiments, when the fluid transfer assembly 2500 (e.g., a syringe assembly) is mechanically coupled to an adapter assembly 2504, the first flow controller 2524 automatically opens before the third flow controller 2544 opens. In several embodiments, when the fluid transfer assembly 2500 (e.g., a syringe assembly) is mechanically coupled to an adapter assembly 2504, the third flow controller 2544 automatically opens before the first flow controller 2524 opens.

In the context of FIGS. 76A and 76B, "automatically opens" means that the act of mechanically coupling the fluid transfer assembly 2500 to the adapter assembly 2504 causes and/or results in the opening of a flow controller. Many other embodiments described herein are configured for automatically opening. In some embodiments, at least one, several, or all flow controllers automatically open when a syringe assembly is mechanically coupled via threads to an adapter assembly or a connector. For example, a syringe assembly can be screwed onto and/or into an adapter assembly or connector.

In several embodiments, when the fluid transfer assembly 2500 (e.g., a syringe assembly) is mechanically uncoupled from an adapter assembly 2504, the first flow controller 2524 automatically closes before the third flow controller 2544 closes. In several embodiments, when the fluid transfer assembly 2500 (e.g., a syringe assembly) is mechanically uncoupled from an adapter assembly 2504, the third flow controller 2544 automatically closes before the first flow controller 2524 closes. In the context of FIGS. 76A and 76B, "automatically closes" means that the act of mechanically uncoupling the fluid transfer assembly 2500 to the adapter assembly 2504 causes a flow controller to close. Many other embodiments described herein are configured for automatically closing.

The second passage 2528 can be fluidly and/or mechanically coupled to the fourth passage 2548. In some embodiments, mechanically coupling the second passage 2528 to the fourth passage 2548 automatically fluidly couples the second passage 2528 to the fourth passage 2548 by moving the second flow controller 2532 and the fourth flow controller 2552 to open positions such that fluid can flow between the second reservoir 2516 and an internal portion of the container assembly 2508.

In some embodiments, placing the container assembly 2508 in fluid communication with the second reservoir 2516 via the second passage 2528 and the fourth passage 2548 requires both the second flow controller 2532 and the fourth flow controller 2552 to be in open positions (e.g., fluid transmission positions). In several embodiments, when the fluid transfer assembly 2500 (e.g., a syringe assembly) is mechanically coupled to an adapter assembly 2504, the second flow controller 2532 automatically opens before the fourth flow controller 2552 opens. In several embodiments, when the fluid transfer assembly 2500 (e.g., a syringe assembly) is mechanically coupled to an adapter assembly 2504, the fourth flow controller 2552 automatically opens before the second flow controller 2532 opens.

In several embodiments, when the fluid transfer assembly 2500 (e.g., a syringe assembly) is mechanically uncoupled from an adapter assembly 2504, the second flow controller 2532 automatically closes before the fourth flow controller 2552 closes. In several embodiments, when the fluid transfer assembly 2500 (e.g., a syringe assembly) is mechanically uncoupled from an adapter assembly 2504, the fourth flow controller 2552 automatically closes before the second flow controller 2532 closes.

In some embodiments, the flow controllers open (e.g., unseal) in the following order as the fluid transfer assembly 2500 is mechanically coupled with the adapter assembly 2504: third flow controller 2544, first flow controller 2524, second flow controller 2532, fourth flow controller 2552. In some embodiments, the order is: first flow controller 2524, third flow controller 2544, second flow controller 2532, fourth flow controller 2552. In some implementations, the order is: third flow controller 2544, first flow controller 2524, fourth flow controller 2552, second flow controller 2532. All other orders are contemplated by this disclosure as well.

In some embodiments, the passage to the liquid reservoir opens (e.g., unseals) before the passage to the gas reservoir opens (e.g., unseals) as the fluid transfer assembly 2500 is mechanically coupled to the adapter assembly 2504. In some embodiments, the passage seal 2560 closes (e.g., seals) before the passage to the liquid reservoir opens (e.g., unseals) as the fluid transfer assembly 2500 is mechanically coupled to the adapter assembly 2504. In some embodiments, this approach can reduce the likelihood of fluid in the syringe assembly and/or in the container escaping into the ambient air (e.g., due to a pressure gradient between the syringe assembly and the container).

Some embodiments include a flow controller that seals all the passages from the ambient air (e.g., even if one of the passages would otherwise leak to the ambient air). This flow controller is depicted as a passage seal 2560 in FIG. 76B, the distal seal 1264 in FIG. 77, the first seal in FIG. 51, and the first seal 1470 in FIG. 41. In some embodiments, this flow controller (e.g., the passage seal 2560 in FIG. 76B, the distal seal 1264 in FIG. 77, the first seal in FIG. 51, and the first seal 1470 in FIG. 41) fluidly isolates a passage joining area 2570 before the opening of the third flow controller 2544, first flow controller 2524, second flow controller 2532, and/or fourth flow controller 2552. The passage joining area 2570 is the area between the fluid transfer assembly 2500 (e.g., a syringe assembly) and the adapter assembly 2504 where the first passage 2520 couples with the third passage 2540 and where the second passage 2528 couples with the fourth passage 2548. In some embodiments, the passage seal 2560 stops fluidly isolating the passage joining area 2570 after the closing of the third flow controller 2544, first flow controller 2524, second flow controller 2532, and/or fourth flow controller 2552. In other words, in some embodiments, the passage seal 2560 moves to an open position after the third flow controller 2544, first flow controller 2524, second flow controller 2532, and/or fourth flow controller 2552 have moved to a closed position.

In some embodiments, while the fluid transfer assembly 2500 is mechanically coupled to the adapter assembly 2504, the passage seal 2560 is in a closed (e.g., sealed) position, while the first flow controller 2524, the third flow controller 2544, the second flow controller 2532, and the fourth flow controller 2552 are in open (e.g., unsealed) positions to place the first passage 2520 in fluid communication with the third passage 2540 and to place the second passage 2528 in fluid communication with the fourth passage 2548, while sealing the first passage 2520 and the third passage 2540 from the second passage 2528 and the fourth passage 2548.

As the fluid transfer assembly 2500 is mechanically uncoupled from the adapter assembly 2504, the first flow controller 2524 can move to a closed (e.g., sealed) position before the third flow controller 2544, the second flow controller 2532, and/or the fourth flow controller 2552 move to a closed position (e.g., while the third flow controller 2544, the second flow controller 2532, and/or the fourth flow controller 2552 are in open positions).

In some embodiments, the flow controllers close (e.g., seal) in the following order as the fluid transfer assembly 2500 is mechanically uncoupled from the adapter assembly 2504: first flow controller 2524, third flow controller 2544, fourth flow controller 2552, second flow controller 2532. In some embodiments, the flow controllers close (e.g., seal) in the following order as the fluid transfer assembly 2500 is mechanically uncoupled from the adapter assembly 2504: first flow controller 2524, fourth flow controller 2552, third flow controller 2544, second flow controller 2532. All other orders are contemplated by this disclosure as well.

In some embodiments, the passage to the gas reservoir closes (e.g., seals) before the passage to the liquid reservoir closes (e.g., seals) as the fluid transfer assembly 2500 is mechanically uncoupled from the adapter assembly 2504. In some embodiments, the passage to the gas reservoir closes (e.g., seals) and the passage to the liquid reservoir closes (e.g., seals) before the passage seal 2560 opens (e.g., unseals) as the fluid transfer assembly 2500 is mechanically uncoupled from the adapter assembly 2504.

Figure 77:
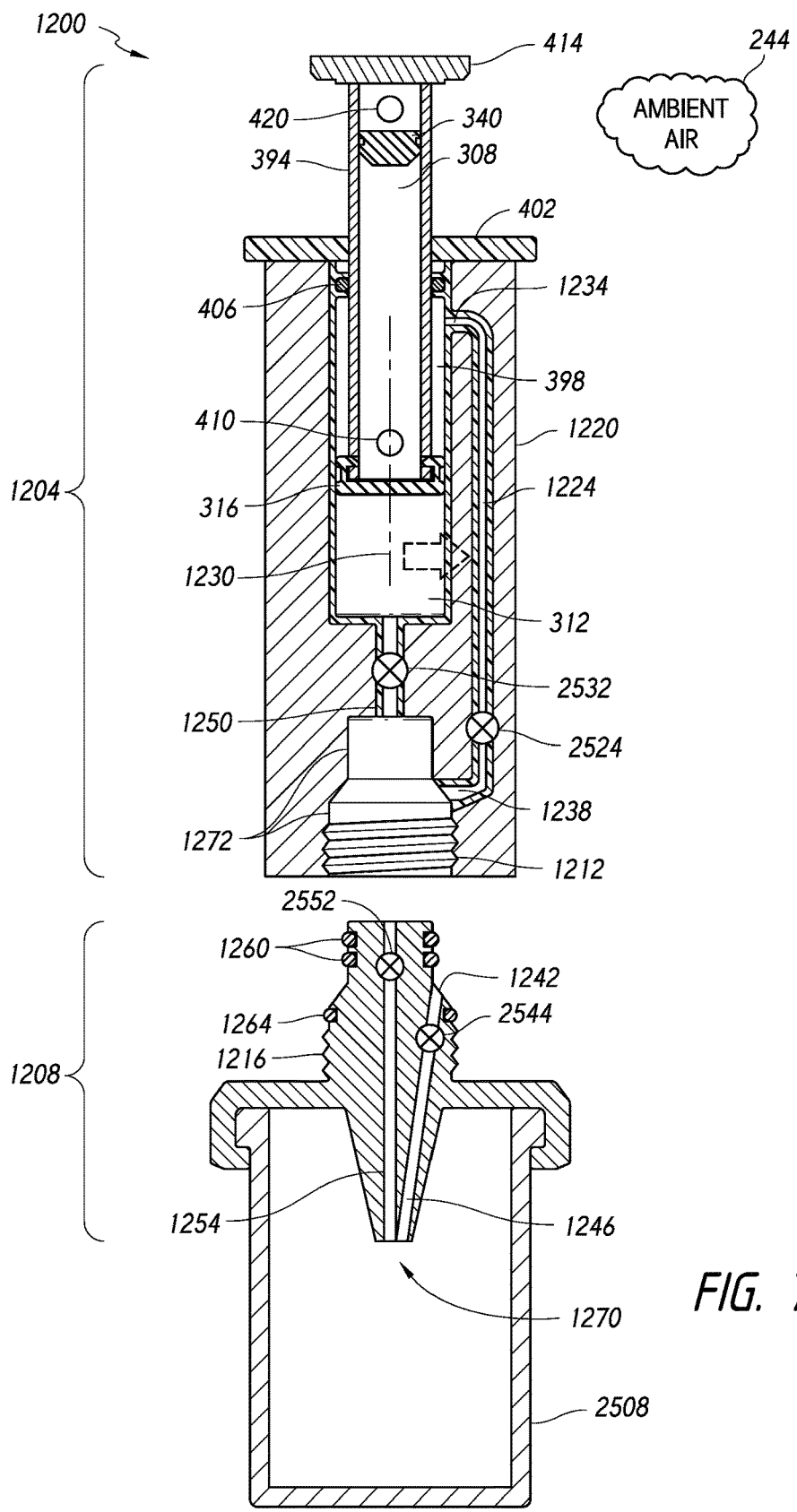
FIG. 77 illustrates a cross-sectional, side view of an embodiment related to the embodiment illustrated in FIGS. 76A and 76B.

FIG. 77 illustrates another embodiment of a pressure regulating syringe system 1200, which is similar to the embodiment illustrated in FIGS. 76A and 76B. The passage seal 2560 in FIG. 76B includes the distal seal 1264 in FIG. 77. The first flow controller 2524 controls flow in the proximal first passage 1224. The second flow controller 2532 controls flow in the proximal second passage 1250. The third flow controller 2544 controls flow in the distal first passage 1246. The fourth flow controller 2552 controls flow in the distal second passage 1254. In the embodiment illustrated in FIG. 77, fluid communication between the first reservoir 308 and the container assembly 2508 can occur when the flow controller (e.g., 2524, 2544) associated with the passage between the first reservoir 308 and the container assembly 2508 is in an open (e.g., unsealed) position. In the embodiment illustrated in FIG. 77, fluid communication between the second reservoir 312 and the container assembly 2508 can occur when the flow controller (e.g., 2532, 2552) associated with the passage between the second reservoir 312 and the container assembly 2508 is in an open (e.g., unsealed) position.

Referring back to FIGS. 38 and 39, the proximal first passage 1416 can be sealed, blocked, and/or closed by moving the third seal 1562. For example, the third seal 1562 can be moved in a distal direction such that the third seal 1562 seals against the inner surface 1580 (as shown in FIG. 38). The proximal first passage 1416 can be unsealed, unblocked, and/or opened when the syringe assembly 1402 is coupled to an adapter such that the adapter engages (e.g., presses) the distal portion 1584 of the passage shaft 1574 in a proximal direction, which moves the third seal 1562 from a sealing, blocking, and/or closing position to an unsealing, unblocking, and/or opening position. Thus, the third seal 1562 and the inner surface 1580 can form the first flow controller 2524 in FIGS. 76A, 76B, and 77.

FIGS. 38 and 39 also show that the proximal second passage 1424 can be alternately sealed, blocked, and/or closed (see FIG. 38) and unsealed, unblocked, and/or opened (see FIG. 39). The distal portion 1584 of the passage shaft 1574 can include a tapered portion that seals, blocks, and/or closes against a tapered portion 1548 of the distal cap 1550 in a seal zone 1590. Thus, the seal zone 1590 in FIG. 38 can form the second flow controller 2532 in FIGS. 76A, 76B, and 77.

Moreover, with reference back to FIG. 36A, the distal first passage 1246 can be unsealed, unblocked, and/or opened by moving the radial protrusion 1508 distally such that the radial protrusion 1508 of the second seal 1486 no longer contacts the inner tapered region 1518 of the adapter assembly 1450. Thus, the radial protrusion 1508 and the inner tapered region 1518 can form the third flow controller 2544 in FIGS. 76A, 76B, and 77.

FIG. 36A illustrates the distal second passage 1254 in an unsealed, unblocked, and/or open position because the second seal 1486 is in a distal location (rather than in a proximal sealing location 1502) so the second seal 1486 does not cover, seal, occlude, and/or block the radial hole 1528. As a result, fluid (such as a medical liquid) can flow through the distal second passage 1254, through the radial hole 1528, and into the proximal second passage 1424 (shown in FIG. 39). Thus, the second seal 1486 and the radial hole 1528 can form the fourth flow controller 2552 in FIGS. 76A, 76B, and 77.

In several embodiments, the adapter 1208 is attached directly to the syringe assembly 1204 rather than requiring an intermediate component to connect the adapter 1208 to the syringe assembly 1204. In some embodiments, the adapter 1208 is attached directly to a container (e.g., container assembly 2508) rather than requiring an intermediate component to connect the adapter 1208 to the container. Direct attachment can reduce the number of components and/or assemblies required to use the syringe assembly 1204 and/or adapter assembly 1208. Referring now to FIGS. 41 and 65, the syringe assembly 1402 can couple (e.g., attach) directly to an adapter assembly 1450 and can couple (e.g., attach) directly to a connector 2200. Thus, the syringe assembly 1402 can be compatible with both the adapter assembly 1450 (e.g., a vial adapter) and the connector 2200 (e.g., a connector configured to couple the syringe assembly 1402 to a tube or bag).

Figure 78:
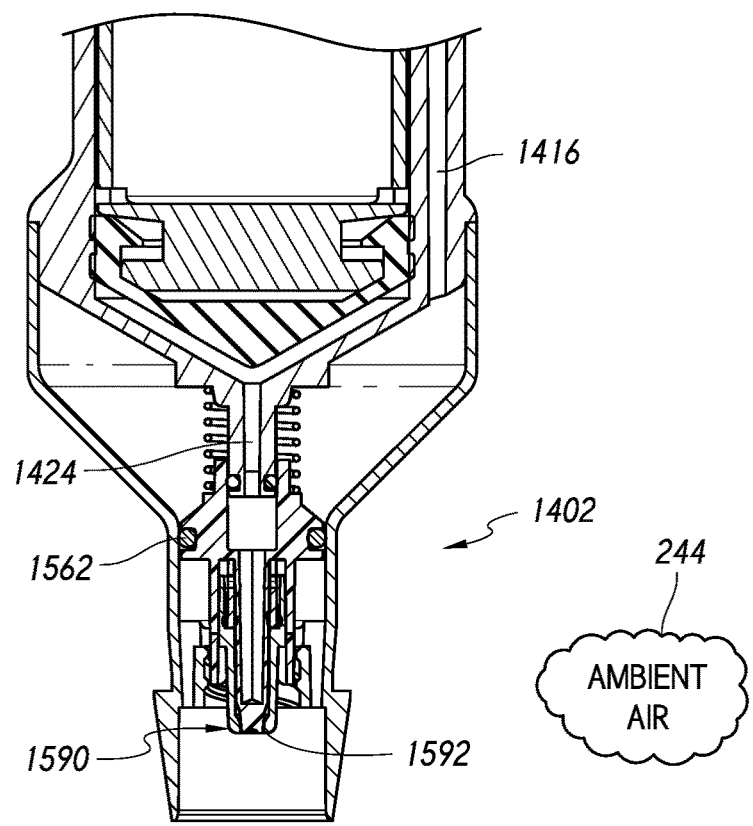
FIG. 78 illustrates a cross-sectional, side view of a distal portion of a syringe assembly just before the syringe assembly is coupled with an adapter, which is attached to a container.
Figure 78:
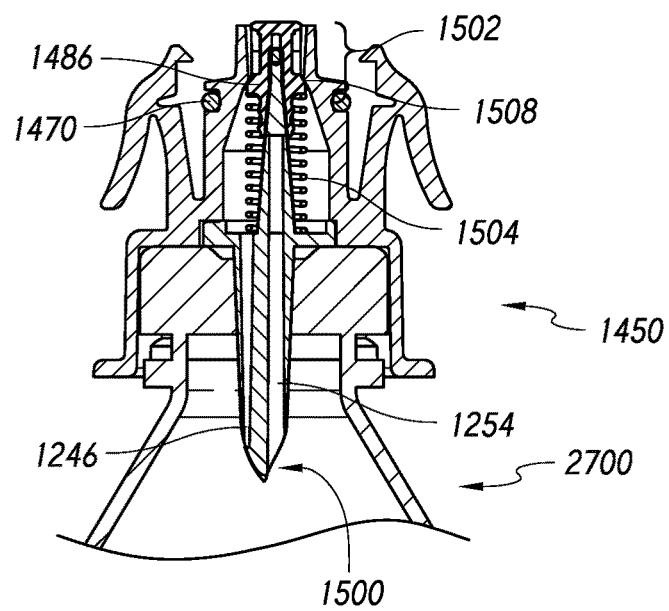

FIG. 78 illustrates a cross-sectional view of a distal portion of a syringe assembly 1402 in a first mode, such as before the syringe assembly 1402 is coupled with an adapter 1450 (which is attached to a container 2700) or after the syringe assembly 1402 and the adapter 1450 are decoupled. The first seal 1470 is in an open position (e.g., because it does not contact a portion of the syringe assembly 1402 to seal a passage joining area). The second seal 1486 is in a closed position to seal the distal first passage 1246 and the distal second passage 1254. The third seal 1562 is in a closed position to seal the proximal first passage 1416. The seal zone 1590 is in a closed position to seal the proximal second passage 1424.

Figure 79:
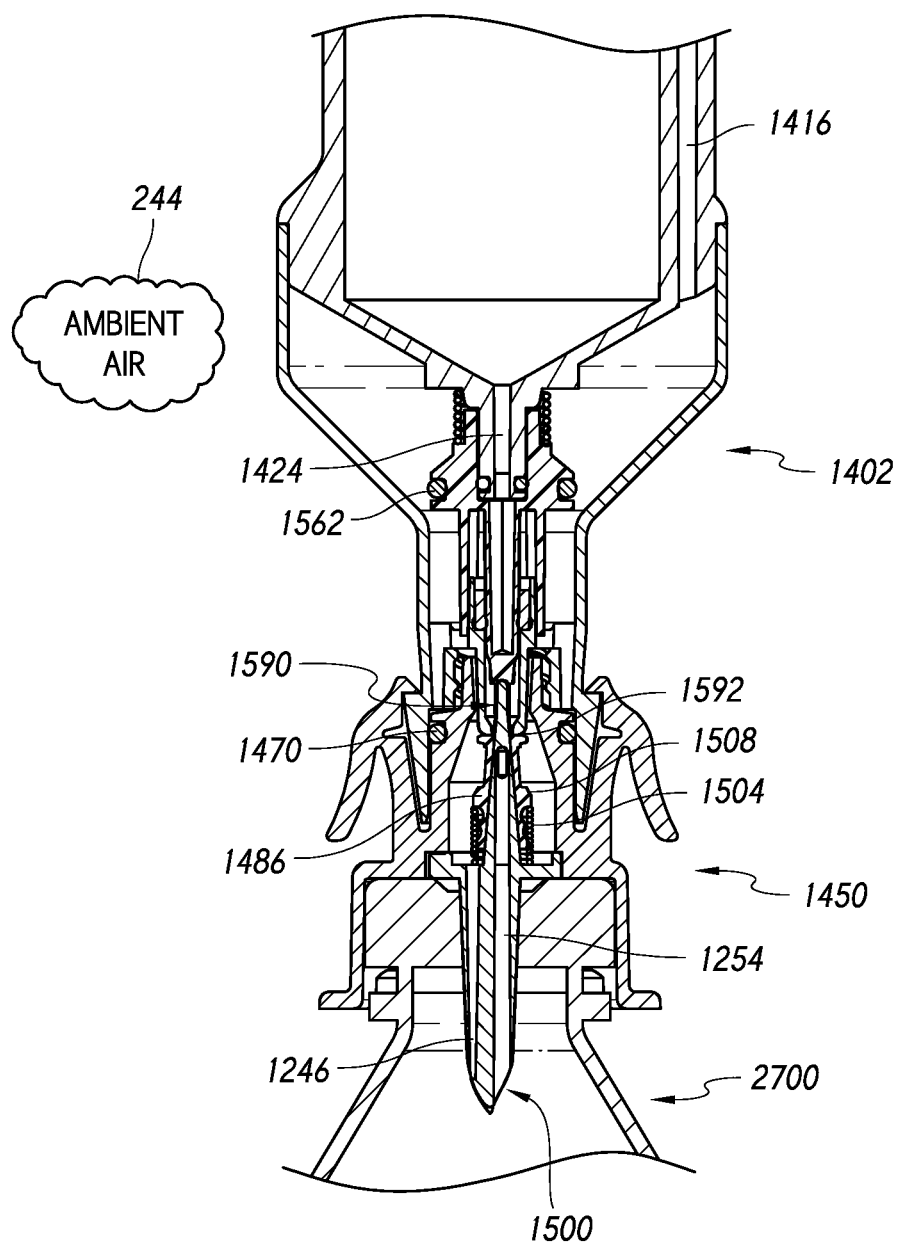
FIG. 79 illustrates a cross-sectional, side view of a distal portion of a syringe assembly just before the syringe assembly is fully coupled with an adapter.

FIG. 79 illustrates a cross-sectional view of a distal portion of a syringe assembly 1402 in a second mode, such as during coupling (e.g., just before the syringe assembly 1402 is fully coupled with an adapter 1450) or during decoupling (e.g., as the syringe assembly 1402 begins to separate from the adapter assembly 1450). The third seal 1562 is sealing against an inner wall, which seals the proximal first passage 1416. As a result, the first reservoir (not shown) is not in fluid communication with the container 2700 even though the distal first passage 1246 is in an open (e.g., unsealed) position. The proximal second passage 1424 and the distal second passage 1254 are in open (e.g., unsealed) positions. As a result, the second reservoir (not shown) is still in fluid communication with the container 2700.

Although various pressure-regulating systems have been disclosed in the context of certain embodiments and examples, the pressure-regulating systems of this disclosure extend beyond the specifically disclosed embodiments to other alternative embodiments and/or uses of the embodiments and certain modifications and equivalents thereof. For example, some embodiments are configured to use a regulating fluid that is a liquid (such as water or saline), rather than a gas. As another example, in certain embodiments, the bag includes bellows. As another example, in certain embodiments, various components are integrated and/or replaced by a single component. Various features and aspects of the disclosed embodiments can be combined with or substituted for one another in order to form varying modes of pressure-regulating systems. Accordingly, it is intended that the scope of the pressure-regulating systems of this disclosure should not be limited by the particular embodiments described above, but should be determined only by a fair reading of the current and/or future claims.

Certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as any subcombination or variation of any subcombination.

Any portion of any of the steps, processes, structures, and/or devices disclosed or illustrated in one embodiment, flowchart, or example in this disclosure can be combined or used with (or instead of) any other portion of any of the steps, processes, structures, and/or devices disclosed or illustrated in a different embodiment, flowchart, or example. The embodiments and examples described herein are not intended to be discrete and separate from each other. Combinations, variations, and other implementations of the disclosed features are within the scope of this disclosure.

Any of the steps and blocks can be adjusted or modified. Other or additional steps can be used. None of the steps or blocks described herein is essential or indispensable. Moreover, while operations may be depicted in the drawings or described in the specification in a particular order, such operations need not be performed in the particular order shown or in sequential order, and that all operations need not be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Also, the separation of various system components in the implementations described above should not be understood as requiring such separation in all implementations, and it should be understood that the described components and systems can generally be integrated together in a single product or packaged into multiple products.

Terms relating to circular shapes as used herein, such as diameter or radius, should be understood not to require perfect circular structures, but rather should be applied to any suitable structure with a cross-sectional region that can be measured from side-to-side. Terms relating to shapes, such as "circular" or "cylindrical" or "semi-circular" or "semi-cylindrical" or any related or similar terms, are not required to conform strictly to the mathematical definitions of circles or cylinders or other structures, but can encompass structures that are reasonably close approximations. Likewise, shapes modified by the word "generally" (e.g., "generally cylindrical") can include reasonably close approximations of the stated shape.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment.

Conjunctive language, such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require at least one of X, at least one of Y, and at least one of Z to each be present.

The terms "comprising," "including," "having," and the like are synonymous and are used inclusively, in an open-ended fashion, and do not exclude additional elements, features, acts, operations and so forth. Also, the term "or" is used in its inclusive sense (and not in its exclusive sense) so that when used, for example, to connect a list of elements, the term "or" means one, some, or all of the elements in the list.

The term "and/or" means that "and" applies to some embodiments and "or" applies to some embodiments. Thus, A, B, and/or C can be replaced with A, B, and C written in one sentence and A, B, or C written in another sentence. A, B, and/or C means that some embodiments can include A and B, some embodiments can include A and C, some embodiments can include B and C, some embodiments can only include A, some embodiments can include only B, some embodiments can include only C, and some embodiments include A, B, and C. The term "and/or" is used to avoid unnecessary redundancy.

The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes or tends toward a particular value, amount, or characteristic. As an example, in certain embodiments, as the context may dictate, the term "generally parallel" can refer to something that departs from exactly parallel by less than or equal to 20 degrees.

Some embodiments have been described in connection with the accompanying drawings. The figures are drawn to scale, but such scale should not be limiting, since dimensions and proportions other than what are shown are contemplated and are within the scope of this disclosure. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

The various features and processes described above may be used independently of one another, or may be combined in various ways. All possible combinations and subcombinations are intended to fall within the scope of this disclosure. In addition, certain method, event, state, or process blocks may be omitted in some implementations. The methods and processes described herein are also not limited to any particular sequence, and the blocks or states relating thereto can be performed in other sequences that are appropriate. For example, described tasks or events may be performed in an order other than the order specifically disclosed. Multiple steps may be combined in a single block or state. The example tasks or events may be performed in serial, in parallel, or in some other manner. Tasks or events may be added to or removed from the disclosed example embodiments. The example systems and components described herein may be configured differently than described. For example, elements may be added to, removed from, or rearranged compared to the disclosed example embodiments.

In summary, various embodiments and examples of pressure-regulating fluid transfer systems and methods have been disclosed. Although the disclosure has been in the context of those embodiments and examples, this disclosure extends beyond the specifically disclosed embodiments to other alternative embodiments and/or other uses of the embodiments, as well as to certain modifications and equivalents thereof. This disclosure expressly contemplates that various features and aspects of the disclosed embodiments can be combined with, or substituted for, one another. Accordingly, the scope of this disclosure should not be limited by the particular disclosed embodiments described above, but should be determined only by a fair reading of the claims that follow.

The following is claimed:

1. A pressure-regulating system configured to transfer medical fluids from the pressure-regulating system to a flexible medical container, the pressure-regulating system comprising:
    an adapter assembly configured to connect with a flexible medical container that has a variable volume; and
    a syringe assembly configured to releasably connect with the adapter assembly and to transfer fluid to and from the flexible medical container via the adapter assembly, the syringe assembly comprising:
        a housing comprising a barrel and a tube;
        the barrel having a proximal portion, a distal portion, a rigid sidewall, and an inner surface;
        the tube being coaxial with the barrel and movable relative to the barrel, the tube having a proximal end, a distal end, and an inner passage, at least the distal end received in the barrel;
        a distal seal that is coupled with the distal end of the tube and that slides along an inner surface of the barrel when the tube is moved relative to the barrel, wherein the distal seal does not permit fluid to pass through the distal seal from a proximal side to a distal side of the seal;
        a regulating reservoir bounded in part by the rigid sidewall of the housing and the distal seal, the regulating reservoir containing an amount of regulating fluid; and
        an access reservoir located in the distal portion of the barrel;
    wherein the pressure-regulating system is configured to operate such that the combined total volume of the regulating reservoir and the access reservoir within the housing is variable, and the regulating reservoir is in fluid communication with an interior of the flexible medical container, when fluid is transferred between the syringe assembly and the flexible medical container.

2. The system of claim 1, wherein:
    when the adapter assembly and the syringe assembly are coupled, the regulating reservoir is configured to deliver regulating fluid to the medical vial and the access reservoir is configured to receive liquid from the vial; and
    wherein, when the adapter assembly and the syringe assembly are not coupled, the regulating reservoir and the access reservoir are each substantially sealed from the ambient environment.

3. The system of claim 1, wherein the pressure-regulating system is further configured to operate such that the combined total volume of the regulating reservoir and the access reservoir decreases when fluid is transferred from the access reservoir to the flexible medical container.

4. The system of claim 1, wherein the pressure-regulating system is further configured to operate such that the combined total volume of the regulating reservoir and the access reservoir increases when fluid is transferred from the flexible medical container to the access reservoir.

5. The system of claim 1, wherein the pressure-regulating system is further configured to operate such that the volume of the regulating reservoir is substantially constant when fluid is transferred between the syringe assembly and the flexible medical container.

6. The system of claim 1, wherein the adapter assembly does not comprise an ambient air inlet.

7. The system of claim 1, wherein the pressure-regulating system is further configured to operate such that substantially no regulating fluid is transferred from the flexible medical container into the regulating reservoir.

8. The system of claim 1, further comprising a proximal seal, the proximal seal having a first side and a second side, the first side bounding a portion of the first reservoir, the second side being in communication with ambient.

9. The system of claim 8, wherein the proximal seal is located radially inward of the rigid sidewall of the barrel.

10. The system of claim 8, wherein the pressure-regulating system is further configured to operate such that the proximal seal moves relative to the housing when the medical fluid is introduced into the variable volume container.

11. The system of claim 1, wherein the flexible medical container comprises an IV bag.

12. A combination of the pressure-regulating system of claim 1 and the flexible medical container.

* * * * *